US009278969B2

(12) United States Patent
Ksander et al.

(10) Patent No.: US 9,278,969 B2
(45) Date of Patent: Mar. 8, 2016

(54) ORGANIC COMPOUNDS

(71) Applicants: Gary Michael Ksander, Amherst, NH (US); Erik Meredith, Hudson, MA (US); Lauren Monovich, Belmont, MA (US); Julien Papillon, Somerville, MA (US); Fariborz Firooznia, Florham Park, NJ (US); Qi-Ying Hu, Needham, MA (US)

(72) Inventors: Gary Michael Ksander, Amherst, NH (US); Erik Meredith, Hudson, MA (US); Lauren Monovich, Belmont, MA (US); Julien Papillon, Somerville, MA (US); Fariborz Firooznia, Florham Park, NJ (US); Qi-Ying Hu, Needham, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/459,567

(22) Filed: Aug. 14, 2014

(65) Prior Publication Data
US 2014/0357621 A1 Dec. 4, 2014

Related U.S. Application Data

(63) Continuation of application No. 13/927,514, filed on Jun. 26, 2013, now Pat. No. 8,835,646, which is a continuation of application No. 13/540,113, filed on Jul. 2, 2012, now abandoned, which is a continuation of application No. 11/508,445, filed on Aug. 23, 2006, now Pat. No. 8,314,097.

(60) Provisional application No. 60/711,442, filed on Aug. 25, 2005.

(51) Int. Cl.
*C07D 401/02* (2006.01)
*C07D 401/10* (2006.01)
*A61K 31/437* (2006.01)
*A61K 31/4353* (2006.01)
*C07D 471/04* (2006.01)
*C07D 487/04* (2006.01)
*A61K 31/4188* (2006.01)
*A61K 31/454* (2006.01)
*A61K 31/5377* (2006.01)
*A61K 45/06* (2006.01)
*A61K 31/55* (2006.01)

(52) U.S. Cl.
CPC .......... *C07D 471/04* (2013.01); *A61K 31/4188* (2013.01); *A61K 31/437* (2013.01); *A61K 31/454* (2013.01); *A61K 31/5377* (2013.01); *A61K 31/55* (2013.01); *A61K 45/06* (2013.01); *C07D 487/04* (2013.01)

(58) Field of Classification Search
CPC .. C07D 401/02; C07D 401/10; A61K 31/437; A61K 31/4353

USPC .......................................... 546/112; 514/300
See application file for complete search history.

(56) References Cited

U.S. PATENT DOCUMENTS

| 4,617,307 | A | 10/1986 | Browne |
| 4,728,645 | A | 3/1988 | Browne |
| 4,889,861 | A | 12/1989 | Browne |
| 4,937,250 | A | 6/1990 | Bowman et al. |
| 4,978,672 | A | 12/1990 | Bowman et al. |
| 5,057,521 | A | 10/1991 | Hausler et al. |

(Continued)

FOREIGN PATENT DOCUMENTS

| CL | 04982009 | 3/2009 |
| EP | 165904 | 6/1985 |

(Continued)

OTHER PUBLICATIONS

Browne. L. J., Gude. C., Rodriguez, H. Steele, R E. Bhatnager. A. Fadrozole hydrochloride a potent, selective, nonsteroidal inhibitor of aromatase for the treatment of estrogen-dependent disease. Journal of Medicinal Chemistry (1991), 34(2). 725-36.

(Continued)

*Primary Examiner* — Niloofar Rahmani
(74) *Attorney, Agent, or Firm* — Michelle Han

(57) ABSTRACT

The present invention provides a compound of formula I:

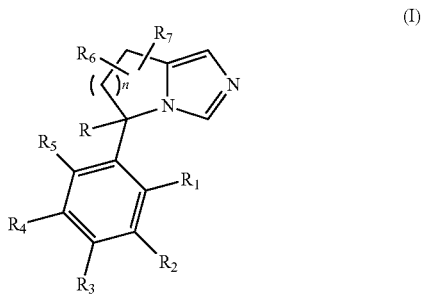

Said compound is inhibitor of aldosterone synthase and aromatase, and thus can be employed for the treatment of a disorder or disease mediated by aldosterone synthase or aromatase. Accordingly, the compound of formula I can be used in treatment of hypokalemia, hypertension, congestive heart failure, atrial fibrillation, renal failure, in particular, chronic renal failure, restenosis, atherosclerosis, syndrome X, obesity, nephropathy, post-myocardial infarction, coronary heart diseases, inflammation, increased formation of collagen, fibrosis such as cardiac or myocardiac fibrosis and remodeling following hypertension and endothelial dysfunction, gynecomastia, osteoporosis, prostate cancer, endometriosis, uterine fibroids, dysfunctional uterine bleeding, endometrial hyperplasia, polycystic ovarian disease, infertility, fibrocystic breast disease, breast cancer and fibrocystic mastopathy. Finally, the present invention also provides a pharmaceutical composition.

4 Claims, No Drawings

(56) References Cited

U.S. PATENT DOCUMENTS

| | | |
|---|---|---|
| 5,066,656 A | 11/1991 | Greco et al. |
| 5,428,160 A * | 6/1995 | Browne .............. C07D 213/38 544/125 |
| 5,491,161 A | 2/1996 | Janssen et al. |
| 5,583,128 A | 12/1996 | Bhatnagar |
| 8,168,794 B2 | 5/2012 | Burger et al. |
| 8,314,097 B2 | 11/2012 | Ksander et al. |
| 8,575,160 B2 | 11/2013 | Sun et al. |
| 2013/0065893 A1 | 3/2013 | Sun et al. |

FOREIGN PATENT DOCUMENTS

| | | |
|---|---|---|
| EP | 236940 | 9/1987 |
| EP | 514015 | 4/1991 |
| EP | 426225 | 5/1991 |
| EP | 433084 | 6/1991 |
| EP | 479570 | 4/1992 |
| EP | 0516278 | 12/1992 |
| EP | 0625155 | 8/2001 |
| JP | 169518 | 10/1991 |
| JP | 09071586 | 9/1995 |
| KR | 100219017 | 12/1996 |
| KR | 1020030048156 | 5/2002 |
| WO | 9218132 | 10/1992 |
| WO | 9315079 | 8/1993 |
| WO | 0107046 | 2/2001 |
| WO | 01/76571 | 10/2001 |
| WO | 0240484 | 5/2002 |
| WO | 2004/046145 | 6/2004 |
| WO | 200612885 | 12/2006 |

OTHER PUBLICATIONS

P Furet, C. Batzl, A. Bhatnagar, E. Francotte, G. Rihs, M. Lang Aromatase inhibitors. synthesis. biological activity and binding mode of azole-type compounds J Med Chem: 1993 36(10): 1393-1400.

Allentoff et al., "Palladium-Catalyzed Aryl Cyanations with [14C] KCN: Synthesis of 14C-JKCN Synthesis of 14C-Labelled Fadrozole, a Potent aromatase Inhibitor", Journal of Labelled Compounds and Radiopharmaceuticals, 2002, 43: pp. 1075-1085.

Fiebeler, et al. "Aldosterone Synthase Inhibitor Ameliorates Angiotensin II-Induced Organ Damage", Circulation 111, pp. 3087-3094 (2005).

Misra et al , "Interphenylene 7-Oxabicyclo [2.2 1] Heptane Oxazoles highly potent. selective, and long-acting thromboxane A2 receptor antagonists". J. Med. Chem., 36. pp. 1401-1417 (1993).

* cited by examiner

ORGANIC COMPOUNDS

The present invention relates to novel imidazole derivatives that are used as aldosterone synthase and aromatase inhibitors, as well as for treatment of a disorder or disease mediated by aldosterone synthase or aromatase.

The present invention provides a compound of formula (I)

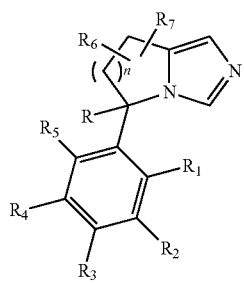

(I)

wherein
n is 1, or 2, or 3;
R is hydrogen, $(C_1-C_7)$ alkyl, or $(C_1-C_7)$ alkenyl, said $(C_1-C_7)$ alkyl and $(C_1-C_7)$ alkenyl being optionally substituted by one to five substituents independently selected from the group consisting of O—$R_8$ and $N(R_8)(R_9)$, wherein $R_8$ and $R_9$ are independently selected from the group consisting of hydrogen, $(C_1-C_7)$ alkyl, acyl, aryl and heteroaryl, each of which is further optionally substituted by one to four substituents independently selected from the group consisting of halo, $(C_1-C_7)$ alkoxy and $(C_1-C_7)$ alkyl; or
R is —C(O)O—$R_{10}$, or —C(O)N($R_{11}$)($R_{12}$), wherein $R_{10}$, $R_{11}$ and $R_{12}$ are selected independently from the group consisting of hydrogen, $(C_1-C_7)$ alkyl, $(C_3-C_8)$ cycloalkyl, aryl, aryl-$(C_1-C_7)$ alkyl, $(C_1-C_7)$ haloalkyl and heteroaryl, each of which is further optionally substituted by one to four substituents independently selected from the group consisting of halo, hydroxyl, $(C_1-C_7)$ alkoxy, $(C_1-C_7)$ alkyl, and aryl, wherein $R_{11}$ and $R_{12}$ taken together with the nitrogen atom to which they are attached optionally form a 3-8-membered ring;
$R_1$, $R_2$, $R_3$, $R_4$, and $R_5$ are selected independently from the group consisting of hydrogen, $(C_1-C_7)$ alkenyl, $(C_1-C_7)$ alkyl, $(C_3-C_8)$ cycloalkyl, halo, cyano, nitro, $H_2N$, $(C_1-C_7)$ haloalkyl, $(C_1-C_7)$ alkoxy, $(C_3-C_8)$ cycloalkoxy, aryloxy, aryl, heteroaryl, —C(O)O$R_{10}$, and —N($R_{13}$)($R_{14}$), said $(C_1-C_7)$ alkyl, $(C_1-C_7)$ alkenyl, $(C_1-C_7)$ alkoxy, aryl and heteroaryl being further optionally substituted by one to three substituents selected from $(C_1-C_7)$ alkyl, hydroxyl, halo, $(C_1-C_7)$ alkoxy, nitro, cyano, $(C_1-C_7)$ dialkylamino, $(C_1-C_7)$ alkoxy-$(C_1-C_7)$ alky-, and $(C_1-C_7)$ haloalkyl, said $R_{10}$ having the same meanings as defined above, said $R_{13}$ and $R_{14}$ are independently selected from the group consisting of hydrogen, $(C_1-C_7)$ alkyl, $(C_3-C_8)$ cycloalkyl, $(C_1-C_7)$ haloalkyl, $(C_1-C_7)$ haloalkoxy, aryl and cyano, with the proviso that no more than three of $R_1$, $R_2$, $R_3$, $R_4$, and $R_5$ are simultaneously hydrogen;
$R_{13}$ and $R_{14}$ taken together with the nitrogen atom to which they are attached optionally form a 3-8-membered ring;
R and $R_1$ taken together optionally form a 5-6-membered ring containing 0 or 1 heteroatom selected from O, N, or S;

$R_6$ and $R_7$ are independently hydrogen, hydroxyl, $(C_1-C_7)$ alkyl, $(C_1-C_7)$ alkoxy, phenyl, or benzyl, wherein phenyl and benzyl are optionally substituted by one to four substituents independently selected from the group consisting of halo, $(C_1-C_7)$; alkoxy and $(C_1-C_7)$ alkyl;
when $R_6$ and $R_7$ are attached to the same carbon atom, they optionally form a moiety (A) represented by the following structure:

(A)

wherein $R_a$ and $R_b$ are independently hydrogen, $(C_1-C_7)$ alkyl, $(C_1-C_7)$ alkoxy, acyl, —COO$R_{16}$ or —CO$R_{15}$, said $R_{15}$ being hydrogen, $(C_1-C_7)$ alkyl, $(C_1-C_7)$ haloalkyl, aryl, or —$NH_2$; or
when $R_6$ and $R_7$ are attached to the same carbon atom, they taken together with said carbon atom optionally form a 3-8-membered ring; or
a pharmaceutically acceptable salt thereof; or an optical isomer thereof; or a mixture of optical isomers.

Preferably, the present invention provides the compound of formula (I), wherein R is hydrogen, $(C_1-C_4)$ alkyl, $(C_1-C_4)$ alkenyl, —C(O)O—$R_{10}$, or —C(O)N($R_{11}$)($R_{12}$), said $(C_1-C_4)$ alkyl and $(C_1-C_4)$ alkenyl are optionally substituted by one to three substituents independently selected from hydroxyl, $(C_1-C_4)$ alkoxy, halo, —$NH_2$, or $(C_1-C_4)$ dialkylamino;
wherein $R_{10}$, $R_{11}$ and $R_{12}$ are independently hydrogen, $(C_1-C_4)$ alkyl, $(C_8-C_{10})$ aryl-$(C_1-C_4)$ alkyl, $(C_3-C_8)$ cycloalkyl, or $(C_1-C_4)$ alkenyl, each of which is optionally substituted by one to three substituents independently selected from halo, hydroxyl, or $(C_1-C_4)$ alkoxy; wherein $R_{11}$ and $R_{12}$ taken together with the nitrogen atom to which they are attached optionally form a 3-8-membered ring;
$R_1$, $R_2$, $R_3$, $R_4$, and $R_5$ are independently selected from hydrogen, halo, cyano, —$NH_2$, $(C_1-C_4)$ dialkylamino, $(C_1-C_4)$ alkoxy, $(C_1-C_4)$ alkenyl, $(C_1-C_4)$ alkyl, $(C_1-C_4)$ haloalkyl, $(C_8-C_{10})$ aryl, or (5-9)-membered heteroaryl, said $(C_1-C_4)$ alkoxy, $(C_1-C_4)$ alkenyl, $(C_1-C_4)$ alkyl and $(C_6-C_{10})$ aryl being optionally substituted by one to three substituents independently selected from halo, $(C_1-C_4)$ alkoxy, $(C_1-C_4)$ alkyl, —$NH_2$, cyano, nitro, $(C_1-C_4)$ alkoxy-$(C_1-C_4)$ alkyl, or $(C_1-C_4)$ haloalkyl, with the proviso that no more than three of $R_1$, $R_2$, $R_3$, $R_4$, and $R_5$ are simultaneously hydrogen; R and $R_1$ taken together optionally form a 5-6-membered ring containing 0 or 1 heteroatom selected from O, N, or S;
$R_6$ and $R_7$ are independently hydrogen, $(C_1-C_4)$ alkyl, $(C_3-C_8)$ cycloalkyl, $(C_1-C_4)$ alkoxy, phenyl, or benzyl, said phenyl and benzyl are optionally substituted by one to three substituents independently selected from halo, $(C_1-C_4)$ alkyl, or $(C_1-C_4)$ alkoxy;
when $R_6$ and $R_7$ are attached to the same carbon atom, they optionally form a moiety (A) described above, wherein $R_a$ and $R_b$ are independently hydrogen, or $(C_1-C_4)$ alkyl, or Ft, and $R_b$ taken together with said carbon atom optionally form a 3-8-membered ring; or a pharmaceutically acceptable salt thereof; or an optical isomer thereof; or a mixture of optical isomers.

In one embodiment, the present invention provides a compound of formula (II)

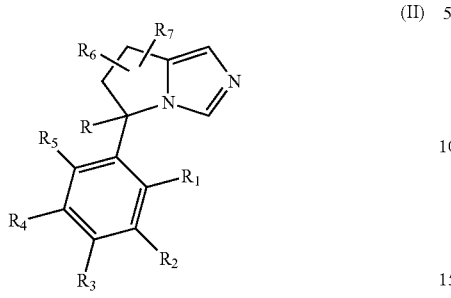

(II)

wherein

R, $R_1$, $R_2$, $R_3$, $R_4$, $R_5$, $R_6$ and $R_7$ have the same meanings as those defined for formula (I) above, or a pharmaceutically acceptable salt thereof; or an optical isomer thereof; or a mixture of optical isomers thereof; or a mixture, of optical isomers thereof.

Preferably, the present invention provides the compound of formula (II), wherein R is hydrogen, $(C_1\text{-}C_4)$ alkyl, $(C_1\text{-}C_4)$ alkenyl, —C(O)O—$R_{10}$, or —C(O)N($R^{11}$)($R^{12}$), said $(C_1\text{-}C_4)$ alkyl and $(C_1\text{-}C_4)$ alkenyl are optionally substituted by one to three substituents independently selected from hydroxyl, $(C_1\text{-}C_4)$ alkoxy, halo, —$NH_2$, or, $(C_1\text{-}C_4)$ dialkylamino;

wherein $R_{10}$, $R_{11}$ and $R_{12}$ are independently hydrogen, $(C_1\text{-}C_4)$ alkyl, $(C_6\text{-}C_{10})$ aryl-$(C_1\text{-}C_4)$ alkyl, $(C_3\text{-}C_8)$ cycloalkyl, or $(C_1\text{-}C_4)$ alkenyl, each of which is optionally substituted by one to three substituents independently selected from halo, hydroxyl, or $(C_1\text{-}C_4)$ alkoxy; wherein $R_{11}$ and $R_{12}$ taken together with the nitrogen atom to which they are attached optionally form a 3-8-membered ring;

$R_1$, $R_2$, $R_3$, $R_4$, and $R_5$ are independently selected from hydrogen, halo, cyano, —$NH_2$, $(C_1\text{-}C_4)$ dialkylamino, $(C_1\text{-}C_4)$ alkoxy, $(C_1\text{-}C_4)$ alkenyl, $(C_1\text{-}C_4)$ alkyl, $(C_1\text{-}C_4)$ haloalkyl, $(C_6\text{-}C_{10})$ aryl, or (5-9)-membered heteroaryl, said $(C_1\text{-}C_4)$ alkoxy, $(C_1\text{-}C_4)$ alkenyl, $(C_1\text{-}C_4)$ alkyl and $(C_6\text{-}C_{10})$ aryl being optionally substituted by one to three substituents independently selected from halo, $(C_1\text{-}C_4)$ alkoxy, $(C_1\text{-}C_4)$ alkyl, —$NH_2$, cyano, nitro, $(C_1\text{-}C_4)$ alkoxy-$(C_1\text{-}C_4)$ alkyl, or $(C_1\text{-}C_4)$ haloalkyl, with the proviso that no more than three of $R_1$, $R_2$, $R_3$, $R_4$, and $R_5$ are simultaneously hydrogen; R and $R_1$ taken together optionally form a 5-6-membered ring containing 0 or 1 heteroatom selected from O, N, or S;

$R_6$ and $R_7$ are independently hydrogen, $(C_1\text{-}C_4)$ alkyl, $(C_3\text{-}C_8)$ cycloalkyl, $(C_1\text{-}C_4)$ alkoxy, phenyl, or benzyl, said phenyl and benzyl are optionally substituted by one to three substituents independently selected from halo, $(C_1\text{-}C_4)$ alkyl, or $(C_1\text{-}C_4)$ alkoxy;

when $R_6$ and $R_7$ are attached to the same carbon atom, they optionally form a moiety (A) described above, wherein $R_a$ and $R_b$ are independently hydrogen, or $(C_1\text{-}C_4)$ alkyl, or $R_a$ and $R_b$ taken together with said carbon atom optionally form a 3-8-membered ring; or a pharmaceutically acceptable salt thereof; or an optical isomer thereof; or a mixture of optical isomers.

In another embodiment, the present invention provides a compound of formula (III)

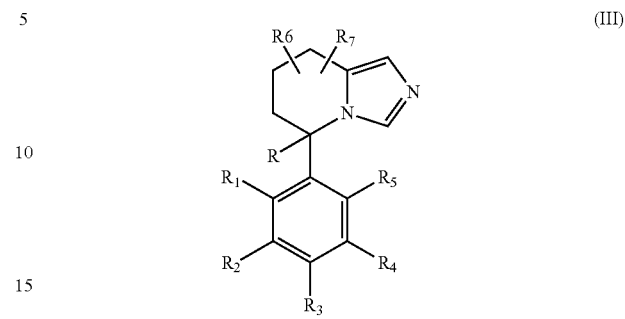

(III)

wherein

R, $R_1$, $R_2$, $R_3$, $R_4$, $R_5$, $R_6$ and $R_7$ have the same meanings as those defined for formula (I) above, or a pharmaceutically acceptable salt thereof; or an optical isomer thereof; or a mixture of optical isomers thereof; or a mixture of optical isomers thereof.

Preferably, the present invention provides the compound of formula (III), wherein R is hydrogen, $(C_1\text{-}C_4)$ alkyl, $(C_1\text{-}C_4)$ alkenyl, —C(O)O—$R_{10}$, or —C(O)N($R^{11}$)($R^{12}$), said $(C_1\text{-}C_4)$ alkyl and $(C_1\text{-}C_4)$ alkenyl are optionally substituted by one to three substituents independently selected from hydroxyl, $(C_1\text{-}C_4)$ alkoxy, halo, —$NH_2$, or $(C_1\text{-}C_4)$ dialkylamino;

wherein $R_{10}$, $R^{11}$ and $R_{12}$ are independently hydrogen, $(C_1\text{-}C_4)$ alkyl, $(C_6\text{-}C_{10})$ aryl-$(C_1\text{-}C_4)$ alkyl-, $(C_3\text{-}C_8)$ cycloalkyl, or $(C_1\text{-}C_4)$ alkenyl, each of which is optionally substituted by one to three substituents independently selected from halo, hydroxyl, or $(C_1\text{-}C_4)$ alkoxy; wherein $R^{11}$ and $R_{12}$ taken together with the nitrogen atom to which they are attached optionally form a 3-8-membered ring;

$R_1$, $R_2$, $R_3$, $R_4$, and $R_5$ are independently selected from hydrogen, halo, cyano, —$NH_2$, $(C_1\text{-}C_4)$ dialkylamino, $(C_1\text{-}C_4)$ alkoxy, $(C_1\text{-}C_4)$ alkenyl, $(C_1\text{-}C_4)$ alkyl, $(C_1\text{-}C_4)$ haloalkyl, $(C_8\text{-}C_{10})$ aryl, or (5-9)-membered heteroaryl, said $(C_1\text{-}C_4)$ alkoxy, $(C_1\text{-}C_4)$ alkenyl, $(C_1\text{-}C_4)$ alkyl and $(C_6\text{-}C_{10})$ aryl being optionally substituted by one to three substituents independently selected from halo, $(C_1\text{-}C_4)$ alkoxy, $(C_1\text{-}C_4)$ alkyl, —$NH_2$, cyano, nitro, $(C_1\text{-}C_4)$ alkoxy-$(C_1\text{-}C_4)$ alkyl, or $(C_1\text{-}C_4)$ haloalkyl, with the proviso that no more than three of $R_1$, $R_2$, $R_3$, $R_4$, and $R_5$ are simultaneously hydrogen; R and $R_1$ taken together optionally form a 5-6-membered ring containing 0 or 1 heteroatom selected from O, N, or S;

$R_6$ and $R_7$ are independently hydrogen, $(C_1\text{-}C_4)$ alkyl, $(C_3\text{-}C_8)$ cycloalkyl, $(C_1\text{-}C_4)$ alkoxy, phenyl, or benzyl, said phenyl and benzyl are optionally substituted by one to three substituents independently selected from halo, $(C_1\text{-}C_4)$ alkyl, or $(C_1\text{-}C_4)$ alkoxy;

when $R_6$ and $R_7$ are attached to the same carbon atom, they optionally form a moiety (A) described above, wherein $R_a$ and $R_b$ are independently hydrogen, or $(C_1\text{-}C_4)$ alkyl, or $R_a$ and $R_b$ taken together with said carbon atom optionally form a 3-8-membered ring; or a pharmaceutically acceptable salt thereof; or an optical isomer thereof; or a mixture of optical isomers.

In another embodiment, the present invention provides a compound of formula (IV)

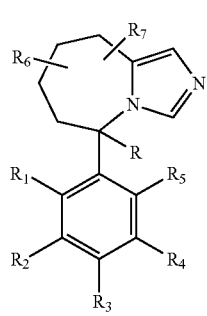

(IV)

wherein

R, $R_1$, $R_2$, $R_3$, $R_4$, $R_5$, $R_6$ and $R_7$ have the same meanings as those defined for formula (I) above, or pharmaceutically acceptable salts thereof; or an optical isomer thereof; or a mixture of optical isomers thereof; or a mixture of optical isomers thereof.

Preferably, the present invention provides the compound of formula (IV), wherein R is hydrogen, ($C_1$-$C_4$) alkyl, ($C_1$-$C_4$) alkenyl, —C(O)O—$R_{10}$, or —C(O)N($R_{11}$)($R_{12}$), said ($C_1$-$C_4$) alkyl and ($C_1$-$C_4$) alkenyl are optionally substituted by one to three substituents independently selected from hydroxyl, ($C_1$-$C_4$) alkoxy, halo, —$NH_2$, or ($C_1$-$C_4$) dialkylamino;

wherein $R_{10}$, $R_{11}$ and $R_{12}$ are independently hydrogen, ($C_1$-$C_4$) alkyl, ($C_3$-$C_{10}$) aryl-($C_1$-$C_4$) alkyl, ($C_3$-$C_8$) cycloalkyl, or ($C_1$-$C_4$) alkenyl, each of which is optionally substituted by one to three substituents independently selected from halo, hydroxyl, or ($C_1$-$C_4$) alkoxy; wherein $R_{11}$ and $R_{12}$ taken together with the nitrogen atom to which they are attached optionally form a 3-8-membered ring;

$R_1$, $R_2$, $R_3$, $R_4$, and $R_5$ are independently selected from hydrogen, halo, cyano, —$NH_2$, ($C_1$-$C_4$) dialkylamino, ($C_1$-$C_4$) alkoxy, ($C_1$-$C_4$) alkenyl, ($C_1$-$C_4$) alkyl, ($C_1$-$C_4$) haloalkyl, ($C_6$-$C_{10}$) aryl, or (5-9)-membered heteroaryl, said ($C_1$-$C_4$) alkoxy, ($C_1$-$C_4$) alkenyl, ($C_1$-$C_4$) alkyl and ($C_6$-$C_{10}$) aryl being optionally substituted by one to three substituents independently selected from halo, ($C_1$-$C_4$) alkoxy, ($C_1$-$C_4$) alkyl, —$NH_2$, cyano, nitro, ($C_1$-$C_4$) alkoxy-($C_1$-$C_4$) alkyl or ($C_1$-$C_4$) haloalkyl, with the proviso that no more than three of $R_1$, $R_2$, $R_3$, $R_4$, and $R_5$ are simultaneously hydrogen; R and $R_1$ taken together optionally form a 5-6-membered ring containing 0 or 1 heteroatom selected from O, N, or S;

$R_6$ and $R_7$ are independently hydrogen, ($C_1$-$C_4$) alkyl, ($C_3$-$C_8$) cycloalkyl, ($C_1$-$C_4$) alkoxy, phenyl, or benzyl, said phenyl and benzyl are optionally substituted by one to three substituents independently selected from halo, ($C_1$-$C_4$) alkyl, or ($C_1$-$C_4$) alkoxy;

when $R_6$ and $R_7$ are attached to the same carbon atom, they optionally form a moiety (A) described above, wherein $R_a$ and $R_b$ are independently hydrogen, or ($C_1$-$C_4$) alkyl, or $R_a$ and $R_b$ taken together with said carbon atom optionally form a 3-8-membered ring; or a pharmaceutically acceptable salt thereof; or an optical isomer thereof; or a mixture of optical isomers.

For purposes of interpreting this specification, the following definitions will apply and whenever appropriate, terms used in the singular will also include the plural and vice versa.

As used herein, the term "alkyl" refers to a fully saturated branched or unbranched hydrocarbon moiety. Preferably the alkyl comprises 1 to 6 carbon atoms, more preferably 1 to 16 carbon atoms, 1 to 10 carbon atoms, 1 to 7 carbon atoms, or 1 to 4 carbon atoms. Representative examples of alkyl include, but are not limited to methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. As used herein, the term "lower alkoxy" refers to the alkoxy groups having about 1-7 preferably about 1-4 carbons.

As used herein, the term "acyl" refers to a group R—C(O)— of from 1 to 10 carbon atoms of a straight, branched, or cyclic configuration or a combination thereof, attached to the parent structure through carbonyl functionality. Such group may be saturated or unsaturated, and aliphatic or aromatic. Preferably, R in the acyl residue is alkyl, or alkoxy, or aryl, or heteroaryl. Also preferably, one or more carbons in the acyl residue may be replaced by nitrogen, oxygen or sulfur as long as the point of attachment to the parent remains at the carbonyl. Examples include but are not limited to, acetyl, benzoyl, propionyl, isobutyryl, t-butoxycarbonyl, benzyloxycarbonyl and the like. Lower acyl refers to acyl containing one to four carbons.

As used herein, the term "cycloalkyl" refers to optionally substituted saturated or unsaturated monocyclic, bicyclic or tricyclic hydrocarbon groups of 3-12 carbon atoms, each of which may be substituted by one or more substituents, such as alkyl, halo, oxo, hydroxy, alkoxy, alkanoyl, acylamino, carbamoyl, alkylamino, dialkylamino, thiol, alkylthio, nitro, cyano, carboxy, alkoxycarbonyl, sulfonyl, sulfonamido, sulfamoyl, heterocyclyl and the like. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

As used herein, the term "cycloalkoxy" refers to —O-cycloalkyl groups.

The term "aryl" refers to monocyclic or bicyclic aromatic, hydrocarbon groups having 6-20 carbon atoms in the ring portion. Preferably, the aryl is a ($C_6$-$C_{10}$) aryl. Non-limiting examples include phenyl, biphenyl, naphthyl or tetrahydronaphthyl, each of which may optionally be substituted by 1-4 substituents, such as alkyl, trifluoromethyl, cycloalkyl, halogen, hydroxy, alkoxy, acyl, alkyl-C(O)—O—, aryl-O—, heteroaryl-O—, amino, HS—, alkyl-S—, aryl-S—, nitro, cyano, carboxy, alkyl-O—C(O)—, carbamoyl, alkyl-S(O)—, sulfonyl, sulfonamido, heterocyclyl and the like, wherein R is independently hydrogen, alkyl, aryl, heteroaryl, aryl-alkyl-, heteroaryl-alkyl and the like.

Furthermore, the term "aryl" as used herein, refers to an aromatic substituent which can be a single aromatic ring, or multiple aromatic rings that are fused together, linked covalently, or linked to a common group such as a methylene or ethylene moiety. The common linking group also can be a carbonyl as in benzophenone or oxygen as in diphenylether or nitrogen as in diphenylamine.

As used herein, the term "carbamoyl" refers to H$_2$NC(O)—, alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aryl-alkyl-NHC(O)—, alkyl(aryl-alkyl)-NC(O)— and the like.

As used herein, the term "sulfonyl" refers to R—SO$_2$—, wherein R is hydrogen, alkyl, aryl, heretoaryl, aryl-alkyl, heteroaryl-alkyl, aryl-O—, heteroaryl-O—, alkoxy, aryloxy, cycloalkyl, or heterocyclyl.

As used herein, the term "sulfonamido" refers to alkyl-S(O)$_2$—NH—, aryl-S(O)$_2$—NH—, aryl-alkyl-S(O)$_2$—NH—, heteroaryl-S(O)$_2$—NH—, heteroaryl-alkyl-S(O)$_2$—NH—, alkyl-S(O)$_2$—N(alkyl)-, aryl-S(O)$_2$—N(alkyl)-, aryl-alkyl-S(O)$_2$—N(alkyl)-, heteroaryl-S(O)$_2$—N(alkyl)-, heteroaryl-alkyl-S(O)$_2$—N(alkyl)- and the like.

As used herein, the term "heterocyclyl" or "heterocyclo" refers to an optionally substituted, fully saturated or unsaturated, aromatic or nonaromatic cyclic group, e.g., which is a 4- to 7-membered monocyclic, 7- to 12-membered bicyclic or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, triazolyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, 1,1,4-trioxo-1,2,5-thiadiazolidin-2-yl and the like.

Exemplary bicyclic heterocyclic groups include indolyl, dihydroidolyl, benzothiazolyl, benzoxazinyl, benzoxazolyl, benzothienyl, benzothiazolyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]-pyridinyl] or furo[2,3-b]pyridinyl), dihydroisoindolyl, 1,3-dioxo-1,3-dihydroisoindol-2-yl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "heterocyclyl" further refers to heterocyclic groups as defined herein substituted with 1, 2 or 3 substituents selected from the groups consisting of the following:

(a) alkyl;
(b) hydroxyl (or protected hydroxy);
(c) halo;
(d) oxo, i.e., =O;
(e) amino, alkylamino or dialkylamino;
(f) alkoxy;
(g) cycloalkyl;
(h) carboxy;
(i) heterocyclooxy, wherein heterocyclooxy denotes a heterocyclic group bonded through an oxygen bridge;
(j) alkyl-O—C(O)—;
(k) mercapto;
(l) nitro;
(m) cyano;
(n) sulfamoyl or sulfonamido;
(o) aryl;
(p) alkyl-C(O)—O—;
(q) aryl-C(O)—O—;
(r) aryl-S—;
(s) aryloxy;
(t) alkyl-S—;
(u) formyl, i.e., HC(O)—;
(v) carbamoyl;
(w) aryl-alkyl-; and
(x) aryl substituted with alkyl, cycloalkyl, alkoxy, hydroxy, amino, alkyl-C(O)—NH—, alkylamino, dialkylamino or halogen.

As used herein, the term "sulfamoyl" refers to H$_2$NS(O)$_2$—, alkyl-NHS(O)$_2$—, (alkyl)$_2$NS(O)$_2$—, aryl-NHS(O)$_2$—, alkyl(aryl)-NS(O)$_2$—, (aryl)$_2$NS(O)$_2$—, heteroaryl-NHS(O)$_2$—, aralkyl-NHS(O)$_2$—, heteroaralkyl-NHS(O)$_2$— and the like.

As used herein, the term "aryloxy" refers to both an —O-aryl and an —O-heteroaryl group, wherein aryl and heteroaryl are defined herein.

As used herein, the term "heteroaryl" refers to a 5-14 membered monocyclic- or bicyclic- or fused polycyclic-ring system, having 1 to 8 heteroatoms selected from N, O or S. Preferably, the heteroaryl is a 5-10 or 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbazolyl, 1-, 3-, 4-, 5-, 6-, 7-, 8-, or 9-carbolinyl, 1-, 2-, 3-, 4-; 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 5-4H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroaryl groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

A heteroaryl group may be mono-, bi-, tri-, or polycyclic, preferably mono-, bi-, or tricyclic, more preferably mono- or bicyclic.

As used herein, the term "halogen" or "halo" refers to fluoro, chloro, bromo, and iodo.

As used herein, the term "acylamino" refers to acyl-NH—, wherein "acyl" is defined herein.

As used herein, the term "alkoxycarbonyl" refers to alkoxy-C(O)—, wherein alkoxy is defined herein.

As used herein, the term "alkanoyl" refers to alkyl-C(O)—, wherein alkyl is defined herein.

As used herein, the term "alkenyl" refers to a straight or branched hydrocarbon group having 2 to 20 carbon atoms and that contains at least one double bonds. The alkenyl groups preferably have about 2 to 8 carbon atoms.

As used, herein, the term "haloalkyl" refers to an alkyl as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. Preferably, the polyhaloalkyl contains up to 12, 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

As used herein, the term "haloalkoxy" refers to haloalkyl-0, wherein haloalkyl is defined herein.

As used herein, the term "alkylamino" refers to alkyl-NH, wherein alkyl is defined herein.

As used herein, the term "dialkylamino" refers to (alkyl)(alkyl)N—, wherein alkyl is defined herein.

As used herein, the term "isomers" refers to different compounds that have the same molecular formula. Also as used herein, the term "an optical isomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Additionally, resolved compounds whose absolute configuration is unknown can be designated by high pressure liquid chromatography (HPLC) retention time ($t_r$) using a chiral adsorbent. Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the term "pharmaceutically acceptable salts" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in *Remington's Pharmaceutical Sciences*, 20th ed., Mack Publishing Company, Easton, Pa., (1985), which is herein incorporated by reference.

As used herein, the term "pharmaceutically acceptable carrier" includes any and all solvents, dispersion media, coatings, surfactants, antioxidants, preservatives (e.g., antibacterial agents, antifungal, agents), isotonic agents, absorption delaying agents, salts, preservatives, drugs, drug stabilizers, binders, excipients, disintegration agents, lubricants; sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The term "therapeutically effective amount" of a compound of the present invention refers to an amount of the compound of the present invention that will elicit the biological or medical response of a subject, or ameliorate symptoms, slow or delay disease progression, or prevent a disease, etc., in a preferred embodiment, the "effective amount" refers to the amount that inhibits or reduces expression of either aldosterone synthase or aromatase.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In, a preferred embodiment, the subject is a human.

As used herein, the term "a disorder" or "a disease" refers to any derangement or abnormality of function; a morbid physical or mental state. See *Dorland's Illustrated Medical Dictionary*, (W.B. Saunders Co. 27th ed. 1988).

As used herein, the term "inhibition" or "inhibiting" refers to the reduction or suppression of a given condition, symptom, or disease, or a significant decrease in the baseline activity of a biological activity or process. Preferably, the condition is due to the abnormal expression of aldosterone synthase or aromatase and the biological activity or process is associated with the abnormal expression of aldosterone synthase or aromatase.

As used herein, the term "treating" or "treatment" of any disease or disorder refers in one embodiment, to ameliorating the disease or disorder (i.e., arresting or reducing the development of the disease or at least one of the clinical symptoms thereof). In another embodiment "treating" or "treatment" refers to ameliorating at least one Physical parameter, which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "abnormal" refers to an activity or feature which differs from a normal activity or feature.

As used herein, the term "abnormal activity" refers to an activity which differs from the activity of the wild-type or native gene or protein, or which differs from the activity of the gene or protein in a healthy subject. The abnormal activity can be stronger or weaker than the normal activity. In one embodiment, the "abnormal activity" includes the abnormal (either over- or under-) production of mRNA transcribed from a gene. In another embodiment, the "abnormal activity" includes the abnormal (either over- or under-) production of polypeptide from a gene. In another embodiment, the abnormal activity refers to a level of a mRNA or polypeptide that is different from a normal level of said mRNA or polypeptide by about 15%, about 25%, about 35%, about 50%, about 65%, about 85%, about 100% or greater. Preferably, the abnormal level of the mRNA or polypeptide can be either higher or lower than the normal level of said mRNA or polypeptide. Yet in another embodiment, the abnormal activity refers to functional activity of a protein that is different from a normal activity of the wild-type protein, due to mutations in the corresponding gene. Preferably, the abnormal activity can be stronger or weaker than the normal activity. The mutations can be in the coding region of the gene or non-coding regions such as transcriptional promoter regions. The mutations can be substitutions, deletions, insertions.

As used herein, the term "a," "an," "the" and similar terms used in the context of the present invention (especially in the context of the claims) are to be construed to cover both the singular and plural unless otherwise indicated herein or clearly contradicted by the context. Recitation of ranges of values herein are merely intended to serve as a shorthand method of referring individually to each separate value falling within the range. Unless otherwise indicated, herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Any asymmetric carbon atom on the compounds of the present invention can be present in the (R)-, (S)- or (R,S)-configuration, preferably in the (R)- or (S)-configuration. Substituents atoms with unsaturated bonds may, if possible, be present in cis-(Z)- or trans (E)-form. Therefore, the compounds of the present invention can be in the form of one of the possible isomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, the imidazolyl moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Finally, compounds of the present invention are either obtained in the free form, as a salt thereof, or as prodrug derivatives thereof.

When a basic group is present in the compounds of the present invention, the compounds can be converted into acid addition salts thereof, in particular, acid addition salts with the imidazolyl moiety of the structure, preferably pharmaceutically acceptable salts thereof. These are formed, with inorganic acids or organic acids. Suitable inorganic acids include but are not limited to, hydrochloric acid, sulfuric acid, a phosphoric or hydrohalic acid. Suitable organic acids include but are not limited to, carboxylic acids, such as $(C_1-C_4)$alkanecarboxylic acids which, for example, are unsubstituted or substituted by halogen, e.g., acetic acid, such as saturated or unsaturated dicarboxylic acids, e.g., oxalic, succinic, maleic or fumaric acid, such as hydroxycarboxylic acids, e.g., glycolic, lactic, malic, tartaric or citric acid, such as amino acids, e.g., aspartic or glutamic acid, organic sulfonic acids; such as $(C_1-C_4)$alkylsulfonic acids, e.g., methanesulfonic acid; or arylsulfonic acids which are unsubstituted or substituted, e.g., by halogen. Preferred are salts formed with hydrochloric acid, methanesulfonic acid and maleic acid.

When an acidic group is present in the compounds of the present invention, the compounds can be converted into salts with pharmaceutically acceptable bases. Such salts include alkali metal salts, like sodium, lithium and potassium salts; alkaline earth metal salts, like calcium and magnesium salts; ammonium salts with organic bases, e.g., trimethylamine salts, diethylamine salts, tris(hydroxymethyl)methylamine salts, dicyclohexylamine salts and N-methyl-D-glucamine salts; salts with amino acids like arginine, lysine and the like. Salts may be formed using conventional methods, advantageously in the presence of an ethereal or alcoholic solvent, such as a lower alkanol. From the solutions of the latter, the salts may be precipitated with ethers, e.g., diethyl ether. Resulting salts may be converted into the free compounds by treatment with acids. These or other salts can also be used for purification of the compounds obtained.

When both a basic group and an acid group are present in the same molecule, the compounds of the present invention can also form internal salts.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally; bioprecursor prodrugs are compounds are inactive or have low activity compared to the corresponding active drug compound, that contains one or more protective groups and are converted to an active form by metabolism or solvolysis. Both the active drug form and any released metabolic products should have acceptably low toxicity. Typically, the formation of active drug compound involves a metabolic process or reaction that is one of the follow types:

1. Oxidative reactions, such as oxidation of alcohol, carbonyl, and acid functions, hydroxyation of aliphatic carbons, hydroxyation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-delakylation, oxidative O- and S-delakylation, oxidative deamination, as well as other oxidative reactions.

2. Reductive reactions, such as reduction of carbonyl groups, reduction of alcoholic groups and carbon-carbon double bonds, reduction of nitrogen-containing functions groups, and other reduction reactions.

3. Reactions without change in the state of oxidation, such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. See, Cheng et al., US20040077595, application Ser. No. 10/656, 838, incorporated herein by reference. Such carrier prodrugs are often advantageous for orally administered drugs. Carrier prodrugs can, for example, be used to improve one or more of the following properties: increased lipophilicity, increased duration of pharmacological effects, increased site-specificity, decreased toxicity and adverse reactions; and/or improvement in drug formulation (e.g., stability, water solubility, suppression of an undesirable organoleptic or physiochemical property). For example, lipophilicity can be increased by esterification of hydroxy groups with lipophilic carboxylic acids, or of carboxylic acid groups with alcohols, e.g., aliphatic alcohols. Wermuth, *The Practice of Medicinal Chemistry*, Ch. 31-32, Ed. Werriuth, Academic Press, San Diego, Calif., 2001.

Exemplary prodrugs are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

In view of the close relationship between the compounds, the compounds in the form of their salts and the pro-drugs, any reference to the compounds of the present invention is to be understood as referring also to the corresponding prodrugs of the compounds of the present invention, as appropriate and expedient.

Furthermore, the compounds of the present invention, including their salts, can also be obtained in the form of their hydrates, or include other solvents used for their crystallization.

The compounds of the present invention have valuable pharmacological properties.

The compounds of the present invention are useful as aldosterone synthase inhibitors. Aldosterone synthase (CYP11B2) is a mitcohcondrial cytochrome P450 enzyme catalyzing the last step of aldosterone production in the adrenal cortex, i.e., the conversion of 11-deoxycorticosterone to aldosterone. Aldosterone synthase has been demonstrated to be expressed in all cardiovascular tissues such as heart, umbilical cord, mesenteric and pulmonary arteries, aorta, endothelium and vascular cells. Moreover, the expression of aldosterone synthase is closely correlated with aldosterone production in cells. It has been observed that elevations of aldosterone activities or aldosterone levels induce different diseases such as congestive heart failure, cardiac or myocardial fibrosis, renal failure, hypertension, ventricular arrhythmia and other adverse effects, etc., and that the inhibition of aldosterone or aldosterone synthase would be useful therapeutic approaches. See e.g., Ulmschenider et al. "Development and evaluation of a pharmacophore model for inhibitors of aldosterone synthase (CYP11B2)," *Bioorganic & Medicinal Chemistry Letters*, 16: 25-30 (2006); Bureik et al., "Development of test systems for the discovery of selective human aldosterone synthase (CYP11B2) and 11β-hydroxylase (CYP11B1) inhibitors, discovery of a new lead compound for the therapy of congestive heart failure, myocardial fibrosis and hypertension," *Moleculare and Cellular Endocrinology*, 217: 249-254 (2004); Bos et al., "Inhibition of catechnolamine-induced cardiac fibrosis by an aldosteron antagonist," *J. Cardiovascular Pharmacol*, 45(1): 8-13 (2005); Jaber and Madias, "Progression of chronic kidney disease: can it be prevented or arrested?" *Am. J. Med.* 118 (12): 1323-1330 (2005); Khan and Movahed, "The role of aldosterone and aldosterone-receptor antagonists in heart failure," *Rev. Cardiovasc Med.*, 5(2): 71-81 (2004); Struthers, "Aldosterone in heart failure: pathophysiology and treatment," *Cyrr. Heart Fail.*, 1(4): 171-175 (2004); Harris and Rangan, "Retardation of kidney failure applying principles to practice," *Ann. Acad. Med. Singapore*, 34(1): 16-23 (2005); Arima, "Aldosterone and the kidney: rapid regulation of renal microcirculation," *Steroids*, online publication November 2005; Brown, "Aldosterone and end-organ damage," *Curr. Opin. Nephrol Hypertens*, 14:235-241 (2005); Grandi, "Antihypertensive therapy: role of aldosteron antagonists," *Curr. Pharmaceutical Design*, 11: 2235-2242 (2005); Declayre and Swynghedauw, "Molecular mechanisms of myocardial remodeling: the role of aldosterone," *J. Mol. Cell. Cardiol.*, 34: 1577-1584 (2002). Accordingly, the compounds of the present invention as aldosterone synthase inhibitors, are also useful for treatment of a disorder or disease mediated by aldosterone synthase or responsive to inhibition of aldosterone synthase. In particular, the compounds of the present invention as aldosterone synthase inhibitors are useful for treatment of a disorder or disease characterized by abnormal aldosterone synthase activity. Preferably, the compounds of the present invention are also useful for treatment of a disorder or disease selected from hypokalemia, hypertension, congestive heart failure, atrial fibrillation, renal failure, in particular, chronic renal failure, restenosis, atherosclerosis, syndrome X, obesity, nephropathy, post-myocardial infarction, coronary heart diseases, inflammation, increased formation of collagen, fibrosis such as cardiac or myocardiac fibrosis and remodeling following hypertension and endothelial dysfunction.

Furthermore, the compounds of the present inventions are useful as aromatase inhibitors. Aromatase is a cytochrome P450 enzyme, it plays a central role in the extragonadal biosynthesis of estrogens such as estradiol, estrone and estrol, and is widely distributed in muscular and adipose tissue (Longcope C, Pratt J H, Schneider S H, Fineberg S E, 1977, *J. Clin. Endocrinol. Metab.* 45:1134-1145). An increase in aromatase activity has been confirmed to be associated with estrogen-dependent disorders or diseases. Accordingly, the compounds of the present invention are also useful for treatment of a disorder or disease characterized by abnormal expression of aromatase. Preferably, the compounds of the present invention are useful for treatment of an estrogen-dependent disorder or disease. More preferably, the compounds of the present invention are useful for treatment of an estrogen-dependent disorder or disease selected from gynecomastia, osteoporosis, prostate cancer, endometriosis, uterine fibroids, dysfunctional uterine bleeding, endometrial hyperplasia, polycystic ovarian disease, infertility, fibrocystic breast disease, breast cancer and fibrocystic mastopathy.

Additionally, the present invention provides:

a compound of the present invention for use as a medicament;

the use of a compound of the present invention for the preparation of a pharmaceutical composition for the delay of progression and/or treatment of a disorder or disease mediated by aldosterone synthase, or responsive to inhibition of aldosterone synthase, or characterized by abnormal activity or expression of aldosterone synthase.

the use of a compound of the present invention for the preparation of a pharmaceutical composition for the delay of progression and/or treatment of a disorder or disease mediated by aromatase, or responsive to inhibition of aromatase, or characterized by abnormal activity or expression of aromatase.

the use of a compound of the present invention for the preparation of a pharmaceutical composition for the delay of progression and/or treatment of a disorder or disease selected from hypokalemia, hypertension, congestive heart failure, atrial fibrillation, renal failure, in particular, chronic renal failure, restenosis, atherosclerosis, syndrome X, obesity, nephropathy, post-myocardial infarction, coronary heart diseases, increased formation of collagen, fibrosis such as cardiac or myocardiac fibrosis and remodeling following hypertension and endothelial dysfunction.

the use of a compound of the present invention for the preparation of a pharmaceutical composition for the delay of progression and/or treatment of a disorder or disease selected from gynecomastia, osteoporosis, prostate cancer, endometriosis, uterine fibroids, dysfunctional uterine bleeding, endometrial hyperplasia, polycystic ovarian disease, infertility, fibrocystic breast disease, breast cancer and fibrocystic mastopathy.

The compounds of formula (I)-(IV) can be prepared by the procedures described in the following sections.

Generally, the compounds of formula (II) can be prepared according to Scheme 1, which contains 13 steps.

Scheme 1

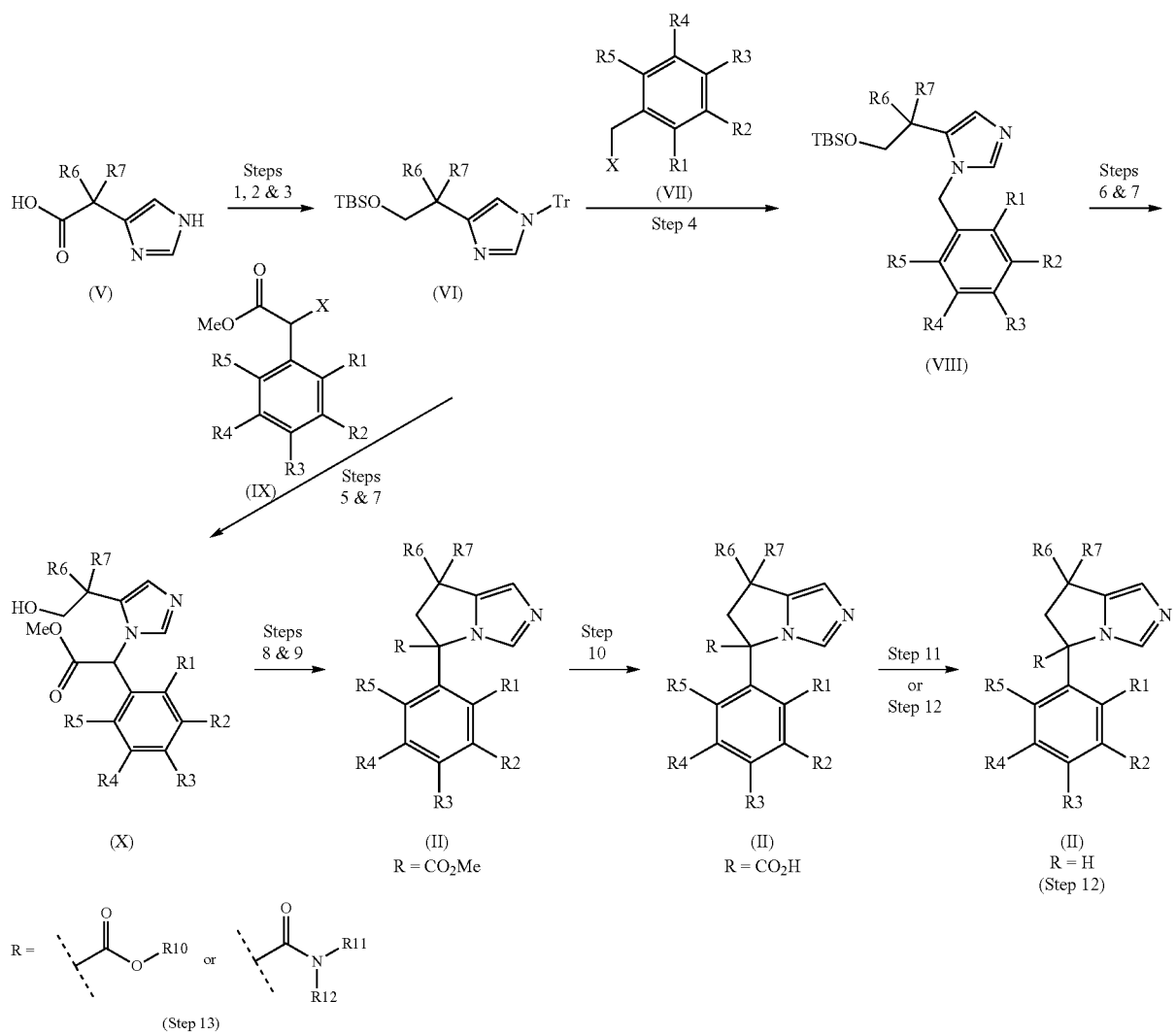

As to the individual steps in the above scheme, step 1 involves the introduction of a suitable protecting group on N1 other imidazole of (V), preferably triphenylmethyl, by reacting (V) with a suitable reagent such as triphenylmethyl chloride, in the presence of pyridine. Step 2 involves the reduction of the carboxylic acid with a suitable reducing reagent, preferably $BH_3 \cdot THF$ complex. Step 3 involves the protection of the alcohol resulting from step 2 as a silyl ether, preferably as t-butyldimethylsilyl ether, with a suitable reagent such as t-butyldimethylsilyl chloride in the presence of a suitable base, preferably $Et_3N$ or imidazole, and an aprotic solvent, preferably DMF or $CH_2Cl_2$ to provide (VI).

Alternatively (VI) can be prepared from (V) by a four step sequence. In step 1 (V) is converted to the corresponding methyl ester upon reaction with methanol in the presence of an acid, preferably HCl. Step 2 involves the protection of N1 of the imidazole, preferably with triphenylmethyl, upon reaction with triphenylmethyl chloride in the presence of a suitable base, preferably $Et_3N$. Step 3 involves the reduction of the ester formed in step 1 upon reaction with a suitable reducing reagent, preferably $LiAlH_4$, in an aprotic solvent, preferably THF. Step 4 involves the protection of the resulting alcohol moiety as a silyl ether to as described in step 3 of the preceding paragraph to provide (VI).

Step 4 involves the reaction of a (VI) with the appropriate alkylating reagent (VII), such as X=Br, in an aprotic solvent, preferably $CH_3CN$ to provide (VIII). Alkylating agents (VII) or (IX) may be prepared by treatment of the corresponding toluene or phenyl acetic acid ester derivative with a suitable brominating agent, e.g. NBS, in the presence of a suitable radical initiator, such as AIBN or benzoyl peroxide. Alternatively, alkylating agents (VII) may be generated by conversion of a substituted benzyl alcohol to the corresponding halide by treatment with, for example, $CBr_4$ and $PPh_3$.

Step 6 involves the reaction of (VIII) with a suitable base, preferably LHMDS, and suitable electrophilic reagent, preferably cyanomethylformate or chloromethylformate. Step 7 involves the removal of the t-butyldimethylsilyl protecting group upon treatment with acid, preferably HCl, to provide ester (X).

Alternatively (X) can be prepared by alkylation of (VI) with an appropriate alkylating reagent (IX), preferably where X=Br, shown in step 5 followed by removal of the silyl protecting group as described in step 7.

Step 8 involves conversion of alcohol (X) to a suitable leaving group, preferably mesylate, by reacting (X) with methanesulfonyl chloride in the presence of a suitable base, preferably $Et_3N$; and an aprotic solvent, preferably $CH_2Cl_2$. Step 9 involves the intramolecular alkylation upon reaction of the mesylate from step 8 with a suitable base, preferably $Et_3N$, in a polar aprotic solvent, preferably. DMF or $CH_3CN$, to provide compounds of formula (I) where $R=CO_2$alkyl.

Additionally, compounds from step 9 where $R=CO_2$alkyl, can be treated with a suitable metal alkoxide, preferably lithium hydroxide in a solvent, for example $H_2O$ and THF, to provide compounds from step 10 where $R=CO_2H$. Step 11 involves decarboxylation of the compounds, where $R=CO_2H$ upon heating in a suitable solvent, preferably DMSO, to provide compounds from step 12 where $R=H$.

Additional compounds of formula (I) may be prepared from conversion of carboxylic acid (I), where $R=CO_2H$, into the corresponding acid chloride upon treatment with a suitable chlorinating reagent, preferably oxalyl chloride, in an aprotic solvent, preferably $CH_2Cl_2$. The acid chloride obtained is then reacted with the appropriate nucleophile, preferably an alcohol or an amine, in the presence of a suitable base to provide compounds of formula (I) where $R=CO_2R_{10}$ or $CO_2NR_{11}NR_{12}$ (step 12).

Alternatively, the compounds of formula (II) can be prepared according to Scheme 2, which contains four steps.

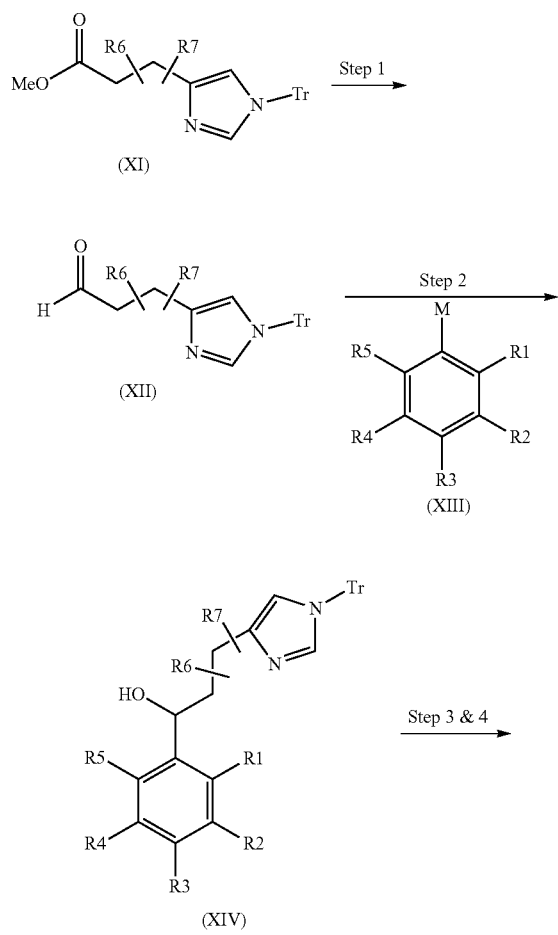

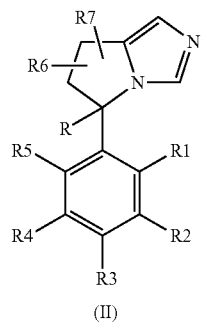

As to the individual steps in the Scheme 2 above, step 1 involves reduction of the known carboxylic ester (XI) to the corresponding aldehyde (XII) upon treatment with a suitable reducing reagent, preferably DIBAL-H, and an aprotic solvent, preferably $CH_2Cl_2$. Step 2 involves the reaction of aldehyde (XII) with an appropriate organometallic reagent (XIII), preferably where M=Li, MgBr, or MgCl, to provide alcohol (XIV). The organometallic reagents (XIII) are obtained from commercial sources or generated under standard conditions by the action of a strong base, e.g. n-BuLi.

Step 3 involves the conversion of the alcohol moiety in (XIV) to a leaving group, preferably mesylate, upon reaction of (XIV) with methanesulfonyl chloride, and a suitable base, preferably $Et_3N$, in a solvent, preferably $CH_2Cl_2$. Step 4 involves the intramolecular N3 alkylation of the imidazole upon warming the mesylate prepared in step 3 in a polar aprotic solvent, preferably $CH_3CN$ or DMF to provide compounds of formula (II).

Alternatively, the compounds of formula (II) can be prepared from other compounds of formula (II), where $R_1$, $R_2$, or $R_3$ represent a halogen or pseudo halogen, e.g., bromide or triflate by palladium or copper catalyzed coupling of a alkyl, alkenyl, or aryl boronic acid, boronic ester, or boroxine; organostannane; organozinc; metal alkoxide; alcohol; amide; or the like to yield the corresponding alkyl, cycloalkyl, aryl, heteroaryl, alkoxy, aryloxy, or acylamino analog. These transformations involve the conversion of compounds of formula (II) where $R_1$, $R_2$, and/or $R_3$ may be equal to a halogen or pseudohalogen, such as Br, to compounds of formula (II) where $R_1$, $R_2$, and/or $R_3$ may be alkyl or aryl by Suzuki cross-coupling with a boronic acid, or the like, in the presence of a catalyst, preferably $Pd(PPh_3)_4$, a base, preferably potassium hydroxide and sodium carbonate, to provide compounds of formula (II). Additional compounds of formula (II) are prepared from existing compounds of formula (II) by independent manipulation of radicals R, $R_1$, $R_2$, $R_3$, $R_4$, and $R_5$ by methods known to those skilled in the art, such as, for example, reduction of a nitro group to an aniline or reduction of an ester to an alcohol.

Alternatively, the compounds of formula (II) can be prepared according to Scheme 3, which contains three steps.

Scheme 3

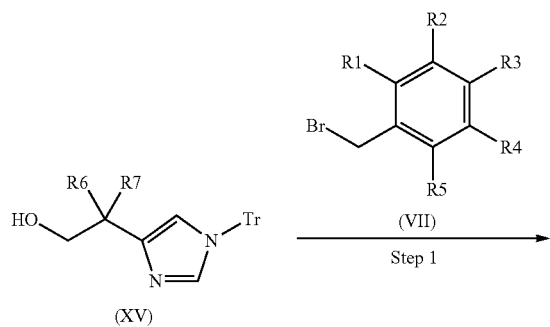

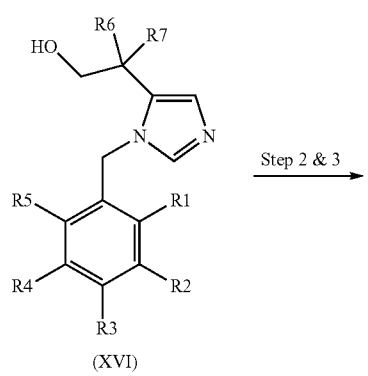

Scheme 4

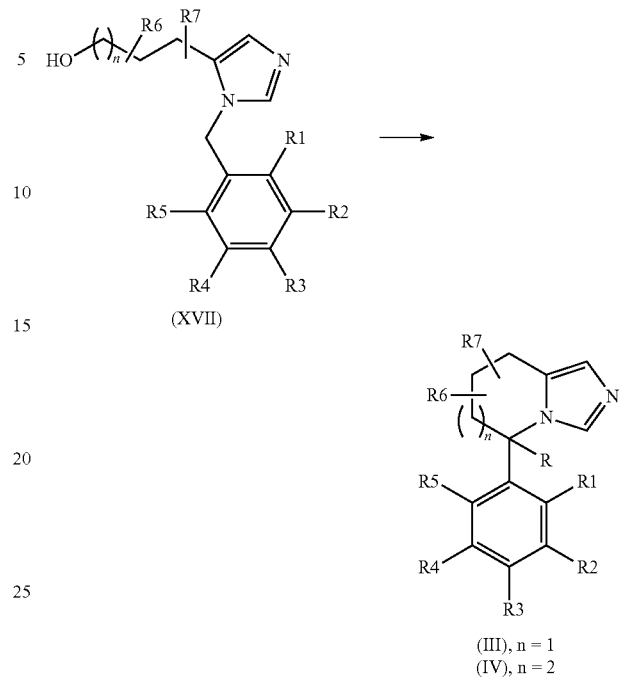

Alternatively, compounds of formula (III) or (IV) can be prepared according to Scheme 5, by conversion of a secondary alcohol (XVIII) to a suitable leaving group, e.g. chloride or mesylate (step 1), and subsequent intramolecular cyclization (step 2) by analogy to steps 3 and 4 of Scheme 2 above.

Scheme 5

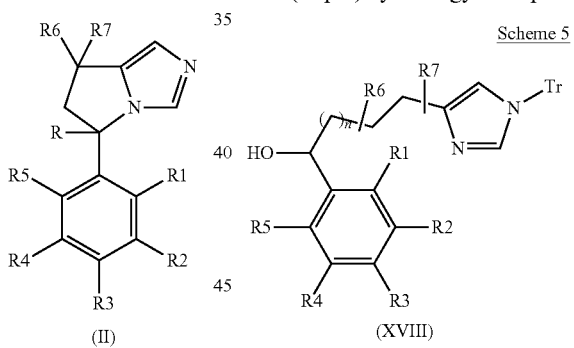

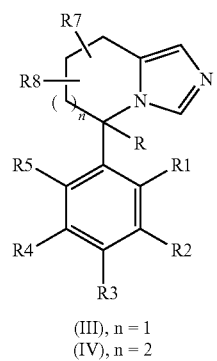

As to the individual steps in Scheme 3, Step 1 involves alkylation of N3 of imidazole (XV) with electrophiles (VII) to provide (XVI). Step 2 involves the conversion of the alcohol of (XVI) to a leaving group, preferably chloride, upon reaction with a suitable chlorinating reagent, preferably thionyl chloride. Step 3 involves the intramolecular alkylation upon reaction of the chloride resulting from step 2 with a base, preferably LDA, to provide compounds of the formula (II) where R=H.

Generally, compounds of formula (III) or (IV) can be prepared according to Scheme 4 by analogy to the cyclization described above as step 2 and 3 in Scheme 3 for the preparation of (II), e.g. by conversion of an alcohol (XVII) to a suitable leaving group, preferably the chloride generated by treatment with SOCl$_2$, followed by deprotonation with strong base, such as t-BuOK, LDA, or LHMDS, or the like, to effect cyclization of the resultant anion onto the leaving group.

Additionally, compounds of formula (III) or (IV) are prepared from existing compounds of formula (III) or (IV) by independent manipulation of radicals R, R$_1$, R$_2$, R$_3$, R$_4$, and R$_5$ by methods known to those skilled in the art, such as, for example, reduction of a nitro group to an aniline or reduction of an ester to an alcohol. For example, compounds of formula (III) or (IV) can be prepared from other compounds of formula (III) or (IV), where $R_1$, $R_2$, or $R_3$ represent a halogen or pseudo halogen, e.g., bromide or triflate by palladium or copper catalyzed coupling of an alkyl, alkenyl, or aryl boronic acid, boronic ester, or boroxine; organostannane; organozinc; metal alkoxide; alcohol; amide; or the like to yield the corresponding alkyl, cycloalkyl, aryl, heteroaryl, alkoxy, aryloxy, or acylamino analog. These transformations involve the conversion of compounds of formula (III) or (IV) where $R_1$, $R_2$, and/or $R_3$ may be equal to a halogen or pseudohalogen, such as Br, to compounds of formula (III) or (IV) where $R_1$, $R_2$, and/or $R_3$ may be alkyl or aryl by Suzuki cross-coupling with a boronic acid, or the like, in the presence of a catalyst, preferably $Pd(PPh_3)_4$, a base, preferably potassium hydroxide and sodium carbonate, to provide compounds of formula (III) or (IV). Additional compounds of formula (III) or (IV) are generated by treatment of compounds (III) or (IV) when R═H with a strong base, for example LHMDS, followed by a suitable elecrophile, for example methyl iodide or allyl bromide to give compounds of formula (III) or (IV) where R is not equal to H.

Additionally, compounds of formula (I) are generated from existing compounds of formula (I) where R and $R_1$ are not equal to H and R and $R_1$ may be reacted to form compounds where R and $R_1$ together comprise a ring.

Intermediate alcohols (XVII) are prepared by deprotection of a silyl ether (XIX), preferably a TBS ether, under, for example, acidic conditions or by reduction of the analogous ester (XX), preferably with $NaBH_4$, according to Scheme 6.

Scheme 6

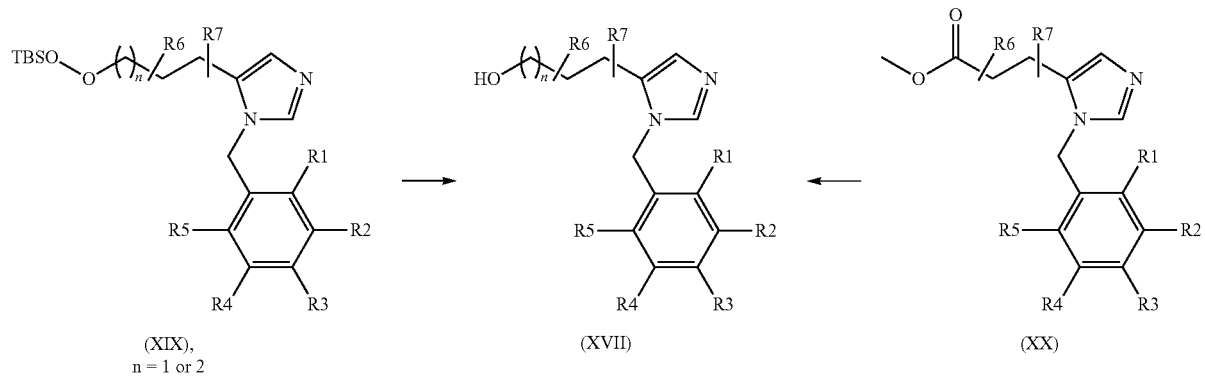

(XIX), n = 1 or 2

(XVII)

(XX)

Ethers (XIX) and esters (XX) are generated by N-alkylation of a suitably protected imidazoles (XXI) or (XXII), respectively, utilizing a suitable electrophile (VII) according to Scheme 7.

Scheme 7

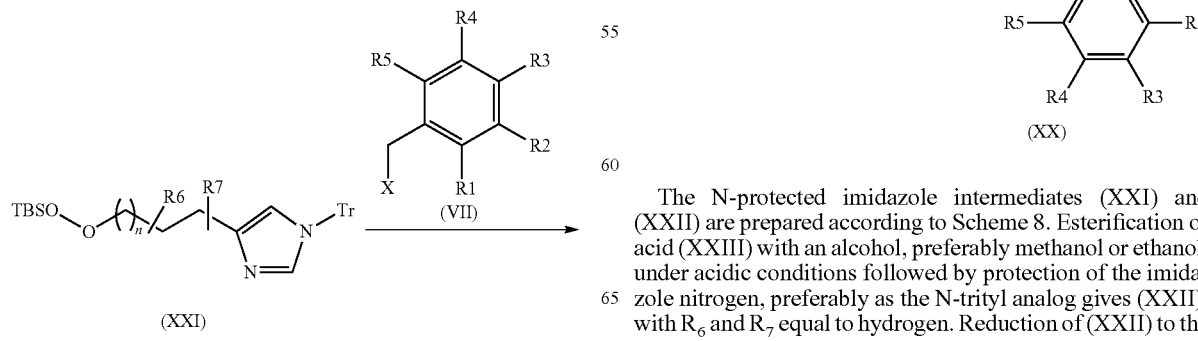

(XXI)

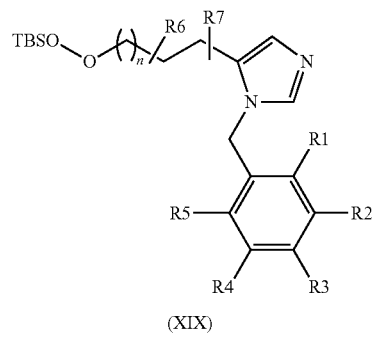

(XIX)

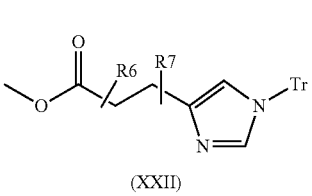

(XXII)

-continued

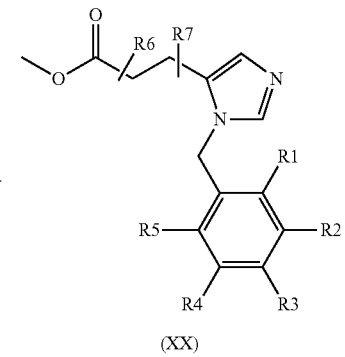

(XX)

-continued

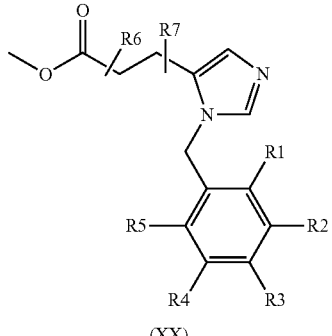

(XX)

The N-protected imidazole intermediates (XXI) and (XXII) are prepared according to Scheme 8. Esterification of acid (XXIII) with an alcohol, preferably methanol or ethanol, under acidic conditions followed by protection of the imidazole nitrogen, preferably as the N-trityl analog gives (XXII), with $R_6$ and $R_7$ equal to hydrogen. Reduction of (XXII) to the alcohol by a suitable reducing agent, preferably $NaBH_4$, followed by protection as the TBS ether gives (XXI). Esters (XXII) where $R_6$ and $R_7$ are not both hydrogen are generated by alkylation of esters (XXII) with a suitable electrophile, e.g. a benzyl bromide, under basic conditions. Conversion of the ester (XXII) to ether (XXI) with $R_6$ and $R_7$ not both hydrogen may be effected by reduction and protection of the resultant alcohol by analogy to above. Substituents $R_6$ and/or $R_7$ not equal to hydrogen may be introduced to the carbon adjacent to the imidazole by treatment of ester (XXV) with a suitable base, e.g. LDA, and electrophile, such as methyl iodide. Esters (XXII) where $R_7$ equals H may be generated by Wittig olefination of ketones (XXIV) by analogy to methods outlined in *Bioorg. Med. Chem.* 2004, 12(9), 2273. Subsequent reduction of the olefinic moiety with a suitable reducing agent, such as hydrogen, utilizing a palladium catalyst yields ester (XXII). Esters (XXV) are produced by alkylations of esters (XXV) where $R_6$ and/or $R_7$ are hydrogen under basic conditions in the presence of a suitable electrophile, e.g. methyl iodide. Homologation of ester (XXV) to ether (XXI) can be achieved by reduction with a suitable reagent, such as LAH, followed by oxidation to the aldehyde, treatment of the aldehyde with the ylide generated from methoxymethyl triphenylphosphonium chloride to produce the homolog aldehyde. Reduction of the aldehyde and subsequent protection of the alcohol yields ethers (XXI).

Compounds of formula (IV) where $R_7$ is defined above, are prepared from aldehyde or ketone (XXIV), by Wittig olefination utilizing a suitably substituted phosphonium salt, for example 3-(tert-butyldimethylsilyloxy)propyl triphenylphoshonium bromide in the presence of a base, preferably n-BuLi according to Scheme 9. Reduction of the resultant olefins yields the saturated ether (XXI) with $R_6$ equal to hydrogen, which may be N-alkylated with a bromide (VII) by analogy to step 4 outlined in Scheme 1 for the conversion of (VI) to (VIII).

Scheme 9

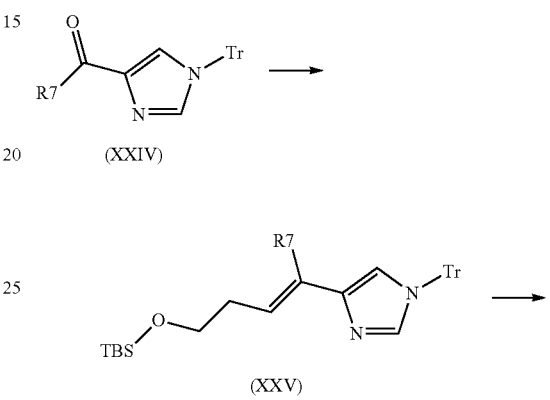

Scheme 8

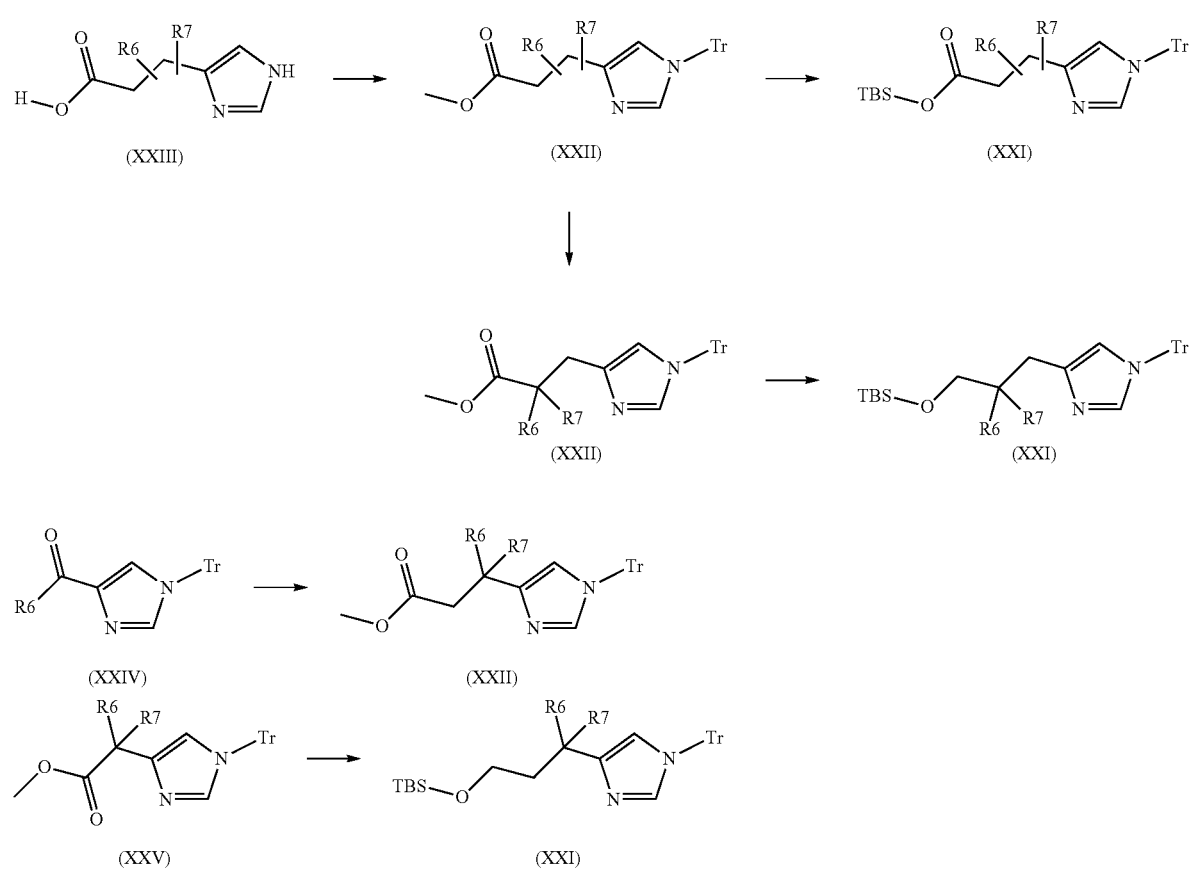

-continued

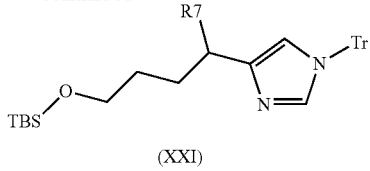

(XXI)

Additionally, substituent $R_6$ not equal to hydrogen may be introduced to compounds of formula (IV) according to Scheme 10 by conversion of ester (XXII) to olefin (XXVI) by a three step process: 1) reduction to the primary alcohol, Swern oxidation to the aldehyde and 3) conversion to the olefin (XXVI) by Wittig olefination. Cross metathesis of olefin (XXVI) with enone (XXVII) utilizing Grubbs' second generation catalyst provides enone (XXVIII), which undergoes copper-mediated conjugate addition with a suitable nucleophile, such as an alkylzinc reagent to give saturated ketone (XXIX). Reduction of (XXIX) with a suitable reagent, such as $NaBH_4$, provides secondary alcohol (XVIII).

groups without the molecular framework being destroyed or other undesired side reactions taking place.

The purpose of introducing protecting groups is to protect the functional groups from undesired reactions with reaction components under the conditions used for carrying out a desired chemical transformation. The need and, choice of protecting groups for a particular reaction is known to those skilled in the art and depends on the nature of the functional group to be protected (hydroxyl group, amino group, etc.), the structure and stability of the molecule of which the substituent is a part and the reaction conditions.

Well-known protecting groups that meet these conditions and their introduction and removal are described, e.g., in McOmie, "Protective Groups in Organic Chemistry", Plenum Press, London, N.Y. (1973); and Greene and Wuts, "Protective Groups in Organic Synthesis", John Wiley and Sons, Inc., NY (1999).

The above-mentioned reactions are carried out according to standard methods, in the presence or absence of diluent, preferably, such as are inert to the reagents and are solvents

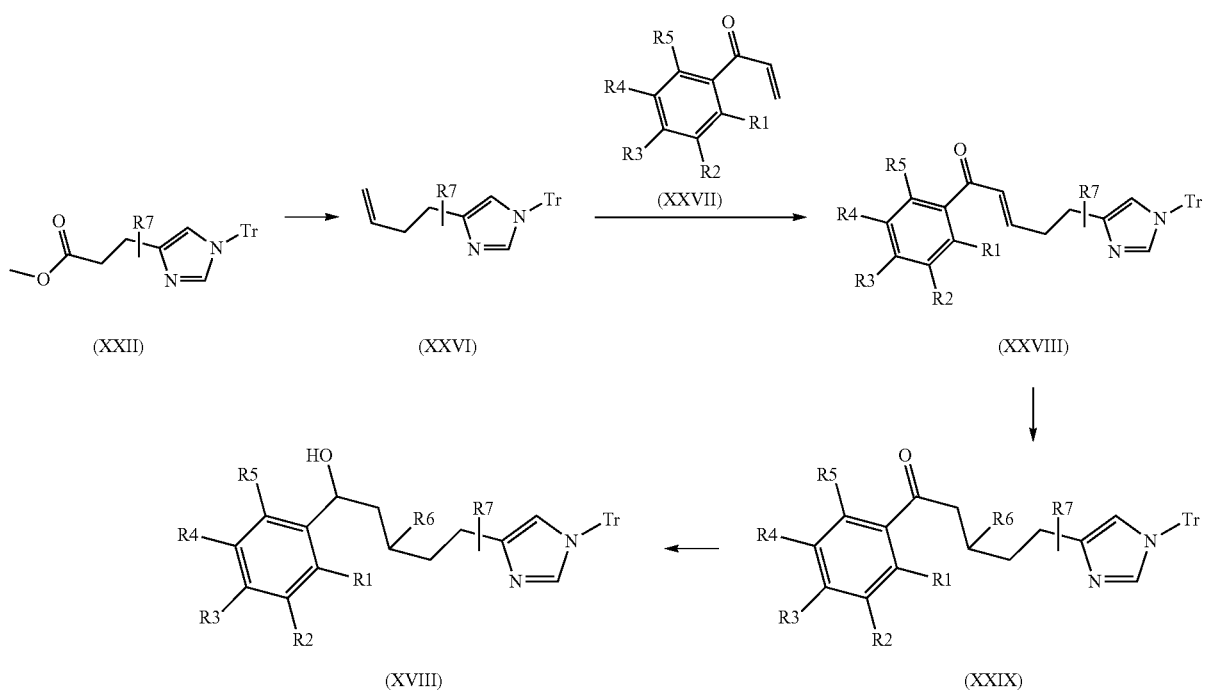

Scheme 10

Generally, enantiomers of the compounds of the present invention can be prepared by methods known to those skilled in the art to resolve racemic mixtures, such as by formation and recrystallization of diastereomeric salts or by chiral chromotagraphy or HPLC separation utilizing chiral stationery phases.

In starting compounds and intermediates which are converted to the compounds of the invention in a manner described herein, functional groups present, such as amino, thiol, carboxyl and hydroxy groups, are optionally protected by conventional protecting groups that are common in preparative organic chemistry. Protected amino, thiol, carboxyl and hydroxyl groups are those that can be converted under mild conditions into free amino thiol, carboxyl and hydroxyl thereof, of catalysts, condensing or said other agents, respectively and/or inert atmospheres, at low temperatures, room temperature or elevated temperatures, preferably at or near the boiling point of the solvents used, and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers etc.

Preferably, the pharmaceutical compositions are tablets and gelatin capsules comprising the active ingredient together with a) diluents, e.g., lactose, dextrose, sucrose, mannitol, sorbitol, cellulose and/or glycine;
b) lubricants, silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium; for example, peanut oil, liquid paraffin or olive oil.

Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure end/Or buffers. In addition, they may also, contain other therapeutically valuable substances. Said compositions are prepared according to conventional mixing, granulating or coating methods, respectively, and contain about 0.1-75%, preferably about 1-50%, of the active ingredient.

Suitable compositions for transdermal application include an effective amount of a compound of the invention with carrier. Advantageous carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations; e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

The present invention further provides anhydrous pharmaceutical compositions and dosage forms comprising the compounds of the present invention as active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutical compositions contain a therapeutically effective amount of a compound of the invention as defined above, either alone or in a combination with one or more therapeutic agents, e.g., each at an effective therapeutic dose as reported in the art. Such therapeutic agents include at least one or two or more selected from the following groups:

(i) angiotensin II receptor antagonist or a pharmaceutically acceptable salt thereof, (ii) HMG-Co-A reductase inhibitor or a pharmaceutically acceptable salt thereof, (iii) angiotensin converting enzyme (ACE) inhibitor or a pharmaceutically acceptable salt thereof, (iv) calcium channel blocker (CCB) or a pharmaceutically acceptable salt thereof, (v) dual angiotensin converting enzyme/neutral endopeptidase (ACE/NEP) inhibitor or a pharmaceutically acceptable salt thereof, (vi) endothelin antagonist or a pharmaceutically acceptable salt thereof, (vii) renin inhibitor or a pharmaceutically acceptable salt thereof, (viii) diuretic or a pharmaceutically acceptable salt thereof, (ix) an ApoA-I mimic;

(x) an anti-diabetic agent;

(xi) an obesity-reducing agent;

(xii) an aldosterone receptor blocker;

(xiii) an endothelin receptor blocker;

(xiv) a CETP inhibitor;

(xv) an inhibitor of Na-K-ATPase membrane pump;

(xvi) a beta-adrenergic receptor blocker or an alpha-adrenergic receptor blocker;

(xvii) a neutral endopeptidase (NEP) inhibitor; and (xviii) an inotropic agent.

An angiotensin II receptor antagonist or a pharmaceutically acceptable salt thereof is understood to be an active ingredients which bind to the $AT_1$-receptor subtype of angiotensin II receptor but do not result in activation of the receptor. As a consequence of the inhibition of the $AT_1$ receptor, these antagonists can, for example, be employed as antihypertensives or for treating congestive heart failure.

The class of $AT_1$ receptor antagonists comprises compounds having differing structural features, essentially preferred are the non-peptidic ones. For example, mention may be made of the compounds which are selected from the group consisting of valsartan, losartan, candesartan, eprosartan, irbesartan, saprisartan, tasosartan, telmisartan, the compound with the designation E-1477 of the following formula

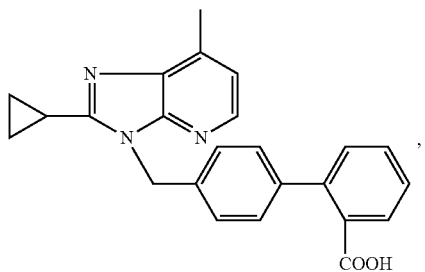 [SMILES: Cc1ccnc2c1nc(C1CC1)n2Cc1ccc(-c2ccccc2C(=O)O)cc1]

the compound with the designation SC-52458 of the following formula

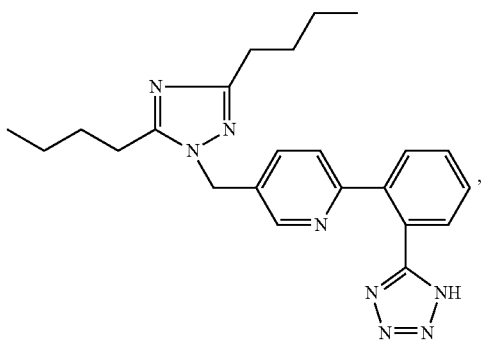 [SMILES: CCCCc1nc(CCCC)n(Cc2ccc(-c3ccccc3-c3nnn[nH]3)nc2)n1]

and the compound with the designation ZD-8731 of the following formula

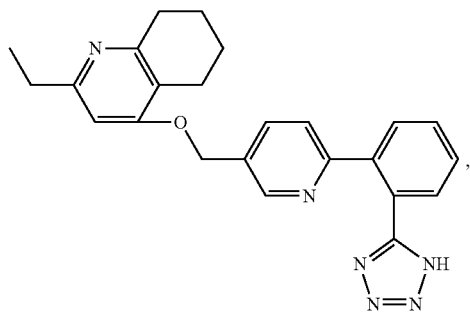 [SMILES: CCc1cc(OCc2ccc(-c3ccccc3-c3nnn[nH]3)nc2)c2c(n1)CCCC2]

or, in each case, a pharmaceutically acceptable salt thereof.

Preferred $AT_1$-receptor antagonist are those agents which have been marketed, most preferred is valsartan or a pharmaceutically acceptable salt thereof.

HMG-Co-A reductase inhibitors (also called beta-hydroxy-beta-methylglutaryl-co-enzyme-A reductase inhibitors) are understood to be those active agents that may be used to lower the lipid levels including cholesterol in blood.

The class of HMG-Co-A reductase inhibitors comprises compounds having differing structural features. For example, mention may be made of the compounds that are selected from the group consisting of atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or, in each case, a pharmaceutically acceptable salt thereof.

Preferred HMG-Co-A reductase inhibitors are those agents which have been marketed, most preferred is fluvastatin and pitavastatin or, in each case, a pharmaceutically acceptable salt thereof.

The interruption of the enzymatic degradation of angiotensin I to angiotensin II with so-called ACE-inhibitors (also called angiotensin converting enzyme inhibitors) is a successful variant for the regulation of blood pressure and thus also makes available a therapeutic method for the treatment of congestive heart failure.

The class of ACE inhibitors comprises compounds having differing structural features. For example, mention may be made of the compounds which are selected from the group consisting alacepril, benazepril, benazeprilat, captopril, ceronapril, cilazapril, delapril, enalapril, enaprilat, fosinopril, imidapril, lisinopril, moveltopril, perindopril, quinapril, ramipril, spirapril, temocapril, and trandolapril, or, in each case, a pharmaceutically acceptable salt thereof.

Preferred ACE inhibitors are those agents that have been marketed, most preferred are benazepril and enalapril.

The class of CCBs essentially comprises dihydropyridines (DHPs) and non-DHPs such as diltiazem-type and verapamil-type CCBs.

A CCB useful in said combination is preferably a DHP representative selected from the group consisting of amlodipine, felodipine, ryosidine, isradipine, lacidipine, nicardipine, nifedipine, niguldipine, niludipine, nimodipine, nisoldipine, nitrendipine, and nicardipine, and is preferably a non-DHP representative selected from the group consisting of flunarizine, prenylamine, diltiazem, fendiline, gallopamil, mibefradil, anipamil, tiapamil and verapamil, and in each case, a pharmaceutically acceptable salt thereof. All these CCBs are therapeutically used, e.g. as anti-hypertensive, anti-angina pectoris or anti-arrhythmic drugs.

Preferred CCBs comprise amlodipine, diltiazem, isradipine, nicardipine, nifedipine, nimodipine, nisoldipine, nitrendipine, and verapamil, or, e.g. dependent on the specific CCB, a pharmaceutically acceptable salt thereof. Especially preferred as DHP is amlodipine or a pharmaceutically acceptable salt, especially the besylate, thereof. An especially preferred representative of non-DHPs is verapamil or a pharmaceutically acceptable salt, especially the hydrochloride, thereof.

A preferred dual angiotensin converting enzyme/neutral endopetidase (ACE/NEP) inhibitor is, for example, omapatrilate (cf. EP 629627), fasidotril or fasidotrilate, or, if appropriable, a pharmaceutically acceptable salt thereof.

A preferred endothelin antagonist is, for example, bosentan (cf. EP 526708 A), furthermore, tezosentan (cf. WO 96/19459), or in each case, a pharmaceutically acceptable salt thereof.

Suitable renin inhibitors include compounds having different structural features. For example, mention may be made of compounds which are selected from the group consisting of ditekiren (chemical name: [1S-[1R*,2R*,4R*(1R*,2R*)]]-1-[(1,1-dimethylethoxy)carbonyl]-L-proly l-L-phenylalanyl-N-[2-hydroxy-5-methyl-1-(2-methylpropyl)-4-[[[2-methyl-1-[[(2-pyridinylmethyl)amino]carbonyl]butyl]amino] carbonyl]hexyl]-N-alfa-methyl-L-histidinamide); terlakiren (chemical name: [R—(R*,S*)]-N-(4-morpholinylcarbonyl)-L-phenylalanyl-N-[1-(cyclohexylmethyl)-2-hydroxy-3-(1-methylethoxy)-3-oxopropyl]-S-methyl-L-cysteineamide); and zankiren (chemical name: [1S-[1R*[R*(R*)],2S*,3R*]]-N-[1-(cyclohexylmethyl)-2,3-dihydroxy-5-methylhexyl]-alfa-[[2-[[(4-methyl-1-piperazinyl)sulfonyl]methyl]-1-oxo-3-phenylpropyl]-amino]-4-thiazolepropanamide), preferably, in each case, the hydrochloride salt thereof, SPP630, SPP635 and SPP800 as developed by Speedel.

Preferred renin inhibitor of the present invention include RO 66-1132 and RO 66-1168 of formula (A) and (B)

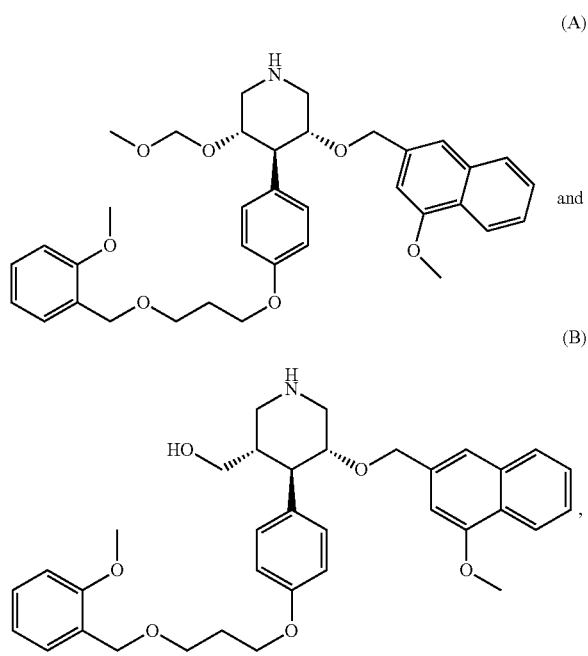

respectively, or a pharmaceutically acceptable salt thereof.

In particular, the present invention relates to a renin inhibitor which is a δ-amino-γ-hydroxy-ω-aryl-alkanoic acid amide derivative of the formula (C)

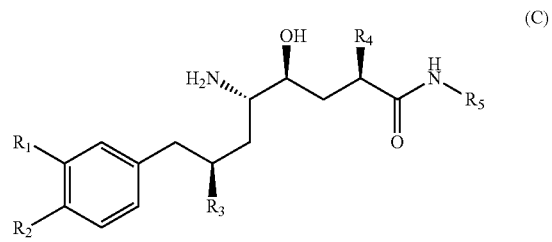

wherein $R_1$ is halogen, $C_{1-6}$halogenalkyl, $C_{1-6}$alkoxy-$C_{1-6}$alkyloxy or $C_{1-6}$alkoxy-$C_{1-6}$alkyl; $R_2$ is halogen, $C_{1-4}$alkyl or $C_{1-4}$alkoxy; $R_3$ and $R_4$ are independently branched $C_{3-6}$alkyl; and $R_5$ is cycloalkyl, $C_{1-6}$alkyl, $C_{1-6}$hydroxyalkyl, $C_{1-6}$aminoalkyl, $C_{1-6}$dialkylamino-$C_{1-6}$alkyl, $C_{1-6}$alkanoylamino-$C_{1-6}$alkyl, HO(O)C—$C_{1-6}$alkyl, $C_{1-6}$alkyl-O—(O)C—$C_{1-6}$alkyl, $H_2N$—C(O)—$C_{1-6}$alkyl, $C_{1-6}$alkyl-HN—C(O)—$C_{1-6}$alkyl or $(C_{1-6}$alkyl$)_2N$—C(O)—$C_{1-6}$alkyl; or a pharmaceutically acceptable salt thereof.

As an alkyl, $R_1$ may be linear or branched and preferably comprise 1 to 6 C atoms, especially 1 or 4 C atoms. Examples are methyl, ethyl, n- and i-propyl, n-, i- and t-butyl, pentyl and hexyl.

As a halogenalkyl, $R_1$ may be linear or branched and preferably comprise 1 to 4 C atoms, especially 1 or 2 C atoms. Examples are fluoromethyl, difluoromethyl, trifluoromethyl, chloromethyl, dichloromethyl, trichloromethyl, 2-chloroethyl and 2,2,2-trifluoroethyl.

As an alkoxy, $R_1$ and $R_2$ may be linear or branched and preferably comprise 1 to 4 C atoms. Examples are methoxy, ethoxy, n- and i-propyloxy, n-, i- and t-butyloxy, pentyloxy and hexyloxy.

As an alkoxyalkyl, $R_1$ may be linear or branched. The alkoxy group preferably comprises 1 to 4 and especially 1 or 2 C atoms, and the alkyl group preferably comprises 1 to 4 C atoms. Examples are methoxymethyl, 2-methoxyethyl, 3-methoxypropyl, 4-methoxybutyl, 5-methoxypentyl, 6-methoxyhexyl, ethoxymethyl, 2-ethoxyethyl, 3-ethoxypropyl, 4-ethoxybutyl, 5-ethoxypentyl, 6-ethoxyhexyl, propyloxymethyl, butyloxymethyl, 2-propyloxyethyl and 2-butyloxyethyl.

As a $C_{1-6}$alkoxy-$C_{1-6}$alkyloxy, $R_1$ may be linear or branched. The alkoxy group preferably comprises 1 to 4 and especially 1 or 2 C atoms, and the alkyloxy group preferably comprises 1 to 4 C atoms. Examples are methoxymethyloxy, 2-methoxyethyloxy, 3-methoxypropyloxy, 4-methoxybutyloxy, 5-methoxypentyloxy, 6-methoxyhexyloxy, ethoxymethyloxy, 2-ethoxyethyloxy, 3-ethoxypropyloxy, 4-ethoxybutyloxy, 5-ethoxypentyloxy, 6-ethcoryhexyloxy, propyloxymethyloxy, butyloxymethyloxy, 2-propyloxyethyloxy and 2-butyloxyethyloxy.

In a preferred embodiment, $R_1$ is methoxy- or ethoxy-$C_{1-4}$alkyloxy, and $R_2$ is preferably methoxy or ethoxy. Particularly preferred are compounds of formula (III), wherein $R_1$ is 3-methoxypropyloxy and $R_2$ is methoxy.

As a branched alkyl, $R_3$ and $R_4$ preferably comprise 0.3 to 6 C atoms. Examples are i-propyl, i- and t-butyl, and branched isomers of pentyl and hexyl. In a preferred embodiment, $R_3$ and $R_4$ in compounds of formula (C) are in each case i-propyl.

As a cycloalkyl, $R_5$ may preferably comprise 3 to 8 ring-carbon atoms, 3 or 5 being especially preferred. Some examples are cyclopropyl, cyclobutyl, cyclopentyl, cyclohexyl and cyclooctyl. The cycloalkyl may optionally be substituted by one or more substituents, such as alkyl, halo, oxo, hydroxy, alkoxy, amino, alkylamino, dialkylamino, thiol, alkylthio, nitro, cyano, heterocyclyl and the like.

As an alkyl, $R_5$ may be linear or branched in the form of alkyl and preferably comprise 1 to 6 C atoms. Examples of alkyl are listed herein above. Methyl, ethyl, n- and i-propyl, n-, i- and t-butyl are preferred.

As a $C_{1-6}$hydroxyalkyl, $R_5$ may be linear or branched and preferably comprise 2 to 6 C atoms. Some examples are 2-hydroxyethyl, 2-hydroxypropyl, 3-hydroxypropyl, 2-, 3- or 4-hydroxybutyl, hydroxypentyl and hydroxyhexyl.

As a $C_{1-6}$alkoxy-$C_{1-6}$alkyl, $R_5$ may be linear or branched. The alkoxy group preferably comprises 1 to 4 C atoms and the alkyl group preferably 2 to 4 C atoms. Some examples are 2-methoxyethyl, 2-methoxypropyl, 3-methoxypropyl, 2-, 3- or 4-methoxybutyl, 2-ethoxyethyl, 2-ethoxypropyl, 3-ethoxypropyl, and 2-, 3- or 4-ethoxybutyl.

As a $C_{1-6}$alkanoyloxy-$C_{1-6}$alkyl, $R_5$ may be linear or branched. The alkanoyloxy group preferably comprises 1 to 4 C atoms and the alkyl group preferably 2 to 4 C atoms.

Some examples are formyloxymethyl, formyloxyethyl, acetyloxyethyl, propionyloxyethyl and butyroyloxyethyl.

As a $C_{1-6}$aminoalkyl, $R_5$ may be linear or branched and preferably comprise 2 to 4 C atoms. Some examples are 2-aminoethyl, 2- or 3-aminopropyl and 2-, 3- or 4-aminobutyl.

As $C_{1-6}$alkylamino-$C_{1-6}$alkyl and $C_{1-6}$dialkylamino-$C_{1-6}$alkyl, $R_5$ may be linear or branched. The alkylamino group preferably comprises $C_{1-4}$alkyl groups and the alkyl group has preferably, 2 to 4 C atoms. Some examples are 2-methylaminoethyl, 2-dimethylaminoethyl, 2-ethylaminoethyl, 2-ethylaminoethyl, 3-methylaminopropyl, 3-dimethylaminopropyl, 4-methylaminobutyl and 4-dimethylaminobutyl.

As a HO(O)C—$C_{1-6}$alkyl, $R_5$ may be linear or branched and the alkyl group preferably comprises 2 to 4 C atoms. Some examples are carboxymethyl, carboxyethyl, carboxypropyl and carboxybutyl.

As a $C_{1-6}$alkyl-O—(O)C—$C_{1-6}$alkyl, $R_5$ may be linear or branched, and the alkyl groups preferably comprise, independently of one another 1 to 4 C atoms. Some examples are methoxycarbonylmethyl, 2-methoxycarbonylethyl, 3-methoxycarbonylpropyl, 4-methoxy-carbonylbutyl, ethoxycarbonylmethyl, 2-ethoxycarbonylethyl, 3-ethoxycarbonylpropyl, and 4-ethoxycarbonylbutyl.

As a $H_2N$—C(O)—$C_{1-6}$alkyl, $R_5$ may be linear or branched, and the alkyl group preferably comprises 2 to 6 C atoms. Some examples are carbamidomethyl, 2-carbamidoethyl, 2-carbamido-2,2-dimethylethyl, 2- or 3-carbamidopropyl, 2-, 3- or 4-carbamidobutyl, 3-carbamido-2-methylpropyl, 3-carbamido-1,2-dimethylpropyl, 3-carbamido-3-ethylpropyl, 3-carbamido-2,2-dimethylpropyl, 2-, 3-, 4- or 5-carbamidopentyl, 4-carbamido-3,3- or -2,2-dimethylbutyl. Preferably, $R_5$ is 2-carbamido-2,2-dimethylethyl.

Accordingly, preferred are δ-amino-γ-hydroxy-ω-aryl-alkanoic acid amide derivatives of formula (C) having the formula

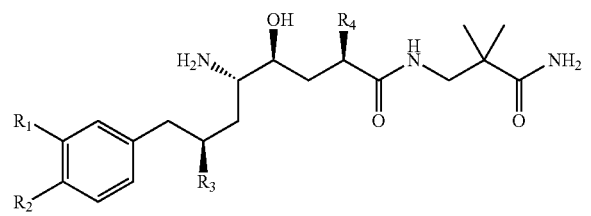

(D)

wherein $R_1$ is 3-methoxypropyloxy; $R_2$ is methoxy; and $R_3$ and $R_4$ are isopropyl; or a pharmaceutically acceptable salt thereof; chemically defined as 2(S),4(S),5(S),7(S)—N-(3-amino-2,2-dimethyl-3-oxopropyl)-2,7-di(1-methylethyl)-4-hydroxy-5-amino-8-[4-methoxy-3-(3-methoxy-propoxy) phenyl]-octanamide, also known as, aliskiren.

The term "aliskiren", if not defined specifically, is to be understood both as the free base and as a salt thereof, especially a pharmaceutically acceptable salt thereof, most preferably a hemi-fumarate salt thereof.

A diuretic is, for example, a thiazide derivative selected from the group consisting of chlorothiazide, hydrochlorothiazide, methylclothiazide, and chlorothalidon. The most preferred is hydrochlorothiazide.

An ApoA-1 mimic is, for example, D4F peptide, especially of formula D-W-F-K-A-F-Y-D-K-V-A-E-K-F-K-E-A-F An anti-diabetic agents include insulin secretion enhancers which are active ingredients that have the property to promote the secretion of insulin from pancreatic β-cells. Examples of insulin secretion enhancers are a biguanide derivative, for example, metformin or, if appropriate, a pharmaceutically acceptable salt thereof, especially the hydrochloride hereof. Other insulin secretion enhancers include sulfonylureas (SU), especially those which promote the secretion of insulin from pancreatic β-cells by transmitting signals of insulin secretion via SU receptors in the cell membrane, including (but are not limited to) tolbutamide; chlorpropamide; tolazamide; acetohexamide; 4-chloro-N-[(1-pyrrolidinylamino) carbonyl]-benzensulfonamide (glycopyramide); glibenclamide (glyburide); gliclazide; 1-butyl-3-metanilylurea; carbutamide; glibonuride; glipizide; gliquidone; glisoxepid; glybuthiazole; glibuzole; glyhexamide; glymidine; glypinamide; phenbutamide; and tolylcyclamide, or pharmaceutically acceptable salts thereof.

Insulin secretion enhancers furthermore include short-acting insulin secretion enhancers, such as the phenylalanine derivative nateglinide [N-(trans-4-isopropylcyclohexylcarbonyl)-D-phenylalanine] (cf. EP 196222 and EP 526171) of the formula

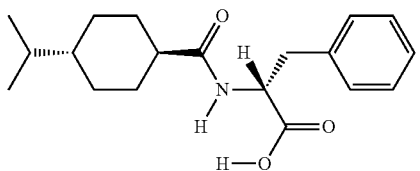 [SMILES: CC(C)[C@H]1CC[C@H](C(=O)N[C@H](Cc2ccccc2)C(=O)O)CC1]

and repaglinide [(S)-2-ethoxy-4-{2-[[3-methyl-1-[2-(1-piperidinyl)phenyl]butyl]amino]-2-oxoethyl}benzoic acid]. Repaglinide is disclosed in EP 589874, EP 147850 A2, in particular Example 11 on page 61, and EP 207331 A1. It can be administered in the forth as it is marketed, e.g. under the trademark NovoNorm™; calcium (2S)-2-benzyl-3-(cis-hexahydro-2-isoindolinlycarbonyl)-propionate dihydrate (mitiglinide cf. EP 507534); furthermore representatives of the new generation of SUs such as glimepiride (cf. EP 31058); in free or pharmaceutically acceptable salt form. The term nateglinide likewise comprises crystal modifications such as disclosed in EP 0526171 B1 or U.S. Pat. No. 5,488,510, respectively, the subject matter of which, especially with respect to the identification, manufacture and characterization of crystal modifications, is herewith incorporated by reference to this application, especially the subject matter of claims 8 to 10 of said U.S. patent (referring to H-form crystal modification) as well as the corresponding references to the B-type crystal modification in EP 196222 B1 the subject matter of which, especially with respect to the identification; manufacture and characterization of the B-form crystal modification. Preferably, in the present invention, the B- or H-type, more preferably the H-type, is used. Nateglinide can be administered in the form as it is marketed e.g. under the trademark STARLIX™.

Insulin secretion enhancers likewise include the long-acting insulin secretion enhancer DPP-IV inhibitors, GLP-1 and GLP-1 agonists.

DPP-IV is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal.

The DPP-IV inhibitor can be peptidic or, preferably, non-peptidic. DPP-IV inhibitors are in each case generically and specifically disclosed e.g. in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications. Preferred are those compounds that are specifically disclosed in Example 3 of WO 98/19998 and Example 1 of WO 00/34241, respectively.

GLP-1 is a insulinotropic proteine which was described, e.g., by W. E. Schmidt et al. in *Diabetologia*, 28, 1985, 704-707 and in U.S. Pat. No. 5,705,483.

The term "GLP-1 agonists" used herein means variants and analogs of GLP-1(7-36)NH$_2$ which are disclosed in particular in U.S. Pat. No. 5,120,712, U.S. Pat. No. 5,118,666, U.S. Pat. No. 5,512,549, WO 91/11457 and by C. Orskov at al in J. Biol. Chem. 264 (1989) 12826. The term "GLP-1 agonists" comprises especially compounds like GLP-1(7-37), in which compound the carboxy-terminal amide functionality of Arg$^{36}$ is displaced with Gly at the 37$^{th}$ position of the GLP-1(7-36) NH$_2$ molecule and variants and analogs thereof including GLN$^9$-GLP-1(7-37), D-GLN$^9$-GLP-1(7-37), acetyl LYS$^9$-GLP-1(7-37), LYS$^{18}$-GLP-1(7-37) and, in particular, GLP-1 (7-37)OH, VAL$^8$-GLP-1(7-37), GLY$^8$-GLP-1(7-37), THR$^8$-GLP-1(7-37), MET$^7$-GLP-1(7-37) and 4-imidazopropionyl-GLP-1. Special preference is also given to the GLP agonist analog exendin-4, described by Greig et al in Diabetologia 1999, 42, 45-50.

An insulin sensitivity enhancer restores impaired insulin receptor function to reduce insulin resistance and consequently enhance the insulin sensitivity.

An appropriate insulin sensitivity enhancer is, for example, an appropriate hypoglycemic thiazolidinedione derivative (glitazone).

An appropriate glitazone is, for example, (S)-((3,4-dihydro-2-(phenyl-methyl)-2H-1-benzopyran-6-yl)methyl-thiazolidine-2,4-dione (englitazone), 5-{[4-(3-(5-methyl-2-phenyl-4-oxazolyl)-1-oxopropyl)-phenyl]-methyl}-thiazolidine-2,4-dione (darglitazone), 5-{[4-(1-methyl-cyclohexl)methoxy)-phenyl]methyl}-thiazolidine-2,4-dione (ciglitazone), 5-{[4-(2-(1-indolyl)ethoxy)phenyl]methyl}-thiazolidine-2,4-dione (DRF2189), 5-{4-[2-(5-methyl-2-phenyl-4-oxazolyl)-ethoxy)]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinyl)methyl] phenyl}methane (YM268), 5-{4-[2-(5-methyl-2-phenyl-4-oxazolyl)-2-hydroxyethoxy]benzyl}-thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy)phenyl]methyl}-thiazolidine-2,4-dione, 5-[3-(4-chloro-phenyl])-2-propynyl]-5-phenylsulfonyl)thiazolidine-2,4-dione, 5-[3-(4-chlorophenyl])-2-propynyl]-5-(4-fluorophenyl-sulfonyl) thiazolidine-2,4-dione, 5-{[4-(2-(methyl-2-pyridinyl-amino)-ethoxy)phenyl]methyl}-thiazolidine-2,4-dione (rosiglitazone), 5-{[4-(2-(5-ethyl-2-pyridyl)ethoxy)phenyl]-methyl}thiazolidine-2,4-dione (pioglitazone), 5-{[4-((3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluoro-benzyloxy)naphthalen-2-ylmethyl]-thiazolidine-2,4-dione (MCC555), 5-{[(2-(2-naphthyl)-benzoxazol-5-yl]-methyl}thiazolidine-2,4-dione (T-174) and 5-(2,4-dioxothiazolidin-5-ylmethyl)-2-methoxy-N-(4-trifluoromethyl-benzyl)benzamide (KRP297). Preferred are pioglitazone, rosiglitazone and troglitazone.

Other anti-diabetic agents include, insulin signalling pathway modulators, like inhibitors of protein tyrosine phosphatases (PTPases), antidiabetic non-small molecule mimetic compounds and inhibitors of glutamine-fructose-6-phosphate amidotransferase (GFAT); compounds influencing a dysregulated hepatic glucose production, like inhibitors of glucose-6-phosphatase (G6 Pase), inhibitors of fructose-1,6-bisphosphatase (F-1,6-BPase), inhibitors of glycogen phosphorylase (GP), glucagon receptor antagonists and inhibitors of phosphoenolpyruvate carboxykinase (PEPCK); pyruvate dehydrogenase kinase (PDHK) inhibitors; inhibitors of gastric emptying; insulin; inhibitors of GSK-3; retinoid X receptor (RXR) agonists; agonists of Beta-3 AR; agonists of uncoupling proteins (UCPs); non-glitazone type PPARγ agonists; dual PPARα/PPARγ agonists; antidiabetic vanadium containing compounds; incretin hormones, like glucagon-like peptide-1 (GLP-1) and GLP-1 agonists; beta-cell imidazoline receptor antagonists; miglitol; and α$_2$-adrenergic antagonists; in which the active ingredients are present in each case in free form or in the form of a pharmaceutically acceptable salt.

An obesity-reducing agent includes lipase inhibitors such as orlistat and appetite suppressants such as sibutramine, phentermine.

An aldosteron receptor blocker includes spironolactone and eplerenone.

An endothelin receptor blacker includes bosentan, etc.

A CETP inhibitor refers to a compound that inhibits the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). The CETP inhibitors include those disclosed in U.S. Pat. No. 6,140,343 and U.S. Pat. No. 6,197,786. CETP inhibitors disclosed in these patents include compounds, such as [2R,4S]-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, which is also known as torcetrapib. CETP inhibitors are also described in U.S. Pat. No. 6,723,752, which includes a number of CETP inhibitors including (2R)-3-{[3-(4-Chloro-3-ethyl-phenoxy)-phenyl]-[[3-(1,1,2,2-tetrafluoro-ethoxy)-phenyl]-methyl]-amino}-1,1,1-trifluoro-2-propanol. CETP inhibitors also include those described in U.S. patent application Ser. No. 10/807,838 filed Mar. 23, 2004. U.S. Pat. No. 5,512,548 discloses certain polypeptide derivatives having activity as CETP inhibitors, also certain CETP-inhibitory rosenonolactone derivatives and phosphate-containing analogs of cholesteryl ester are disclosed in *J. Antibiot.*, 49(8): 815-816 (1996), and *Bioorg. Med. Chem. Lett.*; 6:1951-1954 (1996), respectively. Furthermore, the CETP inhibitors also include those disclosed in WO2000/017165, WO2005/095409 and WO2005/097806.

A Na_K-ATPase inhibitor can be used to inhibit the Na and K exchange across the cell membranes. Such inhibitor can be for example digoxin.

A beta-adrenergic receptor blocker includes but is not limited to: esmolol especially the hydrochloride thereof; acebutolol, which may be prepared as disclosed in U.S. Pat. No. 3,857,952; alprenolol, which may be prepared as disclosed in Netherlands Patent Application No. 6,605,692; amosulalol, which may be prepared as disclosed in U.S. Pat. No. 4,217,305; arotinolol, which may be prepared as disclosed in U.S. Pat. No. 3,932,400; atenolol, which may be prepared as disclosed in U.S. Pat. No. 3,663,607 or U.S. Pat. No. 3,836,671; befunolol, which may be prepared as disclosed in U.S. Pat. No. 3,853,923; betaxolol, which may be prepared as disclosed in U.S. Pat. No. 4,252,984; bevantolol, which may be prepared as disclosed in U.S. Pat. No. 3,857,981; bisoprolol, which may be prepared as disclosed in U.S. Pat. No. 4,171,370; bopindolol, which may be prepared as disclosed in U.S. Pat. No. 4,340,541; bucumolol, which may be prepared as disclosed in U.S. Pat. No. 3,663,570; bufetolol, which may be prepared as disclosed in U.S. Pat. No. 3,723,476; bufuralol, which may be prepared as disclosed in U.S. Pat. No. 3,929,836; bunitrolol, which may be prepared as disclosed in U.S. Pat. Nos. 3,940,489 and 3,961,071; buprandolol, which may be prepared as disclosed in U.S. Pat. No. 3,309,406; butiridine hydrochloride, which may be prepared as disclosed in French Patent No. 1,390,056; butofilolol, which may be prepared as disclosed in U.S. Pat. No. 4,252,825; carazolol, which may be prepared as disclosed in German Patent No. 2,240,599; carteolol, which may be prepared as disclosed in U.S. Pat. No. 3,910,924; Carvedilol, which may be prepared as disclosed in U.S. Pat. No. 4,503,067; celiprolol, which may be prepared as disclosed in U.S. Pat. No. 4,034,009; cetamolol, which may be prepared as disclosed in U.S. Pat. No. 4,059,622; cloranolol, which may be prepared as disclosed in German Patent No. 2,213,044; dilevalol, which may be prepared as disclosed in Clifton et al., Journal of Medicinal Chemistry, 1982, 25, 670; epanolol, which may be prepared as disclosed in European Patent Publication Application No. 41, 491; indenolol, which may be prepared as disclosed in U.S. Pat. No. 4,045,482; labetalol, which may be prepared as disclosed in U.S. Pat. No. 4,012,444; levobunolol, which may be prepared as disclosed in U.S. Pat. No. 4,463,176; mepindolol; which may be prepared as disclosed in Seeman et al., Helv. Chim. Acta, 1971, 54, 241; metipranolol, which may be prepared as disclosed in Czechoslovakian Patent Application No. 128,471; metoprolol, which may be prepared as disclosed in U.S. Pat. No. 3,873,600; moprolol, which may be prepared as disclosed in U.S. Pat. No. 3,501,7691; nadolol, which may be prepared as disclosed in U.S. Pat. No. 3,935,267; nadoxolol, which may be prepared as disclosed in U.S. Pat. No. 3,819,702; nebivalol, which may be prepared as disclosed in U.S. Pat. No. 4,654,362; nipradilol, which may be prepared as disclosed in U.S. Pat. No. 4,394,382; oxprenolol, which may be prepared as disclosed in British Patent No. 1,077,603; perbutolol, which may be prepared as disclosed in U.S. Pat. No. 3,551,493; pindolol, which may be prepared as disclosed in Swiss Patent Nos. 469,002 and 472,404; practolol, which may be prepared as disclosed in U.S. Pat. No. 3,408,387; pronethalol, which may be prepared as disclosed in British Patent No. 909,357; propranolol, which may be prepared as disclosed in U.S. Pat. Nos. 3,337,628 and 3,520,919; sotalol, which may be prepared as disclosed in Uloth et al., *Journal of Medicinal Chemistry*, 1966, 9, 88; sufinalol, which may be prepared as disclosed in German Patent No. 2,728,641; talindol, which may be prepared as disclosed in U.S. Pat. Nos. 3,935,259 and 4,038,313; tertatolol, which may be prepared as disclosed in U.S. Pat. No. 3,960,891; tilisolol, which may be prepared as disclosed in U.S. Pat. No. 4,129,565; timolol, which may be prepared as disclosed in U.S. Pat. No. 3,655,663; toliprolol, which may be prepared as disclosed in U.S. Pat. No. 3,432,545; and xibenolol, which may be prepared as disclosed in U.S. Pat. No. 4,018,824.

An alpha-adrenergic receptor blocker includes but is not limited to: amosulalol, which may be prepared as disclosed in U.S. Pat. No. 4,217,307; arotinolol, which may be prepared as disclosed in U.S. Pat. No. 3,932,400; dapiprazole, which may be prepared as disclosed in U.S. Pat. No. 4,252,721; doxazosin, which may be prepared as disclosed in U.S. Pat. No. 4,188,390; fenspiride, which may be prepared as disclosed in U.S. Pat. No. 3,399,192; indoramin, which may be prepared as disclosed in U.S. Pat. No. 3,527,761; labetolol, which may be prepared as disclosed above; naftopidil, which may be prepared as disclosed in U.S. Pat. No. 3,997,666; nicergoline, which may be prepared as disclosed in U.S. Pat. No. 3,228,943; prazosin, which may be prepared as disclosed in U.S. Pat. No. 3,511,836; tamsulosin, which may be prepared as disclosed in U.S. Pat. No. 4,703,063; tolazoline, which may be prepared as disclosed in U.S. Pat. No. 2,161,938; trimazosin, which may be prepared as disclosed in U.S. Pat. No. 3,669,968; and yohimbine, which may be isolated from natural sources according to methods well known to those skilled in the art.

The natriuretic peptides constitute a family of peptides that include the atrial (ANP), brain-derived (BNP) and C-type natriuretic (CNP) peptides. The natriuretic peptides effect vasodilation, natriuresis, diuresis, decreased aldosterone release, decreased cell growth, and inhibition of the sympathetic nervous system and the renin-angiotensin-aldosterone system indicating their involvement in the regulation of blood pressure and of sodium and water balance. Neutral endopeptidase 24. 11 (NEP) inhibitors impede degradation of natriuretic peptides and elicit pharmacological actions potentially beneficial in the management of several cardiovascular disorders. A NEP inhibitor useful in the said combination is an agent selected from the group represented by candoxatril, sinorphan, SCH 34826 and SCH 42495.

An inotropic agent is selected from the group consisting of: digoxin, digitoxin, digitalis, dobutamine, dopamine, epinephrine, milrinone, aminone and norepinephrine, etc.

A compound of the present invention may be administered either simultaneously, before or after the other active ingredient, either separately by the same or different route of administration or together in the same pharmaceutical formulation.

Furthermore, the combinations as described above can be administered to a subject via simultaneous, separate or sequential administration (use). Simultaneous administration (use) can take place in the form of one fixed combination with two or three or more active ingredients, or by simultaneously administering two or three or more compounds that are formulated independently. Sequential administration (use) preferably means administration of one (or more) compounds or active ingredients of a combination at one time point, other compounds or active ingredients at a different time point, that is, in a chronically staggered manner, preferably such that the combination shows more efficiency than the single compounds administered independently (especially showing synergism). Separate administration (use) preferably means administration of the compounds or active ingredients of the combination independently of each other at different time points, preferably meaning that two, or three or more compounds are administered such that no overlap of measurable blood levels of both compounds are present in an overlapping manner (at the same time).

Also combinations of two or three or more of sequential, separate and simultaneous administrations are possible, preferably such that the combination compound-drugs show a joint therapeutic effect that exceeds the effect found when the combination compound drugs are used independently at time intervals so large that no mutual effect on their therapeutic efficiency can be found, a synergistic effect being especially preferred.

Alternatively, the pharmaceutical compositions contain a therapeutically effective amount of a compound of the invention as defined above, either alone or in a combination with one or more therapeutic agents, e.g., each at an effective therapeutic dose as reported in the art, selected from the group consisting of an antiestrogen; an anti-androgen; a gonadorelin agonist; a topoisomerase I inhibitor; a topoisomerase II inhibitor; a microtubule active agent; an alkylating agent; an anti-neoplastic anti-metabolite; a platin compound; a compound targeting/decreasing a protein or lipid kinase activity or a protein or lipid phosphatase activity, a anti-angiogenic compound; a compound which induces cell differentiation processes; monoclonal antibodies; a cyclooxygenase inhibitor; a bisphosphonate; a heparanase inhibitor; a biological response modifier; an inhibitor of Ras oncogenic isoforms; a telomerase inhibitor; a protease inhibitor, a matrix metalloproteinase inhibitor, a Methionine aminopeptidase inhibitor; a proteasome inhibitor; agents which target, decrease or inhibit the activity of Flt-3; an HSP90 inhibitor; antiproliferative antibodies; an HDAC inhibitor; a compound which targets, decreases or inhibits the activity/function of serine/threonine mTOR kinase; a somatostatin receptor antagonist; an anti-leukemic compound; tumor cell damaging approaches; an EDG binder; a ribonucleotide reductase inhibitor; an S-adenosylmethionine decarboxylase inhibitor; a monoclonal antibody of VEGF or VEGFR; photodynamic therapy; an Angiostatic steroid; an implant containing corticosteroids; an AT1 receptor antagonist; and an ACE inhibitor.

Additionally, the present invention provides:
a pharmaceutical composition or combination of the present invention for use as a medicament;
the use of a pharmaceutical composition or combination of the present invention for the delay of progression and/or treatment of a disorder or disease mediated by aldosterone synthase, or responsive to inhibition of aldosterone synthase, or characterized by abnormal activity or expression of aldosterone synthase.
the use of a pharmaceutical composition or combination of the present invention for the delay of progression and/or treatment of a disorder or disease mediated by aromatase, or responsive to inhibition of aromatase, or characterized by abnormal activity or expression of aromatase.
the use of a pharmaceutical composition or combination of the present invention for the delay of progression and/or treatment of a disorder or disease selected from hypokalemia, hypertension, congestive heart failure, atrial fibrillation, renal failure, in particular, chronic renal failure, restenosis; atherosclerosis, syndrome X, obesity, nephropathy, post-Myocardial infarction, coronary heart diseases, increased formation of collagen, fibrosis such as cardiac or myocardiac fibrosis and remodeling following hypertension and endothelial dysfunction.
the use of a pharmaceutical composition or combination of the present invention for the delay of progression and/or treatment of a disorder or disease selected from gynecomastia, osteoporosis, prostate cancer, endometriosis, uterine fibroids, dysfunctional uterine bleeding, endometrial hyperplasia, polycystic ovarian disease, infertility, fibrocystic breast disease, breast cancer and fibrocystic mastopathy.

The pharmaceutical composition or combination of the present invention can be in unit dosage of about 1-1000 mg of active ingredients for a subject of about 50-70 kg, preferably about 5-500 mg of active ingredients. The therapeutically effective dosage of a compound, the pharmaceutical composition, or the combinations thereof, independent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats; dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, preferably between about 1-100 mg/kg.

The activities of a compound according to the present invention can be assessed by the following in vitro & in vivo methods well-described in the art. See Fieber, A et al. (2005), "Aldosterone Synthase Inhibitor Ameliorates Angiotensin II-Induced Organ Damage," Circulation, 111:3087-3094; see also Stresser D M, Turner S D, McNamara J, et al (2000), "A high-throughput screen to identify inhibitors of aromatase (CYP19)," Anal Biochem; 284:427-30. All the references cited herein are incorporated by reference in their entirety.

In particular, the aldosterone synthase and aromatase inhibitory activities in vitro can be determined by the following assays.

Human adrenocortical carcinoma NCI-H295R cell line is obtained from American Type Culture Collection (Manassas, Va.). Insulin/transferrin/selenium (ITS)-A supplement (100×), DMEM/F-12, antibiotic/antimycotic (100×), and fetal calf serum (FCS) are purchased from Gibco (Grand Island, N.Y.). Anti-mouse PVT scintillation proximity assay (SPA) beads and NBS 96-well plates are obtained from Amersham (Piscataway, N.J.) and Corning (Acton, Mass.), respectively. Solid black 96-well flat bottom plates are purchased from Costar (Corning, N.Y.). Aldosterone and angiotensin (Ang II) are purchased from Sigma (St. Louis, Mo.). D-[1,2,6,7-$^3$H(N)]aldosterone was acquired from PerkinElmer (Boston, Mass.). Nu-serum was a product of BD Biosciences (Franklin Lakes, N.J.). The NADPH regenerating system, dibenzylfluorescein (DBF), and human aromatase Supersomes® are obtained from Gentest (Woburn, Mass.).

For in vitro measurement of aldosterone activity, human adrenocortical carcinoma NCI-H295R cells are seeded in NBS 96-well plates at a density of 25,000 cells/well in 100 μl of a growth medium containing DMEM/F12 supplemented with 10% FCS, 2.5% Nu-serum, 1 μg ITS/ml, and 1× antibiotic/antimycotic. The medium is changed after culturing for 3 days at 37° C. under an atmosphere of 5% $CO_2$/95% air. On the following day, cells are rinsed with 100 μl of DMEM/F12 and incubated with 100 μl of treatment medium containing 1

μM Ang II and a compound at different concentrations in quadruplicate wells at 37° C. for 24 hr. At the end of incubation, 50 μl of medium is withdrawn from each well for measurement of aldosterone production by an RIA using mouse anti-aldosterone monoclonal antibodies.

Measurement of aldosterone activity can also be performed using a 96-well plate format. Each test sample is incubated with 0.02 μCi of D-[1,2,6,7-$^3$H(N)]aldosterone and 0.3 μg of anti-aldosterone antibody in phosphate-buffered saline (PBS) containing 0.1% Triton X-100, 0.1% bovine serum albumin, and 12% glycerol in a total volume of 200 μl at room temperature for 1 hr. Anti-mouse PVT SPA beads (50 μl) are then added to each well and incubated overnight at room temperature prior to counting in a Microbeta plate counter. The amount of aldosterone in each sample is calculated by comparing with a standard curve generated using known quantities of the hormone.

To measure aromatase activity, the human aromatase assay is performed in 96-well flat bottom plates according to a published protocol (Stresser et al, 2000) with minor modifications. Briefly, 10 μl of an NADPH regenerating system containing 2.6 mM NADP$^+$, 6.6 mM glucose 6-phosphate, 6.6 mM MgCl$_2$, and 0.8 U/ml glucose-6-phosphate dehydrogenase in 50 mM potassium phosphate, pH 7.4, is pre-incubated with the test compound at a desired concentration at 30° C. for 10 min in a total volume of 100 μl. Afterwards, 4 pmol of human aromatase, 20 μg of control microsomal protein, and 4 μM DBF in 100 μl of 50 mM potassium phosphate, pH 7.4, is added to each well and incubated at 30° C. for 90 min. The reaction is terminated by the addition of 75 μl of 2 N NaOH to each well. After 2 hr, the product, fluorescein, is measured by a fluorimeter using excitation and emission wavelengths of 485 and 538 nm, respectively.

Full concentration-response curves of the test compound are performed at least 3 times. The IC$_{50}$ values are derived using a non-linear least squares curve-fitting program from Microsoft XLfit.

The in vivo inhibitory activities for aldosterone synthase and aromatase can be determined by the following assays.

Test compounds (i.e., potential aldosterone synthase inhibitors) are profiled in vivo in a conscious rat model of acute secondary hyperaldosteronism. Wild-type rats are instrumented with chronically indwelling arterial and venous cannulas, which are exteriorized through a tether/swivel system. The ambulatory rats are housed in specialized cages to allow blood sampling and parenteral drug, administration without disturbing the animals. Angiotensin II is continuously infused intravenously at a level sufficient to elevate plasma aldosterone concentration (PAC) by ~200-fold to 1-5 nM. This PAC increase is sustained at a stable level for at least 8-9 hours. Test compounds are administered p.o. (via oral gavage) or parenterally (via the arterial catheter) after one hour of angiotensin II infusion at a time when PAC has increased to a steady-state level. Arterial blood samples are collected before and at various times (up to 24 hours) after test agent administration for later determination of PAC and concentration of test agent. From these measurements, various parameters can be derived, e.g., 1) onset and duration of PAC reduction by the test agent 2) pharmacokinetic parameters of the test agent such as half-life, clearance, volume of distribution, and oral bioavailability, 3) dose/PAC response, dose/test-agent concentration, and test-agent concentration/PAC response relationships, and 4) dose and concentration potencies and efficacy of the test agent. A successful test compound decreases PAC in a dose- and time-dependent fashion in the dose range of about 0.01 to about 10 mg/kg i.a. or p.o.

TABLE 1

Inhibitory Activities of the Compounds

| Compound | cellular aldosterone IC$_{50}$ (nM) | % inhibition of aromatase @ 10000 nM |
|---|---|---|
| 4-(6,7-dihydro-5H-pyrrolo[1,2-c]imidazol-5-yl)-3-methylbenzonitrile, enantiomer A | >1000 | 96 |
| 4-(6,7-dihydro-5H-pyrrolo[1,2-c]imidazol-5-yl)-3-methylbenzonitrile, enantiomer B | 7 | 96 |
| 5-(2-chloro-4-cyanophenyl)-6,7-dihydro-5H-pyrrolo[1,2-c]imidazole-5-carboxylic acid (4-methoxybenzyl)methylamide, enantiomer A | >>1000 | 98 |
| 5-(2-chloro-4-cyanophenyl)-6,7-dihydro-5H-pyrrolo[1,2-c]imidazole-5-carboxylic acid (4-methoxybenzyl)methylamide, enantiomer B | 8 | 97 |
| 4'-fluoro-6-(6,7,8,9-tetrahydro-5H-imidazo[1,5-a]azepin-5-yl)biphenyl-3-carbonitrile, enantiomer A | 2 | 97 |
| 4'-fluoro-6-(6,7,8,9-tetrahydro-5H-imidazo[1,5-a]azepin-5-yl)biphenyl-3-carbonitrile, enantiomer B | 50 | 70 |
| 5-(4-Cyano-2-methoxyphenyl)-6,7-dihydro-5H-pyrrolo[1,2-c]imidazole-5-carboxylic acid butyl ester | 6 | 100 |
| 5-(2-Chloro-4-cyanophenyl)-6,7-dihydro-5H-pyrrolo[1,2-c]imidazole-5-carboxylic acid methyl ester | 45 | 96 |
| 5-(4-Cyano-2-methoxyphenyl)-6,7-dihydro-5H-pyrrolo[1,2-c]imidazole-5-carboxylic acid (4-fluorobenzyl)methylamide | 57 | 85 |
| 5-(4-Cyano-2,5-dimethoxyphenyl)-6,7-dihydro-5H-pyrrolo[1,2-c]imidazole-5-carboxylic acid methyl ester | 113 | 98 |
| 3-Chloro-4-[5-(morpholino-4-carbonyl)-6,7-dihydro-5H-pyrrolo[1,2-c]imidazol-5-yl]benzonitrile | 357 | |
| 4-(6,7-Dihydro-5H-pyrrolo[1,2-c]imidazol-5-yl)-3-methoxybenzonitrile | 18 | 100 |
| 3-Amino-4-(6,7-dihydro-5H-pyrrolo[1,2-c]imidazol-5-yl)benzonitrile | 90 | 100 |
| 5-(4-Cyano-2-trifluoromethylphenyl)-6,7-dihydro-5H-pyrrolo[1,2-c]imidazole-5-carboxylic acid methyl ester | 244 | |
| 5-(3-fluoro-4-methoxyphenyl)-6,7-dihydro-5H-pyrrolo[1,2-c]imidazole | 159 | 100 |
| 5-(2-Chloro-4-cyanophenyl)-6,7-dihydro-5H-pyrrolo[1,2-c]imidazole-5-carboxylic acid 4-fluorobenzyl ester, enantiomer A | >>1000 | 91 |
| 5-(2-Chloro-4-cyanophenyl)-6,7-dihydro-5H-pyrrolo[1,2-c]imidazole-5-carboxylic acid 4-fluorobenzyl ester, enantiomer B | 2 | 98 |
| 3-Chloro-4-[5-(piperidine-1-carbonyl)-6,7-dihydro-5H-pyrrolo[1,2-c]imidazol-5-yl]-benzonitrile | 135 | 98 |
| 5-(4-Cyano-2-trifluoromethoxyphenyl)-6,7-dihydro-5H-pyrrolo[1,2-c]imidazole-5-carboxylic acid methyl ester | 2 | 99 |
| 5-(4-Cyano-2-methoxyphenyl)-6,7-dihydro-5H-pyrrolo[1,2-c]imidazole-5-carboxylic acid 2-isopropoxyethyl ester | 5 | 96 |
| 4-(6,7-Dihydro-5H-pyrrolo[1,2-c]imidazol-5-yl)-3-vinylbenzonitrile | 31 | 95 |
| 4-(6,7-Dihydro-5H-pyrrolo[1,2-c]imidazol-5-yl)-2-methylbenzonitrile | 3 | 95 |
| 4-(6,7-Dihydro-5H-pyrrolo[1,2-c]imidazol-5-yl)-2-methoxybenzonitrile | 5 | 97 |
| 4-(6,7-Dihydro-5H-pyrrolo[1,2-c]imidazol-5-yl)-2-vinylbenzonitrile | 8 | 100 |
| 3-Fluoro-4-(7-methylene-6,7-dihydro-5H-pyrrolo[1,2-c]imidazol-5-yl)benzonitrile | 4 | 95 |
| 5'-[2-fluoro-4-cyano-phenyl]-5',6'-dihydrospiro[cyclopropane-1,7'-pyrrolo[1,2-c]imidazole] | 11 | 99 |
| 5-(5-Fluorobiphenyl-2-yl)-5,6,7,8-tetrahydroimidazo[1,5-a]pyridine | 57 | 98 |

TABLE 1-continued

Inhibitory Activities of the Compounds

| Compound | cellular aldosterone IC$_{50}$ (nM) | % inhibition of aromatase @ 10000 nM |
|---|---|---|
| 5-(4-Fluoro-2-thiophen-3-yl-phenyl)-5,6,7,8-tetrahydroimidazo[1,5-a]pyridine | 93 | 88 |
| 6-(5-Methyl-5,6,7,8-tetrahydroimidazo[1,5-a]pyridin-5-yl)biphenyl-3-carbonitrile | 270 | |
| 3-Methoxy-4-(5,6,7,8-tetrahydro-imidazo[1,5-a]pyridin-5-yl)benzonitrile | 270 | 100 |
| cis-3-Fluoro-4-[7-(4-fluoro-benzyl)-5,6,7,8-tetrahydro-imidazo[1,5-a]pyridin-5-yl]benzonitrile | 7 | 100 |
| trans-3-Methoxy-4-[7-(4-fluorobenzyl)-5,6,7,8-tetrahydroimidazo[1,5-a]pyridin-5-yl]benzonitrile | 83 | 100 |
| 4'-Fluoro-6-(9-methyl-6,7,8,9-tetrahydro-5H-imidazo[1,5-a]azepin-5-yl)biphenyl-3-carbonitrile | 2 | 91 |
| 5-(2-Bromo-4-fluorophenyl)-6,7,8,9-tetrahydro-5H-imidazo[1,5-a]azepine | 65 | 92 |
| 4'-Fluoro-6-(9-methyl-6,7,8,9-tetrahydro-5H-imidazo[1,5-a]azepin-5-yl)biphenyl-3-carbonitrile, isomer A | 4 | 98 |
| 4'-Fluoro-6-(9-methyl-6,7,8,9-tetrahydro-5H-imidazo[1,5-a]azepin-5-yl)biphenyl-3-carbonitrile, isomer B | 207 | |
| 4'-Fluoro-6-(9-methyl-6,7,8,9-tetrahydro-5H-imidazo[1,5-a]azepin-5-yl)biphenyl-3-carbonitrile, isomer C | 16 | 81 |
| 4'-Fluoro-6-(9-methyl-6,7,8,9-tetrahydro-5H-imidazo[1,5-a]azepin-5-yl)biphenyl-3-carbonitrile, isomer D | 727 | |
| 2-Bromo-4-(6,7,8,9-tetrahydro-5H-imidazo[1,5-a]azepin-5-yl)benzonitrile | 23 | 100 |
| 3-Pyridin-3-yl-4-(6,7,8,9-tetrahydro-5H-imidazo[1,5-a]azepin-5-yl)benzonitrile | 35 | 97 |
| 4-(5-Allyl-6,7,8,9-tetrahydro-5H-imidazo[1,5-a]azepin-5-yl)-3-bromobenzonitrile | 32 | 97 |
| 3-Chloro-(5-ethyl-6,7,8,9-tetrahydro-5H-imidazo[1,5-a]azepin-5-yl)benzonitrile | 217 | 91 |
| 3-(3,5-Dimethylisoxazol-4-yl)-4-(6,7,8,9-tetrahydro-5H-imidazo[1,5-a]azepin-5-yl)benzonitrile | 40 | 59 |
| 3-Chloro-4-(6,7,8,9-tetrahydro-5H-imidazo[1,5-a]azepin-5-yl)benzonitrile | 48 | 100 |
| 3'-Methylene-2',3',6,7,8,9-hexahydrospiro[imidazo[1,5-a]azepine-5,1'-indene]-5'-carbonitrile | 11 | 100 |

ABBREVIATIONS

DCM: dichloromethane
DIBAL: dIisobutylaiuminum hydride
DMAP: N,N-dimethylaminopyridine
DME: dimethoxyethane
DMF: N,N-dimethylformamide
DMSO: dimethylsulfoxide
ESI: electrospray ionization
h: hours
HPLC: high pressure liquid chromatography
HRMS: high resolution mass spectrometry
IPA: iso-propyl alcohol
IR: infrared spectroscopy
KHMDS: Potassium hexamethyldisilazide
LAH: lithium aluminum hydride
LCMS: liquid chromatography/mass spectrometry
LDA: lithium diisoprovlamide
LHMDS: lithium hexamethyldisilazide
min: minutes
MS: mass spectrometry
NBS: N-bromosuccinimide
NMR: nuclear magnetic resonance
PS-PPh$_3$-Pd(0): polymer supported palladium triphenylphosphine complex
TBSCl: tert-butyldimethylsilyl chloride
TFA: trifluoroacetic acid
THF: tetrahydrofuran
TMEDA: tetramethylethylenediamine
TBS: tert-butyl dimethylsilyl
TMSCl: trimethylsilyl chloride
TLC: thin layer chromatography
Tr: trityl
t$_r$: retention time
TMEDA: tetramethylethylene diamine

EXAMPLES

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art. The compounds in the following examples have been found to have IC$_{50}$ values in the range of about 0.1 nM to about 10,000 nM for both aldosterone synthase and aromatase.

Example 1

Benzyl Bromides

A. 4-Bromomethyl-3-chlorobenzonitrile (cas #21924-83-4)

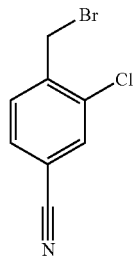

3-Chloro-4-methylbenzonitrile (2.34 g, 15.4 mmol), NBS (3.0 g, 16.9 mmol) and benzoyl peroxide (0.37 g, 1.54 mmol) are taken up in carbon tetrachloride (50 mL, 0.3M) and refluxed until the reaction is judged complete by TLC. The mixture is then allowed to cool to room temperature and is filtered. The filtrate is concentrated and purified via flash column chromatography (0-5% EtOAc/hexanes) to give 4-bromomethyl-3-chlorobenzonitrile as a white solid. HRMS (ESI) m/z 229.9133 (229.9193 calcd for C$_8$H$_6$ClBrN, M+H).

Similarly prepared are the following compounds from the corresponding toluenes:
4-Bromomethyl-3-fluorobenzonitrile (cas #105942-09-4)
4-Bromomethyl-2-bromobenzonitrile (cas #89892-38-6)
4-Bromomethyl-3-methoxybenzonitrile (cas #104436-60-4)

4-Bromomethyl-3-nitrobenzonitrile (cas #223512-70-7)
3-Bromo-4-bromomethylbenzoic acid methyl ester (cas #78946-25-5)

B. 4-Bromomethyl-3-trifluoromethylbenzonitrile

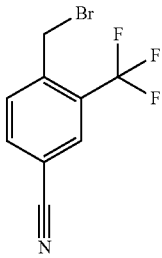 [SMILES: N#Cc1ccc(CBr)c(C(F)(F)F)c1]

4-Methyl-3-trifluoromethylbenzonitrile is brominated with NBS according to Example 1A to give 4-bromomethyl-3-trifluoromethylbenzonitrile. $^1$H NMR (400 MHz, CDCl$_3$) δ (ppm) 7.94 (s, 1H), 7.85 (d, J=8.1 Hz, 1H), 7.76 (d, J=8.1 Hz, 1H), 4.63 (s, 2H).

C. 4-Bromomethyl-3-trifluoromethoxybenzonitrile

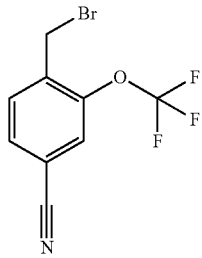 [SMILES: N#Cc1ccc(CBr)c(OC(F)(F)F)c1]

To a mixture of CuBr$_2$ (25.5 g, 114 mmol) in CH$_3$CN (500 mL) at 0° C. is added t-butyl nitrite (17.7 mL, 148 mmol). Then 4-amino-3-trifluoromethoxybenzonitrile (20.0 g, 99.0 mmol) is added in 4 portions over a 10 min period. The mixture is allowed to warm to room temperature and stir overnight. The solvent is removed and the residue is partitioned between Et$_2$O and 1M HCl. The aqueous phase is further extracted with Et$_2$O and the combined organic layers are dried (Na$_2$SO$_4$) and concentrated. Solid residue is then triturated with hexanes to give 4-Bromo-3-trifluoromethoxybenzonitrile as a yellow crystalline solid. $^1$H NMR, (400 MHz, CDCl$_3$) δ (ppm) 7.47 (dd, J=8.0, 2.0 Hz, 1H), 7.59 (m, 1H), 7.80 (d, J=8.0 Hz, 1H).

A mixture of 4-bromo-3-trifluoromethoxybenzonitrile (10.0 g, 37.6 mmol), K$_2$CO$_3$ (15.6 g, 113 mmol), trimethylboroxine (5.5 mL, 39.5 mmol) and DMF (150 mL) is degassed for 10 min with nitrogen before Pd(PPh$_3$)$_4$ (4.34 g, 3.76 mmol) is added. The mixture is then sealed and heated to 120° C. for 14 h. The mixture is then concentrated and then partitioned between Et$_2$O and 50% brine solution. The aqueous phase is further extracted with Et$_2$O and the combined organic layers are dried (Na$_2$SO$_4$) and concentrated. The residue is purified via flash chromatography (10% EtOAc/hexanes) to give 4-methyl-3-trifluoromethoxybenzonitrile. $^1$H NMR (400 MHz, CDCl$_3$) δ (ppm) 2.40 (s, 3H), 7.40 (d, J=7.7 Hz, 1H), 7.50 (s, 1H), 7.51 (dd, J=7.7, 1.5 Hz, 1H). MS (ESI) m/z 202.1.

4-Methyl-3-Trifluoromethoxybenzonitrile is brominated with NBS according to Example 1A to give 4-bromomethyl-3-trifluoromethoxybenzonitrile. $^1$H NMR (400 MHz, CDCl$_3$) δ (ppm) 4.51 (s, 2H), 7.55 (br s, 1H), 7.59 (d, J=8.0 Hz, 1H), 7.64 (d, J=8.0 Hz, 1H).

D. 4-Bromomethyl-2,5-dimethoxybenzonitrile

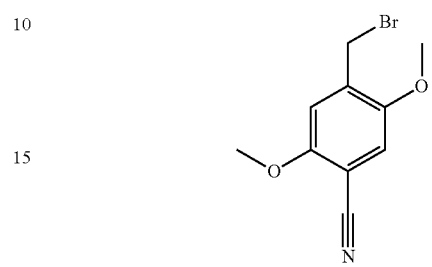

By analogy to steps outlined in J. Med. Chem. 1976, 19(12), 1400-1404. 2,5-dimethoxy-4-methylbenzaldehyde (14.8 g, 82.2 mmol) is dissolved in pyridine (300 mL) and to it, is added hydroxylamine hydrochloride (6.8 g, 98.6 mmol). The suspension is heated at 105° C. for 2 h. Acetic anhydride (15.5 mL, 164 mmol) is then added to the reaction and stirring is continued for another 2 h. The solution is evaporated to dryness and partitioned between EtOAc and saturated aqueous NaHCO$_3$. The organic fraction is dried (Na$_2$SO$_4$) and evaporated to give a yellow solid which is taken up in hexanes and filtered to give 2,5-dimethoxy-4-methylbenzonitrile as a white solid. (cas #51267-09-5) MS (ESI) m/z 178.2 (M+H).

2,5-Dimethoxy-4-methylbenzonitrile (4.06 g, 21.5 mmol) is brominates with NBS according to Example 1A to give 4-bromomethyl-2,5-dimethoxybenzonitrile. $^1$H NMR (400 MHz, CDCl$_3$) δ (ppm) 6.95 (s, 1H), 6.91 (s, 1H), 4.43 (s, 2H), 3.84 (s, 3H), 3.80 (s, 3H).

Similarly prepared is the following:

4-Bromomethyl-3-bromobenzonitrile (cas #89892-39-7). $^1$H NMR (400 MHz, CDCl$_3$) δ (ppm) 7.87 (d, 1H, J=1.2 Hz), 7.60 (dd, 1H, J=7.6, 1.2 Hz), 7.57 (d, 1H, J=7.6 Hz), 4.58 (s, 2H).

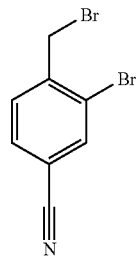 [SMILES: N#Cc1ccc(CBr)c(Br)c1]

D. 2-Bromomethyl-4'-fluorobiphenyl (cas #791078-01-8)

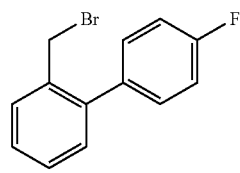 [SMILES: Fc1ccc(-c2ccccc2CBr)cc1]

To a mixture of 4-fluorophenylboronic acid (2.5 g, 13.4 mmol), 2-bromobenzyl alcohol (2.131 g, 20.1 mmol) and Pd(PPh$_3$)$_4$ (0.25 g, 0.216 mmol) in DME (20 mL) is added an aqueous solution of Na$_2$CO$_3$ (11.5 mL, 2.7 M, 31 mmol). The mixture is heated to 115° C. in sealed vessel overnight. The reaction is allowed to cool to room temperature and is diluted with EtOAc and water. The aqueous layer is extracted further with EtOAc (2×). The combined organic layers are washed with water, saturated NH$_4$Cl, brine and dried over Na$_2$SO$_4$. After concentration, the resulting residue is purified by flash chromatography (hexane/CH$_2$Cl$_2$) to give (4'-fluorobiphenyl-2-yl)-methanol as oil. (cas #773871-75-3) $^1$H NMR (400 MHz, CDCl$_3$) δ (ppm) 7.46-7.43 (m, 1H), 7.32-7.22 (m, 4H), 7.18-7.16 (m, 1H), 7.04-6.99 (m, 2H), 4.48 (d, J=5.5 Hz, 2H), 1.68 (br s, 1H).

To a solution of (4'-fluorobiphenyl-2-yl)-methanol (2.58 g, 12.8 mmol) in CH$_2$Cl$_2$ (100 mL), carbon tetrabromide (7.40 g, 22.3 mmol) is added. The solution is cooled to 0° C. and then triphenylphosphine (7.53 g, 28.7 mmol) is added portionwise. The reaction is stirred at 0° C. for 1.5 h and then at room temperature for 90 h before the solvent is removed. The resulting residue is partitioned between Et$_2$O and water and then filtered. The layers are separated and the aqueous layer is extracted with Et$_2$O. The combined organic layers are washed with water, brine and dried over Na$_2$SO$_4$. After concentration, the residue is purified by flash chromatography (hexane) to give 2-bromomethyl-4'-fluorobiphenyl as an oil. (an alternative preparation appears in *J. Med. Chem.* 2004, 47(22), 5441) $^1$H NMR (400 MHz, CDCl$_3$) δ 7.53-7.50 (m, 1H), 7.43-7.31 (m, 4H), 7.24-7.21 (m, 1H), 7.15-6.80 (m, 2H), 4.42 (s, 2H).

E. Bromo-(3-fluoro-4-methoxyphenyl)acetic acid methyl ester

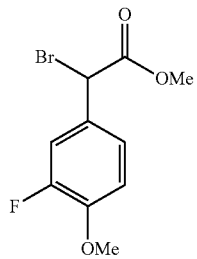 [SMILES: COC(=O)C(Br)c1ccc(OC)c(F)c1]

(3-Fluoro-4-methoxyphenyl)acetic acid (5.0 g, 27.1 mmol) is dissolved in MeOH (100 mL). To it is added concentrated H$_2$SO$_4$ (5 mL) and the solution it warmed to reflux for 2 h. At that point, the solution is evaporated to dryness and taken up in EtOAc. The solution is washed with saturated aqueous NaHCO$_3$, dried (Na$_2$SO$_4$) and evaporated to give (3-fluoro-4-methoxyphenyl)acetic acid methyl ester (cas#588-14-7) as a yellow oil. MS (ESI) m/z 199.3 (M+H).

The (3-fluoro-4-methoxyphenyl)acetic acid methyl ester (5.16 g, 26.0 mmol) is dissolved in carbon tetrachloride (300 mL) along with NBS (5.56 g, 31.3 mmol) and benzoyl peroxide (0.63 g, 2.60 mmol) and refluxed for 2 h. The solution is then allowed to cool to room temperature and is filtered. The filtrate is evaporated and the residue purified via flash column chromatography (EtOAc/hexanes 5:95→EtOAc/hexanes 2:8) to give bromo-(3-fluoro-4-methoxyphenyl)acetic acid methyl ester as a yellow oil. $^1$H NMR (CDCl$_3$) δ 7.37 (d, J=12 Hz, 1H), 7.26-7.23 (m, 1H), 6.93 (t, J=8 Hz, 1H), 5.31 (s, 1H), 3.91 (s, 3H), 3.81 s, 3H).

Example 2

Substituted Imidazole Intermediates

A. 1-Trityl-4-carboxaldehyde-1H-imidazole (cas #33016-47.6)

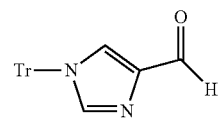

According to procedure outlined in *J. Med. Chem.* 2002, 45(1), 177, to imidazole-4-carboxaldehyde (15.0 g, 156.2 mmol) in DMF (300 mL) is added triethylamine (43.8 ml, 312 mmol) followed by trityl chloride (44.4 g, 159.0 mmol). The reaction mixture is stirred at ambient temperature for 18 h before the solvent is removed in vacuo. The resulting solid is dissolved in dichloromethane and washed with sodium bicarbonate and water. The organic phase is concentrated in vacuo to give the desired material as a solid.

B. 1-(1-Trityl-1H-imidazol-4-yl)ethanol (cas #62256-50-2)

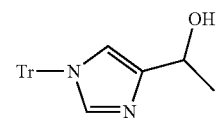

To 1-trityl-4-carboxaldehyde-1H-imidazole (11.7 g, 34.6 mmol) in THF (250 ml) at 0° C. is added methylmagnesium bromide (12.6 mL, 38 mmol, 3.0 M in diethyl ether). The reaction mixture is stirred at 15° C. for 4 h before quenching with water (10 mL), followed by aqueous ammonium chloride. The reaction is extracted into ethyl acetate and washed with 30 mL of saturated aqueous sodium bicarbonate. The organic solvent is removed in vacuo. Chromatography (silica gel, ethyl acetate:hexanes, 1:1 to 1:0) yields the desired product. MS (ESI) m/z 355 (M+H). (prepared similarly in *J. Med. Chem.* 1977, 20(5), 721)

C. 1-(1-Trityl-1H-imidazol-4-yl)ethanone (cas #116796-56-2)

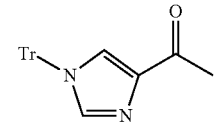

To 1-(1-trityl-1H-imidazol-4-yl)ethanol (8.06 g, 22.7 mmol) in dioxane (400 mL) is added manganese dioxide (9.9 g, 113.8 mmol). The reaction mixture is heated to 90° C. and stirred for 18 h. The reaction is allowed to cool to room temperature and filtered through diatomaceous earth. The

D. (1-Trityl-1H-imidazol-4-yl)acetic acid (cas #168632-03-9)

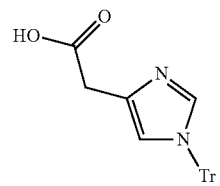

Trityl chloride (51 g, 0.18 mol) is added to a suspension of (1H-imidazol-4-yl)acetic acid hydrochloride (25 g, 0.15 mol) in pyridine (500 mL). This is stirred at room temperature for 16 h, at the end of which MeOH (150 mL) is added. This solution is stirred at room temperature for 1 h. Solvents are evaporated and the residue is taken up in $CH_2Cl_2$ and washed with 1 M aqueous citric acid solution (2×) and brine. The organic phase is dried over anhydrous $Na_2SO_4$ and evaporated to give a sticky residue which when taken up in diethyl ether and evaporated gave the product as a white solid that is used without further purification. MS (ESI) m/z 368.9 (M+H) (Procedure adapted from *J. Org. Chem.* 1993, 58, 4606, also prepared in WO2003013526)

E. 2-(1-Trityl-1H-imidazol-4-yl)ethanol (cas #12760742-9)

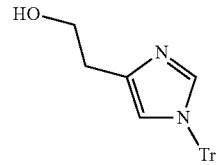

(1-Trityl-1H-imidazol-4-yl)acetic acid (65 g, 0.17 mol) is suspended in THF (400 mL) and cooled to 0° C. To this is added $BH_3$.THF solution (350 mL, 1.0 M). The clear solution obtained is stirred at 0° C. for 30 min before warming to room temperature until LCMS indicated completion of the reaction. The solution is cooled again to 0° C. and quenched carefully with water (250 mL). The resulting solution is diluted with EtOAc (300 mL) and transferred to a separatory funnel and the aqueous layer is extracted with EtOAc. The organic phase is dried over anhydrous $Na_2SO_4$ and evaporated to give a sticky residue which is taken up in ethanolamine (800 mL) and heated to 90° C. for 2 h. The reaction is transferred to a separatory funnel, diluted with EtOAc (1 L) and washed with water (3×600 mL). The organic phase is dried over anhydrous $Na_2SO_4$ and evaporated to give 2-(1-trityl-1H-imidazol-4-yl)-ethanol as a white solid that is used as is without further purification. MS (ESI) m/z 354.8 (M+H) (prepared by alternate method in *J. Med. Chem.* 1996, 39(19), 3806)

F. 4-[2-(tert-Butyldimethylsilanyloxy)ethyl]-1-trityl-1H-imidazole

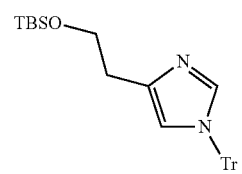

2-(1-Trityl-1H-imidazol-4-yl)ethanol (20 g, 56.5 mmol) is dissolved in $CH_2Cl_2$ (500 mL). To this is added imidazole (11.5 g, 169 mmol) and tert-butyldimethylsilylchloride (10.2 g, 67.8 mmol). The solution is stirred at room temperature until LCMS indicated the reaction is complete. The solution is partitioned between $CH_2Cl_2$ and aqueous saturated $NaHCO_3$. The organic layer is washed further with aqueous saturated $NaHCO_3$ and brine.

The organic phase is dried over anhydrous $Na_2SO_4$ and evaporated to give an oil that is purified via flash column chromatography (EtOAc/hexanes 3:7) to give 3-[2-(tert-butyldimethylsilanyloxy)ethyl]-1-trityl-1H-imidazole as a white solid. MS (ESI) m/z 469.3 (M+H).

G. Methyl 4-[(1-Trityl-1H-imidazol-4-yl)]propanoic acid ester (cas#102676-60-8)

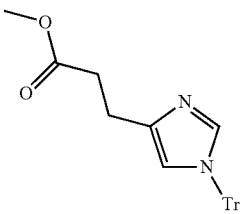

To a white suspension of 3-(1H-imidazole-411)propionic acid (5 g, 35.7 mmol) in MeOH (140 mL) is added dropwise HCl/Dioxane (4M, 29 mL, 116 mmol). The resulting clear solution is slowly warmed up to ambient temperature and stirred overnight. The reaction mixture is concentrated in vacuo and dried on a high vacuum pump to give an oil.

To a solution of 3-(1H-imidazol-4-yl)propionic acid methyl ester hydrochloride (6.8 g, 35.7 mmol) in $CH_3CN$ (160 mL) is added trityl chloride (11.0 g, 39.5 mmol) in portion at 0° C. and followed by triethylamine (40 mL). The white suspension mixture is stirred at ambient temperature overnight. The solvent is evaporated and the residue is suspended in 200 mL $H_2O$-ice and stirred for 1 h. The solid is collected and dried under a high vacuum pump to give a white solid. (prepared in *J. Med. Chem.* 1996, 39(6), 1220.)

H. (1-Trityl-1H-imidazol-4-yl)acetic acid methyl ester (cas#145133-11-5)

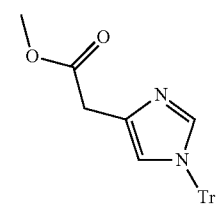

Prepared from the corresponding acid according to the procedure G above. (prepared in U.S. Pat. No. 5,140,034)

--- filtered solvent is removed in vacuo to yield the product. MS (ESI) m/z 353 (M+H) (prepared similarly in *Bioorg. Med. Chem.* 2004, 12(9), 2251.)

I. 4-[3-(tert-Butyldimethylsilanyloxy)propyl]-1-trityl-1H-imidazole

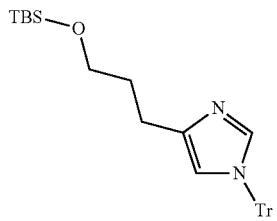

To a suspension of LAH (1.0 g, 26.4 mmol) in THF (80 mL) at 0° C. is added 3-(1-trityl-1H-imidazol-4-yl)propanoic acid methyl ester (6.76 g, 17.1 mmol) in portion. Then the resulting mixture is stirred at ambient temperature overnight. The reaction is quenched with water, 15% sodium hydroxide, and water, then diluted with methylene chloride and filtered. The precipitate on the fitter is washed with methylene chloride. The filtrate is evaporated to dryness to give the crude compound.

To a solution of the above crude compound (7.46 g, 20.3 mmol) in DMF (60 mL) at ambient temperature is added imidazole (2.07 g, 30.4 mmol), tert-butyldimethylsilyl chloride (3.5 g, 23.2 mmol) and followed by DMAP (70 mg). The mixture is stirred at ambient temperature overnight. The mixture is partitioned between EtOAc and brine. The organic layer is washed with brine, dried over $Na_2SO_4$ and concentrated to give the desired compound.

J. 3-(1-Trityl-1H-imidazol-4-yl)butyric acid ethyl ester (cas#698367-52-1)

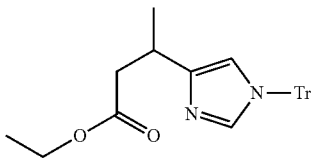

The title ester is prepared according to the strategy outlined in *Bioorg. Med. Chem.* 2004, 12(9), 2273. To a suspension of NaH (60% dispersion in mineral oil, 1.7 g, 42.5 mmol) in THF (10 mL) at ambient temperature is added drop wise triethylphosphonoacetate (8.53 mL, 42.6 mmol). To this mixture is slowly added a solution of 1-(1-trityl-1H-imidazol-4-yl)ethanone (10 g, 28.4 mmol) in THF (100 mL). The resulting mixture is heated at reflux for 3 h. The reaction mixture is poured onto ice and extracted with EtOAc. The organic layer is washed by brine, dried over anhydrous $Na_2SO_4$ and concentrated to give the crude solid.

To a degassed solution of 3-(1-trityl-1H-imidazol-4-yl)but-2-enoic acid ethyl ester (5 g, 11.8 mmol) in ethanol (100 mL) in a Parr bottle is added 5% palladium on carbon (0.5 g). The bottle is purged with nitrogen, evacuated, and hydrogen gas (15 psi) added. The bottle is placed upon a Parr hydrogenation apparatus and shaken for 18 h. The hydrogen is evacuated and the bottle purged with nitrogen gas. The reaction mixture is then filtered through diatomaceous earth and the clear liquid solution collected and the solvent removed in vacuo to give the crude oil, which is subject to flash chromatography (silica gel) eluting with $MeOH:CH_2Cl_2$ to yield the desired compound.

K. 2,2-Dimethyl-2-(1-trityl-1H-imidazol-4-yl)-propionic acid methyl ester

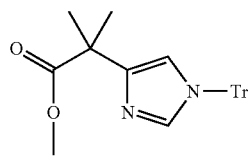

To a solution of (1-trityl-1H-imidazol-4-yl)acetic acid methyl ester (10 g, 26.2 mmol) in THF (150 mL) at 0° C. is added NaH powder (60% dispersion in mineral oil, 3.15 g, 78.8 mmol). The suspension is stirred at 0° C. for 0.5 h then is added $CH_3I$ (4 mL, 64.1 mmol). The resulting mixture is warmed up to ambient temperature and stirred overnight. To the suspension mixture is added Florisil (2.5 g), and the solid is removed by filtration through a Celite pad. The filtrate is concentrated and the residue is partitioned between EtOAc and brine, and the organic layer is washed by brine, dried over anhydrous $Na_2SO_4$ and concentrated to give the crude oil, which is subject to flash chromatography (silica gel) eluting with $MeOH:CH_2Cl_2$ to yield the desired compound.

L. 2,2-Dimethyl-2-(1-trityl-1H-imidazol-4-yl)propionaldehyde (cas#64464-49-9)

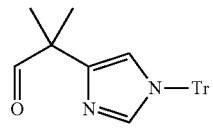

To a solution of 2,2-dimethyl-2-(1-trityl-1H-imidazol-4-yl)propionic acid methyl ester (4.2 g, 10.2 mmol) in THF (40 mL) at 0° C. is added LAH (600 mg, 15.8 mmol). The resulting suspension is stirred at 0° C. for 2 h. The reaction is quenched with water, 15% sodium hydroxide; and water, then diluted with methylene chloride and filtered. The precipitate on the filter is washed with methylene chloride. The filtrate is evaporated to dryness to give the crude compound.

To a solution of the above crude compound (3.83 g, 10.0 mmol) in $CH_2Cl_2$ (50 mL) at ambient temperature is added Dess-Martin periodinane in portion. The resulting clear solution is stirred at ambient temperature for 2 h. The reaction is quenched with 1 N aqueous $Na_2S_2O_3$, saturated aqueous $NaHCO_3$, and extracted with $CH_2Cl_2$. The organic layer is washed by brine, dried over anhydrous $Na_2SO_4$ and concentrated to give the crude oil, which is subject to flash chromatography (silica gel) eluting with $MeOH:CH_2Cl_2$ to yield the desired compound. (prepared by an alternate method in *Bioorg. Med. Chem.* 2004, 12(9), 2251.)

M. 3,3-Dimethyl-3-(1-trityl-1H-imidazol-4-yl)butan-1-ol

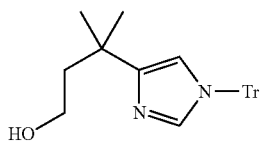

To a suspension of methoxymethyl triphenylphosphonium chloride (11.0 g, 32.1 mmol) in THF (15 mL) at ambient temperature is added t-BuOK/THE (1.0 M, 30 mL, 30 mmol). The resulting mixture is stirred at ambient temperature about 10 min then is added a solution of 2,2-dimethyl-2-(1-trityl-1H-imidazol-4-yl)propionaldehyde (3.6 g, 9.5 mmol) in THF (70 mL). The mixture is stirred at ambient temperature overnight. The reaction is quenched by sat. NH$_4$Cl, and the mixture is partitioned between EtOAc and brine. The organic layer is washed by brine, dried and concentrated to give an oil, which is subjected to flash chromatography (silica gel) eluting with MeOH:CH$_2$Cl$_2$ to yield the desired compound.

To the above compound (1.04 g, 2.55 mmol) in 10% H$_2$O-THF (22 mL) at ambient temperature is added TsOH resin. The mixture is stirred at ambient temperature for 2 h. The reaction mixture is filtered off the resin and washed with CH$_2$Cl$_2$. The organic layer is neutralized and washed with brine, dried and concentrated to give the crude compound.

To the above crude compound in THF (10 mL) at 0° C. is added LAH (150 mg, 3.95 mmol) and the mixture is stirred at 0° C. for 3.0 min. The reaction is quenched with water, 15% sodium hydroxide, and water, then diluted with methylene chloride and filtered. The precipitate on the filter is washed with methylene chloride. The filtrate is evaporated to dryness to give an oil, which is subject to flash chromatography (silica gel) eluting with MeOH:CH$_2$Cl$_2$ to yield the desired compound.

N. 4-[3-(tert-Butyldimethylsilanyloxy)-1,1-dimethyl-propyl]-1-trityl-1H-imidazole

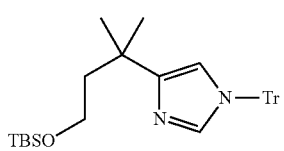

To a solution of 3,3-dimethyl-3-(1-trityl-1H-imidazol-4-yl)butan-1-ol (0.87 g, 2.2 mmol) in CH$_2$Cl$_2$ (10 mL) at ambient temperature is added imidazole (200 mg, 2.94 mmol), tert-butyldimethylsilyl chloride (350 mg, 2.32 mmol). The mixture is stirred at ambient temperature overnight. The mixture is partitioned between EtOAc and brine. The organic layer is washed with brine, dried over Na$_2$SO$_4$ and concentrated to give an oil, which is subject to flash chromatography (silica gel) eluting with MeOH:CH$_2$Cl$_2$ to yield the desired compound.

O. (E and Z)-4-[4-tert-Butyl-dimethyl-silanyloxy)-but-1-enyl]-1-trityl-1H-imidazole

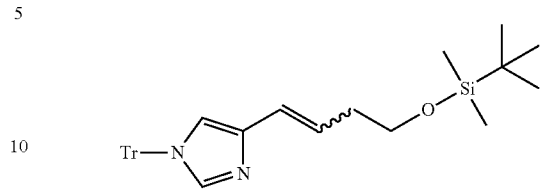

To 3-(tert-butyldimethylsilanyloxy)propyl-1-bromide is converted to the triphenyl phosphonium salt according to literature precedent (*Tetrahedron Letters* 1997, 38(20), 3647-3650). To the bromide (25 g, 95 mmol) in toluene (200 mL) is added triphenylphosphine (40 g, 158 mmol). The reaction mixture is stirred at 105° C. for 18 h. The mixture is then allowed to cool to room temperature over the course of an hour. The white solid is filtered off, washed with hexane (50 mL), then washed with ethyl acetate, and dried under vacuum for 24 h.

To [3-(tert-butyldimethylsilanyloxy)propyl]triphenylphosphonium bromide (35.5 g, 68.9 mmol) is added anhydrous THF (300 mL) via cannula. This suspension is cooled to –78° C. and n-butyllithium in hexanes (2.5 M, 30 mL, 75 mmol) is added via syringe. The mixture is allowed to stir for 20 minutes at –78° C. before a solution of 1-trityl-4-carboxaldehyde-1H-imidazole (20.0 g, 59.1 mmol) in THF (30.0 mL) is added via cannula. The mixture is allowed to warm to room temperature over 30 minutes, then stirred an additional 3.5 h at room temperature. The reaction is quenched by the addition of methanol (20 mL) followed by aqueous saturated ammonium chloride. The reaction mixture is then partitioned between ethyl acetate and saturated aqueous sodium bicarbonate. The organic layer in concentrated in vacuo to yield crude product. Chromatography purification (silica gel, ethyl acetate:hexanes 0:1 to 3:2) yields the product as a white solid, a mixture of cis and trans isomers. MS (ESI) m/z 495 (M+H)

P. (E and Z)-4-[4-tert-Butyldimethylsilanyloxy)-1-methyl-but-1-enyl]-1-trityl-1H-imidazole

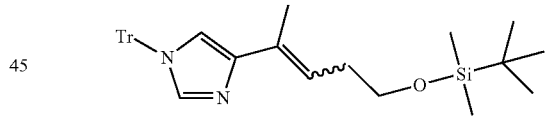

The title compound is prepared from Example 2C in a similar manner to preparation O above. MS (ESI) m/z 509 (M+H)

Q. 4-[4-(tert-Butyldimethylsilanyloxy)butyl]-1-trityl-1H-imidazole

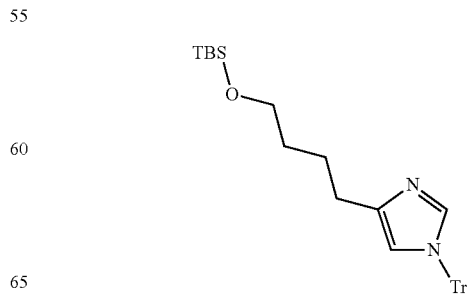

To a mixture of E- and Z-4-[4-tert-butyldimethylsilanyloxy)but-1-enyl]-1-trityl-1H-imidazole (7.4 g, 14.9 mmol) in degassed ethanol in a Parr bottle is added 5% palladium on carbon (0.1 g). The bottle is purged with nitrogen, evacuated, and hydrogen gas (30 psi) added. The bottle is placed upon a Parr hydrogenation apparatus and shaken for 18 hours. The hydrogen is evacuated and the bottle purged with nitrogen gas. The reaction mixture is then filtered through diatomaceous earth and the clear liquid solution collected and the solvent removed in vacuo to give the product as a white solid. MS (ESI) m/z 497 (M+H)

R. 4-[4-(tert-Butyldimethylsilanyloxy)-1-methylbutyl]-1-trityl-1H-imidazole

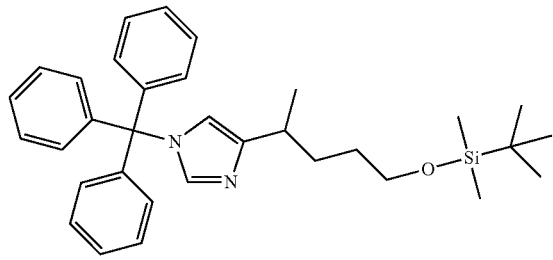 [SMILES: CC(CCCO[Si](C)(C)C(C)(C)C)c1cn(C(c2ccccc2)(c2ccccc2)c2ccccc2)cn1]

The title compound is prepared from a mixture of E- and Z-4-[4-tert-butyldimethylsilanyloxy)-1-methylbut-1-enyl]-1-trityl-1H-imidazole in a similar manner to preparation Q above. MS (ESI) m/z 511 (M+H)

Example 3

A. 4-{5-[2-tert-Butyldimethylsilanyloxy)ethyl]imidazol-1-ylmethyl}-3-chlorobenzonitrile

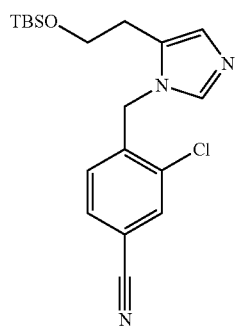 [SMILES: CC(C)(C)[Si](C)(C)OCCc1cncn1Cc1ccc(C#N)cc1Cl]

4-[2-(tert-Butyldimethylsilanyloxy)ethyl]-1-trityl-1H-imidazole (3.98 g, 8.5 mmol) and 4-bromomethyl-3-chlorobenzonitrile (2.93 g, 12.7 mmol) are dissolved in MeCN (40 mL) and heated at 80° C. for 5 h. After cooling to room temperature MeOH (40 mL) and Et$_2$NH (7 mL) are then added and the solution is warmed 70° C. for 1 h. The solution is evaporated to dryness and the residue purified via flash column chromatography (acetone/CH$_2$Cl$_2$ 1:3→MeOH/CH$_2$Cl$_2$ 5:95) to give 4-{5-[2-tert-butyl-dimethylsilanyloxy)ethyl]-imidazol-1-ylmethyl}-3-chlorobenzonitrile as an oil. MS (ESI) m/z 376.3, 378.3 (M+H).

B. {5-[2-Tert-butyldimethylsilanyloxy)ethyl]imidazol-1-yl}-(2-chloro-4-cyanophenyl)acetic acid methyl ester

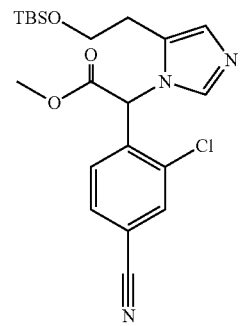 [SMILES: COC(=O)C(c1ccc(C#N)cc1Cl)n1cncc1CCO[Si](C)(C)C(C)(C)C]

4-{5-[2-tert-Butyldimethylsilanyloxy)ethyl]imidazol-1-ylmethyl}-3-chlorobenzonitrile (1.7 g, 4.52 mmol) is dissolved in anhydrous THF (30 mL) and stirred at −78° C. before a THF solution of LHMDS (8.1 mL, 1.0 M) is added. After 15 min, methyl cyanoformate (0.38 mL, 4.74 mmol) is added and the solution is left at −78° C. for 2 h. The excess LHMDS is quenched with aqueous saturated NH$_4$Cl and the mixture is allowed to warm to room temperature. The mixture is then diluted with EtOAc and washed with aqueous saturated NH$_4$Cl (2×). Organic is dried (Na$_2$SO$_4$) and evaporated. The crude residue is purified via flash column chromatography (EtOAc/hexanes 1:1→EtOAc) to give {5-[2-tert-butyldimethylsilanyloxy)ethyl]-imidazol-1-yl}-(2-chloro-4-cyanophenyl)acetic acid methyl ester as an oil. MS (ESI) m/z 434.3, 436.3 (M+H).

C. 5-(2-Chloro-4-cyanophenyl)-6,7-dihydro-5H-pyrrolo[1,2-c]imidazole-5-carboxylic acid methyl ester

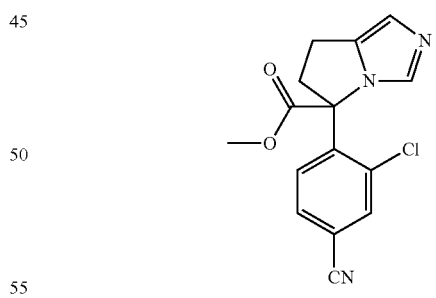

{5-[2-tert-Butyldimethylsilanyloxy)ethyl]-imidazol-1-0}-(2-chloro-4-cyanophenyl)-acetic acid methyl ester (2.8 g, 6.46 mmol) in THF (25 mL) is cooled to 0° C. before a solution of HCl in 1,4-dioxane (10 mL, 4.0 M, 40 mmol) is added. After completion of the reaction as judged by LCMS, the solution is partitioned between EtOAc and aqueous saturated NaHCO$_3$. The organic layer is dried (Na$_2$SO$_4$) and evaporated to give the crude alcohol, (2-chloro-4-cyanophenyl)-[5-(2-hydroxyethyl)imidazol-1-yl]-acetic acid methyl ester that is used without further purification. MS (ESI) m/z 320.1, 322.1 (M+H).

The crude (2-chloro-4-cyanophenyl)-[5-(2-hydroxyethyl) imidazol-1-yl]acetic acid methyl ester (2.06 g, 6.46 mmol) is dissolved in CH$_2$Cl$_2$ (25 mL) and stirred at 0° C. before Et$_3$N (1.4 mL, 9.69 mmol) and methanesulfonyl chloride (0.6 mL, 7.75 mmol) are added. After completion of the reaction, the solution is partitioned between CH$_2$Cl$_2$ and aqueous saturated NaHCO$_3$. The organic layer is dried (Na$_2$SO$_4$) and evaporated to give the crude (2-chloro-4-cyanophenyl)-[5-(2-methanesulfonyloxyethyl)imidazol-1-yl]-acetic acid methyl ester that is used without further purification. MS (ESI) m/z 398.2, 400.2 (M+H).

The crude (2-chloro-4-cyanophenyl)-[5-(2-methanesulfonyloxyethyl)imidazol-1-yl]-acetic acid methyl ester (2.56 g, 6.45 mmol) is dissolved in dry DMF (50 mL) and to it is added K$_2$CO$_3$ (2.67 g, 19.4 mmol), NaI (2.9 g, 19.4 mmol) and Et$_3$N (2.7 mL, 19.4 mmol). The reaction is stirred at 80° C. for 2 h before being concentrated to dryness. The residue is then diluted with EtOAc and washed with water. The organic layer is dried (Na$_2$SO$_4$) and evaporated to give a crude residue that is purified via flash column chromatography (Acetone/ CH$_2$Cl$_2$ 1:3) to give 5-(2-chloro-4-cyanophenyl)-6,7-hydro-5H-pyrrolo[1,2-c]imidazole-5-carboxylic acid methyl ester as an oil. MS (ESI) m/z 302.2, 304.2 (M+H). $^1$H NMR (400 MHz, CDCl$_3$) δ ppm 2.64-2.76 (m, 2H), 2.97-3.06 (m, 1H), 3.84 (s, 3H), 3.86-3.93 (m, 1H), 6.56 (d, J=8.1 Hz, 1H), 6.87 (s, 1H), 7.50 (obs d, J=8.1 Hz, 1H), 7.52 (s, 1H), 7.73 (s, 1H).

D. 5-(2-chloro-4-cyanophenyl)-6,7-dihydro-5H-pyrrolo[1,2-c]imidazole-5-carboxylic acid

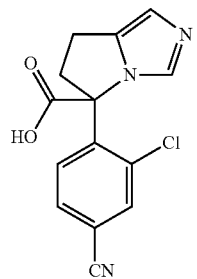 [SMILES: N#Cc1ccc(C2(C(=O)O)CCc3cncn32)c(Cl)c1]

5-(2-chloro-4-cyanophenyl)-6,7-dihydro-5H-pyrrolo[1,2-c]imidazole-5-carboxylic acid methyl ester (0.6 g, 2.0 mmol) is dissolved in THF/water 3:2 (20 mL) and to it, is added LiOH (0.17 g, 4.0 mmol). The mixture is stirred at room temperature for 2 h before being neutralized to pH 6 with 1M HCl. The solution is evaporated to dryness to give acid, 5-(2-chloro-4-cyanophenyl)-6,7-dihydro-5H-pyrrolo[1,2-c]imidazole-5-carboxylic acid as a solid. MS (ESI) m/z 288.2, 290.2 (M+H); $^1$H NMR (400 MHz, MeOD) (ammonium salt) δ ppm 2.64-2.74 (m, 1H), 2.77-2.86 (m, 1H), 2.94-3.02 (m, 1H), 3.74 (ddd, J=13.1, 9.1, 8.0 Hz, 1H), 6.74 (d, J=8.1 Hz, 1H), 6.85 (s, 1H), 7.59 (dd, J=8.1, 1.5 Hz, 1H), 7.84 (d, J=1.8 Hz, 1H), 7.91 (s, 1H).

E. 3-Chloro-4-(6,7-hydro-5H-pyrrolo[1,2-c]imidazol-5-yl)-benzonitrile

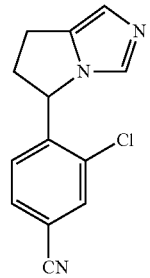 [SMILES: N#Cc1ccc(C2CCc3cncn32)c(Cl)c1]

The 5-(2-chloro-4-cyanophenyl)-6,7-dihydro-5H-pyrrolo[1,2-c]imidazole-5-carboxylic acid (0.02 g, 70 µmol) is dissolved in DMSO (2 mL) and Et$_3$N (0.2 mL) and heated at 100° C. for 2 h. The solution is evaporated to dryness and residue purified via reverse phase HPLC (5-100% MeCN/water w/0.1% TFA) to give 3-chloro-4-(6,7-dihydro-5H-pyrrolo[1,2-c]imidazol-5-yl)-benzonitrile as a white solid. MS (ESI) m/z 244.2, 246.2 (M+H); $^1$H NMR (400 MHz, CDCl$_3$) (TFA salt) δ ppm 2.60-2.73 (m, 1H), 3.08-3.20 (m, 2H), 3.22-3.36 (m, 1H), 6.04 (dd, J=7.6, 5.8 Hz, 1H), 6.91 (d, J=8.1 Hz, 1H), 7.24 (s, 1H), 7.61 (d, J=8.1 Hz, H), 7.81 (d, J=1.5 Hz, 1H), 8.53 (s, 1H).

Similarly prepared are the following compounds (Table 2):

TABLE 2

| Compounds of Formula (II) | |
|---|---|
| Structure | Compound Name and Analytical Data |
| (structure shown) | 5-(4-Cyano-2-methoxyphenyl)-6,7-dihydro-5H-pyrrolo[1,2-d]imidazole-5-carboxylic acid butyl ester. $^1$H NMR (400 MHz, CDCl$_3$) δ ppm 0.88 (t, J = 7.33 Hz, 3 H), 1.21-1.30 (m, 2 H), 1.53-1.61 (m, 2 H), 2.60 (ddd, J = 13.0, 8.4, 3.4, 1 H), 2.66-2.74 (m, 1 H), 2.92-3.00 (m, 1 H), 3.68 (ddd, J = 13.1, 9.1, 8.4 Hz, 1 H), 3.88 (s, 3 H), 4.17 (app t, J = 6.7 Hz, 2 H), 6.59 (d, J = 8.1 Hz, 1 H), 6.81 (s, 1 H), 7.14 (d, J = 1.5 Hz, 1 H), 7.21 (dd, J = 8.1, 1.5 Hz, 1 H), 7.52 (s, 1 H); MS (ESI) m/z 340 (M + H). |

TABLE 2-continued

Compounds of Formula (II)

| Structure | Compound Name and Analytical Data |
|---|---|
| 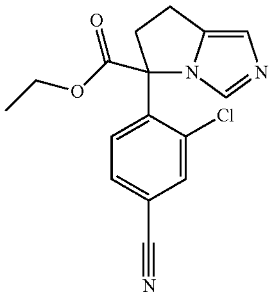 [SMILES: CCOC(=O)C1(c2ccc(C#N)cc2Cl)CCc2cncn21] | 5-(2-Chloro-4-cyanophenyl)-6,7-dihydro-5H-pyrrolo[1,2-c]imidazole-5-carboxylic acid ethyl ester. $^1$H NMR (400 MHz, CDCl$_3$) δ ppm 1.26 (t, J = 7.2 Hz, 3 H), 2.62-2.74 (m, 2 H), 2.96-3.04 (m, 1 H), 3.82-3.91 (m, 1 H), 4.24-4.35 (m, 2 H), 6.55 (d, J = 8.3 Hz, 1 H), 6.86 (s, 1 H), 7.48 (dd, J = 8.2, 1.6 Hz, 1 H), 7.53 (s, 1 H), 7.71 (d, J = 1.8 Hz, 1 H); MS (ESI) m/z 316, 318 (M + H). |
| 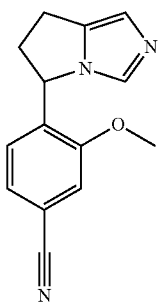 [SMILES: COc1cc(C#N)ccc1C1CCc2cncn21] | 4-(6,7-Dihydro-5H-pyrrolo[1,2-c]imidazol-5-yl)-3-methoxybenzonitrile. $^1$H NMR (400 MHz, CDCl$_3$) δ ppm 2.34-2.45 (m, 1 H), 2.77-2.93 (m, 2 H), 3.02-3.14 (m, 1 H), 3.93 (s, 3 H), 5.68 (dd, J = 8.1, 4.0 Hz, 1 H), 6.65 (d, J = 7.8 Hz, 1 H), 6.82 (s, 1 H), 7.15 (s, 1 H), 7.19 (d, J = 7.8 Hz, 1 H), 7.35 (s, 1 H); MS (ESI) m/z 240 (M + H). |
| 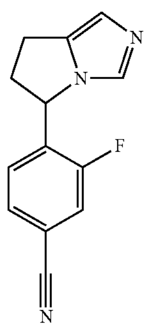 [SMILES: N#Cc1ccc(C2CCc3cncn32)c(F)c1] | 4-(6,7-Dihydro-5H-pyrrolo[1,2-c]imidazol-5-yl)-3-fluorobenzonitrile. $^1$H NMR (400 MHz, CDCl$_3$) δ ppm 2.45-2.55 (m, 1 H), 2.84-2.98 (m, 2 H), 3.10-3.23 (m, 1 H), 5.67 (dd, J = 8.1, 4.3 Hz, 1 H), 6.78-6.84 (m, 1 H), 6.84 (s, 1 H), 7.36 (s, 1 H), 7.38-7.45 (m, 2 H); MS (ESI) m/z 228 (M + H). |
| 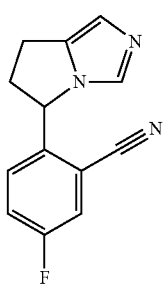 [SMILES: N#Cc1cc(F)ccc1C1CCc2cncn21] | 2-(6,7-Dihydro-5H-pyrrolo[1,2-c]imidazol-5-yl)-5-fluorobenzonitrile. $^1$H NMR (400 MHz, CDCl$_3$) δ ppm 2.45-2.55 (m, 1 H), 2.94 (app t, J = 7.2 Hz, 2 H), 3.19-3.30 (m, 1 H), 5.73 (dd, J = 7.8, 4.8 Hz, 1 H), 6.82-6.90 (m, 2 H), 7.23-7.31 (m, 1 H), 7.37 (s, 1 H), 7.44 (dd, J = 7.7, 2.7 Hz, 1 H); MS (ESI) m/z 228 (M + H). |
| 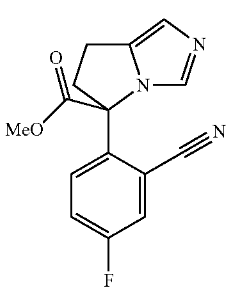 [SMILES: COC(=O)C1(c2ccc(F)cc2C#N)CCc2cncn21] | 5-(2-Cyano-4-fluorophenyl)-6,7-dihydro-5H-pyrrolo[1,2-c]imidazole-5-carboxylic acid methyl ester $^1$H NMR (400 MHz, CDCl$_3$) δ ppm 2.70-2.85 (m, 2 H), 2.99-3.09 (m, 1 H), 3.80-3.88 (m, 1 H), 3.90 (s, 3 H), 6.70 (dd, J = 9.0, 4.9 Hz, 1 H), 6.86 (s, 1 H), 7.20-7.26 (m, 1 H), 7.47 (dd, J = 7.6, 2.8 Hz, 1 H), 7.53 (s, 1 H); MS (ESI) m/z 286 (M + H). |

TABLE 2-continued

Compounds of Formula (II)

| Structure | Compound Name and Analytical Data |
| --- | --- |
| 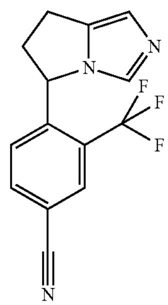 [SMILES: N#Cc1ccc(C2CCc3cncn32)c(C(F)(F)F)c1] | 4-(6,7-Dihydro-5H-pyrrolo[1,2-c]imidazol-5-yl)-3-trifluoromethylbenzonitrile. $^1$H NMR (400 MHz, CDCl$_3$) δ ppm 2.41-2.51 (m, 1 H), 2.96 (app t, J = 7.2 Hz, 2 H), 3.16-3.27 (m, 1 H), 5.76 (dd, J = 7.8, 4.8 Hz, 1 H), 6.87 (br s, 1 H), 6.94 (d, J = 8.1 Hz, 1 H), 7.30 (br s, 1 H), 7.78 (d, J = 8.3 Hz, 1 H), 8.02 (s, 1 H); MS (ESI) m/z 278 (M + H). |
| 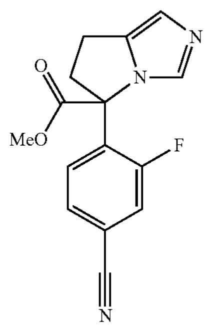 [SMILES: COC(=O)C1(c2ccc(C#N)cc2F)CCc2cncn21] | 5-(4-Cyano-2-fluorophenyl)-6,7-dihydro-5H-pyrrolo[1,2-c]imidazole-5-carboxylic acid methyl ester. $^1$H NMR (400 MHz, CDCl$_3$) δ ppm 2.63-2.79 (m, 2 H), 2.92-3.03 (m, 1 H), 3.61-3.73 (m, 1 H), 3.81 (s, 3 H), 6.72 (app t, J = 8.0 Hz, 1 H), 6.80 (s, 1 H), 7.36-7.43 (m, 2 H), 7.53 (s, 1 H); MS (ESI) m/z 286 (M + H). |
| 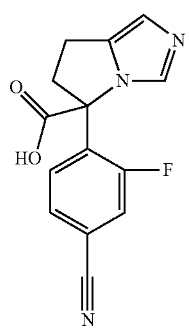 [SMILES: N#Cc1ccc(C2(C(=O)O)CCc3cncn32)c(F)c1] | 5-(4-Cyano-2-fluorophenyl)-6,7-dihydro-5H-pyrrolo[1,2-c]imidazole-5-carboxylic acid. $^1$H NMR (400 MHz, MeOD) (TFA salt) δ ppm 3.19 (m, J = 7.2 Hz, 2 H), 3.25-3.34 (obs m, 1 H), 3.39-3.49 (m, 1 H), 7.31 (s, 1 H), 7.63-7.76 (m, 3 H), 8.95 (s, 1 H); MS (ESI) m/z 272 (M + H)$^+$. |
| 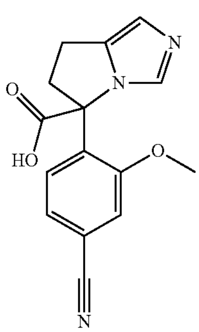 [SMILES: COc1cc(C#N)ccc1C1(C(=O)O)CCc2cncn21] | 5-(4-Cyano-2-methoxyphenyl)-6,7-dihydro-5H-pyrrolo[1,2-c]imidazole-5-carboxylic acid. $^1$H NMR (400 MHz, CD$_3$CN) δ ppm 2.93-3.05 (m, 2 H), 3.06-3.15 (m, 1 H), 3.18-3.26 (m, 1 H), 3.78 (s, 3 H), 7.00 (s, 1 H), 7.30 (dd, J = 8.0, 1.4 Hz, 1 H), 7.34 (s, 1 H), 7.41 (d, J = 8.1 Hz, 1 H), 8.44 (s, 1 H); MS (ESI) m/z 284 (M + H). |

TABLE 2-continued

Compounds of Formula (II)

| Structure | Compound Name and Analytical Data |
|---|---|
| 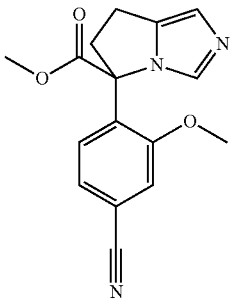 | 5-(4-Cyano-2-methoxyphenyl)-6,7-dihydro-5H-pyrrolo[1,2-c]imidazole-5-carboxylic acid methyl ester. $^1$H NMR (400 MHz, CDCl$_3$) δ ppm 2.55-2.65 (m, 1 H), 2.66-2.76 (m, 1 H), 2.92-3.02 (m, 1 H), 3.63-3.74 (m, 1 H), 3.77 (s, 3 H), 3.90 (s, 3 H), 6.60 (d, J = 8.1 Hz, 1 H), 6.81 (s, 1 H), 7.16 (d, J = 1.3 Hz, 1 H), 7.21 (dd, J = 8.1, 1.5 Hz, 1 H), 7.51 (s, 1 H); MS (ESI) m/z 298 (M + H). |
| 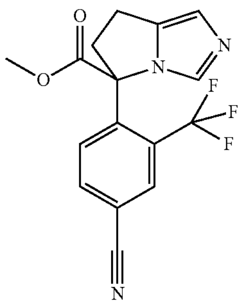 [SMILES: COC(=O)C1(c2ccc(C#N)cc2C(F)(F)F)CCc2cncn21] | 5-(4-Cyano-2-trifluoromethylphenyl)-6,7-dihydro-5H-pyrrolo[1,2-c]imidazole-5-carboxylic acid methyl ester. $^1$H NMR (400 MHz, CDCl$_3$) δ ppm 2.61-2.80 (m, 2 H), 2.92-3.09 (m, 1 H), 3.82 (s, 3 H), 3.84-3.98 (m, 1 H), 6.59 (d, J = 8.6 Hz, 1 H), 6.88 (s, 1 H), 7.45 (s, 1 H), 7.73 (d, J = 8.3 Hz, 1 H), 8.03 (s, 1 H); MS (ESI) m/z 336 (M + H). |
| 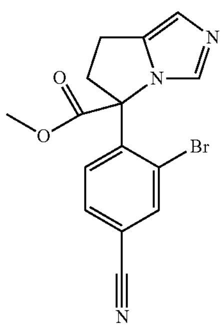 [SMILES: COC(=O)C1(c2ccc(C#N)cc2Br)CCc2cncn21] | 5-(2-Bromo-4-cyanophenyl)-6,7-dihydro-5H-pyrrolo[1,2-c]imidazole-5-carboxylic acid methyl ester. $^1$H NMR (400 MHz, CDCl$_3$) δ ppm 2.62-2.82 (m, 2 H), 3.01 (dd, J = 15.2, 8.3 Hz, 1 H), 3.84 (s, 3 H), 3.86-3.97 (m, 1 H), 6.51 (d, J = 8.1 Hz, 1 H), 6.86 (s, 1 H), 7.50 (s, 1 H), 7.54 (d, J = 8.3 Hz, 1 H), 7.91 (s, 1 H); MS (ESI) m/z 346, 348 (M + H). |
| 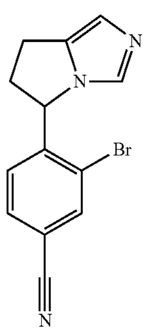 [SMILES: N#Cc1ccc(C2CCc3cncn32)c(Br)c1] | 3-Bromo-4-(6,7-dihydro-5H-pyrrolo[1,2-c]imidazol-5-yl)benzonitrile. $^1$H NMR (400 MHz, CDCl$_3$) δ d ppm 2.39-2.51 (m, 1 H), 2.77-2.98 (m, 2 H), 3.15-3.29 (m, 1 H), 5.71 (dd, J = 8.3, 3.8 Hz, 1 H), 6.62 (d, J = 8.1 Hz, 1 H), 6.86 (s, 1 H), 7.38 (s, 1 H), 7.52 (dd, J = 8.1, 1.5 Hz, 1 H), 7.91 (s, 1 H); MS (ESI) m/z 288, 290 (M + H). |
| 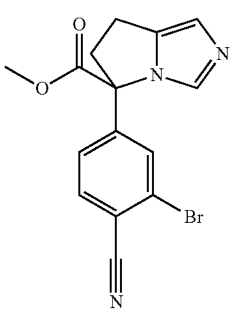 [SMILES: COC(=O)C1(c2ccc(C#N)c(Br)c2)CCc2cncn21] | 5-(3-Bromo-4-cyanophenyl)-6,7-dihydro-5H-pyrrolo[1,2-c]imidazole-5-carboxylic acid methyl ester. $^1$H NMR (400 MHz, CD$_3$CN) (TFA salt) δ ppm 2.87-2.99 (m, 1 H), 2.99-3.10 (m, 2 H), 3.39-3.50 (m, 1 H), 3.85 (s, 3 H), 7.23 (s, 1 H), 7.33 (dd, J = 8.3, 2.0 Hz, 1 H), 7.63 (d, J = 1.8 Hz, 1 H), 7.81 (d, J = 8.3 Hz, 1 H), 8.70 (s, 1 H); MS (ESI) m/z 346, 348 (M + H). |

TABLE 2-continued

Compounds of Formula (II)

| Structure | Compound Name and Analytical Data |
|---|---|
| 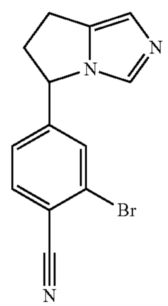 [SMILES: N#Cc1ccc(C2CCc3cncn32)cc1Br] | 2-Bromo-4-(6,7-dihydro-5H-pyrrolo[1,2-c]imidazol-5-yl)benzonitrile. $^1$H NMR (400 MHz, CD$_3$CN) δ ppm 2.40-2.51 (m, 1 H), 2.78-2.94 (m, 2 H), 3.03-3.15 (m, 1 H), 5.44 (dd, J = 8.0, 4.9 Hz, 1 H), 6.67 (s, 1 H), 7.19 (dd, J = 8.1, 1.8 Hz, 1 H), 7.26 (s, 1 H), 7.48 (d, J = 1.8 Hz, 1 H), 7.74 (d, J = 8.1 Hz, 1 H); MS (ESI) m/z 288, 290 (M + H). |
| 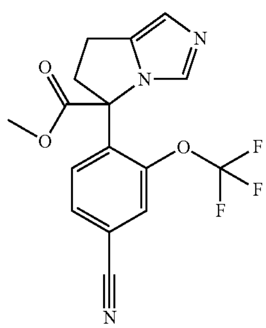 [SMILES: COC(=O)C1(c2ccc(C#N)cc2OC(F)(F)F)CCc2cncn21] | 5-(4-Cyano-2-trifluoromethoxyphenyl)-6,7-dihydro-5H-pyrrolo[1,2-c]imidazole-5-carboxylic acid methyl ester. $^1$H NMR (400 MHz, CDCl$_3$) δ ppm 2.54-2.64 (m, 1 H), 2.69-2.81 (m, 1 H), 2.95-3.08 (m, 1 H), 3.74-3.81 (m, 1 H), 3.83 (s, 3 H), 6.72 (d, J = 8.1 Hz, 1 H), 6.86 (s, 1 H), 7.51 (dd, J = 8.2, 1.4 Hz, 1 H), 7.53 (s, 1 H), 7.56-7.62 (m, 1 H); MS (ESI) m/z 352 (M + H). |
| 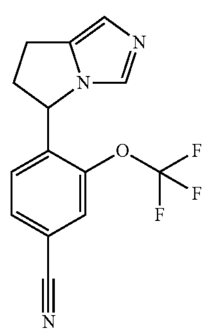 [SMILES: N#Cc1ccc(C2CCc3cncn32)c(OC(F)(F)F)c1] | 4-(6,7-Dihydro-5H-pyrrolo[1,2-c]imidazol-5-yl)-3-trifluoromethoxy benzonitrile. $^1$H NMR (400 MHz, CDCl$_3$) δ ppm 2.40-2.50 (m, 1 H), 2.83-3.00 (m, 2 H), 3.11-3.24 (m, 1 H), 5.69 (dd, J = 8.1, 4.5 Hz, 1 H), 6.86 (d, J = 8.0 Hz, 1 H), 6.85 (s, 1 H), 7.32 (s, 1 H), 7.54 (dd, J = 8.1, 1.3 Hz, 1 H), 7.58-7.63 (m, 1 H); MS (ESI) m/z 294 (M + H). |
| 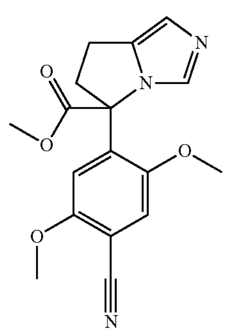 | 5-(4-Cyano-2,5-dimethoxyphenyl)-6,7-dihydro-5H-pyrrolo[1,2-c]imidazole-5-carboxylic acid methyl ester. $^1$H NMR (400 MHz, CDCl$_3$) δ ppm 2.55-2.63 (m, 1 H), 2.68-2.77 (m, 1 H), 2.98 (ddd, J = 15.5, 8.7, 3.0 Hz, 1 H), 3.69 (s, 4H), 3.77 (s, 3 H), 3.82 (s, 3 H), 5.29 (s, 1 H), 6.07 (s, 1 H), 6.82 (s, 1 H), 7.06 (s, 1 H), 7.55 (s, 1 H); MS (ESI) m/z 328 (M + H). |

F. Chiral Resolution of Selected Compounds of Formula II Given as Example 3

1) (R) and (S)-3-Chloro-4-(6,7-dihydro-5H-pyrrolo[1,2-c]imidazol-5-yl)benzonitrile Resolution of the enantiomers of the title compound is achieved by chiral HPLC using ChiralPak IA column with a 70% EtOAc:hexane mobile phase to give enantiomer A ($t_r$=22.4 min) and enantiomer B ($t_r$=41.9 min).

2) (R) and (S)-5-(2-Chloro-4-cyanophenyl)-6,7-dihydro-5H-pyrrolo[1,2-c]imidazole-5-carboxylic acid methyl ester Resolution of the enantiomers of the title compound is achieved by chiral HPLC using ChiralPak AS column with a 15% IPA:hexane mobile phase to give enantiomer A ($t_r$=51.8 min) and enantiomer B ($t_r$=63.2 min).

3) (R) and (S)-4-(6,7-Dihydro-5H-pyrrolo[1,2-c]imidazol-5-yl)-3-methoxybenzonitrile Resolution of the enantiomers of the title compound is achieved by chiral HPLC using ChiralPak AS-H column with a 1% EtOH:MeCN mobile phase to give enantiomer A ($t_r$=16.7 min) and enantiomer B ($t_r$=25.7 min).

4) (R) and (S)-5-(4-Cyano-2-methoxyphenyl)-6,7-dihydro-5H-pyrrolo[1,2-c]imidazole-5-carboxylic acid methyl ester Resolution of the enantiomers of the title compound is achieved by chiral HPLC using ChiralPak AD column with a 30% IPA:hexane mobile phase to give enantiomer A ($t_r$=31.6 min) and enantiomer B ($t_r$=41.7 min).

5) (R) and (S)-4-(6,7-Dihydro-5H-pyrrolo[1,2-c]imidazol-5-yl)-3-fluorobenzonitrile Resolution of the enantiomers of the title compound is achieved by chiral HPLC using ChiralPak AS-H column with a MeCN mobile phase to give enantiomer A ($t_r$=16.7 min) and enantiomer B ($t_r$=22.5 min).

6) (R) and (S)-5-(4-Cyano-2-fluorophenyl)-6,7-dihydro-5H-pyrrolo[1,2-c]imidazole-5-carboxylic acid methyl ester Resolution of the enantiomers of the title compound is achieved by chiral HPLC using ChiralPak AS column with a 20% IPA:hexane mobile phase to give enantiomer A ($t_r$=61.4 min) and enantiomer B ($t_r$=73.8 min).

7) (R) and (S)-3-Bromo-4-(6,7-dihydro-5H-pyrrolo[1,2-c]imidazol-5-yl)benzonitrile Resolution of the enantiomers of the title compound is achieved by chiral HPLC using ChiralPak AS-H column with a 25% IPA:hexane mobile phase to give enantiomer A ($t_r$=44.0 min) and enantiomer B ($t_r$=66.0 min).

8) (R) and (S)-4-(6,7-Dihydro-5H-pyrrolo[1,2-c]imidazol-5-yl)-3-trifluoromethoxybenzonitrile Resolution of the enantiomers of the title compound is achieved by chiral HPLC using ChiralPak AS-H column with a 10% IPA:heptane mobile phase to give enantiomer A ($t_r$=53.4 min) and enantiomer B ($t_r$=59.4 min).

Example 4

A. 4-(6,7-Dihydro-5H-pyrrolo[1,2-c]imidazol-5-yl)-3-methylbenzonitrile

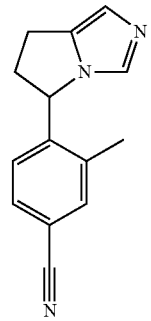

To a solution of 3-bromo-4-(6,7-dihydro-5H-pyrrolo[1,2-c]imidazol-5-yl)benzonitrile (0.100 g, 0.347 mmol) given in Example 3 (table 2) and trimethylboroxine (0.145 g, 1.04 mmol) in DME (3 mL); aqueous solutions of $Na_2CO_3$ (0.69 mL, 2 M) and KOH (0.17 mL, 2 M) are added. After degassing with nitrogen, $Pd(PPh_3)_4$ (0.040 g, 0.035 mmol) is added. The mixture is heated in a microwave reactor at 130° C. 1.5 h. At that point LCMS showed consumption of the starting material. The solution is diluted with ethyl acetate and saturated sodium bicarbonate. The resulting aqueous layer is extracted further with ethyl acetate (3×). The combined organic layers are washed with brine and dried over anhydrous sodium sulfate. After concentration the crude product is filtered through 0.45 μm filter and then purified by preparative HPLC (0% for 5 minutes and 0-34% acetonitrile with 0.1% TFA in 17 minutes). MS (ESI) m/z 224.0 (M+H); $^1$H NMR (400 MHz, $CDCl_3$) δ ppm 2.33-2.42 (m, 1H), 2.43 (s, 3H), 2.84-2.95 (m, 2H), 3.07-3.18 (m, 1H), 5.54 (dd, J=8.1, 4.8 Hz, 1H), 6.65 (d, J=8.1 Hz, 1H), 6.83 (s, 1H), 7.32 (s, 1H), 7.41 (d, J=8.1 Hz, 1H), 7.50 (s, 1H). Resolution of the (R) and (S) enantiomers of the title compound is achieved by chiral HPLC using ChiralPak AS-H column and 9:1 hexane/EtOH to give enantiomer A ($t_r$=84 min) and enantiomer B=104 min).

Similarity prepared are the following:

1) 4-(6,7-Dihydro-5H-pyrrolo[1,2-c]imidazol-5-yl)-3-vinylbenzonitrile. MS (ESI) m/z 236.2 (M+H); $^1$H NMR (400 MHz, $CDCl_3$) δ ppm 2.36-2.51 (m, 1H), 2.83-2.96 (m, 2H), 3.05-3.18 (m, 1H), 5.57 (d, J=11.6 Hz, 1H), 5.63 (dd, J=8.1, 4.5 Hz, 1H), 5.77 (d, J=17.2 Hz, 1H), 6.69 (d, J=8.1 Hz, 1H), 6.85 (s, 1H), 6.90 (dd, J=17.2, 11.1 Hz, 1H), 7.34 (s, 1H), 7.48 (dd, J=8.1, 1.5 Hz, 1H), 7.78 (d, J=1.5 Hz, 1H). Resolution of the (R) and (S) enantiomers of the title compound is achieved by chiral HPLC using ChiralPak AS-H column with a 4:1 Heptane/IPA mobile phase to give enantiomer A ($t_r$=32.3 min) and enantiomer B ($t_r$=58.2 min).

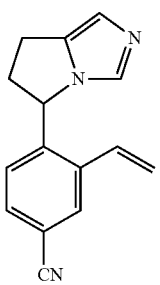 [SMILES: C=Cc1cc(C#N)ccc1C1CCc2cncn21]

2) 4-(6,7-Dihydro-5H-pyrrolo[1,2-c]imidazol-5-yl)-3-((E)-propenyl)benzonitrile. MS (ESI) m/z 250.1 (M+H); $^1$H NMR (400 MHz, CDCl$_3$) δ ppm 1.97 (d, J=6.6 Hz, 3H), 2.37-2.49 (m, 1H), 2.82-2.95 (m, 2H), 3.04-3.18 (m, 1H), 5.62 (dd, J=8.0, 4.7 Hz, 1H), 6.16-6.30 (m, 1H), 6.53 (d, J=15.4 Hz, 1H), 6.66 (d, J=8.1 Hz, 1H), 6.84 (s, 1H), 7.32 (s, 1H), 7.42 (d, J=9.3 Hz, 1H), 7.71 (s, 1H).

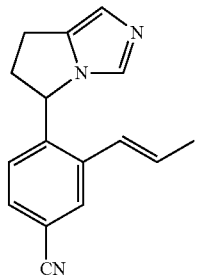 [SMILES: C/C=C/c1cc(C#N)ccc1C1CCc2cncn21]

From 2-Bromo-4-(6,7-dihydro-5H-pyrrolo[1,2-c]imidazol-5-yl)benzonitrile given in Example 3 (table 2) the following are prepared by analogy to example 4A: 1) 4-(6,7-Dihydro-5H-pyrrolo[1,2-c]imidazol-5-yl)-2-vinylbenzonitrile MS (ESI) m/z 236.1 (M+H); $^1$H NMR (400 MHz, CDCl$_3$) δ ppm 2.43-2.56 (m, 1H), 2.85-3.01 (m, 2H), 3.05-3.17 (m, 1H), 5.35 (dd, J=7.8, 5.6 Hz, 1H), 5.57 (d, J=11.1 Hz, 1H), 5.90 (d, J=17.4 Hz, 1H), 6.84 (s, 1H), 7.01-7.10 (m, 2H), 7.31 (s, 1H), 7.35 (d, J=1.3 Hz, 1H), 7.63 (d, J=8.1 Hz, 1H).

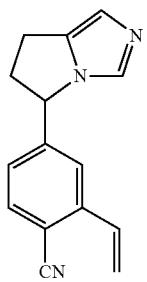 [SMILES: C=Cc1cc(C2CCc3cncn32)ccc1C#N]

2) 4-(6,7-Dihydro-5H-pyrrolo[1,2-c]imidazol-5-yl)-2-methylbenzonitrile MS (ESI) m/z 224.1 (M+H); $^1$H NMR (400 MHz, CD$_3$CN) (TFA salt) δ ppm 2.51 (s, 3H), 2.52-2.61 (m, 1H), 2.94-3.20 (m, 3H), 5.65 (app t, J=6.9 Hz, 1H), 7.19 (s, 1H), 7.18-7.23 (obs m, 1H), 7.26 (s, 1H), 7.70 (d, J=7.8 Hz, 1H), 8.23 (s, 1H).

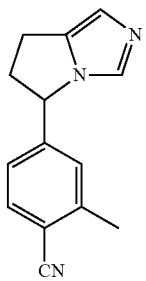 [SMILES: Cc1cc(C2CCc3cncn32)ccc1C#N]

B. 6-(6,7-Dihydro-5H-pyrrolo[1,2-c]imidazol-5-yl)-4'-fluoro-biphenyl-3-carbonitrile

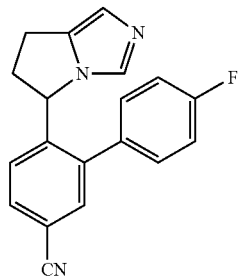 [SMILES: N#Cc1ccc(C2CCc3cncn32)c(-c2ccc(F)cc2)c1]

To a solution of 3-bromo-4-(6,7-dihydro-5H-pyrrolo[1,2-c]imidazol-5-yl)benzonitrile (0.100 g, 0.347 mmol) and 4-fluorophenylboronic acid (0.158 g, 1.04 mmol) in DME (2 mL), aqueous solutions of Na$_2$CO$_3$ (0.69 mL, 2 M) and KOH (0.17 mL, 2 M) are added. After degassing with nitrogen, Pd(PPh$_3$)$_4$ (0.040 g, 0.035 mmol) is added. Mixture is heated in a microwave reactor at 130° C., for 20 minutes. LCMS showed consumption of starting material. The solution is then diluted with ethyl acetate and saturated aqueous sodium bicarbonate. The resulting aqueous layer is extracted further with ethyl acetate (3×). The combined organic layers are washed with brine and dried over anhydrous sodium sulfate. After concentration, crude product is purified by flash chromatography (Hexane/EtOAc, and then 10% MeOH/DCM) followed by preparative HPLC (0-50% acetonitrile with 0.1% TEA in 21 minutes). After concentration and free basing, 6-(6,7-dihydro-5H-pyrrolo[1,2-c]imidazol-5-yl)-4'-fluorobiphenyl-3-carbonitrile is obtained as a white powder. MS (ESI) m/z 304.0 (M+H); $^1$H NMR (400 MHz, CDCl$_3$) δ ppm 2.38-2.54 (m, 1H), 2.76-3.03 (m, 3H), 5.33 (app t, J=6.7 Hz, 1H), 6.79 (s, 1H), 7.01 (d, J=8.1 Hz, 1H), 7.15-7.24 (m, 3H), 7.29 (dd, J=13.4, 5.1 Hz, 2H), 7.54-7.65 (m, 2H).

Similarly prepared are the following:

1) 6-(6,7-Dihydro-5H-pyrrolo[1,2-c]imidazol-5-yl)-4'-methoxybiphenyl-3-carbonitrile MS (ESI) m/z 316.1 (M+H); $^1$H NMR (400 MHz, CDCl$_3$) δ ppm 2.60-2.73 (m, 1H), 2.96-3.10 (m, 2H), 3.12-3.24 (m, 1H), 3.88 (s, 3H), 5.63 (app t, J=7.5 Hz, 1H), 7.03 (d, J=8.6 Hz, 2H), 7.06 (d, J=8.6 Hz, 1H), 7.14 (s, 1H), 7.21 (d, J=8.6 Hz, 2H), 7.65-7.70 (m, 1H), 7.66 (s, 1H), 8.32 (br s, 1H).

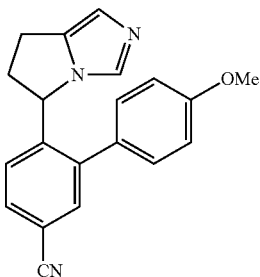 [SMILES: COc1ccc(-c2cc(C#N)ccc2C2CCc3cncn32)cc1]

2) 2-[5-Cyano-2-(6,7-dihydro-5H-pyrrolo[1,2-c]imidazol-5-yl)phenyl]-5-fluoroindole-1-carboxylic acid tert-butyl ester. MS (ESI) m/z 443.2 (M+H)

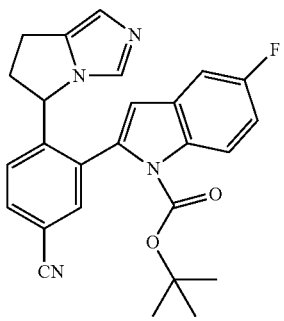 [SMILES: CC(C)(C)OC(=O)n1c(-c2cc(C#N)ccc2C2CCc3cncn32)cc2cc(F)ccc21]

3) 4-(6,7-Dihydro-5H-pyrrolo[1,2-c]imidazol-5-yl)-3-(5-fluoro-1H-indol-2-yl)benzonitrile. MS (ESI) m/z 343.1 (M+H); $^1$H NMR (400 MHz, CDCl$_3$) δ ppm 2.50-2.61 (m, 1H), 2.86-3.04 (m, 2H), 3.06-3.17 (m, 1H), 5.77 (dd, J=8.0, 5.4 Hz, 1H), 6.56 (d, J=1.5 Hz, 1H), 6.81 (s, 1H), 6.94 (d, J=8.3 Hz, 1H), 7.01 (app dt, J=9.1, 2.5 Hz, 1H), 7.09 (s, 1H), 7.30 (dd, J=9.3, 2.3 Hz, 1H), 7.38 (dd, J=8.8, 4.3 Hz, 1H), 7.57 (dd, J=8.2, 1.6 Hz, 1H), 7.85 (d, J=1.5 Hz, 1H), 9.93 (br s, 1H).

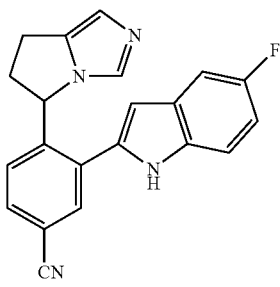 [SMILES: N#Cc1ccc(C2CCc3cncn32)c(-c2cc3cc(F)ccc3[nH]2)c1]

From 2-Bromo-4-(6,7-dihydro-5H-pyrrolo[1,2-c]imidazol-5-yl)benzonitrile given in Example 3 (table 2) the following is prepared by analogy to example 4B:

5-(6,7-Dihydro-5H-pyrrolo[1,2-c]imidazol-5-yl)-4'-fluorobiphenyl-2-carbonitrile. MS (ESI) m/z 304.1 (M+H); $^1$H NMR (400 MHz, CDCl$_3$) δ ppm 2.48-2.62 (m, 1H), 2.89-3.05 (m, 2H), 3.08-3.20 (m, 1H), 5.42 (dd, J=7.7, 5.9 Hz, 1H), 6.95 (s, 1H), 7.04 (app t, J=9.0 Hz, 2H), 7.13-7.21 (m, 3H), 7.46 (dd, J=8.7, 5.2 Hz, 2H), 7.54 (s, 1H).

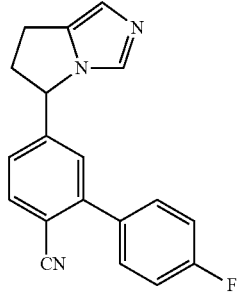 [SMILES: N#Cc1ccc(C2CCc3cncn32)cc1-c1ccc(F)cc1]

C. 4-(6,7-Dihydro-5H-pyrrolo[1,2-c]imidazol-5-yl)-3-(n-propyl)benzonitrile

A suspension of 4-(6,7-Dihydro-5H-pyrrolo[1,2-c]imidazol-5-yl)-3-((E)-propenyl)benzonitrile (0.150 g, 0.602 mmol), 20% (w/w) palladium on carbon (0.040 g), THF (15 mL), and EtOH (15 mL) is stirred under an atmosphere of hydrogen (1 atm) for 60 h. The suspension is the filtered and the filtrate concentrated. The residue is then purified by flash chromatography (Hexane/EtOAc, and then 10% MeOH/EtOAc) to give 4-(6,7-Dihydro-5H-pyrrolo[1,2-c]imidazol-5-yl)-3-(n-propyl)benzonitrile as a white solid. MS (ESI) m/z 252.1 (M+H); $^1$H NMR (400 MHz, CDCl$_3$) δ ppm 1.04 (t, J=7.3 Hz, 3H), 1.63-1.77 (m, 2H), 2.33-2.45 (m, 1H), 2.62-2.80 (m, 2H), 2.92 (app t, J=7.1 Hz, 2H), 3.04-3.19 (m, 1H), 5.58 (dd, J=7.8, 5.6 Hz, 1H), 6.73 (d, J=8.1 Hz, 1H), 6.81 (s, 1H), 7.25 (s, 1H), 7.41 (d, J=8.1 Hz, 1H), 7.51 (s, 1H).

Similarly prepared are the following:

1) 4-(6,7-Dihydro-5H-pyrrolo[1,2-c]imidazol-5-yl)-3-ethylbenzonitrile. MS (ESI) m/z 238.1 (M+H); $^1$H NMR (400 MHz, CDCl$_3$) δ ppm 1.34 (t, J=7.6 Hz, 3H), 2.34-2.47 (m, 1H), 2.68-2.88 (m, 2H), 2.89-2.97 (m, 2H), 3.07-3.19 (m, 1H), 5.59 (dd, J=7.8, 5.1 Hz, 1H), 6.72 (d, J=8.1 Hz, 1H), 6.84 (s, 1H), 7.28 (s, 1H), 7.43 (dd, J=8.1, 1.8 Hz, 1H), 7.55 (d, J=1.3 Hz, 1H). Resolution of the (R) and (S) enantiomers of the title compound is achieved by chiral HPLC using ChiralPak AS-H column and 4:1 heptane/1-PrOH to give enantiomer A (t$_r$=28.1 min) and enantiomer B (t$_r$=43.1 min).

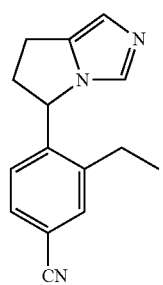 [SMILES: CCc1cc(C#N)ccc1C1CCc2cncn21]

2) 4-(6,7-Dihydro-5H-pyrrolo[1,2-c]imidazol-5-yl)-2-ethylbenzonitrile. MS (ESI) m/z 238.1 (M+H); $^1$H NMR (400 MHz, CDCl$_3$) δ ppm 1.28 (t, J=7.5 Hz, 3H), 2.37-2.55 (m, 1H), 2.78-3.01 (m, 4H), 3.02-3.18 (m, 1H), 5.26-5.40 (m, 1H), 6.82 (br s, 1H), 6.99 (d, J=7.1 Hz, 1H), 7.05 (br s, 1H), 7.30 (br s, 1H), 7.60 (d, J=7.8 Hz, 1H).

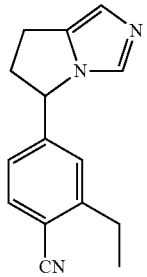 [SMILES: CCc1cc(C2CCc3cncn32)ccc1C#N]

D. 4-(6,7-Dihydro-5H-pyrrolo[1,2-e]imidazol-5-yl)-3-ethoxybenzonitrile

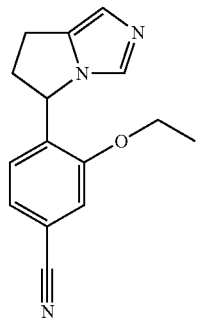 [SMILES: CCOc1cc(C#N)ccc1C1CCc2cncn21]

A solution of 3-bromo-4-(6,7-dihydro-5H-pyrrolo[1,2-c]imidazol-5-yl)benzonitrile (0.090 g, 0.312 mmol) given in Example 3 (table 2), Pd$_2$(dba)$_3$ (0.029 g, 0.031 mmol), BINAP (0.039 g, 0.062 mmol), Cs$_2$CO$_3$ (0.204 g, 0.625 mmol), EtOH (0.091 mL, 1.54 mmol), and DME (4 mL) is heated in a microwave reactor at 135° C. for 1.5 h. At that point LCMS showed consumption of the starting material. The mixture is filtered and then the filtrate is concentrated. The residue is then purified by flash chromatography (0-10% MeOH/DCM) give 4-(6,7-Dihydro-5H-pyrrolo[1,2-c]imidazol-5-yl)-3-ethoxybenzonitrile. MS (ESI) m/z 254.1 (M+H); $^1$H NMR (400 MHz, MeOD) (TFA salt) δ ppm 1.32 (t, J=6.9 Hz, 3H), 2.69-2.82 (m, 1H), 3.07-3.22 (m, 3H), 4.02-4.22 (m, 2H), 5.92-6.03 (m, 1H), 7.27 (d, J=7.8 Hz, 1H), 7.31 (s, 1H), 7.36 (dd, J=7.8, 1.5 Hz, 1H), 7.43 (d, J=1.3 Hz, 1H), 8.68 (s, 1H).

Similarity prepared are the following:

3-Butoxy-4-(6,7-dihydro-5H-pyrrolo[1,2-c]imidazol-5-yl)benzonitrile. MS (ESI) m/z 282.1 (M+H); $^1$H NMR (400 MHz, CDCl$_3$) δ ppm 1.01 (t, J=7.3 Hz, 3H), 1.46-1.59 (m, 2H), 1.78-1.88 (m, 2H), 2.38-2.49 (m, 1H), 2.77-2.93 (m, 2H), 3.02-3.15 (m, 1H), 4.06 (app t, J=6.3 Hz, 2H), 5.67 (dd, J=8.2, 4.2 Hz, 1H), 6.66 (d, J=7.8 Hz, 1H), 6.82 (s, 1H), 7.13 (d, J=1.3 Hz, 1H), 7.17 (dd, J=7.8, 1.3 Hz, 1H), 7.36 (s, 1H).

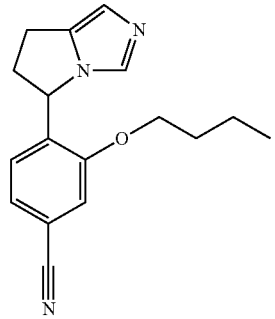 [SMILES: CCCCOc1cc(C#N)ccc1C1CCc2cncn21]

From 2-Bromo-4-(6,7-dihydro-5H-pyrrolo[1,2-c]imidazol-5-yl)benzonitrile given in Example 3 (table 2) the following is prepared by analogy to example 4D:

1) 4-(6,7-Dihydro-5H-pyrrolo[1,2-c]imidazol-5-yl)-2-methoxybenzonitrile. MS (ESI) m/z 240.1 (M+H); $^1$H NMR (400 MHz, CD$_3$CN) (TFA salt) δ ppm 2.97-3.17 (m, 4H), 3.91 (s, 3H), 5.65 (app t, J=7.2 Hz, 1H), 6.90 (dd, J=8.0, 1.4 Hz, 1H), 7.01 (d; J=1.3 Hz, 1H), 7.19 (s, 1H), 7.65 (d, J=8.1 Hz, 1H), 8.23 (s, 1H).

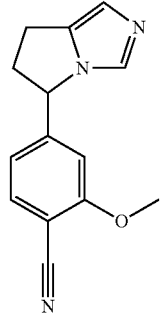 [SMILES: COc1cc(C2CCc3cncn32)ccc1C#N]

2) 4-(6,7-Dihydro-5H-pyrrolo[1,2-c]imidazol-5-yl)-2-pyrrolidin-1-yl-benzonitrile. MS (ESI) m/z 279.1 (M+H); $^1$H NMR (400 MHz, CDCl$_3$) δ ppm 1.97-2.03 (m, 4H), 2.44-2.58 (m, 1H), 2.85-2.98 (m, 2H), 2.99-3.13 (m, 1H), 3.53-3.60 (m, 4H), 5.25 (dd, J=7.7, 5.9 Hz, 1H), 6.26 (d, J=1.3 Hz, 1H), 6.38 (dd, J=8.1, 1.5 Hz, 1H), 6.85 (s, 1H), 7.42 (d, J=8.1 Hz, 1H), 7.44 (s, 1H).

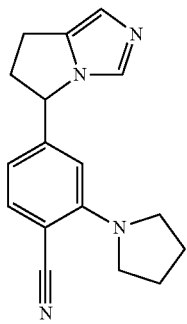 [SMILES: N#Cc1ccc(C2CCc3cncn32)cc1N1CCCC1]

E. 3-Fluoro-4-(5-methyl-6,7-dihydro-5H-pyrrolo[1,2-c]imidazol-5-yl)benzonitrile

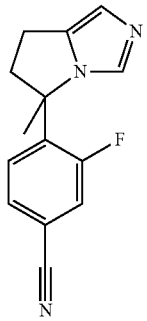

A solution of 4-(6,7-dihydro-5H-pyrrolo[1,2-c]imidazol-5-yl)-4-fluorobenzonitrile (0.050 g, 0.220 mmol) given in Example 3 (table 2), 18-crown-6 (0.006 g, 0.022 mmol), and THF (2 mL) is cooled to −78° C. KHMDS (0.66 mL, 0.5 M) is then added. After 20 min MeI (0.07 mL, 1.10 mmol) is added. After 2.5 h the solution is diluted with saturated aqueous NaHCO$_3$ and DCM. The aqueous layer is further extracted with DCM (3×20 mL). The combined organic layers are dried (Na$_2$SO$_4$), filtered and concentrated. The residue is purified via flash chromatography (50-100% EtOAc/hexanes) to give 3-fluoro-4-(5-methyl-6,7-dihydro-5H-pyrrolo[1,2-c]imidazol-5-yl)benzonitrile as a white solid. MS (ESI) m/z 242.0 (M+H); $^1$H NMR (400 MHz, CDCl$_3$) δ ppm 2.01 (s, 3H), 2.49-2.62 (m, 1H), 2.73-2.99 (m, 3H), 6.35 (app t, J=8.0 Hz, 1H), 6.84 (s, 1H), 7.31 (d, J=8.1 Hz, 1H), 7.40 (d, J=10.9 Hz, 1H), 7.55 (s, 1H).

F. 3-Fluoro-4-(7-methylene-6,7-dihydro-5H-pyrrolo[1,2-c]imidazol-5-yl)benzonitrile

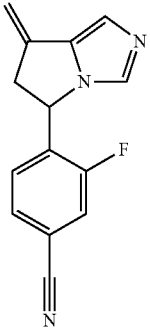 [SMILES: C=C1CC(c2ccc(C#N)cc2F)n2cncc21]

3-Fluoro-4-(5-iodo-imidazol-1-ylmethyl)benzonitrile

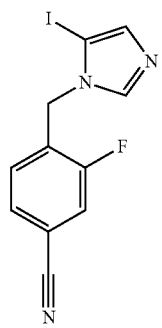 [SMILES: N#Cc1ccc(Cn2cncc2I)c(F)c1]

A mixture of 4-iodo-1-trityl-1H-imidazole (17.1 g, 39.2 mmol) and 4-bromomethyl-3-fluorobenzonitrile (9.65 g, 45.08 mmol) in 150 mL of dry acetonitrile is stirred at room temperature for 7 days. After concentration, the residue is mixed with methanol, and heated to reflux for 1.5 h. The solvent is subsequently removed and the residue is treated with 1M HCl (300 mL). The resulting suspension is filtered and the washed with HCl (1M). The combined solution is adjusted to PH 9-10 by saturated NaHCO$_3$ solution. The resulting precipitation is collected by filtration, dried in vacuum oven. MS (ESI) m/z (M+H) 328.1.

3-Fluoro-4-[1-(5-iodo-imidazol-1-yl)-but-3-enyl]benzonitrile

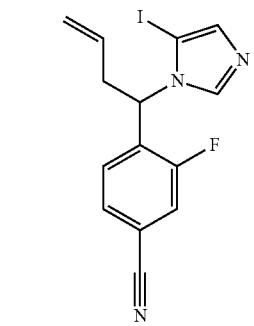 [SMILES: C=CCC(c1ccc(C#N)cc1F)n1cncc1I]

LDA (1.5 M in THF, 20.85 mL, 31.7 mmol) is added dropwise to a suspension of 3-Fluoro-4-(5-iodo-imidazol-1-ylmethyl)benzonitrile (7.98 g, 24.4 mmol) in 150 mL of dry THF at −78° C. After 1 h at this temperature, allyl bromide (2.09 mL, 24.4 mmol) is added slowly, and the resulting mixture is stirred at −78° C. for 3 h. The reaction is quenched with saturated NH$_4$Cl solution, and extracted with CH$_2$Cl$_2$. The combined extracts are washed with brine and dried over anhydrous Na$_2$SO$_4$. After filtration and concentration, the residue is purified by flash column. MS (ESI) m/z (M+H) 368.0.

A mixture of 3-Fluoro-4-[1-(5-iodo-imidazol-1-yl)-but-3-enyl]benzonitrile (2.14 g, 5.83 mmol), PS-PPh$_3$-Pd (0.06 mmol) and Et$_3$N (4.0 mL, 29.15 mmol) in 20 mL of DMF is heated at 150° C. by microwave for 1 h. After filtration and evaporation, the residue is mostly dissolved by 1 M HCl solution. The resulting black mixture is filtered, and the solution is subsequently adjusted to PH 9-10 by saturated NaHCO$_3$ solution. The resulting mixture is extracted with CH$_2$Cl$_2$, and the combined extracts are washed with brine and dried over anhydrous Na$_2$SO$_4$. After filtration and concentration, the residue is purified by flash column. MS (ESI) m/z 240.3 (M+H); $^1$H NMR (400 MHz, CDCl$_3$) δ 7.37-7.33 (m, 2H), 7.32 (s, 1H), 7.18 (s, 1H), 6.82 (t, J=8.0 Hz, 1H), 5.71 (dd, J=12.0 Hz, 4.0 Hz, 1H), 5.35 (t, J=4.0 Hz, 1H), 4.98 (t, J=4.0 Hz, 1H), 3.83-3.76 (m, 1H), 3.05-2.99 (m, 1H). Resolution of the enantiomers of the title compound is achieved by chiral HPLC using the ChiralPak IA column with a EtOH-

G. 5'-[2-fluoro-4-cyano-phenyl]-5',6'-dihydrospiro[cyclopropane-1,7'-pyrrolo[1,2-c]imidazole]

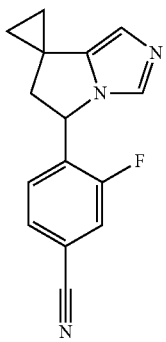 [SMILES: N#Cc1ccc(C2CC3(CC3)c3cncn32)c(F)c1]

A solution of TFA (0.234 mL, 3 mmol) in 0.6 mL of dry CH$_2$Cl$_2$ is added dropwise to a solution of Et$_2$Zn (1M in Hexanes, 3.06 mL, 3.06 mmol) at 0° C. The resulting suspension is subsequently treated with a solution of CH$_2$I$_2$ (0.246 mL, 3.06 mmol) in CH$_2$Cl$_2$ (0.4 mL). After 2 h at 0° C., a solution of 3-fluoro-4-(7-methylene-6,7-dihydro-5H-pyrrolo[1,2-c]imidazol-5-yl)benzonitrile (333.8 mg, 1.392 mmol) in CH$_2$Cl$_2$ is added. After overnight, the reaction is quenched with saturated NaHCO$_3$ solution, and extracted with CH$_2$Cl$_2$ (20 mL×4). The combined extracts are washed with brine, dried over anhydrous Na$_2$SO$_4$. After filtration and evaporation, the residue is purified by chromatography and yield 112 mg of oil. MS (ESI) m/z 254.2 (M+H). $^1$H NMR (400.3 MHz, CDCl$_3$): δ 8.93 (s, 1H), 7.54-7.52 (m, 1H), 7.45 (d, J=8.00 Hz, 1H), 7.35 (m, 1H), 6.83 (s, 1H), 6.27 (brs, 1H), 3.22 (m, 1H), 2.61 (d, J=12 Hz, 1H), 1.33-1.19 (m, 2H), 1.16-1.14 (m, 1H), 0.90-0.85 (m, 1H).

Example 5

A. 5-(3-Fluoro-4-methoxyphenyl)-6,7-dihydro-5H-pyrrolo[1,2-c]imidazole-5-carboxylic acid methyl ester

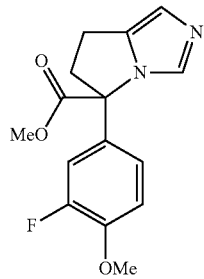 [SMILES: COC(=O)C1(c2ccc(OC)c(F)c2)CCc2cncn21]

4-[2-(tert-Butyl-dimethylsilanyloxy)ethyl]-1-trityl-1H-imidazole (6.5 g, 14.0 mmol) and bromo-(3-fluoro-4-methoxyphenyl)acetic acid methyl ester (5.8 g, 21.0 mmol) are stirred in 60 mL MeCN at room temperature for 2 days. At that point MeOH (50 mL) and Et$_2$NH (50 mL) are then added and the resulting solution heated at 75° C. for 0.5 h. The solution is evaporated and the residue purified via flash column chromatography (EtOAc/DCM 1:9→EtOAc/DCM 1:1) to give {5-[2-(tert-butyldimethylsilanyloxy)ethyl]-imidazol-1-yl}-(3-fluoro-4-methoxyphenyl)acetic acid methyl ester as an oil. MS (ESI) m/z 423.3 (M+H).

The {5-[2-(tert-butyldimethylsilanyloxy)ethyl]-imidazol-1-yl}-(3-fluoro-4-methoxyphenyl)-acetic acid methyl ester (3.1 g, 7.34 mmol) is dissolved in THF (1.00 mL) and cooled down to 0° C. and then HCl in dioxane (11 mL, 4.0 M) is added. After 2 h the solution is evaporated to dryness and the resulting alcohol, (3-fluoro-4-methoxyphenyl)[5-(2-hydroxy-ethyl)-imidazol-1-yl]acetic acid methyl ester, is used without further purification. MS (ESI) m/z 309.2 (M+H).

The (3-fluoro-4-methoxyphenyl)-[5-(2-hydroxyethyl)imidazol-1-yl]-acetic acid methyl ester (2.26 g, 7.34 mmol) is dissolved in DCM (100 mL) and cooled down to 0° C. before Et$_3$N (5.1 mL, 36.7 mmol) and methanesulfonyl chloride (0.7 mL, 8.81 mmol) are added. After 1 h, the solution is transferred to a separatory funnel and partitioned between DCM and saturated aqueous NaHCO$_3$. The organic is dried (Na$_2$SO$_4$) and evaporated to give a crude residue that is purified via flash column chromatography (DCM→MeOH/DCM 5:95) to give the pure intermediate mesylate as yellow oil. MS (ESI) m/z 387.2 (M+H).

The above mesylate (1.8 g, 4.66 mmol) is dissolved in dry THF (50 mL) and cooled down to −78° C. To this solution is added LHMDS (5.6 mL, 1.0M THF). The solution is then allowed to warm gradually to room temperature over 12 h. The solution is then partitioned between EtOAc and saturated aqueous NH$_4$Cl. The organic layer is dried (Na$_2$SO$_4$) and concentrated. The residue is purified via flash column chromatography (DCM→MeOH/DCM 5:95) to give 5-(3-fluoro-4-methoxyphenyl)-6,7-dihydro-5H-pyrrolo[1,2-c]imidazole-5-carboxylic acid methyl ester. MS (ESI) m/z 291.2 (M+H); $^1$H NMR (400 MHz, CDCl$_3$) δ ppm 2.64-2.86 (m, 3H), 3.31-3.40 (m, 1H), 3.79 (s, 3H), 3.84 (s, 3H), 6.62-6.68 (m, 1H), 6.76 (s, 1H), 6.80-6.89 (m, 2H), 7.72 (s, 1H).

B. 5-(3-fluoro-4-methoxyphenyl)-6,7-dihydro-5H-pyrrolo[1,2-c]imidazole

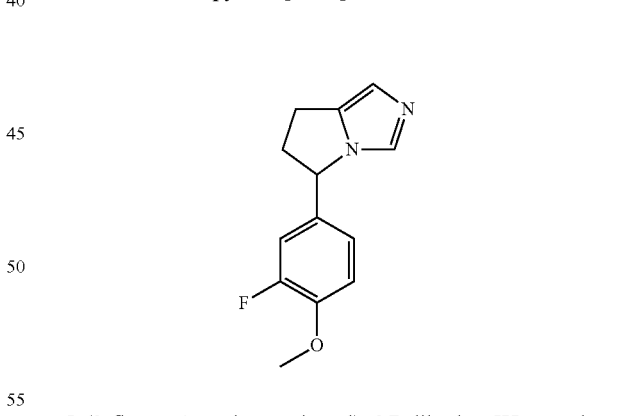

5-(3-fluoro-4-methoxy-phenyl)-6,7-dihydro-5H-pyrrolo[1,2-c]imidazole-5-carboxylic acid methyl ester (0.530 g, 1.82 mmol) is dissolved in THF/water (20 mL) (3:2) and to the solution is added LiOH (0.230 g, 9.58 mmol). After 1 h, the solution is brought to pH 4-5 with 1 M HCl and then evaporated to dryness to give 5-(3-fluoro-4-methoxy-phenyl)-6,7-dihydro-5H-pyrrolo[1,2-c]imidazole-5-carboxylic acid that is used without further purification. MS (ESI) m/z 277.2 (M+H).

The above acid (0.500 g, 1.81 mmol) is dissolved in DMSO (8.0 mL) and Et$_3$N (3.0 mL) and heated in a microwave reactor at 200° C. for 0.5 h. The solution is evaporated to dryness and purified via flash column chromatography (MeOH/DCM 5:95→MeOH/DCM 1:9) to give 5-(3-fluoro-4-methoxy-phenyl)-6,7-dihydro-5H-pyrrolo[1,2-c]imidazole as a pale yellow solid. MS (ESI) m/z 233.3 (M+H); $^1$H NMR (400 MHz, CDCl$_3$) δ ppm 2.44-2.58 (m, 1H), 2.81-3.11 (m, 3H), 3.91 (s, 3H), 5.25 (app t, J=6.8 Hz, 1H), 6.82-6.91 (m, 3H), 6.95 (app t, J=8.6 Hz, 1H), 7.35 (s, 1H).

Example 5a

A. 4-(6,7-dihydro-5H-pyrrolo[1,2-c]imidazol-5-yl)-3,5-difluorobenzonitrile

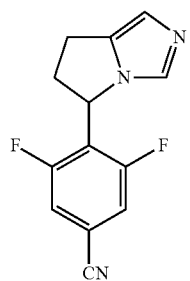 [SMILES: N#Cc1cc(F)c(C2CCc3cncn32)c(F)c1]

3-(1-Trityl-1H-imidazol-4-yl)propionic acid methyl ester (7.75 g, 19.5 mmol), *J. Org. Chem.* 2000, 65, 2229-2230, is dissolved in DCM (300 mL) and cooled to −78° C. To this is added a toluene solution of DIBAL (21.0 mL, 1.5 M). After 2 h MeOH (20 mL) is added followed by saturated aqueous Rochelle salt solution (50 mL). The mixture is partitioned between DCM and saturated aqueous Rochelle salt solution. The organic phase is dried (Na$_2$SO$_4$) and evaporated. The crude residue is purified via flash column chromatography (MeOH/DCM 1:99→MeOH/DCM 5:95) to give the aldehyde, 3-(1-trityl-1H-imidazol-4-yl)propionaldehyde as a yellow gum (cas #184030-88-4). $^1$H NMR (CDCl$_3$) δ 9.83 (s, 1H), 7.38-7.31 (m, 10H), 7.16-7.12 (m, 6H), 6.58 (s, 1H), 2.90 (t, J=8.0 Hz, 2H), 2.83-2.79 (m, 2H).

Diisopropylamine (0.53 mL, 3.75 mmol) is dissolved in 5 mL THF and cooled down to −78° C. To this is added n-BuLi (2.3 mL, 1.6M in hexanes). After 15 min, a solution of 3,5-difluorobenzonitrile (0.52 g, 3.75 mmol) and THF (5 mL) is added and the solution maintained at that temperature for 0.5 h before adding a solution of 3-(1-trityl-1H-imidazol-4-yl)propionaldehyde and THF (20 mL). After 2 h, the solution is diluted with EtOAc and quenched with saturated aqueous NH$_4$Cl. The mixture is then partitioned between EtOAc and saturated aqueous NH$_4$Cl. The organic is dried (Na$_2$SO$_4$) and evaporated. The residue is purified via flash column chromatography (EtOAc/hexanes 2:8→EtOAc) to give 3,5-difluoro-4-[1-hydroxy-3-(1-trityl-1H-imidazol-4-yl)-propyl]benzonitrile as a yellow powder. MS (ESI) m/z 506.2 (M+H).

3,5-Difluoro-4-[1-hydroxy-3-(1-trityl-1H-imidazol-4-yl)-propyl]benzonitrile (0.105 g, 0.21 mmol) is dissolved in DMF (5 mL) and cooled down to 0° C. To this is added Et$_3$N (0.043 mL, 0.31 mmol) and methanesulfonyl chloride (0.019 mL, 0.25 mmol). After 2 h, LCMS showed the presence of the intermediate mesylate [MS (ESI) m/z 584.3 (M+H)]. The solution is evaporated to dryness and dissolved in DMF (5 mL), to which is added K$_2$CO$_3$ (0.086 g, 0.62 mmol) and NaI (0.093 g, 0.62 mmol) and the mixture is heated to 90° C. for 0.5 h. The solution is then evaporated, dissolved in MeCN and filtered. The crude residue is purified via flash column chromatography (MeOH/DCM 1:99→MeOH/DCM 1:9) to give 4-(6,7-dihydro-5H-pyrrolo[1,2-c]imidazol-5-yl)-3,5-difluorobenzonitrile. MS (ESI) m/z 246.2 (M+H); $^1$H NMR (400 MHz, CDCl$_3$) δ ppm 2.72-2.85 (m, 1H), 2.93-3.05 (m, 1H), 3.08-3.21 (m, 2H), 5.75 (app t, J=7.2 Hz, 1H), 6.79 (s, 1H), 7.18-7.41 (m, 3H).

B. 4-(6,7-dihydro-5H-pyrrolo[1,2-c]imidazol-5-yl)-3-fluoro-5-methoxybenzonitrile

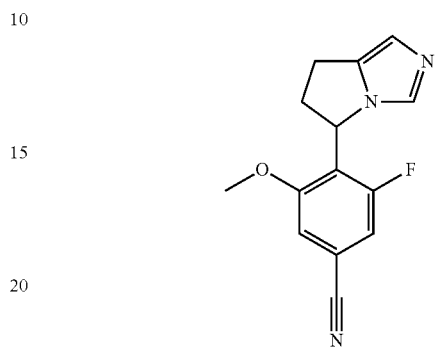

Conditions used to synthesize 3-fluoro-4-[1-hydroxy-3-(1-trityl-1H-imidazol-4-yl)-propyl]-5-methoxybenzonitrile are similar to the procedure above for the synthesis of 3,5-difluoro-4-[1-hydroxy-3-(1-trityl-1H-imidazol-4-yl)-propyl]benzonitrile. MS (ESI) ink 537.2 (M+H).

3-fluoro-4-[1-hydroxy-3-(1-trityl-1H-imidazol-4-yl)-propyl]-5-methoxybenzonitrile (0.283 g, 0.55 mmol) is dissolved in DCM (5 mL) to which thionyl chloride (0.12 mL, 1.64 mmol) is added. The solution is heated at reflux for 1 h before the reaction is allowed to cool to ambient temperature and partitioned between DCM and saturated aqueous NaHCO$_3$. The organic is dried (Na$_2$SO$_4$) and evaporated.

The crude chloride is dissolved in DMF (5 mL), to which is added K$_2$CO$_3$ (0.243 g, 1.76 mmol) and NaI (0.25 g, 1.66 mmol) and the mixture is heated to 120° C. for 0.5 h in a microwave. The solution is then evaporated, dissolved in MeCN and filtered. The crude residue is purified via flash column chromatography (MeOH/DCM 1:99→MeOH/DCM 1:9) and finally HPLC to give 4-(6,7-dihydro-5H-pyrrolo[1,2-c]imidazol-5-yl)-3-fluoro-5-methoxybenzonitrile as the TFA salt. MS (ESI) m/z 258.3 (M+H); $^1$H NMR (400 MHz, CDCl$_3$) (TFA salt) δ ppm 2.79-2.93 (m, 1H), 3.05-3.19 (m, 2H), 3.19-3.31 (m, 1H), 3.86 (s, 3H), 6.05 (app t, J=7.6 Hz, 1H), 7.03 (s, 1H), 7.07 (s, 1H), 7.10 (dd, J=9.6, 1.3 Hz, 1H), 8.32 (s, 1H).

Example 6

A. 4-(6,7-Dihydro-5H-pyrrolo[1,2-c]imidazol-5-yl)-3-nitrobenzonitrile

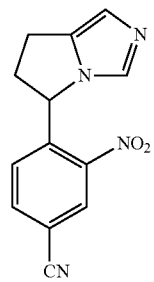

3-[2-(tert-Butyldimethylsilanyloxy)ethyl]-1-trityl-1H-imidazole (1.00 g, 2.13 mmol) and 4-bromomethyl-3-nitrobenzonitrile (cas#223512-70-7, prepared in WO9919301) (0.77 g, 3.20 mmol), prepared via the general benzylic bromination procedure described earlier, are dissolved in MeCN (11 mL) and stirred at room temperature for 15 h. At that time the solution is diluted with MeOH (5 mL) and Et$_2$NH (1 mL) and then warmed to 70° C. for 1.5 h. The solution is then evaporated to dryness and the residue purified via flash column chromatography (20-100% EtOAc/hexanes) to give 4-{5-[2-(tert-butyldimethylsilanyloxy)ethyl]imidazol-1-ylmethyl}-3-nitrobenzonitrile as an oil. MS (ESI) m/z 387.0 (M+H).

4-{5-[2-(tert-Butyldimethylsilanyloxy)ethyl]imidazol-1-ylmethyl}-3-nitrobenzonitrile (0.540 g, 1.40 mmol) is dissolved in THF (8 mL) and MeOH (2 mL) and cooled to 0° C. Then a dioxane solution of HCl (1.75 mL, 4.0 M, 7 mmol) is added. After 0.5 h, the solution is concentrated.

The crude residue, 4-[5-(2-hydroxyethyl)imidazol-1-ylmethyl]-3-nitrobenzonitrile, is then taken up in CH$_2$Cl$_2$ (10 mL), cooled to 0° C., and treated with Et$_3$N (0.58 mL, 4.19 mmol). To this solution is added methanesulfonyl chloride (0.13 mL, 1.68 mmol). After 0.5 h the solution is diluted with CH$_2$Cl$_2$ (10 mL) and saturated aqueous NaHCO$_3$ (20 mL). The organic layer is further extracted with CH$_2$Cl$_2$ (3×20 mL) and the combined layers are dried (Na$_2$SO$_4$) and concentrated to give crude methanesulfonic acid 2-[3-(4-cyano-2-nitrobenzyl)-3H-imidazol-4-yl]ethyl ester. A suspension of the methanesulfonic acid 2-[3-(4-cyano-2-nitrobenzyl)-3H-imidazol-4-yl]-ethyl ester residue, DMF (17 mL), sodium iodide (0.630 g, 4.19 mmol), Et$_3$N (0.58 mL, 4.19 mmol), and potassium carbonate (0.580 g, 4.19 mmol) is heated to 60° C. for 1 hour and then 75° C. for an additional 2 h. At that point the suspension is concentrated and diluted with CH$_2$Cl$_2$ (20 mL) and saturated aqueous NaHCO$_3$ (20 mL). The organic layer is further extracted with CH$_2$Cl$_2$ (3×20 mL) and the combined layers are dried (Na$_2$SO$_4$). The residue is then purified via HPLC (reversed phase, CH$_3$CN/H$_2$O) to give 4-(6,7-dihydro-5H-pyrrolo[1,2-c]imidazol-5-yl)-3-nitrobenzonitrile as a solid. MS (ESI) m/z 254.9 (M+H); $^1$H NMR (400 MHz, CDCl$_3$) δ ppm 2.48-2.57 (m, 1H), 2.81-2.92 (m, 1H), 2.92-3.01 (m, 1H), 3.35-3.47 (m, 1H), 6.03 (dd, J=8.6, 3.5 Hz, 1H), 6.80 (d, J=8.3 Hz, 1H), 6.89 (s, 1H), 7.36 (s, 1H), 7.81 (dd, J=7.8, 1.8 Hz, 1H), 8.41 (d, J=1.8 Hz, 1H).

B. 3-Amino-4-(6,7-dihydro-5H-pyrrolo[1,2-c]imidazol-5-yl)benzonitrile

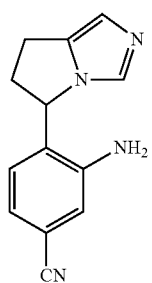 [SMILES: N#Cc1ccc(C2CCc3cncn32)c(N)c1]

4-(6,7-Dihydro-5H-pyrrolo[1,2-c]imidazol-5-yl)-3-nitrobenzonitrile (0.054 g, 0.212 mmol) is dissolved in THF (2 mL) and EtOH (2 mL) and 5% palladium on carbon (wet) (15 mg) is then added. The mixture is placed under an atmosphere of hydrogen overnight. The mixture is then filtered and concentrated. The residue is purified via HPLC (reversed phase, CH$_3$CN/H$_2$O) to give 3-amino-4-(6,7-dihydro-5H-pyrrolo[1,2-c]imidazol-5-yl)benzonitrile as a solid. MS (ESI) m/z 225.0 (M+H); $^1$H NMR (400 MHz, CH$_3$CN) (TFA salt) δ ppm 2.45-2.57 (m, 1H), 2.99-3.16 (m, 3H), 4.47 (br s, 2H), 5.68-5.75 (m, 1H), 6.69 (d, J=7.8 Hz, 1H), 6.98 (d, J=1.5 Hz, 1H), 7.09 (d, J=1.8 Hz, 1H), 7.21 (s, 1H), 8.32 (s, 1H).

C. 1-[5-Cyano-2-(6,7-dihydro-5H-pyrrolo[1,2-c]imidazol-5-yl)phenyl]-3-ethylurea

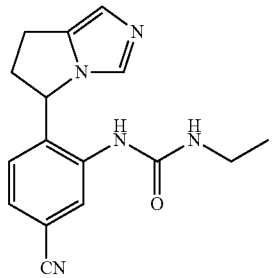 [SMILES: CCNC(=O)Nc1cc(C#N)ccc1C1CCc2cncn21]

To a solution of 3-Amino-4-(6,7-dihydro-5H-pyrrolo[1,2-c]imidazol-5-yl)benzonitrile (0.090 g, 0.420 mmol), given as example 6B, and DMF (5 mL) is added ethylisocyanate (0.040 mL, 0.510 mmol). The solution is heated to 70° C. in a microwave reactor for 1.5 h followed by heating at 70° C. in an oil bath overnight. The solution is then concentrated and the residue purified via flash chromatography (1-10% MeOH/CH$_2$Cl$_2$) to give 1-[5-Cyano-2-(6,7-dihydro-5H-pyrrolo[1,2-d]imidazol-5-yl)phenyl]-3-ethylurea. MS (ESI) m/z 296.1 (M+H); $^1$H NMR (400 MHz, CDCl$_3$) δ ppm 1.16 (t, J=7.2 Hz, 3H), 2.47-2.62 (m, 1H), 2.82-3.04 (m, 2H), 3.05-3.17 (m, 1H), 3.21-3.33 (m, 2H), 5.63 (app t, J=6.8 Hz, 1H), 5.80 (br s, 1H), 6.82 (s, 1H), 6.91 (d, J=8.1 Hz, 1H), 7.30 (dd, J=8.1, 1.5 Hz, 1H), 7.39 (s, 1H), 7.53 (br s, 1H), 7.97 (d, J=1.3 Hz, 1H).

D. N-[5-Cyano-2-(6,7-dihydro-5H-pyrrolo[1,2-c]imidazol-5-yl)-phenyl]-butyramide

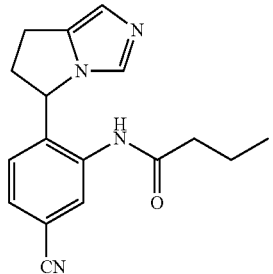 [SMILES: CCCC(=O)Nc1cc(C#N)ccc1C1CCc2cncn21]

A DMF (3 mL) solution of 3-Amino-4-(6,7-dihydro-5H-pyrrolo[1,2-c]imidazol-5-yl)benzonitrile (0.095 g, 0.42 mmol), given as example 6B, is treated with Et$_3$N (0.09 mL, 0.64 mmol) and butyryl chloride (0.05 mL, 0.51 mmol) at room temperature. After 1 h the solution is concentrated. Purification via prep HPLC gives N-[5-Cyano-2-(6,7-dihydro-5H-pyrrolo[1,2-c]imidazol-5-yl)-phenyl]-butyramide. MS (ESI) m/z 295.1 (M+H); $^1$H NMR (400 MHz, CDCl$_3$) δ ppm 1.01 (t, J=7.3 Hz, 3H), 1.67-1.80 (m, 2H), 2.35 (t, J=7.5 Hz, 2H), 2.49-2.61 (m, 1H), 2.88-3.01 (m, 2H), 3.05-3.18 (m, 1H), 5.56 (dd, J=8.0, 5.9 Hz, 1H), 6.84 (s, 1H), 6.97 (d, J=8.1 Hz, 1H), 7.40 (s, 1H), 7.45 (dd, J=8.1, 1.5 Hz, 1H), 7.70 (br s, 1H), 7.91 (s, 1H).

Example 7

A. 5-(4'-fluorobiphenyl-2-yl)-6,7-dihydro-5H-pyrrolo[1,2-c]imidazole

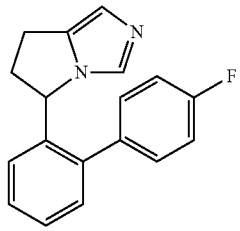 [SMILES: Fc1ccc(-c2ccccc2C2CCc3cncn32)cc1]

To a suspension of 2-(1-trityl-1H-imidazol-4-yl)ethanol (0.65 g, 1.80 mmol), acetonitrile (9 mL) and $CH_2Cl_2$ (12 mL) is added a solution of 2-bromomethyl-4'-fluorobiphenyl (0.478 g, 1.80 mmol) in $CH_2Cl_2$ (2 mL). The resulting mixture is stirred at room temperature overnight. The solution is concentrated and the residue is taken up in MeOH and heated to 75° C. for 3.5 h. The solution is then concentrated and the residue is partitioned between $CH_2Cl_2$ and aqueous 5% $NaHCO_3$. The aqueous layer is then extracted with $CH_2Cl_2$ (3×). The combined organic layers are then washed with brine and dried over $Na_2SO_4$. The residue is then purified by flash chromatography ($CH_2Cl_2$/MeOH) give 2-[3-(4'-fluorobiphenyl-2-ylmethyl)-3H-imidazol-4-yl]ethanol. MS (ESI) m/z 297.1 (M+H).

To a solution of 2-[3-(4'-fluorobiphenyl-2-ylmethyl)-3H-imidazol-4-yl]ethanol (0.341 g, 1.15 mmol) in $CH_2Cl_2$ (10 mL) is added, thionyl chloride (0.11 mL, 1.50 mmol) at 0° C. The mixture is then heated to reflux for 3 h before the solvent is removed and the residue dried under reduced pressure to give 5-(2-chloroethyl)-1-(4'-fluorobiphenyl-2-ylmethyl)-1H-imidazole. The residue is taken up in THF (60 mL). TMEDA (0.71 ml, 4.72 mmol) is added, followed by a hexane/THF solution of LDA (2.62 mL, 1.8 M) at −78° C. The resulting mixture is stirred at −78° C. for 5 h. The excess LDA is then quenched by the addition of saturated $NH_4Cl$. The mixture is then diluted with $CH_2Cl_2$ and water. The organic layer is separated and washed with water, brine and dried over $Na_2SO_4$. After concentration, the residue is purified by flash chromatography ($CH_2Cl_2$/MeOH) to give 5-(4'-fluorobiphenyl-2-yl)-6,7-dihydro-5H-pyrrolo[1,2-c]imidazole. MS (ESI), m/z 279.1 (M+H). Resolution of the (R) and (S) enantiomers of the title compound is achieved by chiral HPLC using ChiralPak AD column and 13% IPA:hexane to give enantiomer A ($t_r$=9.6 min) and enantiomer B=12.6 min). For enantiomer B: $^1H$ NMR (400 MHz, $CDCl_3$) (HCl salt) δ ppm 2.68-2.79 (m, 1H), 2.95-3.06 (m, 2H), 3.13-3.22 (m, 1H), 5.55 (app t, J=7.6 Hz, 1H), 6.96 (dd, J=7.6, 1.5 Hz, 1H), 7.13 (s, 1H), 7.18 (app t, J=8.6 Hz, 2H), 7.27-7.32 (m, 2H), 7.33-7.38 (m, 1H), 7.40-7.49 (m, 2H), 8.01 (s, 1H).

Similarly prepared is the following:

5-Biphenyl-2-yl-6,7-dihydro-5H-pyrrolo[1,2-c]imidazole. MS (ESI) m/z 261.3 (M+H). Resolution of the (R) and (S) enantiomers of the title compound is achieved by chiral HPLC using ChiralPak AD column and 13% IPA:hexane to give enantiomer A ($t_r$=9.1 min) and enantiomer B=12.4 min). For enantiomer B: $^1H$ NMR (400 MHz, MeOD) (TFA salt) δ ppm 2.65-2.74 (m, 1H), 3.00 (ddd, J=15.6, 10.8, 8.5 Hz, 2H), 3.09-3.19 (m, 1H), 5.67-5.73 (m, 1H), 7.08-7.14 (m, 1H), 7.27 (s, 1H), 7.32-7.41 (m, 3H), 7.42-7.50 (m, 5H), 8.66 (s, 1H).

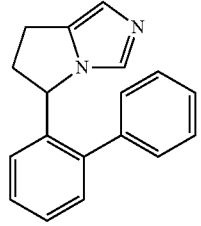 [SMILES: c1ccc(-c2ccccc2C2CCc3cncn32)cc1]

Example 8

A. 5-(4-Cyano-2-fluorophenyl)-6,7-dihydro-5H-pyrrolo[1,2-c]imidazole-5-carboxylic acid isopropyl ester

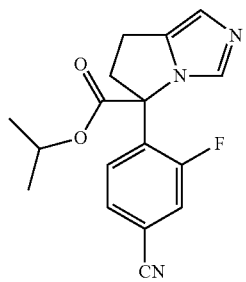 [SMILES: CC(C)OC(=O)C1(c2ccc(C#N)cc2F)CCc2cncn21]

To a solution of 5-(4-cyano-2-fluorophenyl)-6,7-dihydro-5H-pyrrolo[1,2-c]imidazole-5-carboxylic acid methyl ester (0.186 g, 0.652 mmol) in THF (15 mL), an aqueous solution of LiOH (0.065 mL, 2 M) is added. The solution is stirred at room temperature for 20 min, at which time LCMS showed only starting material. At that time additional $H_2O$ (1.5 mL) is added. After an additional 1 h the starting material had been consumed. The solution is then neutralized to pH 5-6 with 1 N HCl and evaporated to dryness. The crude acid, 5-(4-cyano-2-fluoro-phenyl)-6,7-dihydro-5H-pyrrolo[1,2-c]imidazole-5-carboxylic acid is used without further purification. MS (ESI) m/z 272.0 (M+H).

5-(4-Cyano-2-fluorophenyl)-6,7-dihydro-5H-pyrrolo[1,2-c]imidazole-5-carboxylic acid (0.15 g, 0.279 mmol) is suspended in $CH_2Cl_2$ (3 mL) and DMF (0.01 ml) and cooled to 0° C. A solution of oxalyl chloride (0.31 mL, 2 M) in $CH_2Cl_2$ is added dropwise. After 1 h i-PrOH (3 mL) is added. After 2 h $Et_3N$ is added until basic and the solution is concentrated. The resulting slurry is dissolved in $CH_2Cl_2$, washed with aqueous saturated $NaHCO_3/H_2O$ (1:1) and brine, then dried over $Na_2SO_4$. After concentration, the residue is purified by HPLC (2-38% $MeCN/H_2O$ containing 0.1% TFA) to give 5-(4-cyano-2-fluorophenyl)-6,7-dihydro-5H-pyrrolo[1,2-c]imidazole-5-carboxylic acid isopropyl ester as solid. MS (ESI) m/z 314.0 (M+H); $^1H$ NMR (400 MHz, $CD_3CN$) (TFA salt) δ ppm 1.22 (d, J=6.06 Hz, 3H), 1.23 (d, J=6.06 Hz, 3H), 3.01-3.18 (m, 3H), 3.38-3.45 (m, 1H), 5.08-5.18 (m, 1H), 7.20 (s, 1H), 7.34 (app t, J=8.08 Hz, 1H), 7.62-7.68 (m, 2H) 8.52 (s, 1H).

Similarly prepared are the following:

1) 5-(2-Chloro-4-cyanophenyl)-6,7-dihydro-5H-pyrrolo[1,2-c]imidazole-5-carboxylic acid isopropyl ester. MS (ESI) m/z 330.2, 332.2 (M+H); $^1$H NMR (400 MHz, CDCl$_3$) δ ppm 1.23 (d, J=6.3 Hz, 3H), 1.27 (d, J=6.3 Hz, 3H), 2.63-2.77 (m, 2H), 2.94-3.07 (m, 1H), 3.81-3.93 (m, 1H), 5.09-5.22 (m, 1H), 6.54 (d, J=8.1 Hz, 1H), 6.89 (s, 1H), 7.50 (dd, J=8.2, 1.6 Hz, 1H), 7.58 (s, 1H), 7.73 (d, J=1.5 Hz, 1H).

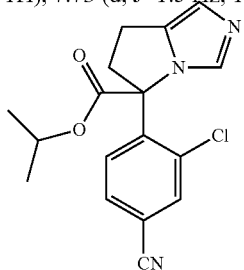 [SMILES: CC(C)OC(=O)C1(c2ccc(C#N)cc2Cl)CCc2cncn21]

2) 5-(4-Cyano-2-methoxyphenyl)-6,7-dihydro-5H-pyrrolo[1,2-c]imidazole-5-carboxylic acid isopropyl ester. MS (ESI) m/z 326.3 (M+H); $^1$H NMR (400 MHz, CDCl$_3$) δ ppm 1.18 (d, J=6.3 Hz, 3H), 1.23 (d, J=6.3 Hz, 3H), 2.55-2.64 (m, 1H), 2.65-2.76 (m, 1H), 2.97 (ddd, J=15.4, 9.4, 2.8 Hz, 1H), 3.61-3.71 (m, 1H), 3.88 (s, 3H), 5.04-5.14 (m, 1H), 6.57 (d, J=8.1 Hz, 1H), 6.83 (s, 1H), 7.14 (d, J=1.3 Hz, 1H), 7.21 (dd, J=8.0, 1.4 Hz, 1H), 7.58 (s, 1H).

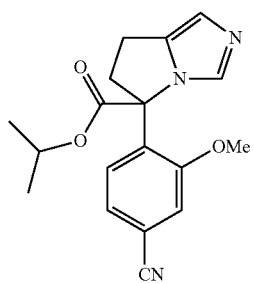 [SMILES: COc1cc(C#N)ccc1C1(C(=O)OC(C)C)CCc2cncn21]

3) 5-(2-Chloro-4-cyanophenyl)-6,7-dihydro-5H-pyrrolo[1,2-c]imidazole-5-carboxylic acid 2-isopropoxyethyl ester. MS (ESI) m/z 374.2, 376.2 (M+H); $^1$H NMR (400 MHz, CDCl$_3$) (HCl salt) δ ppm 1.08 (d, J=6.1 Hz, 3H), 1.10 (d, J=6.1 Hz, 3H), 2.89-3.02 (m, 2H), 3.17-3.28 (m, 1H), 3.52-3.59 (m, 1'H), 3.61 (app t, J=4.5 Hz, 2H), 3.88-3.96 (m, 1H), 4.25-4.33 (m, 1H), 4.57-4.65 (m, 1H), 6.73 (d, J=8.1 Hz, 1H), 7.29 (s, 1H), 7.61 (s, 1H), 7.81 (s, 1H), 8.69 (s, 1H), 10.6 (br s, 1H). Resolution of the (R) and (S) enantiomers of the title compound is achieved by chiral HPLC using the ChiralPak IA column with a 2:8 IPA/hexane mobile phase to give enantiomer A (t$_r$=23.9 min) and enantiomer B (t$_r$=38.6 min).

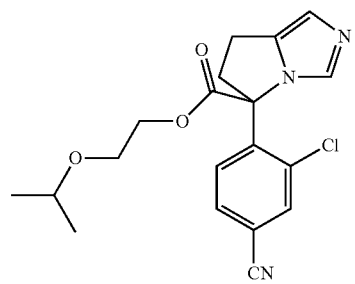 [SMILES: CC(C)OCCOC(=O)C1(c2ccc(C#N)cc2Cl)CCc2cncn21]

4) 5-(4-Cyano-2-methoxyphenyl)-6,7-dihydro-5H-pyrrolo[1,2-c]imidazole-5-carboxylic acid 2-isopropoxyethyl ester. MS (ESI) m/z 370.2 (M+H); $^1$H NMR (400 MHz, CDCl$_3$) δ ppm 1.08 (d, J=6.1, 3H); 1.10 (d, J=6.1, 3H), 2.58-2.78 (m, 2H), 2.92-3.03 (m, 1H), 3.44-3.58 (m, 3H), 3.62-3.73 (m, 1H), 3.90 (s, 3H), 4.14-4.23 (m, 1H), 4.35-4.44 (m, 1H), 6.57 (d, J=8.1 Hz, 1H), 6.84 (s, 1H), 7.15 (d, J=1.3 Hz, 1H), 7.21 (dd, J=7.8, 1.3 Hz, 1H), 7.69 (s, 1H).

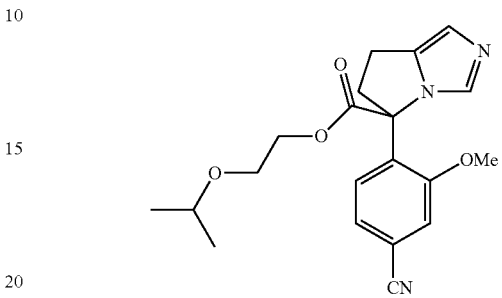

5) 5-(2-Chloro-4-cyanophenyl)-6,7-dihydro-5H-pyrrolo[1,2-c]imidazole-5-carboxylic acid 4-fluorobenzyl ester. MS (ESI) m/z 396.1, 398.1 (M+H); $^1$H NMR (400 MHz, CDCl$_3$) δ ppm 2.68-2.80 (m, 2H), 2.99-3.09 (m, 1H), 3.84-3.91 (m, 1H), 5.22 (ABq, J=11.9 Hz, 2H), 6.56 (d, J=8.3 Hz, 1H), 6.92 (s, 1H), 7.01-7.08 (m, 2H), 7.23-7.28 (m, 2H), 7.50 (dd, J=8.2, 1.6 Hz, 1H), 7.57 (s, 1H), 7.70 (d, J=1.5 Hz, 1H). Resolution of the (R) and (S) enantiomers of the title compound is achieved by chiral HPLC using ChiralPak IA column and 3:7 i-PrOH/hexanes to give enantiomer A (t$_r$=39.2 min) and enantiomer B (t$_r$=60.3 min).

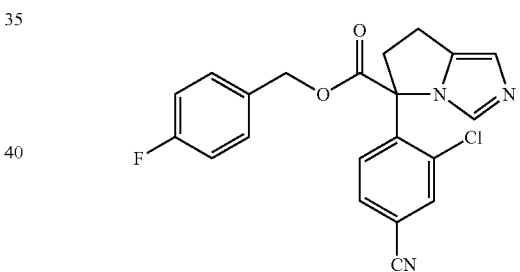

6) 5-(4-Cyano-2-methoxyphenyl)-6,7-dihydro-5H-pyrrolo[1,2-c]imidazole-5-carboxylic acid 4-fluorobenzyl ester. MS (ESI) m/z 392.1 (M+H); $^1$H NMR (400 MHz, CDCl$_3$) δ ppm 2.59 (ddd, J=13.0, 8.1, 3.0 Hz, 1H), 2.65-2.75 (m, 1H), 2.92-3.00 (m, 1H), 3.55 (s, 3H), 3.61-3.71 (m, 1H), 5.15 (ABq, J=11.9 Hz, 2H), 6.58 (d, J=7.8 Hz, 1H), 6.81 (s, 1H), 7.00-7.08 (m, 3H), 7.20 (dd, J=8.0, 1.4 Hz, 1H), 7.23-7.29 (m, 2H), 7.47 (s, 1H).

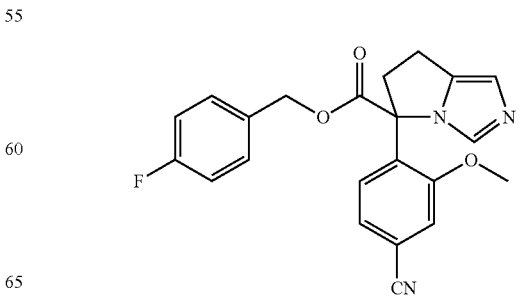

Example 9

A. 5-(4-Cyano-2-methoxyphenyl)-6,7-dihydro-5H-pyrrolo[1,2-c]imidazole-5-carboxylic acid (4-fluorobenzyl)methylamide

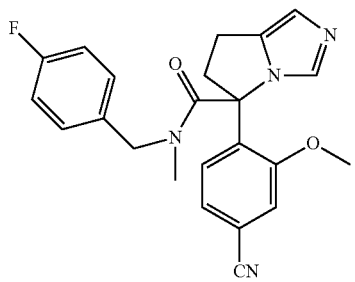 [SMILES: COc1cc(C#N)ccc1C1(C(=O)N(C)Cc2ccc(F)cc2)CCc2cncn21]

Crude 5-(4-cyano-2-methoxyphenyl)-6,7-dihydro-5H-pyrrolo[1,2-c]imidazole-5-carboxylic acid (0.168 g, 0.59 mmol) is suspended in $CH_2Cl_2$ (3 mL) and cooled to 0° C. To it is added DMF (0.2 mL) followed by the addition of a $CH_2Cl_2$ solution of oxalyl chloride (0.6 mL, 2.0 M). After 2 h, 4-fluoro-N-methylbenzylamine (0.23 mL, 1.78 mmol) is added. The reaction is stirred for another 2 h, evaporated to dryness, and partitioned between EtOAc and saturated aqueous $NaHCO_3$. The organic phase is dried ($Na_2SO_4$), filtered, and concentrated. The crude residue is purified via flash column chromatography (2-5% MeOH/$CH_2Cl_2$) to give 5-(4-cyano-2-methoxyphenyl)-6,7-dihydro-5H-pyrrolo[1,2-c]imidazole-5-carboxylic acid (4-fluorobenzyl)methylamide as a yellow solid. MS (ESI) m/z 405.2 (M+H); $^1$H NMR (400 MHz, CDCl$_3$) δ ppm 2.60 (s, 3H), 2.76-2.88 (m, 2H), 2.95-3.04 (m, 1H), 3.57-3.69 (m, 1H), 3.74 (s, 3H), 4.43 (d, J=14.4 Hz, 1H), 4.58-4.70 (m, 1H), 6.79 (s, 1H), 6.86-6.94 (m, 1H), 6.96-7.05 (m, 2H), 7.10 (s, 1H), 7.19-7.25 (m, 3H), 7.55 (s, 1H). Resolution of the (R) and (S) enantiomers of the title compound is achieved by chiral HPLC using ChiralPak AD column with a 6:4 EtOH/hexane mobile phase to give enantiomer A (t$_r$=30.2 min) and enantiomer B (t$_r$=36.0 min).

Similarly prepared are the following:

1) 5-(2-Chloro-4-cyanophenyl)-6,7-dihydro-5H-pyrrolo[1,2-c]imidazole-5-carboxylic acid ethylamide. MS (ESI) m/z 315.0, 317.0 (M+H); $^1$H NMR (400 MHz, CDCl$_3$) (TFA salt) δ ppm 1.09 (t, J=7.2 Hz, 3H), 2.72-2.81 (m, 1H), 2.84 (m, 1H), 3.15-3.27 (m, 2H), 3.32-3.42 (m, 1H), 4.12-4.22 (m, 1H), 6.81 (d, J=8.1 Hz, 1H), 7.11 (s, 1H), 7.53 (obs d, J=7.3 Hz, 1H), 7.54 (s, 1H), 7.78 (s, 1H) 9.52 (s, 1H).

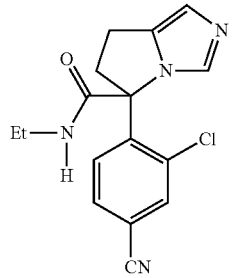 [SMILES: CCNC(=O)C1(c2ccc(C#N)cc2Cl)CCc2cncn21]

2) 5-(2-Chloro-4-cyanophenyl)-6,7-dihydro-5H-pyrrolo[1,2-c]imidazole-5-carboxylic acid methylamide. MS (ESI) m/z 301.0, 303.0 (M+H); $^1$H NMR (400 MHz, CDCl$_3$) (TFA salt) δ ppm 2.74-2.79 (obs m, 1H), 2.80 (d, J=4.6 Hz, 3H), 2.85-2.94 (m, 1H), 3.19-3.28 (m, 1H), 4.13-4.22 (m, 1H), 6.83 (d, J=8.1 Hz, 1H), 7.11 (s, 1H), 7.53 (dd, J=8.2, 1.4 Hz, 1H), 7.62 (br s, 1H), 7.77 (d, J=1.5 Hz, 1H), 9.48 (s, 1H).

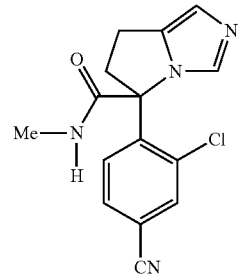 [SMILES: CNC(=O)C1(c2ccc(C#N)cc2Cl)CCc2cncn21]

3) 5-(2-Chloro-4-cyanophenyl)-6,7-dihydro-5H-pyrrolo[1,2-c]imidazole-5-carboxylic acid dimethylamide. MS (ESI) m/z 315.0, 317.0 (M+H); $^1$H NMR (400 MHz, CDCl$_3$) (TFA salt) δ ppm 2.73 (s, 3H), 3.10 (s, 3H), 3.17-3.22 (m, 2H), 3.35-3.44 (m, 2H), 3.52-3.62 (m, 2H), 7.15 (s, 1H), 7.42 (d, J=8.1 Hz, 1H), 7.72 (dd, J=8.2, 1.6 Hz, 1H), 7.84 (d, J=1.5 Hz, 1H), 8.61 (s, 1H).

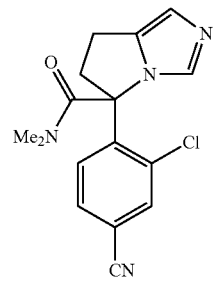

4) 3-Chloro-4-[5-(morpholino-4-carbonyl)-6,7-dihydro-5H-pyrrolo[1,2-c]imidazol-5-yl]benzonitrile. MS (ESI) m/z 356.9, 358.9 (M+H); $^1$H NMR (400 MHz, CDCl$_3$) (TFA salt) δ ppm 2.97-3.64 (m, 8H), 3.74 (br s, 4H), 7.15 (s, 1H), 7.39-7.53 (m, 1H), 7.71 (d, J=7.3 Hz, 1H), 7.85 (s, 1H), 8.66 (s, 1H).

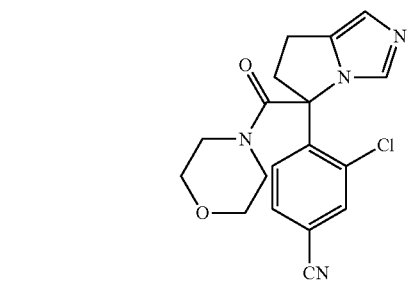 [SMILES: N#Cc1ccc(C2(C(=O)N3CCOCC3)CCc3cncn32)c(Cl)c1]

5) 5-(2-Chloro-4-cyanophenyl)-6,7-dihydro-5H-pyrrolo[1,2-c]imidazole-5-carboxylic acid (2-methoxyethyl)methylamide. MS (ESI) m/z 359.0, 361.0 (M+H); $^1$H NMR (400 MHz, CDCl$_3$) (HCl salt) δ ppm 2.78 (s, 3H), 2.98-3.12 (m, 1H), 3.13-3.40 (m, 6H), 3.42-3.75 (m, 1H), 7.09 (s, 1H), 7.62 (br s, 1H), 7.73 (s, 1H), 8.46 (s, 1H).

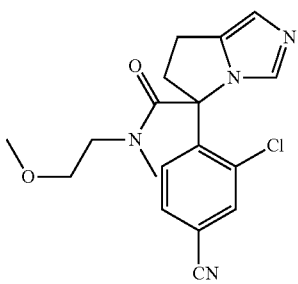 [SMILES: COCCN(C)C(=O)C1(c2ccc(C#N)cc2Cl)CCc2cncn21]

6) 5-(2-Chloro-4-cyanophenyl)-6,7-dihydro-5H-pyrrolo[1,2-c]imidazole-5-carboxylic acid (4-fluorobenzyl)methylamide. MS (ESI) m/z 409.2, 411.2 (M+H). MS (ESI) m/z 405.1 (M+H); ¹H NMR (400 MHz, CDCl₃) δ ppm 2.61 (br s, 3H), 2.64-2.86 (m, 2H), 2.98-3.10 (m, 1H), 3.97-4.12 (m, 1H), 4.37-4.51 (m, 1H), 4.68-4.84 (m, 1H), 6.63-6.77 (m, 1H), 6.91 (s, 1H), 7.01 (app t, J=8.6 Hz, 2H), 7.15-7.26 (m, 2H), 7.48-7.58 (m, 2H), 7.73 (br s, 1H).

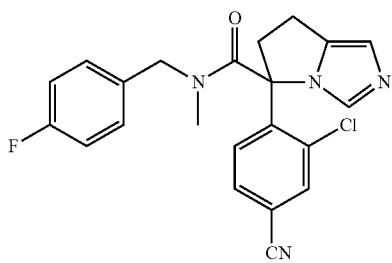 [SMILES: CN(Cc1ccc(F)cc1)C(=O)C1(c2ccc(C#N)cc2Cl)CCc2cncn21]

7) 5-(4-Cyano-2-methoxyphenyl)-6,7-dihydro-5H-pyrrolo[1,2-c]imidazole-5-carboxylic acid (2-fluorobenzyl)methylamide. MS (ESI) m/z 405.1 (M+H); ¹H NMR (400 MHz, CDCl₃) δ ppm 2.68 (br s, 3H), 2.72-2.92 (m, 2H), 3.00 (app dd, J=13.6, 7.8 Hz, 1H), 3.57-3.89 (m, 1H), 3.67 (s, 3H), 4.49-4.82 (m, 2H), 6.77 (s, 1H), 6.91 (br s, 1H), 6.99-7.18 (m, 3H), 7.18-7.32 (m, 2H), 7.43 (br s, 1H), 7.54 (br s, 1H).

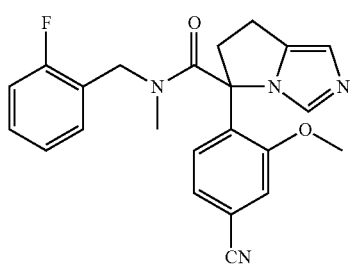 [SMILES: COc1cc(C#N)ccc1C1(C(=O)N(C)Cc2ccccc2F)CCc2cncn21]

8) 5-(4-Cyano-2-methoxyphenyl)-6,7-dihydro-5H-pyrrolo[1,2-c]imidazole-5-carboxylic acid (3-fluorobenzyl)methylamide. MS (ESI) m/z 405.1 (M+H); ¹H NMR (400 MHz, CDCl₃) δ ppm 2.63 (br s, 3H), 2.73-2.84 (m, 1H), 2.84-2.93 (m, 1H), 2.97-3.07 (m, 1H), 3.59-3.73 (m, 1H), 3.82 (br s, 3H), 4.44 (d, J=14.4 Hz, 1H), 4.76 (m, 1H), 6.80 (s, 1H), 6.92 (d, J=7.8 Hz, 1H), 6.96-7.07 (m, 2H), 7.10-7.17 (m, 1H), 7.19-7.35 (m, 3H), 7.58 (s, 1H).

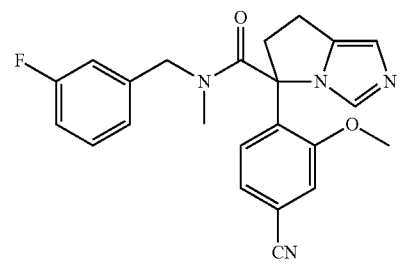 [SMILES: COc1cc(C#N)ccc1C1(C(=O)N(C)Cc2cccc(F)c2)CCc2cncn21]

9) 5-(2-Chloro-4-cyanophenyl)-6,7-dihydro-5H-pyrrolo[1,2-c]imidazole-5-carboxylic acid (4-methoxybenzyl)methylamide. MS (ESI) m/z 421.1, 423.1 (M+H); ¹H NMR (400 MHz, CDCl₃) δ ppm 2.57 (br s, 3H), 2.60-2.77 (m, 2H), 2.95-3.06 (m, 1H), 3.79 (s, 3H), 4.04-4.18 (m, 1H), 4.28-4.40 (m, 1H), 4.71-4.87 (m, 1H), 6.54-6.66 (m, 1H), 6.78-6.90 (m, 4H), 7.10-7.20 (m, 1H), 7.38-7.53 (m, 2H), 7.72 (br s, 1H). Resolution of the (R) and (S) enantiomers of the title compound is achieved by chiral HPLC using a ChiralPak IA column and CH₃CN to give enantiomer A (t$_r$=25.9 min) and enantiomer B (t$_r$=40.3 min).

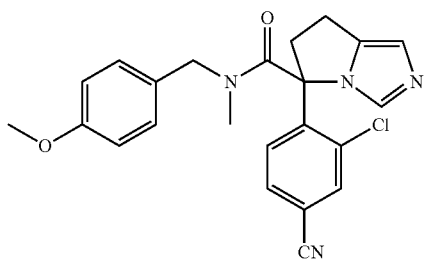 [SMILES: COc1ccc(CN(C)C(=O)C2(c3ccc(C#N)cc3Cl)CCc3cncn32)cc1]

10) 5-(2-Chloro-4-cyanophenyl)-6,7-dihydro-5H-pyrrolo[1,2-c]imidazole-5-carboxylic acid isobutylmethylamide. MS (ESI) m/z 357.1, 359.1 (M+H); ¹H NMR (400 MHz, CDCl₃) δ ppm 0.87-0.93 (m, 6H), 1.95-2.12 (m, 1H), 2.59-2.80 (m, 2H), 2.69 (s, 3H), 2.96-3.06 (m, 1H), 3.06-3.18 (m, 1H), 3.31-3.46 (m, 1H), 3.95-4.12 (m, 1H), 6.61-6.75 (m, 1H), 6.88 (s, 1H), 7.53 (dd, J=8.2, 1.6 Hz, 1H), 7.60 (br s, 1H), 7.75 (s, 1H).

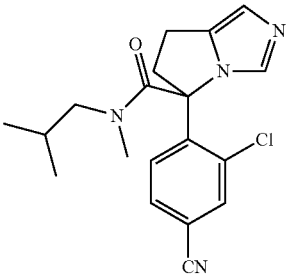 [SMILES: CC(C)CN(C)C(=O)C1(c2ccc(C#N)cc2Cl)CCc2cncn21]

11) 5-(2-Bromo-4-cyanophenyl)-6,7-dihydro-5H-pyrrolo[1,2-c]imidazole-5-carboxylic acid ethylamide. MS (ESI) m/z 359.0, 361.0 (M+H); ¹H NMR (400 MHz, CDCl₃) δ ppm 1.17 (t, J=7.2 Hz, 3H), 2.54-4.68 (m, 1H), 2.86 (ddd, J=13.4, 8.1, 2.5 Hz, 1H), 2.99 (ddd, J=15.5, 9.0, 1.8 Hz, 1H), 3.33-3.45 (m, 2H), 3.85-3.97 (m, 1H), 5.57 (app t, J=5.4 Hz, 1H), 6.60 (d, J=8.1 Hz, 1H), 6.86 (s, 1H), 7.53 (s, 1H), 7.57 (dd, J=8.2, 1.6 Hz, 1H), 7.96 (d, J=1.8 Hz, 1H).

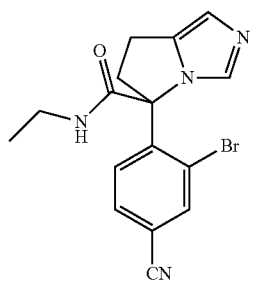 [SMILES: CCNC(=O)C1(c2ccc(C#N)cc2Br)CCc2cncn21]

12) 5-(2-Bromo-4-cyanophenyl)-6,7-dihydro-5H-pyrrolo[1,2-c]imidazole-5-carboxylic acid cyclohexylmethylamide. MS (ESI) m/z 427.2, 429.2 (M+H); $^1$H NMR (400 MHz, CDCl$_3$) δ ppm 0.80-0.97 (m, 2H), 1.06-1.29 (m, 3H), 1.44-1.58 (m, 1H), 1.57-1.76 (m, 5H), 2.56-2.70 (m, 1H), 2.83-2.94 (m, 1H), 2.94-3.03 (m, 1H), 3.08-3.25 (m, 2H), 3.83-3.96 (m, 1H), 5.63 (t, J=5.7 Hz, 1H), 6.63 (d, J=8.3 Hz, 1H), 6.85 (s, 1H), 7.49 (s, 1H), 7.57 (dd, J=8.2, 1.6 Hz, 1H), 7.96 (d, J=1.5 Hz, 1H).

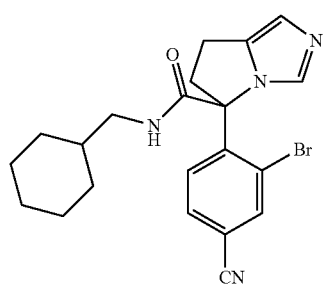 [SMILES: N#Cc1ccc(C2(C(=O)NCC3CCCCC3)CCc3cncn32)c(Br)c1]

13) 5-(2-Bromo-4-cyanophenyl)-6,7-dihydro-5H-pyrrolo[1,2-c]imidazole-5-carboxylic acid (2,2,2-trifluoroethyl)amide. MS (ESI) m/z 413.0, 415.0 (M+H); $^1$H NMR (400 MHz, CDCl$_3$) δ ppm 2.56-2.67 (m, 1H), 2.87 (ddd, J=13.3, 8.1, 2.5 Hz, 1H), 3.01 (ddd, J=15.9, 8.8, 1.6 Hz, 1H), 3.78-3.92 (m, 1H), 3.94-4.04 (m, 1H), 4.05-4.20 (m, 1H), 6.48 (d, J=8.3 Hz, 1H), 6.65 (s, 1H), 7.05 (br s, 1H), 7.41 (s, 1H), 7.48 (dd, J=8.1, 1.5 Hz, 1H), 7.94 (d, J=1.5 Hz, 1H).

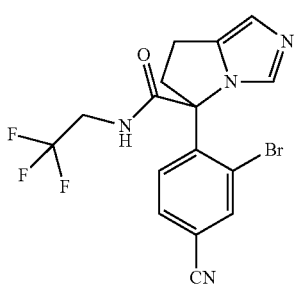 [SMILES: N#Cc1ccc(C2(C(=O)NCC(F)(F)F)CCc3cncn32)c(Br)c1]

14) 5-(2-Chloro-4-cyanophenyl)-6,7-dihydro-5H-pyrrolo[1,2-c]imidazole-5-carboxylic acid (2,2-dimethoxyethyl)amide. MS (ESI) m/z 375.1, 377.1 (M+H); $^1$H NMR (400 MHz, CDCl$_3$) δ ppm 2.57-2.70 (m, 1H), 2.81 (ddd, J=13.3, 8.0, 2.4 Hz, 1H), 2.95-3.05 (m, 1H), 3.30-3.36 (m, 1H), 3.36 (s, 3H), 3.38 (s, 3H), 3.58 (ddd, J=13.8, 6.4, 4.8 Hz, 1H), 3.84-3.94 (m, 1H), 4.39 (t, J=4.9 Hz, 1H), J=5.7 Hz, 1H), 6.63 (d, J=8.1 Hz, 1H), 6.85 (s, 1H), 7.54 (dd, J=8.1, 1.8 Hz, 1H), 7.64 (s, 1H), 7.76 (d, J=1.5 Hz, 1H).

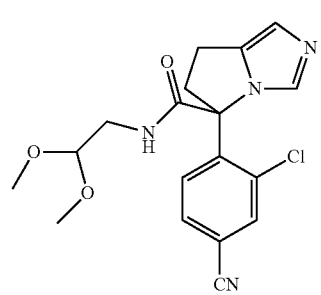 [SMILES: COC(CNC(=O)C1(c2ccc(C#N)cc2Cl)CCc2cncn21)OC]

15) 5-(2-Chloro-4-cyanophenyl)-6,7-dihydro-5H-pyrrolo[1,2-c]imidazole-5-carboxylic acid (2-hydroxyethyl)amide. MS (ESI) m/z 331.2, 333.2 (M+H); $^1$H NMR (400 MHz, DMSO-d$_6$) δ ppm 2.52-2.62 (m, 1H), 2.88 (dd, J=13.8, 8.7 Hz, 1H), 3.05-3.15 (m, 1H), 3.21-3.30 (m, 1H), 3.34-3.49 (m, 2H), 3.71-3.84 (m, 1H), 4.64 (t, J=5.3 Hz, 2H), 6.45 (d, J=8.1 Hz, 1H), 6.74 (s, 1H), 7.64 (s, 1H), 7.85 (dd, J=8.2, 1.6 Hz, 1H), 8.02 (t, J=5.6 Hz, 1H), 8.16 (d, J=1.5 Hz, 1H).

16) 5-(2-Chloro-4-cyanophenyl)-6,7-dihydro-5H-pyrrolo[1,2-c]imidazole-5-carboxylic acid amide. MS (ESI) m/z 287.3, 289.3 (M+H); $^1$H NMR (400 MHz, DMSO-d$_6$) δ ppm 2.53-2.66 (m, 2H), 2.84-2.94 (m, 1H), 3.69-3.78 (m, 1H), 6.53 (d, J=8.1 Hz, 1H), 6.74 (s; 1H), 7.57 (s, 1H), 7.64 (s, 1H), 7.71 (s, 1H), 7.84 (dd, J=8.2, 1.6 Hz, 1H), 8.17 (d, J=1.5 Hz, 1H).

17) 3-Chloro-4-[5-(piperidine-1-carbonyl)-6,7-dihydro-5H-pyrrolo[1,2-c]imidazol-5-yl]benzonitrile. MS (ESI) m/z 355.3, 357.3 (M+H); $^1$H NMR (400 MHz, CDCl$_3$) δ ppm 1.20 (br s, 2H), 1.60 (br s, 4H), 2.58-2.75 (m, 2H), 2.96-3.07 (m, 1H), 3.13-3.42 (m, 3H), 3.84-4.02 (m, 1H), 3.99-4.12 (m, 1H), 6.71 (d, J=7.8 Hz, 1H), 6.87 (s, 1H), 7.54 (dd, J=8.2, 1.6 Hz, 1H), 7.56 (s, 1H), 7.76 (d, J=1.5 Hz, 1H).

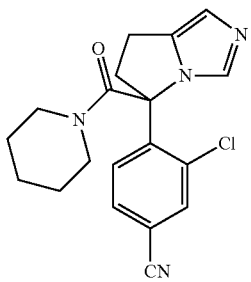 [SMILES: N#Cc1ccc(C2(C(=O)N3CCCCC3)CCc3cncn32)c(Cl)c1]

18) 3-Methoxy-4-[5-(piperidine-1-carbonyl)-6,7-dihydro-5H-pyrrolo[1,2-c]imidazol-5-yl]benzonitrile. MS (ESI) m/z 351.1 (M+H); $^1$H NMR (400 MHz, CDCl$_3$) δ ppm 1.58 (br s, 4H), 1.88 (br s, 2H), 2.72-2.89 (m, 2H), 2.95-3.06 (m, 1H), 3.32 (br s, 4H), 3.59-3.74 (m, 1H), 3.92 (s, 3H), 6.77 (s, 1H), 6.87-6.99 (m, 1H), 7.19 (d, J=1.5 Hz, 1H), 7.24-7.30 (m, 1H), 7.54 (s, 1H).

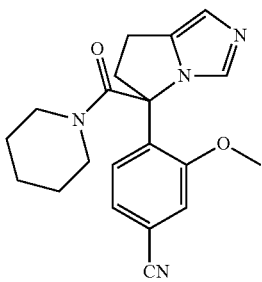 [SMILES: COc1cc(C#N)ccc1C1(C(=O)N2CCCCC2)CCc2cncn21]

19) 5-(2-Chloro-4-cyanophenyl)-6,7-dihydro-5H-pyrrolo[1,2-c]imidazole-5-carboxylic acid cyclohexylmethylamide. MS (ESI) m/z 383.3, 385.3 (M+H); $^1$H NMR (400 MHz, CDCl$_3$) δ ppm 1.24-1.86 (m, 10H), 2.54 (s, 3H), 2.56-2.78 (m, 2H), 2.93-3.11 (m, 1H), 3.15-3.32 (m, 1H), 3.98-4.16 (m, 1H), 6.63 (d, J=8.1 Hz, 1H), 6.86 (s, 1H), 7.44-7.60 (m, 2H), 7.74 (s, 1H).

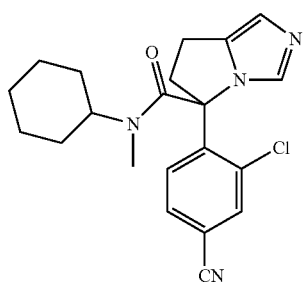 [SMILES: CN(C(=O)C1(c2ccc(C#N)cc2Cl)CCc2cncn21)C1CCCCC1]

20) 5-(2-Chloro-4-cyanophenyl)-6,7-dihydro-5H-pyrrolo[1,2-c]imidazole-5-carboxylic acid methylphenethylamide. MS (ESI) m/z 405.3, 407.3 (M+H); $^1$H NMR (400 MHz, CDCl$_3$) δ ppm 2.56 (br s, 3H), 2.60-2.76 (m, 2H), 2.79-3.25 (m, 3H), 3.55 (d, J=10.4 Hz, 1H), 3.67-3.83 (m, 1H), 3.98-4.13 (m, 1H), 6.62 (d, J=7.8 Hz, 1H), 6.88 (s, 1H), 7.13-7.36 (m, 5H), 7.44 (br s, 1H), 7.50 (d, J=7.8. Hz, 1H), 7.76 (br s, 1H).

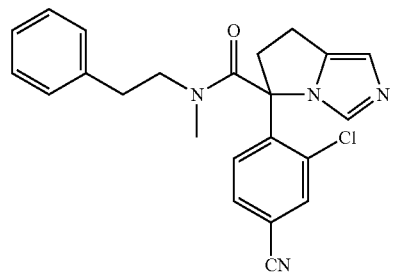 [SMILES: CN(CCc1ccccc1)C(=O)C1(c2ccc(C#N)cc2Cl)CCc2cncn21]

21) 5-(4-Cyano-2-methoxyphenyl)-6,7-dihydro-5H-pyrrolo[1,2-c]imidazole-5-carboxylic acid (3-methoxybenzyl)methylamide. MS (ESI) m/z 417.4 (M+H); $^1$H NMR (400 MHz, CDCl$_3$) δ ppm 2.62 (br s, 3H), 2.76-2.88 (m, 1H), 2.88-2.99 (m, 1H), 2.98-3.09 (m, 1H), 3.58-3.73 (m, 1H), 3.80 (s, 3H), 3.82 (br s, 3H), 4.43-4.72 (m, 2H), 6.75-6.89 (m, 4H), 6.95 (d, J=7.6 Hz, 1H), 7.10-7.19 (m, 1H), 7.24 (d, J=9.9 Hz, 2H), 7.62 (br s, 1H).

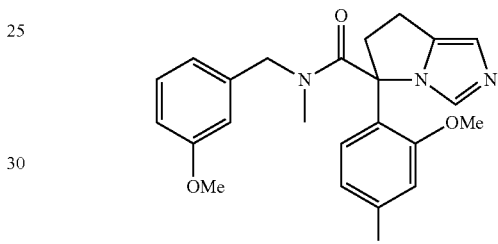

22) 5-(4-Cyano-2-methoxyphenyl)-6,7-dihydro-5H-pyrrolo[1,2-c]imidazole-5-carboxylic acid (4-methoxybenzyl)methylamide. MS (ESI) m/z 417.1 (M+H); $^1$H NMR (400 MHz, CDCl$_3$) δ ppm 2.59 (br s, 3H), 2.71-2.92 (m, 2H), 2.94-3.06 (m, 1H), 3.58-3.70 (m, 1H), 3.75 (br s, 3H), 3.80 (s, 3H), 4.36-4.48 (m, 1H), 4.54-4.72 (m, 1H), 6.78 (s, 1H), 6.81-6.95 (m, 3H), 7.11 (br s, 1H), 7.14-7.27 (m, 3H), 7.53 (br s, 1H). Resolution of the (R) and (S) enantiomers of the title compound is achieved by chiral HPLC using ChiralPak AS-H column with a 3:7 EtOH/Heptane mobile phase to give enantiomer A (t$_r$=28.9 min) and enantiomer 8 (t$_r$=92.3 min).

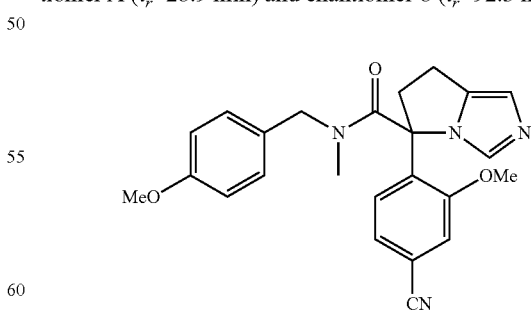

23) 5-(4-Cyano-2-methoxyphenyl)-6,7-dihydro-5H-pyrrolo[1,2-c]imidazole-5-carboxylic acid (2-methoxybenzyl)methylamide. MS (ESI) m/z 417.1 (M+H);

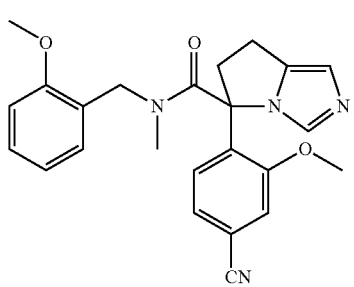 [SMILES: COc1ccccc1CN(C)C(=O)C1(c2ccc(C#N)cc2OC)CCc2cncn21]

B. 1,2,6',7'-Tetrahydro-2-oxo-1-(2,2,2-trifluoroethyl)spiro[3H-indole-3,5'-[5H]pyrrolo[1,2-c]imidazole]-6-carbonitrile

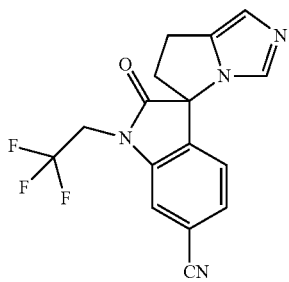 [SMILES: N#Cc1ccc2c(c1)N(CC(F)(F)F)C(=O)C21CCc2cncn21]

A suspension of 5-(2-Bromo-4-cyanophenyl)-6,7-dihydro-5H-pyrrolo[1,2-c]imidazole-5-carboxylic acid (2,2,2-trifluoroethyl)amide (0.168 g, 0.405 mmol), given in example 9, CuI (0.004 g, 0.021 mmol), N,N'-dimethylethylene diamine (0.005 mL, 0.042 mmol), Cs$_2$CO$_3$ (0.198 g, 0.609 mmol), and THF (15 mL) is heated to 110° C. for 60 h. The mixture is then filtered and concentrated. The residue is purified via flash chromatography (EtOAc/hexanes) to give 1,2,6',7'-Tetrahydro-2-oxo-1-(2,2,2-trifluoroethyl)spiro[3H-indole-3,5'-[5H]pyrrolo[1,2-c]imidazole]-6-carbonitrile. MS (ESI) m/z 333.1 (M+H); $^1$H NMR (400 MHz, CDCl$_3$) δ ppm 2.85-2.96 (m, 1H), 3.03-3.18 (m, 2H), 3.27-3.39 (m, 1H), 4.20-4.34 (m, 1H), 4.43-4.57 (m, 1H), 6.86 (s, 1H), 7.04 (s, 1H), 7.30 (s, 1H), 7.35 (d, J=7.8 Hz, 1H), 7.52 (dd, J=7.6, 1.3 Hz, 1H).

Similarly prepared are the following:

1) 1-(Cyclohexylmethyl)-1,2,6',7'-tetrahydro-2-oxospiro[3H-indole-3,5'-[5H]pyrrolo[1,2-c]imidazole]-6-carbonitrile. MS (ESI) m/z 347.1 (M+H); $^1$H NMR (400 MHz, CDCl$_3$) δ ppm 0.99-1.14 (m, 2H), 1.21 (d, J=9.3 Hz, 2H), 1.61-1.72 (m, 4H), 1.73-1.89 (m, 3H), 2.79-2.91 (m, 1H), 2.99-3.15 (m, 2H), 3.27-3.37 (m, 1H), 3.58 (dd, J=7.5, 2.7 Hz, 2H), 6.84 (s, 1H), 7.02 (s, 1H), 7.16 (d, J=0.8 Hz, 1H), 7.28 (d, J=7.6 Hz, 1H), 7.42 (d, J=7.7, 1.4 Hz, 1H).

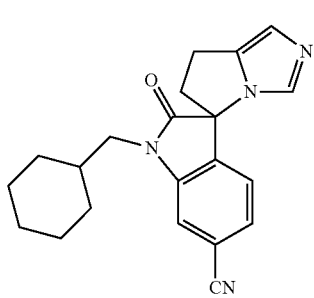 [SMILES: N#Cc1ccc2c(c1)N(CC1CCCCC1)C(=O)C21CCc2cncn21]

2) 1-Ethyl-1,2,6',7'-tetrahydro-2-oxospiro[3H-indole-3,5'-[5H]pyrrolo[1,2-c]imidazole]-6-carbonitrile. MS (ESI) m/z 279.1 (M+H); $^1$H NMR (400 MHz, CDCl$_3$) δ ppm 1.34 (t, J=7.3 Hz, 3H), 2.77-2.89 (m, 1H), 2.99-3.15 (m, 2H), 3.27-338 (m, 1H), 3.73-3.90 (m, 2H), 6.85 (s, 1H), 7.06 (s, 1H), 7.19 (s, 1H), 7.29 (d, J=7.6 Hz, 1H), 7.43 (dd, J=7.6, 1.3 Hz, 1H).

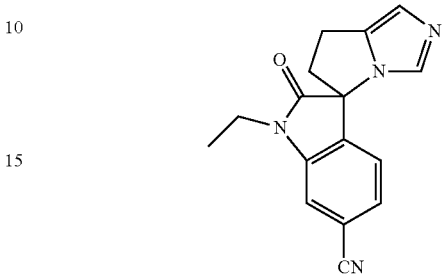

Example 10

5-(4-Ethoxycarbonyl-2-fluorophenyl)-6,7-dihydro-5H-pyrrolo[1,2-c]imidazole-5-carboxylic acid

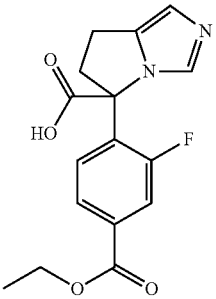 [SMILES: CCOC(=O)c1ccc(C2(C(=O)O)CCc3cncn32)c(F)c1]

To a solution of 5-(4-cyano-2-fluorophenyl)-6,7-dihydro-5H-pyrrolo[1,2-c]imidazole-5-carboxylic acid methyl ester (0.250 g, 0.877 mmol) in THF/EtOH (2:1, 21 mL) is added an aqueous solution of LiOH (0.88 mL, 2 M) is added. After 2.5 h the solution is concentrated and the resulting residue is purified by HPLC (2-23% MeCN/water containing 0.1% TFA). The title compound, 5-(4-ethoxycarbonyl-2-fluorophenyl)-6,7-dihydro-5H-pyrrolo[1,2-c]imidazole-5-carboxylic acid, is isolated as a minor product. MS (ESI) m/z 319.0 (M+H).

Example 11

4-(5-Hydroxymethyl-6,7-dihydro-5H-pyrrolo[1,2-c]imidazol-5-yl)-3-methoxybenzonitrile

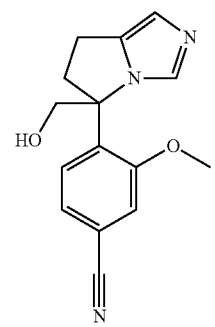 [SMILES: COc1cc(C#N)ccc1C1(CO)CCc2cncn21]

5-(4-Cyano-2-methoxyphenyl)-6,7-dihydro-5H-pyrrolo [1,2-c]imidazole-5-carboxylic acid methyl ester (0.100 g, 0.336 mmol) is dissolved in THF (3 mL) and cooled to −10° C. A THF solution of lithium borohydride (0.08 mL, 2 M) is then added. The solution is removed from the cold bath and allowed to warm to room temperature before being heated to 40° C. at which time additional lithium borohydride (0.08 mL, 2 M) is added. The solution is maintained at that temperature for 1.5 h before being allowed to cool to room temperature and being quenched by the addition of 1 M HCl. Following aqueous workup the residue is warmed to 80° C. in ethanolamine/CH$_3$CN (1:3) for 1 h. The solution is then concentrated and the residue purified via prep HPLC (reversed phase; 5-100% CH$_3$CN/H$_2$O and 0.1% TFA). Conversion to the free base provided 4-(5-hydroxymethyl-6,7-dihydro-5H-pyrrolo[1,2-c]imidazol-5-yl)-3-methoxybenzonitrile as a white solid. MS (ESI) m/z 270.1 (M+H); $^1$H NMR (400 MHz, CDCl$_3$) δ ppm 2.55-2.67 (m, 1H), 2.78-2.96 (m, 3H), 3.91 (s, 3H), 4.10 (d, J=11.6 Hz, 1H), 4.46 (d, J=11.6 Hz, 1H), 6.57 (d, J=8.3 Hz, 1H), 6.73 (s, 1H), 7.13-7.18 (obs m, 1H), 7.16 (s, 1H), 7.52 (s, 1H).

Example 12

A. 3-[3-(2-Bromobenzyl)-3H-imidazol-4-yl]propionic acid methyl ester

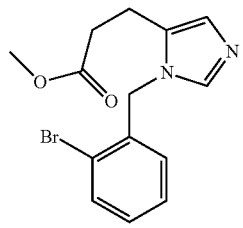 [SMILES: COC(=O)CCc1cncn1Cc1ccccc1Br]

To a solution of 3-(1-trityl-1H-imidazol-4-yl)propanoic acid methyl ester (5.0 g, 12.6 mmol) in CH$_3$CN (80 mL) is added a solution of 2-bromobenzylbromide (2.84 g, 11.4 mmol) in CH$_3$CN (20 mL). The resulting clear solution is stirred at ambient temperature over the weekend. The mixture is concentrated and the remaining oil is taken up in 85 mL methanol and heated up at 70° C. for 2 h. Then the mixture is concentrated to give a yellow oil, which is taken up in EtOAc and washed with saturated aqueous NaHCO$_3$ and brine, dried over anhydrous Na$_2$SO$_4$, and concentrated to yield a viscous oil. The crude reaction mixture is subjected to flash chromatography (silica gel) eluting with MeOH:CH$_2$Cl$_2$ to give the desired compound. MS (ESI) m/z 323 (M+H).

B. 3-[3-(2-Bromobenzyl)-3H-imidazol-4-yl]propan-1-ol

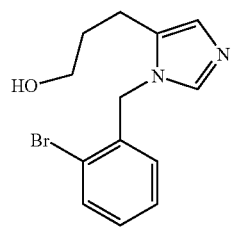 [SMILES: OCCCc1cncn1Cc1ccccc1Br]

To a solution of 3-[3-(2-bromobenzyl)-3H-imidazol-4-yl] propionic acid methyl ester (1.89 g, 5.85 mmol) in MeOH at 0° C. is added NaBH$_4$ and the resulting mixture is stirred at 0° C. for 1 h and warmed up to ambient temperature. The mixture is stirred at ambient temperature for 3 h and is quenched with saturated aqueous NH$_4$Cl, and is adjusted pH to 7 with saturated aqueous Na$_2$CO$_3$. Then the reaction mixture is concentrated and extracted by CH$_2$Cl$_2$. The organic layer is washed with half saturated aqueous NaCl, dried over anhydrous Na$_2$SO$_4$, and concentrated to yield a white solid. MS (ESI) m/z 295 (M+H).

C. 1-(2-Bromobenzyl)-5-(3-chloropropyl)-1H-imidazole

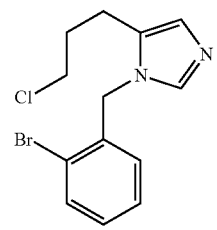 [SMILES: ClCCCc1cncn1Cc1ccccc1Br]

To a solution of SOCl$_2$ (0.55 mL, 7.54 mmol) in CH$_2$Cl$_2$ (15 mL) at 0° C. is added 3-[3-(2-bromobenzyl)-3H-imidazol-4-yl]propan-1-ol in portion and the resulting white suspension is refluxed for 1.5 h. The mixture is cooled with ice and collected to give a buff-colored solid, which is partitioned between CH$_2$Cl$_2$ and saturated aqueous NaHCO$_3$. The organic layer is washed with brine, dried over anhydrous Na$_2$SO$_4$, and concentrated to give an oil. MS (ESI) m/z 313 (M+H).

D. 5-(2-Bromophenyl)-5,6,7,8,-tetrahydro-imidazo [1,5-a]pyridine

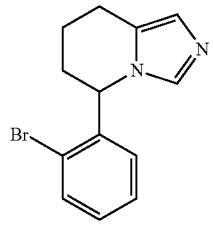 [SMILES: Brc1ccccc1C1CCCc2cncn21]

To a slurry of 1-(2-bromobenzyl)-5-(3-chloropropyl)-1H-imidazole (0.662 g, 2.12 mmol) and TMEDA (0.683 mL, 4.55 mmol) in THF (10 mL) at −78° C. is added LDA (1.8 M in heptane/THF/ethylbenzene, 2.5 mL, 4.5 mmol) and the yellow clear solution is stirred at −78° C. After 3.5 hr, the reaction is quenched by saturated aqueous NH$_4$Cl, and the mixture is partitioned between EtOAc and saturated aqueous NaHCO$_3$. The organic layer is washed with brine, dried and concentrated to give an oil, which is subjected to flash chromatography (silica gel) eluting with MeOH:CH$_2$Cl$_2$ to yield the desired compound. MS (ESI) m/z 277 (M+H).

Similarly prepared is:
5-(4-Bromophenyl)-5,6,7,8-tetrahydro-imidazo[1,5-a]pyridine. MS (ESI) m/z 277 (M+H).

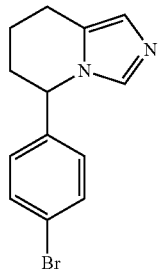 [SMILES: Brc1ccc(C2CCCc3cncn32)cc1]

The following compound is prepared in a similar fashion using LHMDS (1.0 M in THF) as base instead of LDA for the cyclization: 5-(2-Bromo-4-fluorophenyl)-5,6,7,8-tetrahydro-imidazo[1,5-a]pyridine. MS (ESI) m/z 295 (M+H).

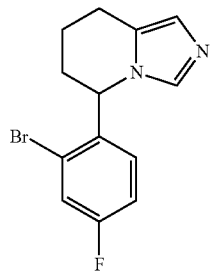 [SMILES: Fc1ccc(C2CCCc3cncn32)c(Br)c1]

From the material outlined in Example 2J above, the procedure above gave the cyclized material: 5-(2-Bromophenyl)-8-methyl-5,6,7,8-tetrahydro-imidazo[1,5-a]pyridine. MS (ESI) m/z 291 (M+H).

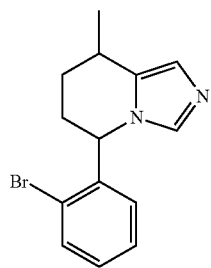 [SMILES: CC1CCC(c2ccccc2Br)n2cncc21]

Example 13

A. 5-(2-Thiophen-2-yl-phenyl)-5,6,7,8-tetrahydro-imidazo[1,5-a]pyridine

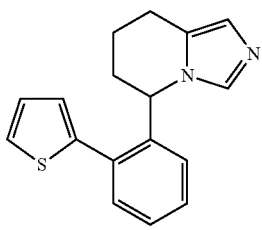 [SMILES: c1csc(-c2ccccc2C2CCCc3cncn32)c1]

To a solution of 5-(2-bromophenyl)-5,6,7,8,-tetrahydroimidazo[1,5-a]pyridine, Example 12D (120 mg, 0.43 mmol) in DME (2 mL) is added thiophene-2-boronic acid (166 mg, 1.3 mmol), aqueous $Na_2CO_3$ (2M, 1.0 mL, 2.0 mmol), and $Pd(PPh_3)_4$ (20 mg). The reaction mixture is refluxed overnight. The mixture is partitioned between EtOAc and 1M NaOH. The organic layer is washed by sat. $NaHCO_3$, dried and concentrated to give an oil. The crude reaction mixture is subjected to flash chromatography (silica gel) eluting with acetone:hexane to yield the desired compound. MS (ESI) m/z 280 (M+H); $^1$H NMR (400 MHz, $CDCl_3$) δ ppm 1.58-1.74 (m, 1H), 1.85-2.01 (m, 2H), 2.14-2.27 (m, 1H), 2.74-2.94 (m, 2H), 5.45 (dd, J=8.6, 5.1 Hz, 1H), 6.81 (s, 1H), 7.00-7.05 (m, 2H), 7.06 (s, 1H), 7.10 (dd, J=5.3, 3.5 Hz, 1H), 7.31-7.37 (m, 2H), 7.39 (dd, J=5.2, 1.1 Hz, 1H), 7.41-7.46 (m, 1H).

B. 5-(2-Thiophen-3-yl-phenyl)-5,6,7,8-tetrahydroimidazo[1,5-a]pyridine

Thereafter, in a similar fashion, is also prepared the following compound except for the Suzuki coupling procedure:

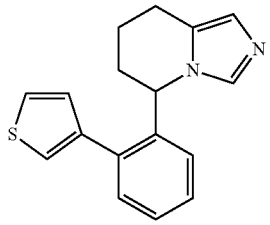 [SMILES: c1ccc(C2CCCc3cncn32)c(-c2ccsc2)c1]

To a solution of 5-(2-bromophenyl)-5,6,7,8,-tetrahydroimidazo[1,5-a]pyridine (95 mg, 0.343 mmol) in DME (2 mL) is added thiophene-3-boronic acid (53 mg, 0.414 mmol), aqueous $Na_2CO_3$ (2M, 0.5 mL, 1.0 mmol), and $Pd(PPh_3)_4$ (20 mg). The reaction mixture is run under microwave irradiation at 120° C. for 20 min. The mixture is partitioned between EtOAc and brine. The organic layer is washed by brine, dried over $Na_2SO_4$ and concentrated to give an oil. The crude reaction mixture is subjected to flash chromatography eluting with acetone:hexane to yield the desired compound. MS (ESI) m/z 280 (M+H).

Similarly prepared are the following:
1) 5-Biphenyl-2-yl-5,6,7,8-tetrahydroimidazo[1,5-a]pyridine. MS (ESI) m/z 275 (M+H).

2) 5-(2-Furan-2-yl-phenyl)-5,6,7,8-tetrahydroimidazo[1,5-a]pyridine. MS (ESI) m/z 264 (M+H).

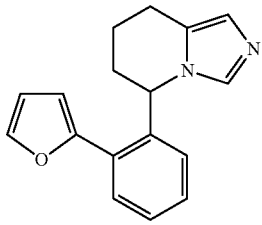 [SMILES: c1coc(-c2ccccc2C2CCCc3cncn32)c1]

The following compounds are prepared in a similar fashion except using PS-PPh$_3$-Pd(0) resin instead of Pd(PPh$_3$)$_4$ for the Suzuki coupling reaction:

3) 5-(4'-Fluorobiphenyl-2-yl)-5,6,7,8-tetrahydroimidazo[1,5-a]pyridine. MS (ESI) m/z 293 (M+H); $^1$H NMR (400 MHz, MeOD) δ ppm 1.55-1.76 (m, 1H), 1.86-2.07 (m, 2H), 2.06-2.26 (m, 1H), 2.68-3.01 (m, 2H), 5.32 (dd, J=8.6, 5.1 Hz, 1H), 6.78 (s, 1H), 6.99-7.09 (m, 1H), 7.17-7.29 (m, 3H), 7.29-7.38 (m, 1H), 7.38-7.51 (m, 4H).

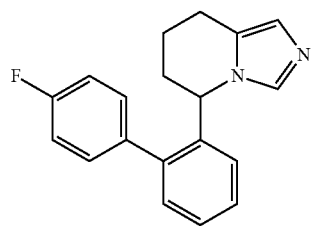 [SMILES: Fc1ccc(-c2ccccc2C2CCCc3cncn32)cc1]

Similarly, following the same Suzuki coupling procedure is prepared:

4) 5-(4'-Trifluoromethylbiphenyl-2-yl)-5,6,7,8-tetrahydroimidazo[1,5-a]pyridine. MS (ESI) m/z 343 (M+H).

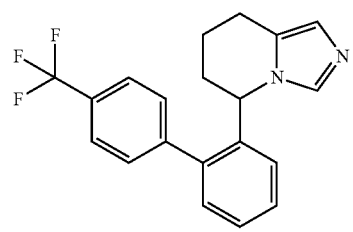 [SMILES: FC(F)(F)c1ccc(-c2ccccc2C2CCCc3cncn32)cc1]

5) 5-(4'-Methoxybiphenyl-2-yl)-5,6,7,8-tetrahydroimidazo[1,5-a]pyridine. MS (ESI) m/z 305 (M+H).

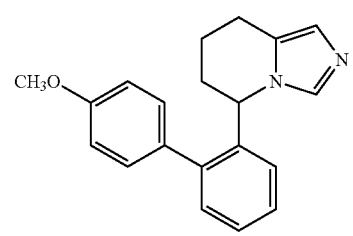

6) 5-(2'-Chlorobiphenyl-2-yl)-5,6,7,8-tetrahydroimidazo[1,5-a]pyridine. MS (ESI) m/z 309, 311 (M+H).

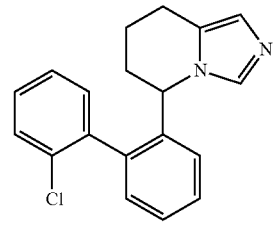 [SMILES: Clc1ccccc1-c1ccccc1C1CCCc2cncn21]

7) 5-(3'-Chlorobiphenyl-2-yl)-5,6,7,8-tetrahydroimidazo[1,5-a]pyridine. MS (ESI) m/z 309, 311 (M+H); $^1$H NMR (400 MHz, MeOD) δ ppm 1.47-1.74 (m, 1H), 1.84-2.03 (m, 2H), 2.08-2.23 (m, 1H), 2.71-2.99 (m, 2H), 5.30 (dd, J=8.6, 5.3 Hz, 1H), 6.78 (s, 1H), 7.00-7.10 (m, 1H), 7.24 (s, 1H), 7.27-7.39 (m, 2H), 7.41-7.47 (m, 3H), 7.47-7.53 (m, 2H).

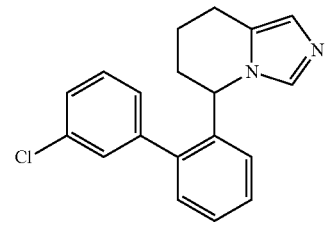 [SMILES: Clc1cccc(-c2ccccc2C2CCCc3cncn32)c1]

8) 5-(4'-Chlorobiphenyl-2-yl)-5,6,7,8-tetrahydro-imidazo[1,5-a]pyridine. MS (ESI) m/z 309, 311 (M+H); $^1$H NMR (400 MHz, MeOD) δ ppm 1.51-1.70 (m, 1H), 1.81-2.01 (m, 2H), 2.03-2.21 (m, 1H), 2.66-2.96 (m, 2H), 5.29 (dd, J=8.5, 5.2 Hz, 1H), 6.75 (s, 1H), 6.95-7.07 (m, 1H), 7.19 (s, 1H), 7.25-7.32 (m, 1H), 7.34-7.44 (m, 4H), 7.44-7.54 (m, 2H).

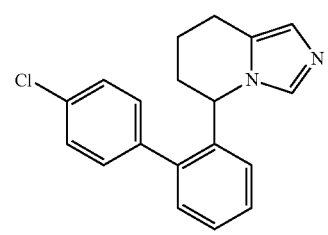 [SMILES: Clc1ccc(-c2ccccc2C2CCCc3cncn32)cc1]

9) 5-(3',5'-Dichlorobiphenyl-2-yl)-5,6,7,8-tetrahydroimidazo[1,5-a]pyridine. MS (ESI) m/z 343, 345, 347 (M+H).

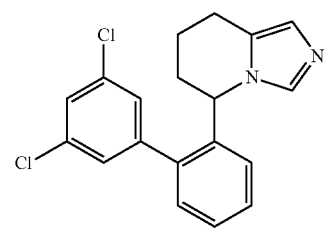 [SMILES: Clc1cc(Cl)cc(-c2ccccc2C2CCCc3cncn32)c1]

10) 5-(3',5'-Difluorobiphenyl-2-yl)-5,6,7,8-tetrahydroimidazo[1,5-a]pyridine. MS (ESI) m/z 311 (M+H); $^1$H NMR (400 MHz, CDCl$_3$) δ ppm 1.49-1.70 (m, 1H), 1.76-1.90 (m, 1H), 1.90-2.00 (m, 1H), 2.02-2.16 (m, 1H), 2.68-2.83 (m, 1H), 2.88 (dt, J=16.2, 5.1 Hz, 1H), 5.15 (dd, J=9.1, 5.1 Hz, 1H), 6.81 (s, 1H), 6.82-6.91 (m, 3H), 7.05 (s, 1H), 7.06-7.10 (m, 1H), 7.20-7.26 (m, 1H), 7.32-7.41 (m, 2H).

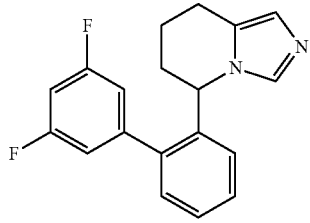 [SMILES: Fc1cc(F)cc(-c2ccccc2C2CCCc3cncn32)c1]

11) 5-(3',5'-Dimethylbiphenyl-2-yl)-5,6,7,8-tetrahydroimidazo[1,5-a]pyridine. MS (ESI) m/z 303 (M+H).

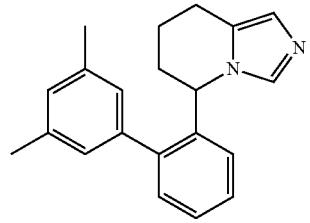 [SMILES: Cc1cc(C)cc(-c2ccccc2C2CCCc3cncn32)c1]

12) 5-(3'-Chloro-4'-fluorobiphenyl-2-yl)-5,6,7,8-tetrahydroimidazo[1,5-a]pyridine. MS (ESI) m/z 327, 329 (M+H).

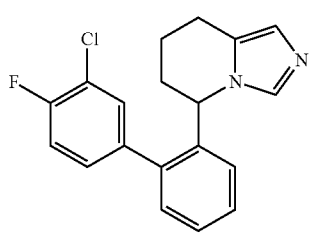 [SMILES: Fc1ccc(-c2ccccc2C2CCCc3cncn32)cc1Cl]

13) 5-(3',4'-Dichlorobiphenyl-2-yl)-5,6,7,8-tetrahydroimidezo[1,5-a]pyridine. MS (ESI) m/z 343, 345, 347 (M+H).

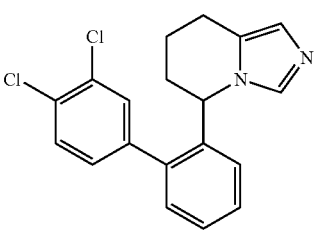 [SMILES: Clc1ccc(-c2ccccc2C2CCCc3cncn32)cc1Cl]

14) 5-(4'-Isopropylbiphenyl-2-yl)-5,6,7,8-tetrahydroimidazo[1,5,-a]pyridine. MS (ESI) m/z 317 (M+H).

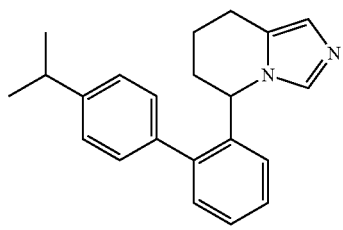 [SMILES: CC(C)c1ccc(-c2ccccc2C2CCCc3cncn32)cc1]

15) 5-(2'-Fluorobiphenyl-2-yl)-5,6,7,8-tetrahydroimidazo[1,5-a]pyridine. MS (ESI) m/z 293 (M+H).

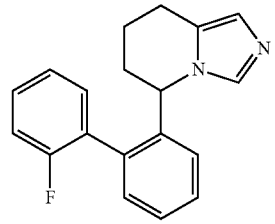

16) 5-(2'-Methoxybiphenyl-2-yl)-5,6,7,8-tetrahydroimidazo[1,5-a]pyridine. MS (ESI) m/z 305 (M+H).

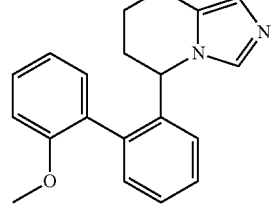

17) N,N-Dimethyl-[2'-(5,6,7,8-tetrahydroimidazo[1,5-a]pyridin-5-yl)-biphenyl-4-yl]amine. MS (ESI) m/z 318 (M+H).

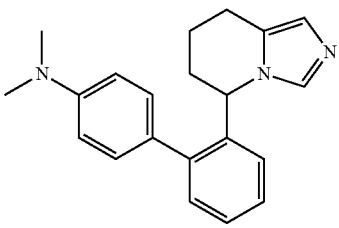 [SMILES: CN(C)c1ccc(-c2ccccc2C2CCCc3cncn32)cc1]

18) 5-(2'-Trifluoromethylbiphenyl-2-yl)-5,6,7,8-tetrahydroimidazo[1,5-a]pyridine. MS (ESI) m/z 343 (M+H).

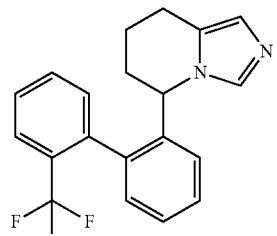

19) 5-(2'-Methylbiphenyl-2-yl)-5,6,7,8-tetrahydroimidazo[1,5-a]pyridine. MS (ESI) m/z 289 (M+H).

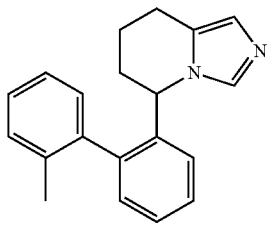

20) 5-(2'-Ethoxybiphenyl-2-yl)-5,6,7,8-tetrahydroimidazo[1,5-a]pyridine. MS (ESI) m/z 319 (M+H).

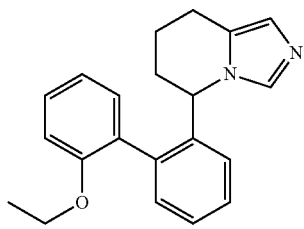 [SMILES: CCOc1ccccc1-c1ccccc1C1CCCc2cncn21]

21) 5-(2'-Methoxymethyl-biphenyl-2-yl)-5,6,7,8-tetrahydroimidazo[1,5-a]pyridine. MS (ESI) m/z 319 (M+H).

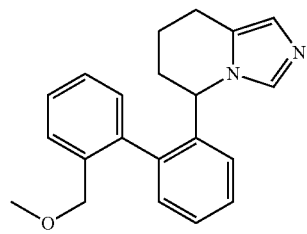 [SMILES: COCc1ccccc1-c1ccccc1C1CCCc2cncn21]

By analogy to the compounds described above the following are prepared from 5-(2-Bromo-4-fluorophenyl)-5,6,7,8-tetrahydro-imidazo[1,5-a]pyridine, given as example 12D:

1) 5-(5-Fluorobiphenyl-2-yl)-5,6,7,8-tetrahydroimidazo[1,5-a]pyridine. MS (ESI) m/z 293 (M+H). Resolution of the (R) and (S) enantiomers of the title compound is achieved by chiral HPLC using the ChiralPak AD column with a IPA/hexanes mobile phase to give enantiomer A and enantiomer B. For enantiomer B: $^1$H NMR (400 MHz, CDCl$_3$) δ ppm 1.42-1.67 (m, 1H), 1.76-1.88 (m, 1H), 1.88-1.97 (m, 1H), 2.01-2.13 (m, 1H), 2.65-2.80 (m, 1H), 2.86 (dt, J=15.9, 5.1 Hz, 1H), 5.13 (dd, J=9.5, 4.9 Hz, 1H), 6.78 (s, 1H), 6.97-7.02 (m, 1H), 7.02-7.10 (m, 3H), 7.28-7.36 (m, 2H), 7.36-7.49 (m, 3H).

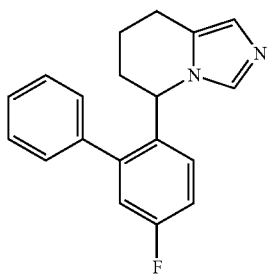 [SMILES: Fc1ccc(C2CCCc3cncn32)c(-c2ccccc2)c1]

2) 5-(5,4'-Difluorobiphenyl-2-yl)-5,6,7,8-tetrahydroimidazo[1,5-a]pyridine. MS (ESI) m/z 311 (M+H); $^1$H NMR (400 MHz, CDCl$_3$) δ ppm 1.33-1.60 (m, 1H), 1.66-1.79 (m, 1H), 1.79-1.91 (m, 1H), 1.90-2.03 (m, 1H), 2.60-2.73 (m, 1H), 2.79 (dt, J=16.2, 4.6 Hz, 1H), 5.01 (dd, J=9.6, 4.8 Hz, 1H), 6.72 (s, 1H), 6.89 (dt, J=9.1, 1.5 Hz, 1H), 6.92-7.00 (m, 3H), 7.01-7.13 (m, 2H), 7.16-7.24 (m, 2H).

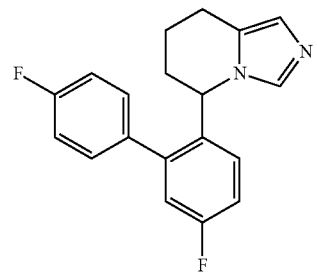 [SMILES: Fc1ccc(-c2cc(F)ccc2C2CCCc3cncn32)cc1]

3) 5-(5,2'-Difluorobiphenyl-2-yl)-5,6,7,8-tetrahydroimidazo[1,5-a]pyridine. MS (ESI) m/z 311 (M+H).

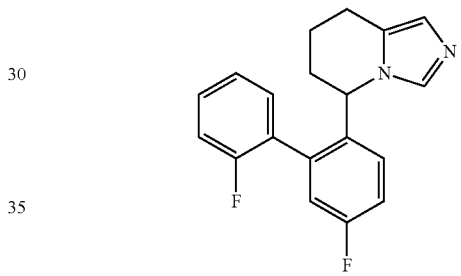

4) 5-(2'-Chloro-5-fluorobiphenyl-2-yl)-5,6,7,8-tetrahydroimidazo[1,5-a]pyridine. MS (ESI) m/z 327 (M+H).

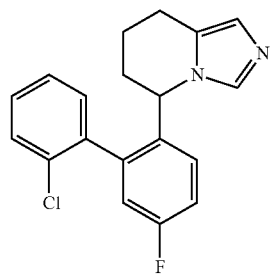 [SMILES: Fc1ccc(C2CCCc3cncn32)c(-c2ccccc2Cl)c1]

5) 5-(4-Fluoro-2-thiophen-3-yl-phenyl)-5,6,7,8-tetrahydroimidazo[1,5-a]pyridine. MS (ESI) m/z 299 (M+H): $^1$H NMR (400 MHz, CDCl$_3$) δ ppm 1.58-1.68 (m, 1H), 1.74-2.02 (m, 2H), 2.05-2.22 (m, 1H), 2.67-2.82 (m, 1H), 2.88 (dt, J=16.2, 4.8 Hz, 1H), 5.24 (dd, J=9.2, 4.9 Hz, 1H), 6.80 (s, 1H), 6.99-7.06 (m, 4H), 7.08 (dd, J=4.9, 1.1 Hz, 1H), 7.21 (dd, J=2.9, 1.1 Hz, 1H), 7.43 (dd, J=4.8, 3.0 Hz, 1H).

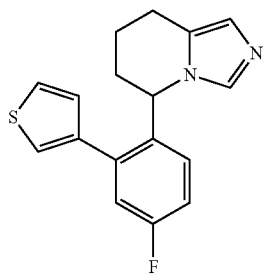 [SMILES: Fc1ccc(C2CCCc3cncn32)c(-c2ccsc2)c1]

C. 5-(2-Pyridin-3-yl-phenyl)-5,6,7,8-tetrahydroimidazo[1,5-a]pyridine

The following compound is prepared in a similar fashion using the modified Suzuki coupling procedure:

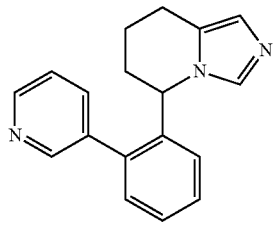 [SMILES: c1cncc(-c2ccccc2C2CCCc3cncn32)c1]

To a solution of 5-(2-bromophenyl)-5,6,7,8,-tetrahydroimidazo[1,5-a]pyridine (89 mg, 0.321 mmol) in dioxane (2 mL) is added pyridine-3-boronic acid 1,3-propanediol cyclic ester (105 mg, 0.644 mmol), $K_3PO_4$ (105 mg, 0.707 mmol), and PS-PPh$_3$Pd (0) resin (0.13 mmol/g, 100 mg). The reaction mixture is run on a microwave at 130° C. for 20 min. The mixture is partitioned between EtOAc and brine. The organic layer is washed with brine, dried over $Na_2SO_4$ and concentrated to give an oil. The crude reaction mixture is subjected to flash chromatography (silica gel) eluting with MeOH:CH$_2$Cl$_2$ to yield the desired compound. MS (ESI) m/z 275 (M+H).

Similarly prepared are the following:

1) 5-(2-Pyridin-4-yl-phenyl)-5,6,7,8-tetrahydroimidazo[1,5-a]pyridine. MS (ESI) m/z 275 (M+H)

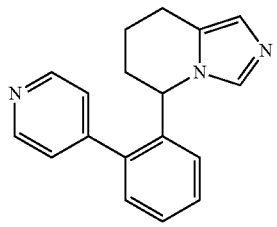 [SMILES: c1ccc(C2CCCc3cncn32)c(-c2ccncc2)c1]

2) 2'-(5,6,7,8-Tetrahydroimidazo[1,5-a]pyridine-5-yl)biphenyl-2-carbonitrile. MS (ESI) m/z 300 (M+H).

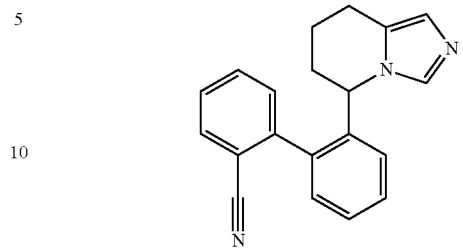

D. (R) and (S)-5-Biphenyl-2-yl-5,6,7,8-tetrahydroimidazo[1,5-a]pyridine

Resolution of the enantiomers of the title compound is achieved by chiral HPLC using the ChiralPak AD column with a 25% IPA/Hexane mobile phase to give enantiomer A ($t_r$=5.3 min) and enantiomer B ($t_r$=8.1 min). For enantiomer B: $^1$H NMR (400 MHz, DMSO-d$_6$) δ ppm 1.34-1.59 (m, 1H), 1.64-1.87 (m, 2H), 1.90-2.12 (m, 1H), 2.72 (t, J=6.2 Hz, 2H), 5.23 (dd, J=8.0, 5.2 Hz, 1H), 6.65 (s, 1H), 6.81-6.95 (m, 1H), 7.12 (s, 1H), 7.20-7.28 (m, 1H), 7.34-7.40 (m, 2H), 7.40-7.44 (m, 3H), 7.44-7.52 (m, 2H).

Similarly resolved are the following:

1) (R) and (S)-5-(2'-Chlorobiphenyl-2-yl)-5,6,7,8-tetrahydroimidazo[1,5-a]pyridine

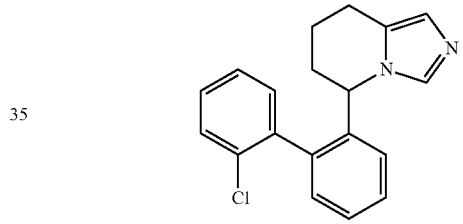

ChiralPak AD column with a 20% IPA/Hexane mobile phase to give enantiomer A ($t_r$=7.0 min) and enantiomer B ($t_r$=8.8 min).

2) (R) and (S)-5-(2'-Trifluoromethylbiphenyl-2-yl)-5,6,7,8-tetrahydroimidazo[1,5-a]pyridine

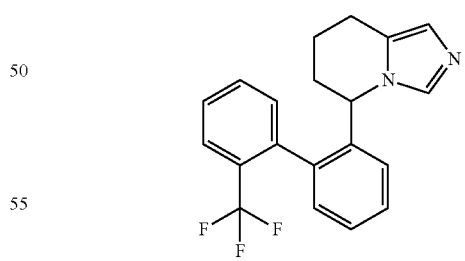

ChiralPak AS column with a 10% IPA/Hexane mobile phase to give enantiomer A ($t_r$=15 min) and enantiomer B ($t_r$=21 min). For enantiomer B: $^1$H NMR (400 MHz, CDCl$_3$) δ ppm 1.45-1.54 (m, 1H), 1.78-1.90 (m, 1H), 1.90-1.98 (m, 1H), 1.99-2.09 (m, 1H), 2.67-2.81 (m, 1H), 2.81-2.92 (m, 1H), 4.74 (dd, J=10.1, 4.5 Hz, 1H), 6.78 (s, 1H), 7.08 (s, 1H), 7.16 (d, J=7.6 Hz, 1H), 7.20-7.28 (m, 1H), 7.30-7.43 (m, 3H), 7.52 (t, J=7.6 Hz, 1H), 7.58 (t, J=7.1 Hz, 1H), 7.80 (d, J=7.6 Hz, 1H).

E. 5-(2-Cyclopropylphenyl)-5,6,7,8-tetrahydroimidazo[1,5-a]pyridine

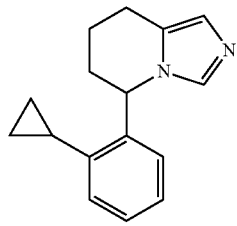 [SMILES: c1ccc(C2CCCc3cncn32)c(C2CC2)c1]

From 5-(2-bromophenyl)-5,6,7,8,-tetrahydro-imidazo[1,5-a]pyridine, Example 12D, is converted to the title compound according to the method outlined in *Tet. Lett.* 2002, 43, 6987. MS (ESI) m/z 239 (M+H); ¹H NMR (400 MHz, CDCl₃) δ ppm 0.78 (br s, 2H), 1.02 (br s, 2H), 1.79 (br s, 1H), 2.00 (br s, 3H), 2.31 (br s, 1H), 2.84-2.97 (m, 2H), 5.83 (dd, J=7.6, 5.3 Hz, 1H), 6.79 (d, J=7.6 Hz, 1H), 6.85 (s, 1H), 7.09-7.13 (m, 2H), 7.15 (t, J=7.3 Hz, 1H), 7.23 (t, J=7.3 Hz, 1H).

Similarly prepared from 5-(4-Bromophenyl)-5,6,7,8-tetrahydro-imidazo[1,5-a]pyridine is: 5-(4-Cyclopropylphenyl)-5,6,7,8-tetrahydroimidazo[1,5-a]pyridine, MS (ESI) m/z 239 (M+H); ¹H NMR (400 MHz, MeOD) δ ppm 0.68 (br s, 2H), 0.96 (br s, 2H), 1.71-1.83 (m, 1H), 1.87-2.04 (m, 3H), 2.22-2.33 (m, 1H), 2.81-2.94 (m, 2H), 5.26 (dd, J=7.8, 5.1 Hz, 1H), 6.74 (s, 1H), 7.00 (d, J=8.3 Hz, 2H), 7.09 (d, J=8.3 Hz, 2H), 7.14 (br s, 1H).

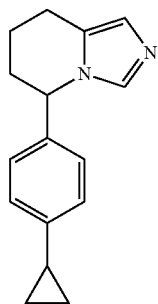 [SMILES: c1cc(C2CCCc3cncn32)ccc1C1CC1]

F. 5-Biphenyl-2-yl-8-methyl-5,6,7,8-tetrahydro-imidazo[1,5-a]pyridine

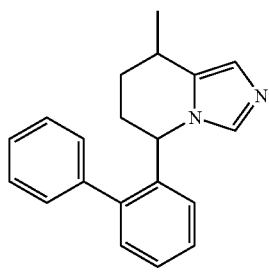 [SMILES: CC1CCC(c2ccccc2-c2ccccc2)n2cncc21]

To a solution of 5-(2-bromophenyl)-8-methyl-5,6,7,8-tetrahydro-imidazo[1,5-a]pyridine (573 mg, 1.97 mmol) in DME (10 mL) is added phenylboronic acid (480 mg, 3.94 mmol), aqueous Na₂CO₃ (2M, 4 mL, 8.0 mmol), and Pd(PPh₃)₄ (500 mg). The reaction mixture is stirred at reflux overnight. The mixture is partitioned between EtOAc and brine. The organic layer is washed by brine, dried over Na₂SO₄ and concentrated to give an oil, which is subjected to flash chromatography (silica gel) eluting with MeOH:CH₂Cl₂ to yield the desired compound. MS (ESI) m/z 289 (M+H)

Resolution of the stereoisomers of the title compound is achieved by chiral HPLC using the ChiralPak AD column with a 15% IPA/Hexane mobile phase to give isomer A (t$_r$=7.8 min), isomer B (t$_r$=9.9 min), isomer C (t$_r$=17 min) and isomer D (t$_r$=24 min). For isomer B: ¹H NMR (400 MHz, CDCl₃) δ ppm 1.35 (d, J=6.8 Hz, 3H), 1.45-1.58 (m, 1H), 1.63-1.74 (m, 1H), 1.84-2.00 (m, 2H), 2.88-3.00 (m, 1H), 5.41 (t, J=5.4 Hz, 1H), 6.68 (d, J=7.3 Hz, 1H), 6.86 (s, 1H), 7.15 (s, 1H), 7.20-7.51 (m, 8H).

Example 14

A. 6-[5-(3-Hydroxypropyl)-imidazol-1-ylmethyl]biphenyl-4-carbonitrile

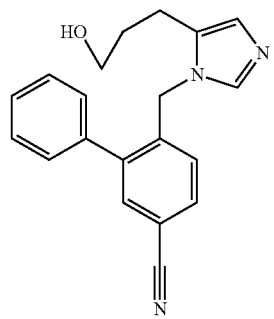 [SMILES: N#Cc1ccc(Cn2cncc2CCCO)c(-c2ccccc2)c1]

To a solution of 3-bromo-4-[5-(3-hydroxypropyl)-imidazol-1-ylmethyl]benzonitrile (1.02 g, 3.2 mmol) that is prepared by alkylation of imidazole from Example 21 with bromide described in Example 1C followed by removal of the silyl protecting group by analogy to the first step in Example 3C in DME (10 mL) is added phenylboronic acid (586 mg, 4.8 mmol), aqueous Na₂CO₃ (2M, 4.8 mL, 9.6 mmol), and PS-PPh₃-Pd (0) resin (0.13 mmol/g, 1 g). The reaction mixture is run in a microwave at 130° C. for 20 min. The mixture is partitioned between EtOAc and brine. The organic layer is washed with brine, dried over Na₂SO₄ and concentrated to give oil.

B. 6-[5-(3-Chloropropyl)-imidazol-1-ylmethyl]biphenyl-3-carbonitrile

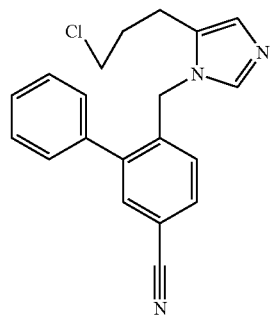 [SMILES: N#Cc1ccc(Cn2cncc2CCCCl)c(-c2ccccc2)c1]

To a solution of SOCl$_2$ (0.382 mL, 5.24 mmol) in CH$_2$Cl$_2$ (20 mL) at 0° C. is added 6-[5-(3-hydroxypropyl)imidazol-1-ylmethyl]biphenyl-3-carbonitrile in portion and the resulting white suspension is refluxed for 1.5 h. The mixture is cooled in ice and partitioned between CH$_2$Cl$_2$ and saturated aqueous NaHCO$_3$. The organic layer is washed with brine, dried over anhydrous Na$_2$SO$_4$ and concentrated to give an oily foam.

C. 6-(5,6,7,8-Tetrahydroimidazo[1,5-a]pyridin-5-yl)-biphenyl-3-carbonitrile

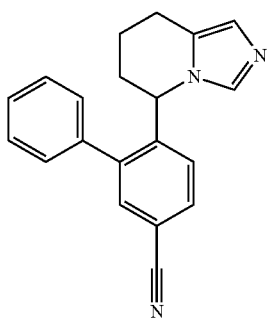 [SMILES: N#Cc1ccc(C2CCCc3cncn32)c(-c2ccccc2)c1]

To a solution of 6-[5-(3-chloropropyl)imidazol-1-ylmethyl]biphenyl-3-carbonitrile (1.0 g, 3.0 mmol) in THF (16 mL) at 0° C. is added t-BuOK/THF (1.0 M, 6 mL, 6.0 mmol). The mixture is warmed up to ambient temperature and stirred for 2 h. The reaction mixture is quenched by saturated aqueous NH$_4$Cl and partitioned between CH$_2$Cl$_2$ and brine. The organic layer is washed by brine, dried over anhydrous Na$_2$SO$_4$ and concentrated to give the crude oil, which is subjected to flash chromatography (silica gel) eluting with MeOH:CH$_2$Cl$_2$ to yield the desired compound. MS (ESI) m/z 300 (M+H); $^1$H NMR (400 MHz, CDCl$_3$) δ ppm 1.50-1.66 (m, 1H), 1.73-1.83 (m, 1H), 1.83-1.95 (m, 1H), 1.95-2.16 (m, 1H), 2.68-2.95 (m, 2H), 5.28 (dd, J=8.5, 5.2 Hz, 1H), 6.83 (s, 1H), 7.01-7.15 (m, 2H), 7.27-7.35 (m, 2H), 7.43-7.54 (m, 3H), 7.58 (s, 1H), 7.62 (d, J=8.3 Hz, 1H). Resolution of the enantiomers of the title compound is achieved by Chiral HPLC using the ChiralPak AD column with a 20% IPA/Hexane mobile phase.

Example 15

A. 3-Bromo-4-(5,6,7,8-tetrahydro-imidazo[1,5-a]pyridin-5-yl)benzonitrile

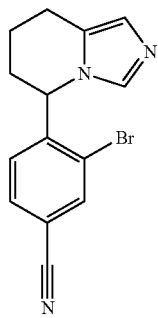 [SMILES: N#Cc1ccc(C2CCCc3cncn32)c(Br)c1]

4-{5-[3-Hydroxypropyl]imidazol-1-ylmethyl}-3-bromobenzonitrile is converted to the corresponding chloride according to Example 14B. The resulting chloride is treated with a base, such as t-BuOK as in Example 14C above, to effect cyclization to the title compound. MS (ESI) m/z 302.1, 304.1 (M+H); $^1$H NMR (400 MHz, MeOD) δ ppm 1.74-1.85 (m, 2H), 2.08-2.17 (m, 1H), 2.34-2.43 (m, 1H), 2.82-2.91 (m, 1H), 2.93-3.00 (m, 1H), 5.88 (t, J=5.6 Hz, 1H), 6.75 (d, J=8.1 Hz, 1H), 6.82 (d, J=1.0 Hz, 1H), 7.34 (s, 1H), 7.69 (dd, J=8.1, 1.5 Hz, 1H), 8.09 (d, J=1.5 Hz, 1H).

Similarly prepared are the following:

1) 3-Fluoro-4-(5,6,7,8-tetrahydro-imidazo[1,5-a]pyridin-5-yl)benzonitrile MS (ESI) m/z 242.1 (M+H); $^1$H NMR (400 MHz, MeOD) (HCl salt) δ ppm 1.88-1.98 (m, 1H), 2.02-2.11 (m, 1H), 2.14-2.24 (m, 1H), 2.39-2.47 (m, 1H), 2.92-3.00 (m, 1H), 3.02-3.09 (m, 1H), 5.83 (dd, J=9.1, 5.3 Hz, 1H), 7.37-7.39 (m, 1H), 7.42 (dd, J=10.4, 8.8 Hz, 1H), 7.67 (dd, J=6.8, 2.0 Hz, 1H), 7.86-7.90 (m, 1H), 8.65 (s, 1H). Resolution of the (R) and (S) enantiomers of the title compound is achieved by chiral HPLC using ChiralPak AS-H column and 30 IPA:hexane to give enantiomer A (t$_r$=24 min) and enantiomer B (t$_r$=30 min).

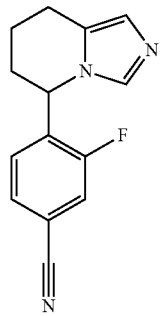

2) 3-Chloro-4-(5,6,7,8-tetrahydro-imidazo[1,5-a]pyridin-5-yl)benzonitrile MS (ESI) m/z 258.1, 260.1 (M+H); $^1$H NMR (400 MHz, MeOD) δ ppm 1.74-1.85 (m, 2H), 2.07-2.17 (m, 1H), 2.33-2.44 (m, 1H), 2.81-2.91 (m, 1H), 2.91-3.00 (m, 1H), 5.92 (d, J=5.3 Hz, 1H), 6.76 (dd, J=8.1 Hz, 1H), 6.82 (s, 1H), 7.35 (s, 1H), 7.65 (dd, J=8.1, 1.5 Hz, 1H), 7.89-7.95 (m, 1H).

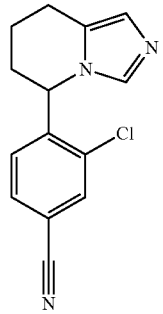

3) 3-Methoxy-4-(5,6,7,8-tetrahydro-imidazo[1,5-a]pyridin-5-yl)benzonitrile MS (ESI) m/z 254.1 (M+H); $^1$H NMR (400 MHz, MeOD) (HCl salt) δ ppm 1.85-1.95 (m, 1H), 1.95-2.04 (m, 1H), 2.18-2.28 (m, 1H), 2.31-2.41 (m, 1H), 2.99 (s, 2H), 3.88-3.94 (m, 3H), 5.85-5.92 (m, 1H), 7.09 (d, J=7.8 Hz, 1H), 7.32-7.41 (m, 2H), 7.48 (s, 1H), 8.53 (s, 1H).

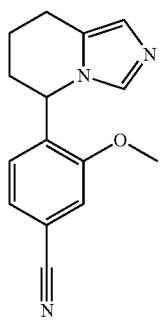 [SMILES: COc1cc(C#N)ccc1C1CCCc2cncn21]

B. 3-Methyl-4-(5,6,7,8-tetrahydro-imidazo[1,5-a]pyridin-5-yl)benzonitrile

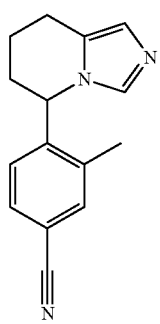 [SMILES: Cc1cc(C#N)ccc1C1CCCc2cncn21]

3-Bromo-4-(5,6,7,8-tetrahydro-imidazo[1,5-a]pyridin-5-yl)benzonitrile, prepared above, is converted to the corresponding toluene by the method outlined in *Tet. Lett.* 2000, 41, 6237. MS (ESI) m/z 238.1 (M+H); ¹H NMR (400 MHz, MeOD) δ ppm 1.77-1.89 (m, 2H), 1.91-2.00 (m, 1H), 2.29-2.39 (m, 1H), 2.45 (s, 3H), 2.86-2.93 (m, 2H), 5.71 (t, J=6.1 Hz, 1H), 6.77 (d, J=8.1 Hz, 1H), 6.81 (s, 1H), 7.29 (s, 1H), 7.49 (d, J=8.1 Hz, 1H), 7.61 (s, 1H).

C. 3-Cyclopropyl-4-(5,6,7,8-tetrahydro-imidazo[1,5-a]pyridin-5-yl)benzonitrile

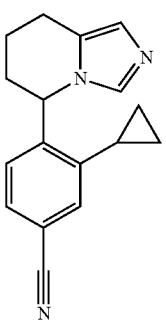 [SMILES: N#Cc1ccc(C2CCCc3cncn32)c(C2CC2)c1]

3-Bromo-4-(5,6,7,8-tetrahydro-imidazo[1,5-a]pyridin-5-yl)benzonitrile, prepared above, is converted to the corresponding cyclopropane by the method outlined in *Tet. Lett.* 2002, 43, 6987. MS (ESI) m/z 264.1 (M+H); ¹H NMR (400 MHz, MeOD) δ ppm 0.69-0.80 (m, 2H), 0.94-1.06 (m, 2H), 1.69-1.80 (m, 2H), 1.93-2.04 (m, 2H), 2.24-2.34 (m, 1H), 2.76-2.86 (m, 2H), 5.95 (d, J=6.1 Hz, 1H), 6.64-6.72 (m, 2H), 7.15 (s, 1H), 7.35 (s, 1H), 7.39 (d, J=8.1 Hz, 1H).

Example 17

5-(4-Cyano-phenyl)-5,6,7,8-tetrahydro-imidazo[1,5-a]pyridine-5-carboxylic acid methyl ester ¹H NMR (400 MHz, CDCl₃) δ ppm 1.87-1.77 (m, 2H), 2.10-2.17 (m, 1H), 2.78-2.88 (m, 3H), 3.83 (s, 3H), 6.87 (s, 1H), 7.11 (d, J=8.3 Hz, 2H), 7.46 (s, 1H), 7.64 (d, J=8.3 Hz, 2H).

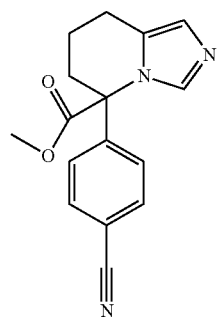 [SMILES: COC(=O)C1(c2ccc(C#N)cc2)CCCc2cncn21]

Example 18

4-((R)-1-Bromo-5,6,7,8-tetrahydroimidazo[1,5-a]pyridin-5-yl)benzonitrile

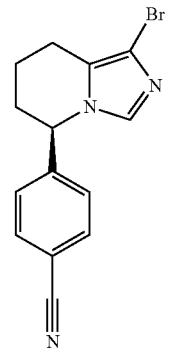

To (R)-4-(5,6,7,8-Tetrahydroimidazo[1,5-a]yridine-5-yl)benzonitrile (1.2 g, 5.4 mmol) in acetonitrile (50 mL) at 0° C. is added NBS (0.96 g, 5.4 mmol). The reaction is stirred until complete consumption of the starting material (about 2 h) before concentrating under reduced pressure. The residue is partitioned between CH₂Cl₂ and brine. The separated organic phase is washed with fresh brine (2×), dried (Na₂SO₄), and concentrated under reduced pressure. The residue is purified by flash chromatography eluting with 2.5% MeOH in CH₂Cl₂. The resulting foam is diluted with CH₂Cl₂ and HCl (g) is bubbled through for 10 min. The product is isolated by concentrating under reduced pressure. ¹H NMR (400 MHz, MeOD) (HCl salt) δ ppm 1.88-1.99 (m, 1H), 2.01-2.17 (m, 2H), 2.34-2.50 (m, 1H), 2.80-2.95 (m, 2H), 5.64 (dd, J=8.6, 5.1 Hz, 1H), 7.50 (d, J=8.3 Hz, 2H), 7.80 (d, J=8.3 Hz, 2H), 8.54 (s, 1H).

Example 18

A. 3-[3-(2-Bromobenzyl)-3H-imidazol-4-yl]-3-methylbutan-1-ol

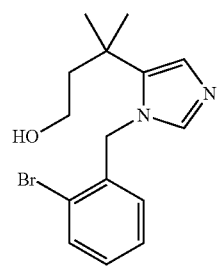 [SMILES: CC(C)(CCO)c1cncn1Cc1ccccc1Br]

To a solution of 4-[3-(tert-butyldimethylsilanyloxy)-1,1-dimethylpropyl]-1-trityl-1H-imidazole (650 mg, 1.27 mmol) in CH₃CN (10 mL) at ambient temperature is added a solution of 2-bromobenzyl bromide (420 mg, 1.68 mmol) in CH₃CN (10 mL). The resulting solution is stirred at 80° C. for 6 h. The mixture is cooled to ambient temperature and diethylamine (2 mL) is added, followed by MeOH (10 mL) and the mixture is heated at 75° C. for 1 hr and stirred at ambient temperature overnight. To the reaction mixture is added HCl/dioxane (4 M, 5 mL, 20 mmol) and stirred at ambient temperature for 1 h. The mixture is neutralized with saturated aqueous NaHCO₃ and concentrated. The residue is partitioned between CH₂Cl₂ and brine. The organic layer is washed with brine, dried over Na₂SO₄ and concentrated to give an oil, which is subjected to flash chromatography (silica gel) eluting with MeOH:CH₂Cl₂ to yield the desired compound. MS (ESI) m/z 323 (M+H).

B. 1-(2-Bromobenzyl)-5-(3-chloro-1,1-dimethylpropyl)-1H-imidazole

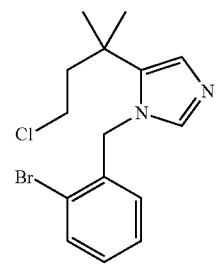 [SMILES: CC(C)(CCCl)c1cncn1Cc1ccccc1Br]

By analogy to Example 14B, the title compound is prepared from alcohol 18A. MS (ESI) m/z 341 (M+H).

C. 5-(2-Bromophenyl)-8,8-dimethyl-5,6,7,8-tetrahydro-imidazo[1,5-a]pyridine

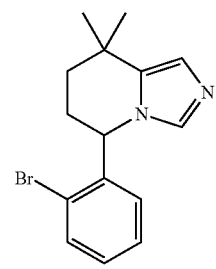

Compound 16B is cyclized according to the procedure outlined in 14C. MS (ESI) m/z 305 (M+H).

D. 5-Biphenyl-2-yl-8,8-dimethyl-5,6,7,8-tetrahydroimidazo[1,5-a]pyridine

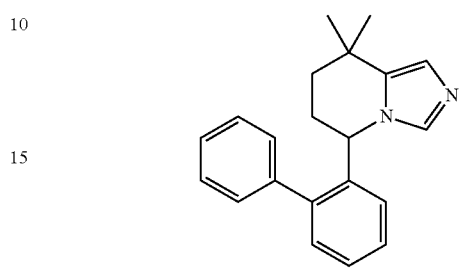

The title compound is prepared from the bromide 16C by the method described in Example 13A. MS (ESI) m/z 303 (M+H); ¹H NMR (400 MHz, CDCl₃) δ ppm 1.40 (s, 3H), 1.44 (s, 3H), 1.59-1.74 (m, 1H), 1.76-1.92 (m, 1H), 2.12-2.32 (m, 2H), 5.19-5.35 (m, 1H), 6.94-7.05 (m, 1H), 7.22 (s, 1H), 7.29-7.34 (m, 2H), 7.34-7.40 (m, 1H), 7.40-7.52 (m, 5H), 7.89 (s, 1H).

Example 19

A. 6-(5-Methyl-5,6,7,8-tetrahydroimidazo[1,5-a]pyridin-5-yl)biphenyl-3-carbonitrile

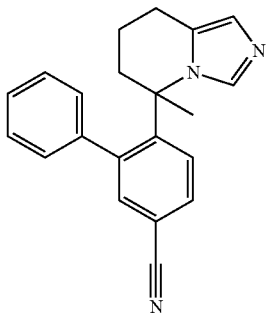 [SMILES: CC1(c2ccc(C#N)cc2-c2ccccc2)CCCc2cncn21]

To a solution of 6-(5,6,7,8-tetrahydroimidazo[1,5-a]pyridin-5-yl)biphenyl-3-carbonitrile (53 mg, 0.177 mmol) in THF (2 mL) at −40° C. is added LHMDS (1.0 M in THF, 0.27 mL, 0.27 mmol). The resulting brown solution is stirred at −30° C. for 0.5 h. To the reaction mixture is added methyl iodide (0.017 mL, 0.272 mmol) and the mixture is warmed up to ambient temperature and stirred overnight. The reaction mixture is quenched by saturated aqueous NH₄Cl and the reaction is partitioned between CH₂Cl₂ and brine. The organic layer is washed with brine, dried over anhydrous Na₂SO₄ and concentrated to give the crude oil, which is subject to flash chromatography (silica gel) eluting with MeOH:CH₂Cl₂ to yield the desired compound. MS (ESI) m/z 314 (M+H).

Similarly prepared is:

6-(5-Allyl-5,6,7,5-tetrahydroimidazo[1,5-a]pyridine-5-yl)biphenyl-3-carbonitrile

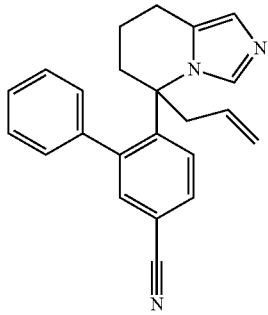 [SMILES: C=CCC1(c2ccc(C#N)cc2-c2ccccc2)CCCc2cncn21]

6-(5-Allyl-5,6,7,8-tetrahydroimidazo[1,5-a]pyridine-5-yl)biphenyl-3-carbonitrile is prepared from 6-(5,6,7,8-tetrahydroimidazo[1,5-a]pyridin-5-yl)biphenyl-3-carbonitrile and allyl bromide by analogy to 19A above. MS (ESI) m/z 340 (M+H); $^1$H NMR (400 MHz, CDCl$_3$) δ ppm (HCl salt) 1.73-1.98 (m, 2H), 2.02-2.16 (m, 1H), 2.23-2.38 (m, 1H), 2.54-2.65 (m, 1H), 2.68-2.83 (m, 1H), 2.86-3.02 (m, 1H), 3.00-3.14 (m, 1H), 5.11 (d, J=17.2 Hz, 1H), 5.23 (d, J=10.1 Hz, 1H), 5.44-5.69 (m, 1H), 6.87 (d, J=7.3 Hz, 1H), 6.92 (s, 1H), 7.02-7.12 (m, 1H), 7.13-7.22 (m, 1H), 7.27-7.39 (m, 3H), 7.45 (d, J=2.0 Hz, 1H), 7.71 (dd, J=8.5, 1.9 Hz, 1H), 8.31 (s, 1H).

B. 6-(5-n-Propyl-5,6,7,8-tetrahydro-imidazo[1,5-a]pyridine-5-yl)biphenyl-3-carbonitrile

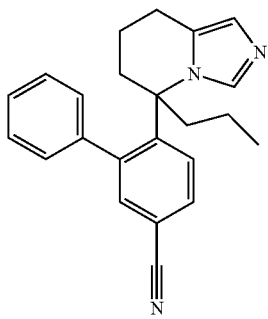 [SMILES: CCCC1(c2ccc(C#N)cc2-c2ccccc2)CCCc2cncn21]

To a solution of 6-(5-allyl-5,6,7,8-tetrahydroimidazo[1,5-a]pyridine-5-yl)biphenyl-3-carbonitrile (35' mg, 0.103 mmol) in EtOH (2 mL) at ambient temperature is added H$_2$NNH$_2$/THF (1.0 M, 15 mL, 15 mmol) and saturated aqueous CuSO$_4$ (0.1 mL). The reaction mixture is stirred at ambient temperature overnight. The mixture is concentrated and dissolved in EtOAc, which is washed with water, dried over anhydrous Na$_2$SO$_4$ and concentrated to give the crude oil, which is subjected to flash chromatography (silica gel) eluting with MeOH:CH$_2$Cl$_2$ to yield the desired compound. MS (ESI) m/z 342 (M+H); $^1$H NMR (400 MHz, CDCl$_3$) δ ppm (HCl salt) 0.95 (t, J=7.2 Hz, 3H), 1.21-1.33 (m, 2H), 1.80-1.90 (m, 2H), 1.90-2.02 (m, 1H), 2.09-2.37 (m, 3H), 2.59-2.68 (m, 1H), 2.71-2.85 (m, 1H), 6.81-6.88 (m, 1H), 6.90-6.98 (m, 2H), 7.19-7.25 (m, 1H), 7.27-7.39 (m, 3H), 7.43 (d, J=1.8 Hz, 1H), 7.71 (dd, J=8.3, 2.0 Hz, 1H), 8.10-8.18 (m, 1H).

Example 20 cis- and trans-3-Fluoro-4-[7-(4-fluorobenzyl)-5,6,7,8-tetrahydroimidazo[1,5-a]pyridin-5-yl]benzonitrile

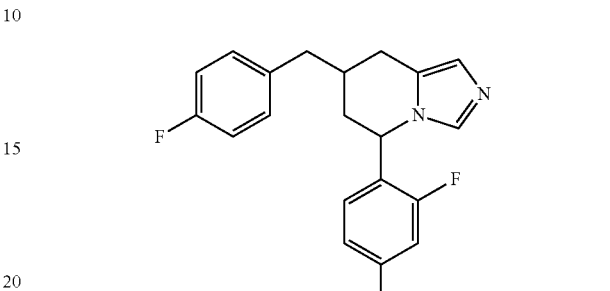

The ester obtained in Example 2G (5.0 g, 12.6 mmol) is dried azeotropically with toluene and then dissolved in THF (20 mL). This solution is added dropwise to a solution of LHMDS (1M in hexanes, 15.7 mL, 15.7 mmol) in THF (20 mL) at −75° C. (dry ice-acetone bath). After 10 min, 4-fluorobenzyl bromide (3.57 g, 18.9 mmol) is added dropwise. The mixture is stirred at −75° C. for 4 h, whereupon 10% aqueous acetic add is added and the cooling bath is removed. After extraction with ethyl acetate, the organic phase is dried over Na$_2$SO$_4$ and concentrated in vacuo. Purification by silica gel chromatography (ethyl acetate=hexanes, 85:15) afforded the product as oil.

The ester obtained above (2.15 g, 4.26 mmol) is dissolved in THF (15 mL) and cooled to −20° C. LiAlH$_4$ (1M in THF, 10.7 mL, 10.7 mmol) is added and the cooling bath is removed. After 1 h at room temperature, saturated aqueous NaHCO$_3$ is carefully added. After extraction with ethyl acetate, the organic phase is dried over Na$_2$SO$_4$ and concentrated in vacuo to afford the product as oil.

The alcohol obtained above (3.6 g, 7.56 mmol), TBSCl (1.25 g, 8.31 mmol), DMAP (0.092 g, 0.756 mmol) and imidazole (1.54 g, 22.6 mmol) are dissolved in DMF (10 mL) and heated to 75° C. for 4 h. After diluting with ethyl acetate, the mixture is washed three times with water. The organic phase is dried over Na$_2$SO$_4$ and concentrated in vacuo to afford the product as an oil.

The silyl ether obtained above (2.0 g, 3.38 mmol) and 2-fluoro-4-cyanobenzyl bromide (0.94 g, 4.40 mmol) are dissolved in acetonitrile (10 mL) and refluxed overnight. After cooling to room temperature methanol (5 mL) is added and the mixture is refluxed for 3 h, whereupon the volatiles are removed in vacuo. The residue is purified by silica gel chromatography (dichloromethane-methanol, 19:1) to afford the product as an oil.

The alcohol obtained above (0.65 g, 1.70 mmol) is dissolved in carbon tetrachloride (5 mL) and thionyl chloride (0.51 g, 4.29 mmol) is added. The mixture is refluxed for 1.5 h, cooled to room temperature and quenched with saturated aqueous NaHCO$_3$. The aqueous phase is extracted with dichloromethane. The combined organic phase is dried over Na$_2$SO$_4$ and concentrated in vacuo. Purification by silica gel chromatography (dichloromethane-methanol, 19:1) afforded the product as an oil.

The chloride obtained above (0.46 g, 1.20 mmol) is dissolved in THF (45 mL) and cooled to 0° C. Potassium tert-butoxide (1.0M in THF, 4.8 mL, 4.8 mmol) is added dropwise and after another 30 min, 1.0% aqueous acetic acid is added. After extraction with ethyl acetate, the organic phase is dried over $Na_2SO_4$ and concentrated in vacuo. Purification by silica gel chromatography (dichloromethane-methanol, 9:1) afforded the clean cis isomer and a mixture of cis and trans isomers. The clean trans isomer is obtained by preparative HPLC purification of the mixture. MS (ESI) m/z 350 (M+H); For cis isomer, $^1$H NMR (400 MHz, MeOD) δ ppm 1.64-1.73 (m, 1H), 2.05-2.20 (m, 2H), 2.35 (dd, J=15.0, 12.8 Hz, 1H), 2.65 (d, J=6.8 Hz, 2H), 2.81-2.88 (m, 1H), 5.40 (dd, J=11.5, 4.9 Hz, 1H), 6.61 (s, 1H), 6.87-6.96 (m, 2H), 7.05 (s, 1H), 7.09-7.18 (m, 2H), 7.35 (t, J=7.6 Hz, 1H), 7.47-7.57 (m, 2H); For trans isomer, $^1$H NMR (400 MHz, MeOD) δ ppm 1.85-2.13 (m, 3H), 2.39 (dd, J=16.0, 11.0 Hz, 1H), 2.49-2.61 (m, 2H), 2.87 (dd, J=16.0, 4.7 Hz, 1H), 5.90 (dd, J=5.2, 3.4 Hz, 1H), 6.40 (t, J=7.8 Hz, 1H), 6.71 (s, 1H), 6.81-6.90 (m, 2H), 6.95-7.01 (m, 2H), 7.38 (dd, J=8.1, 1.3 Hz, 1H), 7.40 (s, 1H), 7.47-7.50 (d, J=10.2, 1.3 Hz, 1H).

Similarly prepared is the following:

trans-3-Methoxy-4-[7-(4-fluorobenzyl)-5,6,7,8-tetrahydroimidazo[1,5-a]pyridin-5-yl]benzonitrile. MS (ESI) m/z 362 (M+H); $^1$H NMR (400 MHz, CDCl$_3$) (TFA salt) δ ppm 1.88-2.12 (m, 3H), 2.40 (dd, J=16.0, 9.6 Hz, 1H), 2.54 (dd, J=13.6, 7.6 Hz, 1H), 2.63 (dd, J=13.6, 6.1 Hz, 1H), 2.89 (dd, J=16.0, 4.4 Hz, 1H), 3.89 (s, 3H), 5.80 (dd, J=5.3, 3.0 Hz, 1H), 6.26 (d, J=7.8 Hz, 1H), 6.82 (s, 1H), 6.88-7.04 (m, 4H), 7.09-7.16 (m, 2H), 7.22 (s, 1H).

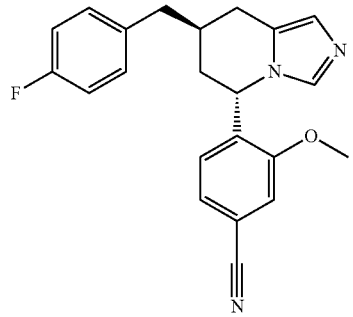 [SMILES: COc1cc(C#N)ccc1[C@@H]1C[C@@H](Cc2ccc(F)cc2)Cc2cncn21]

Example 21

A. 3-Bromo-4-{4-[4-(tert-butyldimethylsilanyloxy)butyl]imidazol-1-ylmethyl}benzonitrile

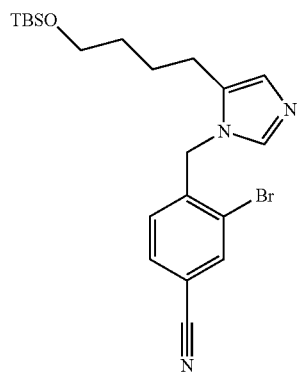 [SMILES: CC(C)(C)[Si](C)(C)OCCCCc1cncn1Cc1ccc(C#N)cc1Br]

To 4-[4-(tert-butyldimethylsilanyloxy)butyl]-1-trityl-1H-imidazole (3.95 g, 7.95 mmol) is added acetonitrile (300 mL). To this solution is added 3-bromo-4-bromomethylbenzonitrile (2.14 g, 7.78 mmol). The solution is stirred at 40° C. for 18 h. The solvent is then removed in vacuo and methanol (300 ml) is added. The solution is heated to 55° C. and stirred for 1.5 h. Saturated sodium bicarbonate is then added and stirred for 10 min. The organic solvent is removed in vacuo, and the crude product extracted into ethyl acetate and washed with water. The organic solvent is removed in vacuo to give the crude product. Chromatography (silica gel, 1:0 to 1:1 to 0:1 hexanes:ethyl acetate) gives the pure product. MS (ESI) m/z 448, 450 (M+H).

Following this protocol is also prepared:

1) 3-Chloro-4-{4-[4-(tert-butyldimethylsilanyloxy)butyl]-imidazol-1-ylmethyl}benzonitrile. MS (ESI) m/z 404, 406 (M+H).

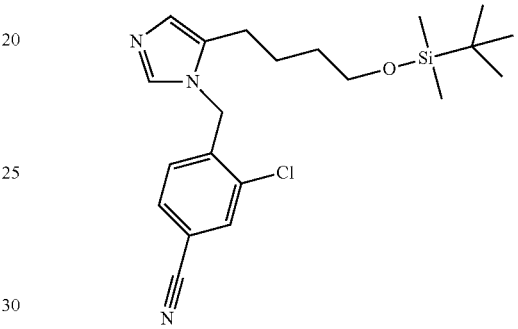

2) 3-Methoxy-4-{4-[4-(tert-butyldimethylsilanyloxy)butyl]-imidazol-1-ylmethyl}benzonitrile. MS (ESI) m/z 400 (M+H).

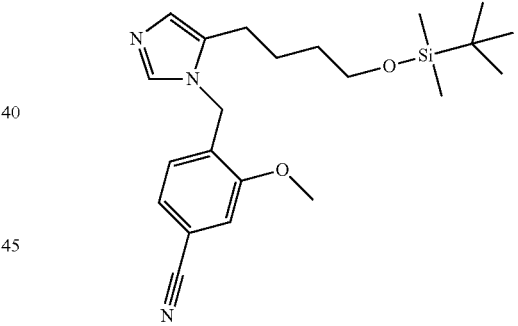

3) 3-Fluoro-4-{4-[4-(tert-butyldimethylsilanyloxy)butyl]-imidazol-1-ylmethyl}benzonitrile. MS (ESI) m/z 388 (M+H).

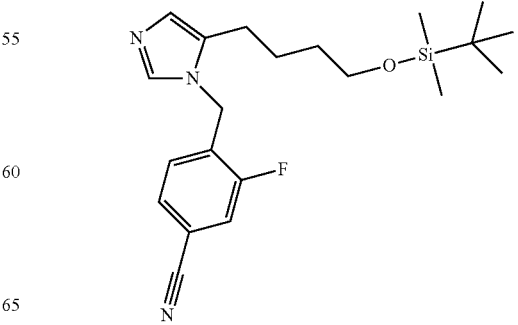

4) 2-Bromo-4-{4-[4-tert-butyldimethylsilanyloxy)butyl]-imidazol-1-ylmethyl}benzonitrile. MS (ESI) m/z 448, 450 (M+H).

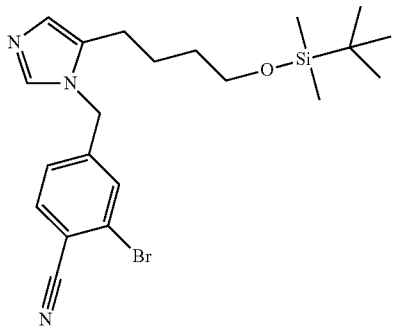 [SMILES: CC(C)(C)[Si](C)(C)OCCCCc1cncn1Cc1ccc(C#N)c(Br)c1]

5) 1-(2-Bromo-4-Fluorobenzyl)-5-[4-tert-butyldimethylsilanyloxy)butyl]-1H-imidazole. MS (ESI) m/z 441, 443 (M+H).

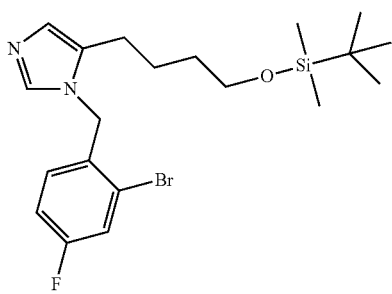 [SMILES: CC(C)(C)[Si](C)(C)OCCCCc1cncn1Cc1ccc(F)cc1Br]

6) 1-2-Bromo-benzyl-5-[4-(tert-butyldimethylsilanyloxy)-butyl]-1H-imidazole. MS (ESI) m/z 423, 425 (M+H).

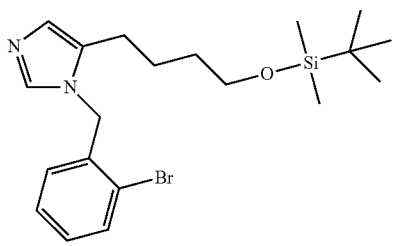 [SMILES: CC(C)(C)[Si](C)(C)OCCCCc1cncn1Cc1ccccc1Br]

7) 3-Bromo-4-[5-(4-tert-butyldimethylsilanyloxy)-1-methylbutylimidazol-1-ylmethyl-]benzonitrile. MS (ESI) m/z 462, 464 (M+H).

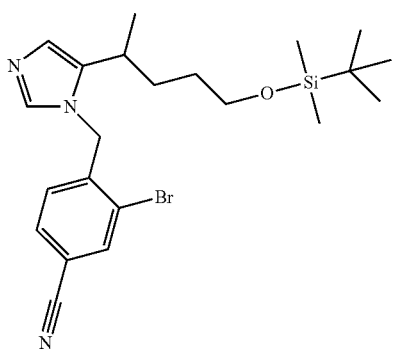 [SMILES: CC(CCCO[Si](C)(C)C(C)(C)C)c1cncn1Cc1ccc(C#N)cc1Br]

8) 3-Bromo-4-{5-[4-(tert-butyldimethylsilanyloxy)butyl]-imidazol-1-ylmethyl}-benzoic acid methyl ester. MS (ESI) m/z 481, 484 (M+H).

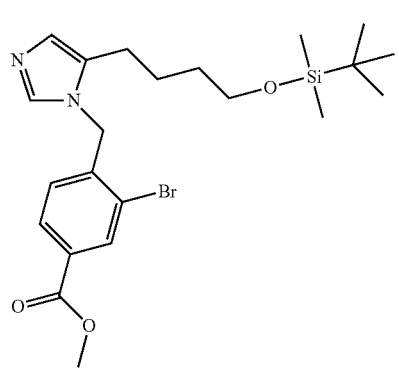 [SMILES: COC(=O)c1ccc(Cn2cncc2CCCCO[Si](C)(C)C(C)(C)C)c(Br)c1]

Example 22

3-Bromo-4-[5-(4-chlorobutyl)-imidazol-1-ylmethyl]benzonitrile

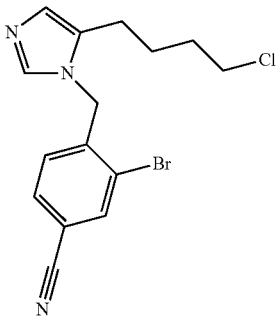 [SMILES: N#Cc1ccc(Cn2cncc2CCCCCl)c(Br)c1]

To 3-bromo-4-{4-[4-tert-butyldimethylsilanyloxybutyl]-imidazol-1-ylmethyl}-benzonitrile (1.09 g, 2.4 mmol) is added methanol (100 ml). To this solution is added hydrogen chloride, as a 4 M solution in dioxane (1.0 ml, 4.0 mmol). The solution is stirred 30 minutes. The solvent is then removed in vacuo to give the product as the hydrogen chloride salt. The product is extracted into methylene chloride and washed with saturated sodium bicarbonate. The organic phase is taken and the solvent removed in vacuo to give the intermediate alcohol as the free base. To this intermediate is added methylene chloride (100 ml). To this solution is added thionyl chloride (1.0 ml, 13.6 mmol) at room temperature. The solution is heated to 40° C. and stirred 3 h. The solution is allowed to cool, and the solvent and excess thionyl chloride is removed in vacuo. The resulting solid is extracted into methylene chloride and washed with saturated sodium bicarbonate. The organic phase is taken and removed in vacuo to give the product. MS (ESI) m/z 352, 354, 356 (M+H).

Following this protocol is also prepared:

1) 3-Chloro-4-[5-(4-chlorobutyl)imidazol-1-ylmethyl]benzonitrile. MS (ESI) m/z 308, 310, 312 (M+H).

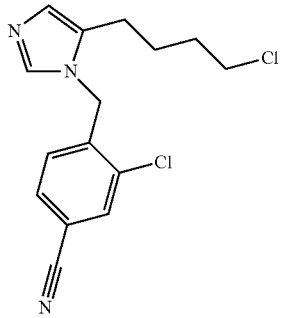 [SMILES: N#Cc1ccc(Cn2cncc2CCCCCl)c(Cl)c1]

2) 3-Methoxy-4-[5-(4-chlorobutyl)imidazol-1-ylmethyl]benzonitrile. MS (ESI) m/z 304, 306 (M+H).

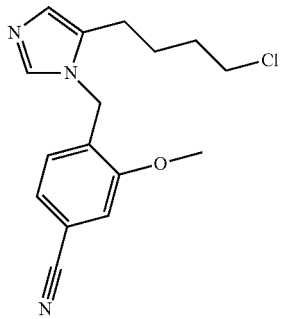 [SMILES: COc1cc(C#N)ccc1Cn1cncc1CCCCCl]

3). 3-Fluoro-4-[5-(4-chlorobutyl)-imidazol-1-ylmethyl]benzonitrile. MS (ESI) m/z 292, 294 (M+H).

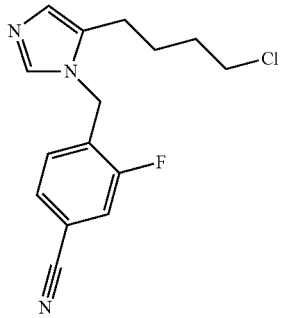 [SMILES: N#Cc1ccc(Cn2cncc2CCCCCl)c(F)c1]

4) 2-Bromo-4-[5-(4-chlorobutyl)imidazol-1-ylmethyl]benzonitrile. MS (ESI) m/z 352, 354, 356 (M+H).

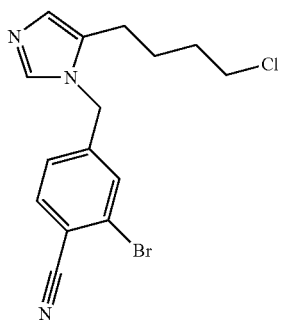 [SMILES: N#Cc1ccc(Cn2cncc2CCCCCl)cc1Br]

5) 3-Bromo-4-{5-(4-chloro-1-methylbutyl)-imidazol-1-ylmethyl]benzonitrile. MS (ESI) m/z 366, 368, 370 (M+H).

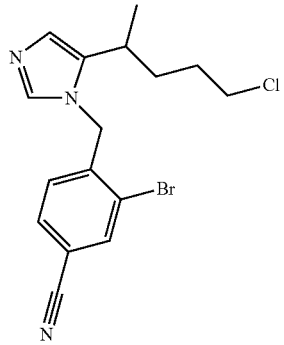 [SMILES: CC(CCCCl)c1cncn1Cc1ccc(C#N)cc1Br]

6) 1-(2-Bromobenzyl)-5-(4-chlorobutyl)-1H-imidazole. MS (ESI) m/z 327, 329, 331 (M+H).

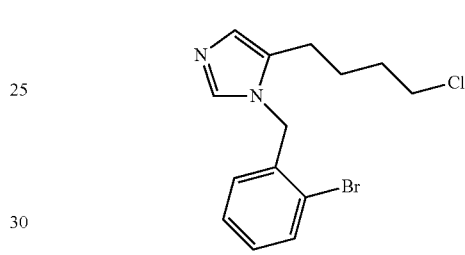

7) 1-(2-Bromo-4-fluorobenzyl)-5-(4-chlorobutyl)-1H-imidazole. MS (ESI) m/z 345, 347, 349 (M+H).

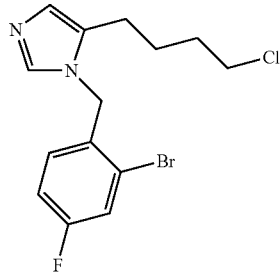 [SMILES: Fc1ccc(Cn2cncc2CCCCCl)c(Br)c1]

8) 3-Bromo-4-[5-(4-chlorobutyl)imidazol-1-ylmethyl]benzoic acid methyl ester. MS (ESI) m/z 385, 387, 389 (M+H).

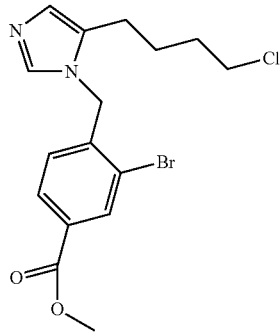 [SMILES: COC(=O)c1ccc(Cn2cncc2CCCCCl)c(Br)c1]

Example 23

3-Bromo-4-(6,7,8,9-tetrahydro-5H-imidazo[1,5-a]-azepin-5-yl)benzonitrile

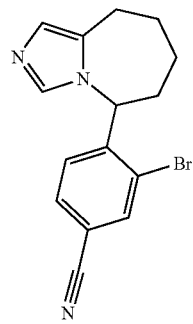

To 3-Bromo-4-[5-(4-chlorobutyl)imidazol-1-ylmethyl]benzonitrile (0.672 g, 1.9 mmol) is added anhydrous THF (40 mL). The solution is deoxygenated with nitrogen bubbled through it for 15 minutes. A solution of potassium t-butoxide in THF (3.41 ml, 1M, 3.41 mmol) is added. The reaction is allowed to proceed for 2 h at room temperature. The reaction is then quenched by the addition of methanol (3 mL) followed by aqueous ammonium chloride. The product is extracted into ethyl acetate and washed with saturated sodium bicarbonate. The organic layer is removed in vacuo to give crude product. Chromatography (reverse phase HPLC, gradient 1:9 acetonitrile:water to 7:3 acetonitrile:water, over 8 minutes, pH 2) gives the pure product. MS (ESI) m/z 316, 318 (M+H)

Resolution of the (R) and (S) enantiomers of the title compound is achieved by chiral HPLC using the ChiralPak IA column with a 20% IPA:hexane mobile phase to give enantiomer A ($t_r$=24.0 min) and enantiomer B ($t_r$=29 minutes).

Similarly prepared are the following:

1) 3-Fluoro-4-(6,7,8,9-tetrahydro-5H-imidazo[1,5-a]azepin-5-yl)benzonitrile. MS (ESI) m/z 256 (M+H).

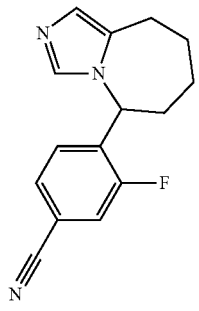 [SMILES: N#Cc1ccc(C2CCCCc3cncn32)c(F)c1]

Resolution of the (R) and (S) enantiomers of the above compound is achieved by chiral HPLC using the ChiralPak IA column with a 20% IPA:hexane mobile phase to give enantiomer A ($t_r$=18.2 min) and enantiomer B ($t_r$=20.3 minutes). For enantiomer A: $^1$H NMR (400 MHz, CDCl$_3$) δ ppm 1.38-1.67 (m, 2H), 1.72-1.93 (m, 2H), 1.96-2.14 (m, 1H), 2.44-2.74 (m, 2H), 2.97 (dd, J=15.4, 6.3 Hz, 1H), 5.73 (dd, J=6.1, 2.8 Hz, 1H), 6.80-6.94 (m, 2H), 7.23 (s, 1H), 7.39-7.42 (m, 1H), 7.43 (s, 1H).

2) 3-Chloro-4-(6,7,8,9-tetrahydro-5H-imidazo[1,5-a]azepin-5-yl)benzonitrile. MS (ESI) m/z 272, 274 (M+H); $^1$H NMR (400 MHz, CDCl$_3$) δ ppm 1.50-1.87 (m, 4H), 1.97-2.19 (m, 1H), 2.42-2.61 (m, 1H), 2.67-2.85 (m, 1H), 2.85-3.00 (m, 1H), 5.71 (dd, J=7.2, 2.7 Hz, 1H), 6.83 (s, 1H), 6.98 (s, 1H), 7.17 (d, J=8.1 Hz, 1H), 7.56 (dd, J=8.1, 1.5 Hz; 1H), 7.72 (d, J=1.5 Hz, 1H).

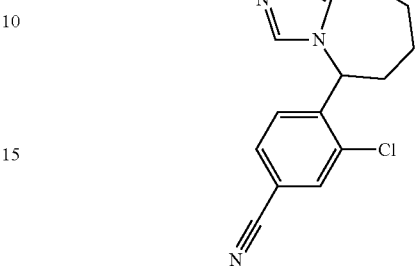

Resolution of the (R) and (S) enantiomers of the above compound is achieved by chiral HPLC using the ChiralPak IA column with a 20% IPA:hexane mobile phase to give enantiomer A ($t_r$=24.0 min) and enantiomer B=29.0 minutes).

3) 3-Bromo-4-(9-methyl-6,7,8,9-tetrahydro-5H-imidazo[1,5-a]azepin-5-yl)benzonitrile MS (ESI) m/z 330, 332 (M+H).

4) 2-Bromo-4-(6,7,8,9-tetrahydro-5H-imidazo[1,5-a]azepin-5-yl)benzonitrile. MS (ESI) m/z 316, 318 (M+H); $^1$H NMR (400 MHz, CDCl$_3$) δ ppm 1.39-1.57 (m, 2H), 1.73-1.96 (m, 2H), 2.04-2.17 (m, 1H), 2.18-2.37 (m, 1H), 2.47-2.73 (m, 1H), 2.81-3.03 (m, 1H), 5.50-5.70 (m, 1H), 6.90 (s, 1H), 6.93-7.00 (m, 1H), 7.29 (s, 1H), 7.35 (s, 1H), 7.65 (d, J=8.1 Hz, 1H).

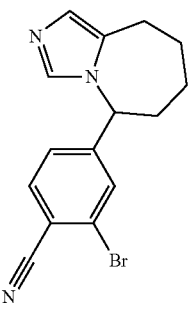 [SMILES: N#Cc1ccc(C2CCCCc3cncn32)cc1Br]

Example 24

5-(2-Bromophenyl)-6,7,8,9-tetrahydro-5H-imidazo[1,5-a]azepine

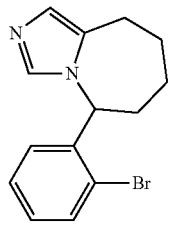 [SMILES: Brc1ccccc1C1CCCCc2cncn21]

To 5-(2-bromophenyl)-6,7,8,9-tetrahydro-5H-imidazo[1,5-a]azepine (1.65 g, 4.75 mmol) is added anhydrous THF (100 mL). Nitrogen is bubbled through this solution for 15 minutes and LHMDS (10 mL, 1.0 M, 10 mmol) is added. The reaction is allowed to proceed for 2 h at room temperature. The reaction is then quenched by the addition of methanol (5 mL) followed by aqueous ammonium chloride. The product is extracted into ethyl acetate and washed with saturated sodium bicarbonate. The organic layer is removed in vacuo to give the crude product. Chromatography (reverse phase HPLC, gradient 1:9 acetonitrile:water to 7:3 acetonitrile:water, over 8 minutes, pH 2) gives the pure product. MS (ESI) m/z 291, 293 (M+H); $^1$H NMR (400 MHz, CDCl$_3$) δ ppm 1.54-1.67 (m, 1H), 1.70-1.83 (m, 1H), 1.83-1.96 (m, 2H), 2.12-2.23 (m, 1H), 2.27-2.40 (m, 1H), 2.77-2.87 (m, 1H), 2.91-3.01 (m, 1H), 5.58 (dd, J=8.5, 1.9 Hz, 1H), 6.81 (s, 1H), 6.82 (s, 1H), 7.20-7.29 (m, 2H), 7.33-7.41 (m, 1H), 7.64 (dd, J=8.1, 1.3 Hz, 1H).

Similarly prepared are the following:

1) 5-(2-Bromo-4-fluorophenyl)-6,7,8,9-tetrahydro-5H-imidazo[1,5-a]azepine. MS (ESI) m/z 309, 311 (M+H); $^1$H NMR (400 MHz, CDCl$_3$) δ ppm 1.54-1.63 (m, 1H), 1.72-1.94 (m, 3H), 2.10-2.33 (m, 2H), 2.75-2.97 (m, 2H), 5.53 (d, J=8.3 Hz, 1H), 6.78 (s, 1H), 6.81 (s, 1H), 7.01-7.13 (m, 1H), 7.16-7.28 (m, 1H), 7.40 (dd, J=8.1, 2.5 Hz, 1H).

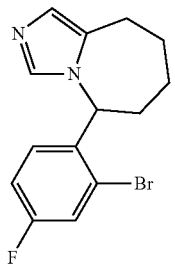

2) 3-Bromo-4-(6,7,8,9-tetrahydro-5H-imidazo[1,5-a]azepin-5-yl)benzoic acid methyl ester. MS (ESI) m/z 349, 351 (M+H).

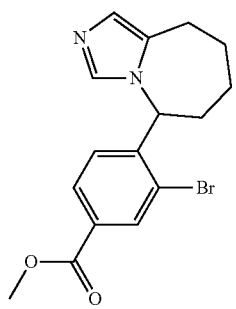 [SMILES: COC(=O)c1ccc(C2CCCCc3cncn32)c(Br)c1]

3) 3-Methoxy-4-(6,7,8,9-tetrahydro-5H-imidazo[1,5-a]azepin-5-yl)benzonitrile. MS (ESI) m/z 268 (M+H).

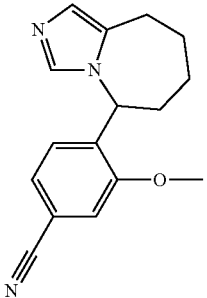 [SMILES: COc1cc(C#N)ccc1C1CCCCc2cncn21]

Example 25

4% Fluoro-6-(6,7,8,9-tetrahydro-5H-imidazo[1,5-a]azepin-5-yl)biphenyl-3-carbonitrile

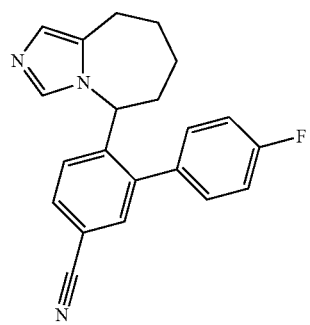 [SMILES: N#Cc1ccc(C2CCCCc3cncn32)c(-c2ccc(F)cc2)c1]

To 3-bromo-4-(6,7,8,9-tetrahydro-5H-imidazo[1,5-a]azepin-5-yl)benzonitrile (0.507 g, 1.59 mmol) is added DME (7.0 mL). To this is added aqueous 2M sodium carbonate (3.0 mL, 6 mmol) followed by 4-fluorophenylboronic acid (0.552 g, 3.97 mmol). This mixture is transferred to a microwave safe vial. Tetrakis(triphenylphosphine) palladium(0) (0.03 g, 0.025 mmol) is added, and the vessel sealed. The mixture is stirred briefly (30 seconds) and placed in a microwave for 25 minutes at 125° C. The vial is allowed to cool and unsealed. The mixture is extracted into ethyl acetate and washed with saturated sodium bicarbonate. The organic layer is removed in vacuo. The resulting material is subjected to chromatography (Silica gel, 1:50 to 1:25 methanol:methylene chloride) to give the desired product. MS (ESI) m/z 332 (M+H)

Resolution of the (R) and (S) enantiomers of the title compound is achieved by chiral HPLC using the ChiralPak IA column with a 20% IPA:hexane mobile phase to give enantiomer A (t$_r$=17.6 min) and enantiomer B (t$_r$=23.0 minutes). For enantiomer, A: $^1$H NMR (400 MHz, CDCl$_3$) δ ppm 1.40-1.57 (m, 2H), 1.77-1.92 (m, 2H), 1.94-2.04 (m, 2H), 2.43 (dd, J=15.0, 9.7 Hz, 1H), 2.85 (dd, J=15.4, 7.3 Hz, 1H), 5.13 (dd, J=7.5, 3.2 Hz, 1H), 6.83 (s, 1H), 6.92 (s, 1H), 7.01-7.12 (m, 4H), 7.51 (d, J=8.3 Hz, 1H), 7.63 (d, J=1.8 Hz, 1H), 7.75 (dd, J=8.1, 1.8 Hz, 1H).

Similarly prepared are the following:

1) 5-Biphenyl-2-yl-6,7,8,9-tetrahydri-5H-imidazo[1,5-a]azepine. MS (ESI) m/z 289 (M+H); $^1$H NMR (400 MHz, CDCl$_3$) δ ppm 1.35-1.56 (m, 2H), 1.80-1.89 (m, 1H), 1.89-1.98 (m, 1H), 1.99-2.08 (m, 2H), 2.28-2.41 (m, 1H), 2.87 (dd, J=15.3, 6.2 Hz, 1H), 5.05-5.15 (m, 1H), 6.80 (br s, 1H), 6.97 (br s, 1H), 7.03-7.10 (m, 2H), 7.31-7.36 (m, 4H), 7.40-7.48 (m, 3H).

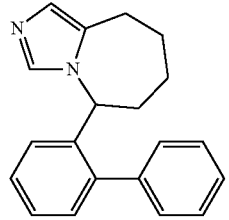 [SMILES: c1ccc(-c2ccccc2C2CCCCc3cncn32)cc1]

Resolution of the (R) and (S) enantiomers of the above compound is achieved by chiral HPLC using the ChiralPak AS column with a 20% IPA:hexane mobile phase to give enantiomer A (t$_r$=7.5 min) and enantiomer B (t$_r$=10.8 minutes).

2) 5-(4'-Fluorobiphenyl-2-yl)6,7,8,9-tetrahydro-5H-imidazo[1,5-a]azepine MS (ESI) m/z 307 (M+H); $^1$H NMR (400 MHz, CDCl$_3$) δ ppm 1.34-1.56 (m, 2H), 1.81-1.99 (m, 2H), 2.02-2.09 (m, 2H), 2.28-2.41 (m, 1H), 2.89 (dd, J=15.2, 6.6 Hz, 1H), 4.98-5.05 (m, 1H), 6.79 (s, 1H), 6.90 (s, 1H), 7.02 (d, J=7.6 Hz, 4H), 7.28-7.34 (m, 1H), 7.39-7.52 (m, 3H).

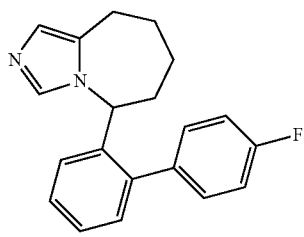 [SMILES: Fc1ccc(-c2ccccc2C2CCCCc3cncn32)cc1]

Resolution of the (R) and (S) enantiomers of the above compound is achieved by chiral HPLC using the ChiralPak AS column with a 15% IPA:hexane mobile phase to give enantiomer A (t$_r$=9.3 min) and enantiomer B (t$_r$=11.6 minutes).

3) 5-(2'-Chlorobiphenyl-2-yl)6,7,8,9-tetrahydro-5H-imidazo[1,5-a]azepine. MS (ESI) m/z 323, 325 (M+H).

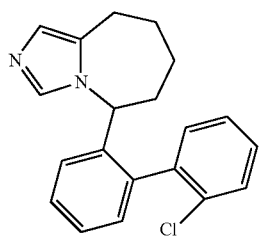 [SMILES: Clc1ccccc1-c1ccccc1C1CCCCc2cncn21]

4) 2'-(6,7,8,9)-Tetrahydro-5H-imidazo[1,5-a]azepin-5-yl)biphenyl-4-carbonitrile. MS (ESI) m/z 314 (M+H); $^1$H NMR (400 MHz, CDCl$_3$) δ ppm 1.33-1.58 (m, 2H), 1.84-1.96 (m, 1H), 1.96-2.16 (m, 3H), 2.26-2.38 (m, 1H), 2.92 (dd, J=15.3, 6.7 Hz, 1H), 4.90-4.97 (m, 1H), 6.83 (s, 1H), 6.94 (s, 1H), 7.17 (d, J=7.6 Hz, 2H), 7.28-7.37 (m, 1H), 7.45-7.57 (m, 3H), 7.65 (d, J=8.3 Hz, 2H).

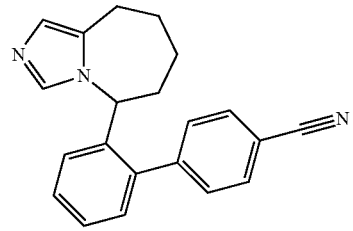 [SMILES: N#Cc1ccc(-c2ccccc2C2CCCCc3cncn32)cc1]

5) 5-(2'-Trifluoromethylbiphenyl-2-yl)6,7,8,9-tetrahydro-5H-imidazo[1,5-a]azepine MS (ESI) m/z 357 (M+H); $^1$H NMR (400 MHz, CDCl$_3$) δ ppm 1.27-1.39 (m, 1H), 1.41-1.55 (m, 1H), 1.86-1.95 (m, 1H), 1.97-2.13 (m, 3H), 2.14-2.25 (m, 1H), 2.84 (dd, J=15.4, 6.1 Hz, 1H), 4.61 (d, J=9.9 Hz, 1H), 6.80 (s, 1H), 6.87 (d, J=7.6 Hz, 1H), 6.98 (s, 1H), 7.29 (d, J=7.6 Hz, 1H), 7.37 (t, J=7.6 Hz, 1H), 7.44-7.51 (m, 2H), 7.56 (d, J=3.8 Hz, 2H), 7.78 (d, J=8.1 Hz, 1H).

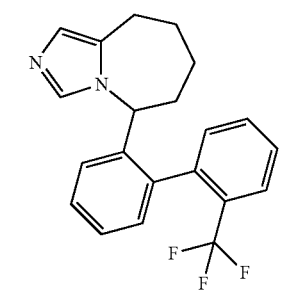 [SMILES: FC(F)(F)c1ccccc1-c1ccccc1C1CCCCc2cncn21]

6) 5-(3'-Nitrobiphenyl-2-yl)-6,7,8,9-tetrahydro-5H-imidazo[1,5-a]azepine. MS (ESI) m/z 334 (M+H); $^1$H NMR (400 MHz, CDCl$_3$) δ ppm 1.34-1.58 (m, 2H), 1.84-1.93 (m, 1H), 1.95-2.17 (m, 3H), 2.25-2.36 (m, 1H), 2.90 (dd, J=15.3, 6.7 Hz, 1H), 4.97 (dd, J=9.1, 1.5 Hz, 1H), 6.81 (s, 1H), 6.91 (s, 1H), 7.23-7.28 (m, 1H), 7.34-7.38 (m, 1H), 7.45-7.57 (m, 4H), 8.07 (t, J=1.9 Hz, 1H), 8.18-8.25 (m, 1H).

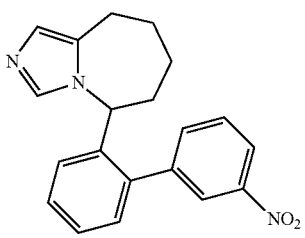 [SMILES: O=[N+]([O-])c1cccc(-c2ccccc2C2CCCCc3cncn32)c1]

7) 5-(5-Fluorobiphenyl-2-yl)-6,7,8,9-tetrahydro-5H-imidazo[1,5-a]azepine. MS (ESI) m/z 307 (M+H).

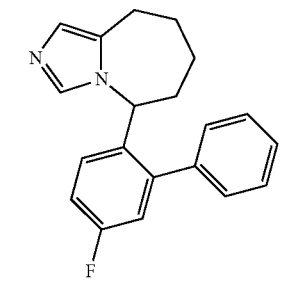 [SMILES: Fc1ccc(C2CCCCc3cncn32)c(-c2ccccc2)c1]

8) 4'-Fluoro-6-(9-methyl-6,7,8,9-tetrahydro-5H-imidazo[1,5-a]azepin-5-yl)biphenyl-3-carbonitrile. MS (ESI) m/z 346 (M+H).

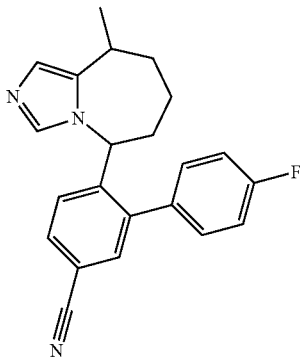 [SMILES: CC1CCCC(c2ccc(C#N)cc2-c2ccc(F)cc2)n2cncc21]

Resolution of the (R)(R), (R)(S), (S)(R), and (S)(S) isomers of the above compound is achieved by chiral HPLC using the ChiralPak IA column with a 15% IPA:hexane mobile phase to give isomer A ($t_r$=18.1 min), isomer B ($t_r$=21.8 minutes), isomer C ($t_r$=24.8 minutes) and isomer D=27.5 minutes). For isomer D: $^1$H NMR (400 MHz, CDCl$_3$) δ ppm 1.31-1.35 (m, 1H), 1.40 (d, J=6.8 Hz, 3H), 1.64-1.77 (m, 1H), 1.91-2.00 (m, 1H), 2.10-2.23 (m, 2H), 2.26-2.34 (m, 1H), 2.51-2.60 (m, 1H), 5.24 (d, J=10.1 Hz, 1H), 6.94-7.02 (m, 2H), 7.08-7.15 (m, 3H), 7.70 (d, J=1.8 Hz, 1H), 7.77 (d, J=8.1 Hz, 1H), 7.85 (s, 1H), 7.89 (dd, J=8.2, 1.6 Hz, 1H).

9) 3-(3,5-Dimethylisoxazol-4-yl)-4-(6,7,8,9-tetrahydro-5H-imidazo[1,5-a]azepin-5-yl)benzonitrile. MS (ESI) m/z 333 (M+H)

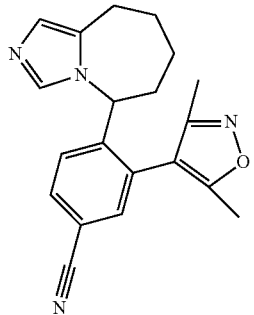 [SMILES: Cc1noc(C)c1-c1cc(C#N)ccc1C1CCCCc2cncn21]

10) 3-Pyridin-4-yl-4-(6,7,8,9-tetrahydro-5H-imidazo[1,5-a]azepin-5-yl)benzonitrile. MS (ESI) m/z 315 (M+H); $^1$H NMR (400 MHz, CDCl$_3$) δ ppm 1.37-1.63 (m, 2H), 1.77-1.95 (m, 2H), 1.96-2.10 (m, 2H), 2.35-2.52 (m, 1H), 2.86 (dd, J=15.5, 7.2 Hz, 1H), 5.04-5.13 (m, 1H), 6.85 (s, 1H), 6.89 (s, 1H), 6.98-7.07 (m, 2H), 7.58 (d, J=8.1 Hz, 1H), 7.64 (d, J=1.5 Hz, 1H), 7.82 (dd, J=8.3, 1.8 Hz, 1H), 8.67 (d, J=6.1 Hz, 2H).

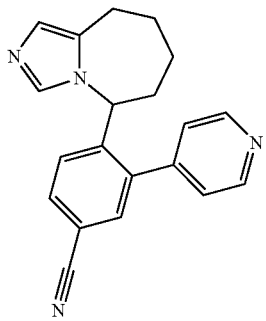 [SMILES: N#Cc1ccc(C2CCCCc3cncn32)c(-c2ccncc2)c1]

11) 3-Pyridin-3-yl-4-(6,7,8,9-tetrahydro-5H-imidazo[1,5-a]azepin-5-yl)benzonitrile. MS (ESI) m/z 315 (M+H); $^1$H NMR (400 MHz, CDCl$_3$) (HCl salt) δ ppm 1.41-1.63 (m, 2H), 1.70-1.93 (m, 2H), 1.95-2.13 (m, 2H), 2.29-2.54 (m, 1H), 2.84 (dd, J=15.4, 7.3 Hz, 1H), 5.11 (t, J=5.1 Hz, 1H), 6.82 (s, 1H), 6.90 (s, 1H), 7.28-7.39 (m, 2H), 7.55 (d, J=8.3 Hz, 1H), 7.64 (d, J=1.5 Hz, 1H), 7.80 (dd, J=8.1, 1.8 Hz, 1H), 8.39-8.53 (m, 1H), 8.68 (t, J=3.3 Hz, 1H).

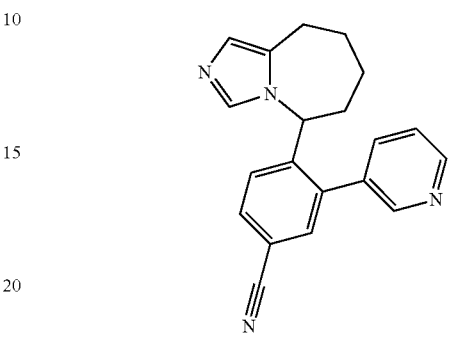

12) 5-(6,7,8,9-Tetrahydro-5H-imidazo[1,5-a]azepin-5-yl)biphenyl-2-carbonitrile. MS (ESI) m/z 314 (M+H).

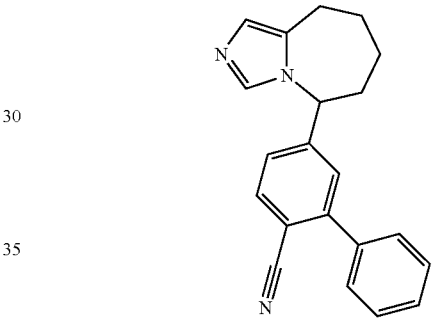

Example 26

4-(5-Allyl-6,7,8,9-tetrahydro-5H-imidazo[1,5-a]azepin-5-yl)-3-bromobenzonitrile

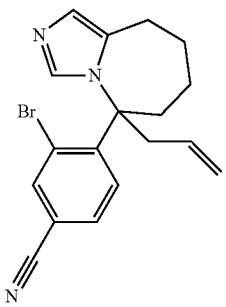 [SMILES: C=CCC1(c2ccc(C#N)cc2Br)CCCCc2cncn21]

To 4-(6,7,8,9-tetrahydro-5H-imidazo[1,5-a]azepin-5-yl)-3-bromobenzonitrile (0.330 g, 1.04 mmol) is added anhydrous tetrahydrofuran (60 mL). Nitrogen is bubbled through the solution for 15 minutes. LDA in THF (2.2 mL, 1.0M, 2.2 mmol) is added at room temperature. The reaction is allowed to stir for 15 min at room temperature. Allyl bromide (12.78 g, 90.6 mmol) is then added. The reaction is allowed to stir for an additional 5 min. The reaction is then quenched by the addition of methanol (2 mL) followed by aqueous ammonium chloride. The product is extracted into ethyl acetate and washed with saturated aqueous sodium bicarbonate. The organic layer removed in vacuo to give crude product. Chromatography (silica gel, methanol:methylene chloride, gradient 0% methanol to 5% methanol over 30 minutes gives the pure product. MS (ESI) m/z 356, 358 (M+H); $^1$H NMR (400 MHz, CDCl$_3$) δ ppm 1.35-1.52 (m, 2H), 1.67-1.77 (m, 1H), 1.84-2.00 (m, 3H), 2.82 (dd, J=15.3, 5.7 Hz, 1H), 3.15-3.41 (m, 3H), 5.14-5.30 (m, 2H), 5.67-5.82 (m, 1H), 6.26 (d, J=8.1 Hz, 1H), 6.86 (s, 1H), 7.45 (dd, J=8.3, 1.8 Hz, 1H), 7.79 (s, 1H), 7.94 (d, J=1.8 Hz, 1H).

Similarly prepared are the following:

1) 3-Chloro-(5-ethyl-6,7,8,9-tetrahydro-5H-imidazo[1,5-a]azepin-5-yl)benzonitrile. MS (ESI) m/z 300, 302 (M+H); $^1$H NMR (400 MHz, CDCl$_3$) δ ppm 1.07 (t, J=7.3 Hz, 3H), 1.24-1.52 (m, 2H), 1.60-1.79 (m, 1H), 1.86-2.07 (m, 3H), 2.19-2.44 (m, 1H), 2.50-2.62 (m, 1H), 2.84 (dd, J=15.4, 5.8 Hz, 1H), 3.18 (dd, J=14.8, 5.7 Hz, 1H), 6.21 (d, J=8.3 Hz, 1H), 6.88 (s, 1H), 7.40 (dd, J=8.5, 1.9 Hz, 1H), 7.65 (s, 1H), 7.71 (d, J=1.8 Hz, 1H).

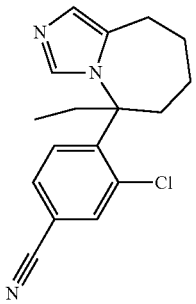 [SMILES: CCC1(c2ccc(C#N)cc2Cl)CCCCc2cncn21]

2) 6-(5-Ethyl-6,7,8,9-tetrahydro-5H-imidazo[1,5-a]azepin-5-yl)-4'-fluorobiphenyl-3-carbonitrile. MS (ESI) m/z 360 (M+H).

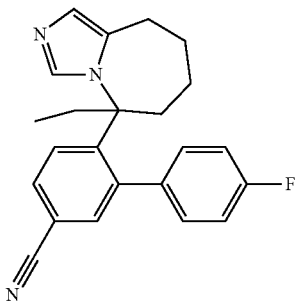 [SMILES: CCC1(c2ccc(C#N)cc2-c2ccc(F)cc2)CCCCc2cncn21]

3) 6-(5-Methyl-6,7,8,9-tetrahydro-5H-imidazo[1,5-a]azepin-5-yl)-4'-fluorobiphenyl-3-carbonitrile. MS (ESI) m/z 346 (M+H).

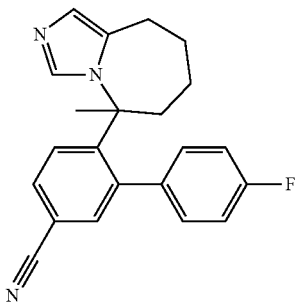 [SMILES: CC1(c2ccc(C#N)cc2-c2ccc(F)cc2)CCCCc2cncn21]

Example 27

3'-Methylene-2',3',6,7,8,9-hexahydrospiro[imidazo[1,5-a]azepine-5,1'-indene]-5'-carbonitrile

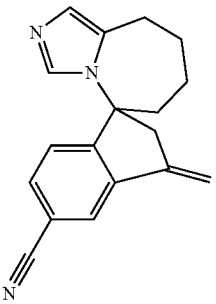 [SMILES: C=C1CC2(CCCCc3cncn32)c2ccc(C#N)cc21]

To 4-(5-allyl-6,7,8,9-tetrahydro-5H-imidazo[1,5-a]azepin-5-yl)-3-bromobenzonitrile (0.275 g, 0.76 mmol) is added DME (3.0 mL). To this solution is added aqueous 2M sodium carbonate (1.5 ml, 3.0 mmol) followed by 4-fluorophenylboronic acid (0.269 g, 1.92 mmol). This mixture is transferred to a microwave safe vial Tetrakis(triphenylphosphine) palladium(0) (0.04 g, 0.034 mmol) is added, and the vessel sealed. The mixture is stirred briefly (30 seconds) and place in a microwave for 25 minutes at 130° C. The vial is allowed to cool and unsealed. The mixture is extracted with ethyl acetate and washed with saturated aqueous sodium bicarbonate. The separated organic layer is concentrated in vacuo. The resulting material is subjected to two sequential chromatography procedures (1: Silica gel, 1:50 to 1:25 methanol:methylene chloride. 2: Reverse phase HPLC, gradient 10-95% Acetonitrile:Water, pH2, over 8 minutes) to give the product. MS (ESI) m/z 276 (M+H); $^1$H NMR (400 MHz, CDCl$_3$) δ ppm 1.47-1.61 (m, 1H), 1.85-1.99 (m, 1H), 2.01-2.16 (m, 3H), 2.25-2.36 (m, 1H), 2.63 (t, 1H), 2.99 (d, J=16.4 Hz, 1H), 3.10 (dd, J=15.5, 5.7 Hz, 1H), 3.23-3.32 (m, 1H), 5.21-5.25 (m, 1H), 5.62-5.67 (m, 1H), 6.50 (s, 1H), 6.78 (s, 1H), 7.54-7.58 (m, 1H), 7.66-7.70 (m, 1H), 7.88 (s, 1H).

Example 28

7-Benzyl-5-(3,5-dimethoxy-phenyl)-6,7,8,9-tetrahydro-5H-imidazo[1,5-a]azepine

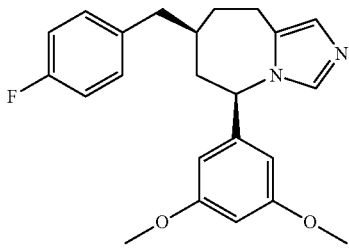 [SMILES: COc1cc(OC)cc([C@H]2C[C@@H](Cc3ccc(F)cc3)CCc3cncn32)c1]

A. 3-(1-trityl-1H-imidazol-4-yl)propionaldehyde

To a solution of DMSO (3.57 g, 45.6 mmol) in dichloromethane (100 mL) at −78° C. under nitrogen is added oxalyl chloride (2.0M in DCM, 17.1 mL, 34.2 mmol). After 20 min at −78° C., the alcohol prepared in step 2 (8.41 g, 22.82 mmol) in dichloromethane (30 mL) is cannulated dropwise. After 30 min at −78° C., triethylamine (9.24 g, 91.3 mmol) is added dropwise and the mixture is allowed to warm to room temperature. The mixture is diluted with diethyl ether (800 mL) and washed with saturated aqueous ammonium chloride (2×200 mL) and brine (200 mL). The combined organic phase is dried over magnesium sulfate and filtered. After concentration in vacuo, the product is obtained as an orange gum.

B. 4-but-3-enyl-1-trityl-1H-imidazole tert-BuOK (5.78 g, 51.53 mmol) is dissolved in THF (80 mL) and added to a suspension of methyltriphenylphosphonium bromide (20.00 g, 56.00 mmol) in THF (120 mL) at 0° C. under nitrogen. After 30 min at 0° C., the aldehyde obtained in step 3 (8.5 g) in THF (40 mL) is cannulated dropwise. The cooling bath is removed and after 1 h, the mixture is diluted with ethyl acetate (800 mL) and washed with saturated aqueous ammonium chloride (400 mL) and brine (400 mL). The combined organic phase is dried over magnesium sulfate and filter. The residue is purified by silica gel flash chromatography (elution with hexanes-ethyl acetate, 1:1) to give the alkene (6.72 g) as a pale yellow solid.

C. (E)-1-(3,5-dimethoxyphenyl)-5-(1-trityl-1H-imidazol-4-yl)pent-2-en-1-one

Toluene (100 mL) is added to (PPh$_3$)$_2$Pd(BnCl) (0.151 g, 0.199 mmol) and 3,5-dimethoxybenzoyl chloride (4.00 g, 19.94 mmol) under nitrogen, followed with tributylvinyltin (6.11 g, 21.93 mmol). The yellow solution is heated to 80° C., to give a paler yellow solution. After 1.5 h, the mixture is partially concentrated and poured onto a column of 10% wt KF in silica gel. Elution with hexanes then hexanes-ethyl acetate 10 to 15% gave 1-(3,5-dimethoxyphenyl)propenone (3.57 g) as pale yellow oil.

A portion (1.32 g, 6.86 mmol) is added to a solution of the alkene prepared above (1.00 g, 2.74 mmol) in dichloromethane (25 mL). p-Toluenesulfonic acid (0.574 g, 3.018 mmol) is added, the solution is degassed by bubbling nitrogen for 25 min, and it is then refluxed for 30 min. After cooling, second generation Grubbs' catalyst (0.116 g, 0.137 mmol) is added and the purple solution is heated to reflux. After 45 min, the mixture is cooled, diluted with ether and washed with saturated aqueous sodium bicarbonate and brine. After drying over MgSO$_4$ and filtering, silica gel (2 g) is added and the mixture is concentrated in vacuo. The residue is absorbed on a pad of silica gel in a sintered funnel, followed by elution with ethyl acetate-hexanes, 1:1 to 4:1. The filtrate is concentrated in vacuo to give a residue which is purified by flash silica gel chromatography (hexanes-ethyl acetate, 1:1 to 3:7) to afford the product as a brown gum.

D. 3-benzyl-1-(3,5-dimethoxyphenyl)-5-(1-trityl-1H-imidazol-4-yl)pentan-1-one Zinc foil (0.556 g, 8.512 mmol) is cut in small pieces and covered with THF (0.5 mL) in a dry flask under nitrogen. Dibromoethane (0.132 g, 0.704 mmol) is added and the flask is gently heated with a heat gun for two minutes, whereupon TMSCl (0.039 g, 0.355 mmol) is added. The mixture is stirred at room temperature for 10 min and benzyl bromide (passed through a plug of alumina, 1.20 g, 7.04 mmol) in THF (2 mL) is added dropwise over 10 min. The colorless mixture is stirred for another 2 h and a portion (1.87 M assumed based on 85% yield and 3.2 mL measured volume, 2.00 mL, 3.74 mmol) is added to a solution of CuCN (0.231 g, 2.580 mmol) and LiCl (dried at 150° C. under vacuum for 2 h, 0.234 g, 5.512 mmol) in THF (15 mL) at −78° C. The mixture is warmed to −20° C., stirred at this temperature for 5 min and recooled to −78° C. TMSCl (0.68 g, 5.28 mmol) is added, followed with the ketone prepared in above (0.620 g, 1.173 mmol) in THF (10 mL) over 10 min to give a yellow slurry. After 3 h, the mixture is place in a −25° C. bath (cryobath) and stirred at this temperature for 30 h, whereupon it is diluted with ether, quenched with 10% v/v aqueous ammonia-aqueous saturated ammonium chloride, and stirred vigorously for 15 min. The organic layer is washed with brine. After drying over MgSO$_4$, filtering and concentrating in vacuo, the residue (0.63 g) is taken up in ether (100 mL) and stirred with aqueous 1 M HCl for 5 min. The organic phase is separated, washed with saturated aqueous sodium bicarbonate, brine and dried over MgSO$_4$. After drying over MgSO$_4$ and filtering, the mixture is concentrated in vacuo to give the crude product.

E. 3-Benzyl-1-(3,5-dimethoxyphenyl)-5-(1-trityl-1H-imidazol-4-yl)pentan-1-ol The crude ketone prepared above (0.53 g, 0.854 mmol) is dissolved in dichloromethane (4 mL) and methanol (8 mL), and sodium borohydride (0.129 g, 3.415 mmol) is added. After 30 min, water (25 mL) is added and the volatiles are evaporated in vacuo. The aqueous phase is extracted with dichloromethane and the combined organic phase is dried over MgSO$_4$, filtered through a cotton plug and concentrated in vacuo. Purification by silica gel flash chromatography (elution with hexanes-ethyl acetate, 1:1 to 3:7) afforded the alcohol as white foam and a 1:1 mixture of diastereomers.

F. 7-Benzyl-5-(3,5-dimethoxy-phenyl)-6,7,8,9-tetrahydro-5H-imidazo[1,5-a]azepine The alcohol prepared above (0.150 g, 0.241 mmol) is dissolved in dichloromethane (10 mL) and thionyl chloride (0.100 g, 0.843 mmol) is added. After 30 min, 10 drops of saturated aqueous sodium bicarbonate are added. The mixture is dried over MgSO$_4$, filtered and concentrated in vacuo. The mixture is redissolved in dry acetonitrile and heated to reflux. After 48 h, methanol (5 mL) is added and after 2 h and the mixture is evaporated to dryness in vacuo and taken up in 1M aqueous HCl and ethyl acetate. The aqueous phase is washed with ether. The pH is adjusted to ca. 10 with 2M aqueous sodium hydroxide and it is extracted with dichloromethane. The combined dichloromethane fractions are dried over MgSO$_4$, filtered and concentrated in vacuo. The residue is purified by silica gel flash chromatography (elution with dichloromethane-methanol, 19:1 to 9:1) to afford the cis diastereomer. MS (ESI) m/z 363 (M+H); $^1$H NMR (400 MHz, CDCl$_3$) (HCl salt) δ ppm 1.17-1.27 (m, 1H), 1.84 (dt, J=14.1, 10.9 Hz, 1H), 1.98-2.10 (m, 2H), 2.25 (d, J=14.1° Hz, 1H), 2.53-2.65 (m, 3H), 3.01 (ddd, J=15.4, 6.3, 1.8 Hz, 1H), 379 (s, 6H), 4.89 (d, j=10.4 Hz, 1H), 6.44-6.52 (m, 3H), 6.76 (br s, 2H), 7.11-7.22 (m; 3H), 7.25-730 (m, 2H)

Other Embodiments

Other embodiments will be evident to those of skill in the art. It should be understood that the foregoing detailed description is provided for clarity only and is merely exemplary. The spirit and scope of the present invention are not limited to the above examples, but are encompassed by the following claims.

What is claimed is:

1. A compound of formula (III)

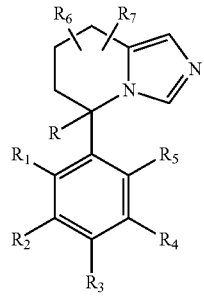

(III)

wherein
R is hydrogen, $(C_1-C_4)$ alkyl, $(C_2-C_4)$ alkenyl, —C(O)O—$R_{10}$, or —C(O)N($R_{11}$)($R_{12}$), said $(C_1-C_4)$ alkyl and $(C_2-C_4)$ alkenyl are optionally substituted by one to three substituents independently selected from hydroxyl, $(C_1-C_4)$ alkoxy, halo, —NH$_2$, or $(C_1-C_4)$-[(alkyl)(alkyl)N—];

wherein $R_{10}$, $R_{11}$ and $R_{12}$ are independently hydrogen, $(C_1-C_4)$ alkyl, $(C_6-C_{10})$ aryl-$(C_1-C_4)$ alkyl-, $(C_3-C_8)$ cycloalkyl, or $(C_2-C_4)$ alkenyl, each of which is optionally substituted by one to three substituents independently selected from halo, hydroxyl, or $(C_1-C_4)$ alkoxy;

$R_1$ is a $(C_1-C_4)$ alkoxy;

$R_2$, $R_3$, $R_4$, and $R_5$ are independently selected from hydrogen, halo, cyano, —NH$_2$, $(C_1-C_4)$-[(alkyl)(alkyl)N—], $(C_1-C_4)$ alkoxy, $(C_2-C_4)$ alkenyl, $(C_1-C_4)$ alkyl, $(C_1-C_4)$ haloalkyl, $(C_6-C_{10})$ aryl, or (5-9)-membered heteroaryl, said $(C_1-C_4)$ alkoxy, $(C_2-C_4)$ alkenyl, $(C_1-C_4)$ alkyl and $(C_6-C_{10})$ aryl being optionally substituted by one to three substituents independently selected from halo, $(C_1-C_4)$ alkoxy, $(C_1-C_4)$ alkyl, —NH$_2$, cyano, nitro, $(C_1-C_4)$ alkoxy-$(C_1-C_4)$ alkyl-, or $(C_1-C_4)$ haloalkyl, with the proviso that no more than three of $R_2$, $R_3$, $R_4$, and $R_5$ are simultaneously hydrogen;

$R_6$ and $R_7$ are independently hydrogen, $(C_1-C_4)$ alkyl, $(C_3-C_8)$ cycloalkyl, $(C_1-C_4)$ alkoxy, phenyl, or benzyl, said phenyl and benzyl are optionally substituted by one to three substituents independently selected from halo, $(C_1-C_4)$ alkyl, or $(C_1-C_4)$ alkoxy;

when $R_6$ and $R_7$ are attached to the same carbon atom, they optionally form a moiety (A) represented by the following structure:

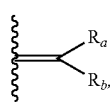

(A)

wherein $R_a$ and $R_b$ are independently hydrogen, or $(C_1-C_4)$ alkyl, or $R_a$ and $R_b$ taken together with said carbon atom optionally form a 3-8-membered ring;

or a pharmaceutically acceptable salt thereof; or an optical isomer thereof; or a mixture of optical isomers.

2. A pharmaceutical composition comprising a therapeutically effective amount of a compound according to claim 1 and one or more pharmaceutically acceptable carriers.

3. A pharmaceutical composition comprising a therapeutically effective amount of a compound according to claim 1 and one or two or more therapeutically active agents selected from angiotensin II receptor antagonist or a pharmaceutically acceptable salt thereof, HMG-Co-A reductase inhibitor or a pharmaceutically acceptable salt thereof; angiotensin converting enzyme (ACE) Inhibitor or a pharmaceutically acceptable salt thereof; calcium channel blocker (CCB) or a pharmaceutically acceptable salt thereof; dual angiotensin converting enzyme/neutral endopeptidase (ACE/NEP) inhibitor or a pharmaceutically acceptable salt thereof; endothelin antagonist or a pharmaceutically acceptable salt thereof; renin inhibitor or a pharmaceutically acceptable salt thereof; diuretic or a pharmaceutically acceptable salt thereof; an ApoA-I mimic; an anti-diabetic agent; an obesity-reducing agent; an aldosterone receptor blocker; an endothelin receptor blocker; a CETP inhibitor; an inhibitor of Na-K-ATPase membrane pump; a beta-adrenergic receptor blocker or an alpha-adrenergic receptor blocker; a neutral endopeptidase (NEP) inhibitor; and an inotropic agent.

4. A pharmaceutical combination comprising a therapeutically effective amount of a compound according to claim 1 and one or two or more therapeutically active agents selected from an antiestrogen; an anti-androgen; a gonadorelin agonist; a topoisomerase I inhibitor; a topoisomerase II inhibitor; a microtubule active agent; an alkylating agent; an anti-neoplastic anti-metabolite; a platin compound; a compound targeting/decreasing a protein or lipid kinase activity or a protein or lipid phosphatase activity, a anti-angiogenic compound; a compound which induces cell differentiation processes; monoclonal antibodies; a cyclooxygenase inhibitor; a bisphosphonate; a heparanase inhibitor; a biological response modifier; an inhibitor of Ras oncogenic isoforms; a telomerase inhibitor; a protease inhibitor, a matrix metalloproteinase inhibitor, a methionine aminopeptidase inhibitor; a proteasome inhibitor; agents which target, decrease or inhibit the activity of Flt-3; an HSP90 inhibitor; antiproliferative antibodies; an HDAC inhibitor; a compound which targets, decreases or inhibits the activity/function of serine/theronine mTOR kinase; a somatostatin receptor antagonist; an anti-leukemic compound; tumor cell damaging approaches; an EDG binder; a ribonucleotide reductase inhibitor; an S-adenosylmethionine decarboxylase inhibitor; a monoclonal antibody of VEGF or VEGFR; an Angiostatic steroid; an implant containing corticosteroids; an AT1 receptor antagonist; and an ACE inhibitor.

* * * * *